United States Patent
Lobl et al.

(10) Patent No.: US 6,596,752 B1
(45) Date of Patent: Jul. 22, 2003

(54) INHIBITORS OF $\alpha_4\beta_1$ MEDIATED CELL ADHESION

(75) Inventors: Thomas J. Lobl, Foster City, CA (US); Bradley R. Teegarden, San Diego, CA (US); Alexander Polinsky, San Diego, CA (US); Gilbert M. Rishton, Thousand Oaks, CA (US); Masafumi Yamagishi, Hyogo-ken (JP); Steven Tanis, Kalamazoo, MI (US); Jed F. Fisher, Three Rivers, MI (US); Edward W. Thomas, Kalamazoo, MI (US); Robert A. Chrusciel, Portage, MI (US)

(73) Assignees: Tanabe Seiyaku Co., Ltd., Osaka (JP); Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 10/193,137

(22) Filed: Jul. 12, 2002

Related U.S. Application Data

(62) Division of application No. 09/102,584, filed on Jun. 23, 1998, now Pat. No. 6,482,849
(60) Provisional application No. 60/050,515, filed on Jun. 23, 1997.

(51) Int. Cl.[7] .................. A61K 31/415; A61K 31/535; A61K 31/47; A61K 31/44; A61K 31/40
(52) U.S. Cl. .................. 514/401; 514/237.5; 514/307; 514/350; 514/354; 514/400; 514/419; 514/423; 514/448; 514/471; 514/478; 514/530; 514/562; 514/563; 514/566; 544/165; 546/145; 546/298; 546/316; 546/323; 548/338.1; 548/376.1; 548/495; 548/537; 549/69; 549/487; 549/493; 566/13; 566/27; 562/430; 562/432
(58) Field of Search .................. 514/237.5, 307, 514/350, 354, 355, 400, 401, 419, 423, 448, 471, 478, 530, 562, 563, 566; 544/165; 546/145, 298, 316, 323; 548/338.1, 376.1, 495, 537; 549/69, 487, 493; 560/13, 27; 562/430, 432

(56) References Cited

U.S. PATENT DOCUMENTS

| | | | |
|---|---|---|---|
| 4,517,686 A | 5/1985 | Ruoslahti et al. | 623/11 |
| 4,578,079 A | 3/1986 | Ruoslahti et al. | 623/11 |
| 4,589,881 A | 5/1986 | Pierschbacher et al. | 623/11 |
| 4,614,517 A | 9/1986 | Ruoslahti et al. | 623/11 |
| 4,661,111 A | 4/1987 | Ruoslahti et al. | 623/11 |
| 4,683,291 A | 7/1987 | Zimmerman et al. | 530/324 |
| 4,792,525 A | 12/1988 | Ruoslahti et al. | 435/240.243 |
| 4,816,484 A | 3/1989 | Tovoshima et al. | 514/563 |
| 6,221,367 B1 | 4/2001 | Milstein et al. | 424/400 |

FOREIGN PATENT DOCUMENTS

| | | |
|---|---|---|
| WO | WO9622966 | 8/1996 |
| WO | WO 9853814 | 12/1998 |
| WO | WO 9853817 | 12/1998 |
| WO | WO 9853818 | 12/1998 |
| WO | WO 9854207 | 12/1998 |
| WO | WO 9906390 | 2/1999 |
| WO | WO 9906431 | 2/1999 |
| WO | WO 9906432 | 2/1999 |
| WO | WO 9906433 | 2/1999 |
| WO | WO 9906434 | 2/1999 |
| WO | WO 9906435 | 2/1999 |
| WO | WO 9906436 | 2/1999 |
| WO | WO 9906437 | 2/1999 |
| WO | WO 9910312 | 3/1999 |
| WO | WO 9910313 | 3/1999 |
| WO | WO 9926615 | 6/1999 |
| WO | WO 9926921 | 6/1999 |
| WO | WO 9926922 | 6/1999 |
| WO | WO 9935163 | 7/1999 |
| WO | WO 9937618 | 7/1999 |
| WO | WO 9943642 | 9/1999 |
| WO | WO 9948879 | 9/1999 |
| WO | WO 9961465 | 12/1999 |
| WO | WO 9964390 | 12/1999 |
| WO | WO 9964395 | 12/1999 |

OTHER PUBLICATIONS

M.D. Pierschbacher et al., Proc. Natl. Acad. Sci., 81:5985–5988 (Oct. 1984).
K. T. Wanner et al., Liebigs Annalen Der Chemie, 5:477–484 (1993).
J.L. Guan et al., Cell, 60:53–61 (Jan. 1990).
R.O. Hynes, Cell, 48:549–554 (Feb. 1987).
M.E. Hemler, Annu. Rev. Immunol., 8:365–400(1990).
R. Pytela et al., Cell, 40:191–198 (Jan. 1985).
C. Rüegg et al., J. Cell Biol., 117 (1) :179–189 (Apr. 1992).
D.P. Andrew et al., J. Immunol., 153:3847–3861(1994).
M.J. Briskin et al., Nature, 363:461–464(Jun. 1993).
A.M. Shyjan et al., J. Immunol.,156:2851–2857(1996).
T.M. Carlos et al., Immunol. Rev., 114:5–28(1990).
L. Osborn, Cell, 62:3–6(Jul. 1990).

(List continued on next page.)

*Primary Examiner*—Peter O'Sullivan
(74) *Attorney, Agent, or Firm*—Birch, Stewart, Kolasch & Birch, LLP

(57) ABSTRACT

The present invention relates to small molecules according to the formula [I]:

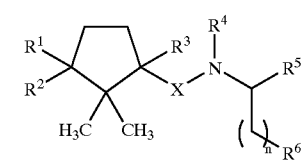

which are potent inhibitors of $\alpha_4\beta_1$ mediated adhesion to either VCAM or CS-1 and which can be used for treating or preventing $\alpha_4\beta_1$ adhesion mediated conditions in a mammal such as a human.

15 Claims, No Drawings

OTHER PUBLICATIONS

T.A. Springer, Nature, 346:425–434 (Aug. 1990).
J.G. Geng et al., Nature, 343:757–760 (Feb. 1990).
L.M. Stoolman, Cell, 56:907–910 (Mar. 1989).
A.C.H.M. Van Dinther–Janssen et al., J. Immunol., 147:4207–4210 (Dec. 1991).
A. Laffón et al., J. Clin. Invest., 88:546–552 (Aug. 1991).
J. Morales–Ducret et al., J. Immunol. 149:1424–1431 (Aug. 1992).
G. M. Walsh et al., J. Immunol., 146:3419–3423 (May 1990).
B.S. Bochner et al., J. Exp. Med., 173:1553–1556 (Jun. 1991).
W. M. Abraham et al., J. Clin. Invest., 93:776–787 (Feb. 1994).
V. B. Weg et al., J. Exp. Med., 177:561–566 (Feb. 1993).
D.K. Podolsky et al., J. Clin. Invest., 92:372–380 (Jul. 1993).
R.G. Bell et al., J. Immunol. 151(9):4790–4802 (Nov. 1993).
T.A. Yednock et al., Nature, 356:63–66 (Mar. 1993).
J.L. Baron et al., J. Exp. Med., 177:57–68 (Jan. 1993).
J.L. Baron et al., J. Clin. Invest., 93:1700–1708 (Apr. 1994).
X.D. Yang et al., Proc. Natl. Acad. Sci., 90:10494–10498 (1993).
L.C. Burkly et al., Diabetes, 43:529–534 (Apr. 1994).
E.A. Wayner et al., J. Cell Biol., 109:1321–1330 (Sep. 1989).
M.I. Cybulsky et al., Science, 251:788–791 (Feb. 1991).

INHIBITORS OF $\alpha_4\beta_1$ MEDIATED CELL ADHESION

This application is a divisional of application Ser. No. 09/102,584, filed on Jun. 23, 1998, now U.S. Pat. No. 6,482,849 which is the conversion of Application No. 60/050,515, filed on Jun. 23, 1997, the entire contents of which are hereby incorporated by reference and for which priority is claimed under 35 U.S.C. §120.

BACKGROUND OF THE INVENTION

1. Field of the Invention

The present invention relates to small molecules that are potent inhibitors of $\alpha_4\beta_1$ mediated adhesion to either VCAM or CS-1 and which could be useful for the treatment of inflammatory diseases.

2. Description of Related Art

The extracellular matrix (ECM) is the major component of connective tissue which provides structural integrity, and promotes cell migration and differentiation. As part of these functions, extracellular matrix molecules such as fibronectin, collagen, laminin, von Willebrand factor, is thrombospondin, fibrinogen, and tenascin have been shown to support adhesion of cells in vitro. This adhesive interaction is critical for a number of biological processes including hemostasis, thrombosis, wound healing, tumor metastasis, immunity and inflammation.

Fibronectin (FN) is the prototype ECM molecule. The major cell attachment site in the fibronectin molecule has been reproduced synthetically with the amino acid sequence arginine-glycine-aspartic acid, or RGD using single letter nomenclature. Peptides containing the RGD sequence which either inhibit or promote cell adhesion have been described (U.S. Pat. Nos. 4,589,881; 4,661,111; 4,517,686; 4,683,291; 4,578,079; 4,614,517; and 4,792,525) Changes in the peptide as small as the exchange of alanine for glycine or glutamic acid for aspartic acid, which constitute the addition of a single methyl or methylene group to the tripeptide, eliminates these activities (Pierschbacher et al., *Proc. Natl. Acad. Sci. USA* 81:5985 (1984)). Recently, a second FN cell binding domain has been identified within the alternatively spliced region of the A chain of the molecule, known as the connecting segment 1 (CS-1). The most active cell-binding site within this alternatively spliced region is composed of 25 amino acids where the carboxy terminus contains the sequence EILDVPST. The amino acid sequence EILDVPST forms a recognition motif on FN for cell surface receptors. (Wayner et al., *J. Cell Biol.* 109:1321 (1989); Guan et al., *Cell* 60:53 (1990)).

The receptors which recognize these sites on FN belong to a gene superfamily called integrins which consist of heterodimeric complexes of non-covalently associated alpha and beta subunits. A common β subunit combines with unique α subunits to form an adhesion receptor of defined specificity. To date, 8β subunits have been identified which can dimerize with 16 distinct α subunits forming 22 distinct integrins. The β1 subfamily, also known as the VLA family (Very Late Activation Antigens), binds to ECM molecules such as FN, collagen and laminin. For reviews, see, Hynes, *Cell* 48:549 (1987); Hemler, *Annu. Rev. Immunol.* 8:365 (1990). Leukocyte interaction with FN at the two spatially separate binding domains is mediated by two distinct integrins. The RGD site is recognized by the integrin $\alpha_5\beta_1$, while, EILDV is recognized by $\alpha_4\beta_1$ (Pytela et al., *Cell* 40:191 (1985); Wayner et al., *J. Cell Biol.* 109:1321 (1989); Guan et al, *Cell* 60:53 (1990)).

Vascular endothelial cells form the interface between blood and tissues and control the passage of leukocytes as well as plasma fluid into tissues. A variety of signals generated at the site of inflammation can activate both endothelial cells as well as circulating leukocytes so that they become more adhesive to one another. Following this initial adhesion the leukocytes migrate into the tissues to perform host defense functions. Several adhesion molecules have been identified which are involved in leukocyte-endothelial interactions.

In the $\beta_1$ subfamily, in addition to binding to fibronectin, $\alpha_4\beta_1$ interacts with a cytokine inducible protein on endothelial cells termed vascular cell adhesion molecule (VCAM). Further involved in the leukocyte-endothelial adhesion process is the $\beta_2$ integrin subfamily. $\beta_2$ integrins include CD11a/CD18, CD11b/CD18, and CD11c/CD18. In addition, the $\beta_7$ subunit associates with $\alpha_4$ to form a unique $\alpha_4\beta_7$ heterodimer which binds to FN, to VCAM, and to Mucosal Addressin Cell Adhesion Molecule-1 (MAdCAM) (Ruegg et al, *J. Cell.Biol.* 117:179 (1992); Andrew et al., *J. Immunol.* 153:3847 (1994); Briskin et al., *Nature* 363:461 (1993); Shyjan et al, *J. Immunol.* 156:2851 (1996)). $\alpha_4$ integrins are widely expressed on different cell types including hematopoietic progenitors, lymphocytes, natural killer cells, monocytes, eosinophils, basophils, and mast cells (Helmer, M. E., *Annu. Rev. Immunol.* 8:365 (1990)). Other molecules on endothelial cells which bind to the leukocytes include ICAM-1, ICAM-2, E-selectin and P-selectin (Carlos and Harlan, *Immunol. Rev.* 114:1 (1990); Osborn, L., *Cell* 62:3 (1990); Springer T., *Nature* 346:425 (1990); Geng et al., *Nature* 347:757 (1990); Stoolman, *Cell* 56:907 (1989)).

A number of in vitro and in vivo studies indicate that $\alpha_4\beta_1$ plays a critical role in the pathogenesis of a variety of diseases. Monoclonal antibodies directed against $\alpha_4$ have been tested in a variety of disease models. Anti-$\alpha_4$ antibodies block adhesion of lymphocytes to synovial endothelial cells; this adhesion plays a potential role in rheumatoid arthritis (van Dinther-Janssen et al, *J. Immunol.* 147:4207 (1991)). $\alpha_4$ has also been implicated with respect to rheumatoid arthritis in separate studies (Laffon et al, *J. Clin. Invest.* 88:546 (1991); Morales-Ducret et al, *J. Immunol.* 149:1424 (1992)). A significant number of studies have evaluated the role of $\alpha_4$ in allergy and asthma. For example, monoclonal antibodies to $\alpha_4$ block adhesion of basophils and eosinophils to cytokine activated endothelial cells (Walsh et al, *J. Immunol.* 146:3419 (1991); Bochner et al, *J. Exp. Med.* 173:1553 (1991)). Monoclonal antibodies to $\alpha_4$ were also effective in several lung antigen challenge models (Abraham et al, *J. Clin. Invest.* 93:776 (1994); Weg et al, *J. Exp. Med.* 177:561 (1993)). The cotton-top tamarin, which experiences spontaneous chronic colitis, showed a significant attenuation of their colitis when anti-$\alpha_4$ antibody was administered (Podolsky et al, *J. Clin. Invest.* 92:372 (1993); Bell et al, *J. Immunol.* 151:4790 (1993)). In a rat and mouse model, autoimmune encephalomyelitis was blocked by anti-$\alpha_4$ antibody (Yednock et al, *Nature* 356:63 (1992); Baron et al, *J. Exp. Med.* 177:57 (1993)). Anti-$\alpha_4$ monoclonal antibodies also inhibit insulitis and delay the onset of diabetes in the non-obese diabetic mouse (Baron et al, *J. Clin. Invest.* 93:1700 (1994); Yang et al, *Proc. Natl. Acad. Sci. USA* 90:10494 (1993); Burkly et al, *Diabetes* 43:529 (1994)). α4 is also implicated in atherosclerosis due to its endothelial expression during atherogenesis (Cybulsky et al, *Science* 251:788 (1991)). The migration of leukocytes to an inflammatory site can also be blocked by anti-$\alpha_4$ antibodies. In addition to the blocking of migration, inhibitors of leukocyte endothelial adhesion may block the costimulatory signals mediated by integrins and thus inhibit overproduction of inflammatory cytokines. In a separate set of experiments not using anti-$\alpha_4$ antibodies, the peptides GRDGSP or EILDV were tested against contact hypersensitivity response. The contact hypersensitivity response was found to be blocked by GRDGSP or EILDV suggesting that both $\alpha_4\beta_1$ and $\alpha_5\beta_1$ are involved in this inflammatory response.

Other ailments which may involve $\alpha_4\beta_1$-mediated conditions include the inflammatory disorders rheumatoid arthritis, allergic disorders, asthma, spontaneous chronic colitis, insulitis, contact hypersensitivity response, atherosclerosis and autoimmune encephalomyelitis. These studies illustrate that small molecules that are potent inhibitors of $\alpha_4\beta_1$ mediated adhesion to either VCAM-1 or CS-1 may be used as a form of treatment in numerous inflammatory diseases. However, these inflammatory conditions could be expanded to include adult respiratory distress syndrome, AIDS, cardiovascular diseases, thrombosis or harmful platelet aggregation, reocclusion following thrombolysls, allograft rejection, reperfusion injury, psoriasis, eczema, contact dermatitis and other skin inflammatory diseases, osteoporosis, osteoarthritis, atherosclerosis, neoplastic diseases including metastasis of neoplastic or cancerous growth, wound healing enhancement, treatment of certain eye diseases such as detaching retina, Type I diabetes, multiple sclerosis, systemic lupus erythematosus (SLE), inflammatory and immunoinflammatory conditions including ophthalmic inflammatory conditions and inflammatory bowel diseases, ulcerative colitis, regional enteritis and other autoimmune diseases. Accordingly, a compound which could inhibit these conditions is desirable.

SUMMARY OF THE INVENTION

The present invention is directed to a compound of the formula [I]:

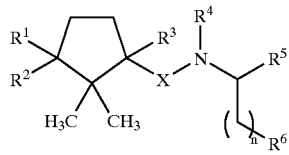

[I]

In the above formula [I], n is an integer of 0 or 1, $R^1$ is a hydrogen atom or a methyl group, and $R^2$ can be selected from the following: a —CN group; a —COOH group; a —($C_{1-6}$alkylene)OH group, preferably a —($C_{1-3}$alkylene)OH group; a $CH_2O(C_{1-6}$ alkyl) group, preferably a —$CH_2O$ ($C_{1-3}$ alkyl) group; a —($C_{1-3}$ alkylene)COOH group, preferably a —($C_{1-3}$ alkylene)COOH group; a —$CH_2O(C_{1-6}$ alkylene)O($C_{1-6}$ alkyl) group, preferably a —$CH_2O(C_{1-3}$ alkylene)O($C_{1-6}$ alkyl) group or a —$CH_2O(C_{1-6}$ alkylene)O($C_{1-3}$ alkyl) group, more preferably a —$CH_2O(C_{1-3}$ alkylene)O($C_{1-3}$ alkyl) group; a —$CH_2O(C_{1-6}$ alkylene)COOH group, preferably a —$CH_2O(C_{1-3}$ alkylene)COOH group; a —($C_{2-7}$ alkenylene)COOH group, preferably a —($C_{2-4}$ alkenylene)COOH group; a —CO($C_{1-6}$ alkylene)COOH group, preferably a —CO($C_{1-3}$ alkylene)COOH group; a —CO($C_{2-7}$ alkenylene)COOH group, preferably a —CO($C_{2-4}$ alkenylene)COOH group; a —CO($C_{1-6}$ alkylene)O($C_{1-6}$ alkyl) group, preferably a —CO($C_{1-3}$ alkylene)O($C_{1-6}$ alkyl) group or a —CO($C_{1-6}$ alkylene)O($C_{1-3}$ alkyl) group, more preferably a —CO($C_{1-3}$ alkylene)O($C_{1-3}$ alkyl) group; a —CO($C_{1-6}$ alkylene)CO($C_{1-6}$ alkyl) group, preferably a —CO($C_{1-3}$ alkylene)CO($C_{1-6}$ alkyl) group or a —CO($C_{1-6}$ alkylene)CO($C_{1-3}$ alkyl) group, more preferably a —CO($C_{1-3}$ alkylene)CO($C_{1-3}$ alkyl) group; a —CONH($C_{1-6}$ alkyl) group, preferably a —CONH($C_{1-3}$ alkyl) group; a —CONHO($C_{1-6}$ alkyl) group, preferably a —CONHO($C_{1-3}$ alkyl) group; a —CONH($C_{1-6}$ alkylene)COOH group, preferably a —CONH ($C_{1-3}$ alkylene)COOH group, a —$CONH_2$ group; a —CONH($C_{3-7}$ cycloalkyl) group, preferably a —CONH($C_{3-6}$ cycloalkyl) group; a group as follows:

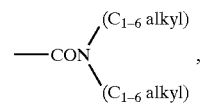

a —$CONHOCH_2Ph$ group; a —CONH($C_{1-6}$ alkylene)CN group, preferably a —CONH($C_{1-3}$ alkylene)CN group; a —COO($C_{1-6}$ alkyl) group, preferably a —COO($C_{1-3}$ alkyl) group; a —$CH_2O(C_{1-6}$ alkylene)$CONH_2$ group, preferably a —$CH_2O(C_{1-3}$ alkylene)$CONH_2$ group; a —CONH($C_{1-6}$ alkylene)$CONH_2$ group, preferably a —CONH($C_{1-3}$ alkylene)$CONH_2$ group; a —CONHOH group; a —$NHCOOCH_2Ph$ group; or a group selected from the following formula:

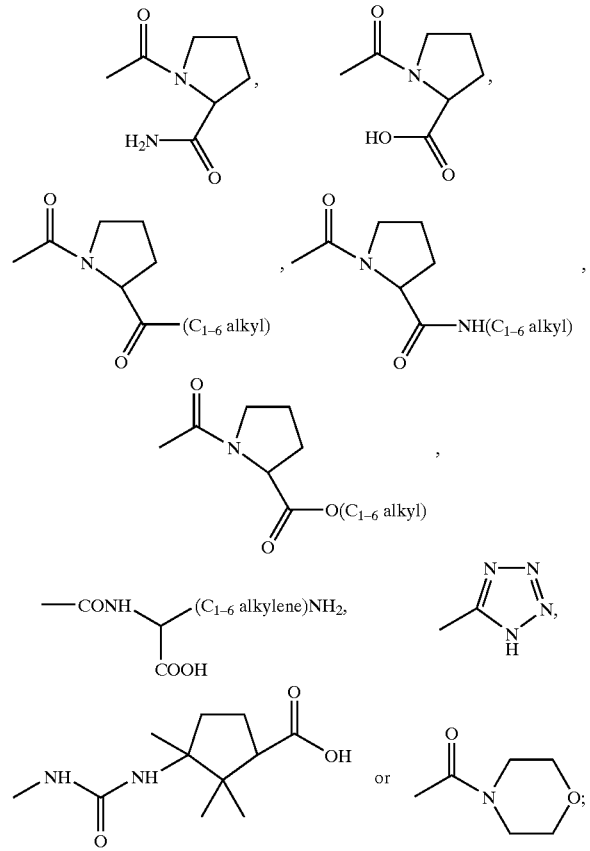

In the above Formula (I), in $R^2$, the $C_{1-6}$ alkylene is preferably $C_{1-3}$ aklylene, the $C_{2-7}$ alkenylene is preferably $C_{2-4}$ alkenylene, the $C_{1-6}$ alkyl is preferably $C_{1-3}$ alkyl and the $C_{3-7}$ cycloalkyl is preferably $C_{3-6}$ cycloalkyl.

In the above formula [I], $R^3$ can be a hydrogen atom or a methyl group, X can be a methylene group or a —CO— group, and $R^4$ can selected from the following: a hydrogen atom; or a $C_{1-6}$ alkyl group, preferably a $C_{1-3}$ alkyl group.

In the above formula [I], $R^5$ can be a group selected from the following: a —COOH group or an ester or an amide thereof; a —(C$_{1-6}$ alkylene)COOH group, preferably a —(C$_{1-3}$ alkylene)COOH group, or an ester or an amide thereof; a —(C$_{1-7}$ alkylene)O(C$_{1-6}$ alkyl) group, preferably a —(C$_{1-4}$ alkylene)O(C$_{1-6}$ alkyl) group or a —(C$_{1-7}$ alkylene)O(C$_{1-3}$ alkyl) group, more preferably a —(C$_{1-4}$ alkylene)O(C$_{1-3}$ alkyl) group; a —(C$_{1-7}$ alkylene)OH group, preferably a —(C$_{1-4}$ alkylene)OH group; a —COO(C$_{1-6}$ alkyl) group, preferably a —COO(C$_{1-3}$ alkyl) group; a —CONH(C$_{1-6}$ alkyl) group, preferably a —CONH(C$_{1-3}$ alkyl) group; or a —CONH$_2$ group.

In the above formula [I], R$^6$ can be a substituted or unsubstituted monocyclic or bicyclic aryl group, a substituted or unsubstituted monocyclic or bicyclic heteroaryl group, a substituted or unsubstituted monocyclic or bicyclic arylcarbonylamino-C$_{1-6}$ alkyl group, a substituted or unsubstituted monocyclic or bicyclic aliphatic heterocyclic carbonyl group, a 9-fluorenylmethyloxycarbonylamino-C$_{1-6}$ alkyl group, a 3-tosylguanidino-C$_{1-6}$ alkyl group,

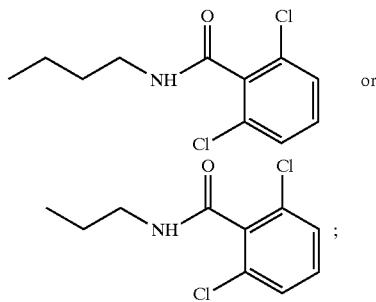

or provided that R$^1$ and R$^3$ must be different and when R$^2$ or R$^6$ is a —COOH group or contains a —COOH group, then a pharmaceutically acceptable ester or a pharmaceutically acceptable amide thereof are included and also with the proviso that [1S-[1α,(R*),3α]]-α-[[(3-Carboxy-2,2,3-trimethylcyclopentyl)carbonyl]amino]-4-(2,6-dichlorobenzoyl)-γ-oxo-1-pyrazinebutanoic acid methyl ester or [1S-[1α,(R*),3α]]-β-[[(3-Carboxy-2,2,3-trimethylcyclopentyl)carbonyl]amino]-4-(2,6-dichlorobenzoyl)-γ-oxo-1-pyrazinebutanoic acid methyl ester are excluded.

In the above formula [I], in R$^6$, an aryl group or aryl moiety in the arylcabonylamino group is a 5- or 6-membered aromatic hydrocarbon ring; and including any bicyclic group in which any of the above ring is fused to another above ring; and substituted by zero (0) to three (3) substituents.

Examples of aryl can include phenyl, a C$_{1-6}$ alkoxyphenyl group and naphthyl group. Each of these moieties may be substituted as appropriate.

In R$^6$, a heteroaryl is a 5- or 6-membered partially saturated or unsaturated ring containing from one (1) to four (4) heteroatoms selected from the group consisting of nitrogen, oxygen and sulfur; and including any bicyclic group in which any of the above heterocyclic rings is fused to a benzene ring, C$_3$–C$_8$ cycloalkyl, or another heterocycle; and if chemically feasible, the nitrogen and sulfur atoms may be in the oxidized forms; and substituted by zero (0) to three (3) substituents.

Examples of heteroaryl can include 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazinyl, 2-quinolyl, 3-quinolyl, 1-isoquinolyl, 3-isoquinolyl, 4-isoquinolyl, 2-quinazolinyl, 4-quinazolinyl, 2-quinoxalinyl, 1-phthalazinyl, 2-imidazolyl, 4-imidazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-indolinyl, 3-indolyl, 3-indazolyl, 2-benzoazolyl, 2-benzothiazolyl, 2-benzimidazolyl, 2-benzofuryl, 3-benzofuryl, 2-furyl, 3-furyl, 2-thienyl, 3-thienyl, 2-pyrrolyl, 3-pyrrolyl, 1,2,4-oxadiazolyl-3-yl, 1,2,4-oxadiazol-5-yl, 1,2,4-thiadiazol-3-yl, 1,2,4-thiadiazol-5-yl, 1,2,4-triazol-3-yl, 1,2,4-triazol-5-yl, 1,2,3,4-tetrazol-5-yl, 5-oxazolyl, 1-pyrrolyl, 1-pyrazolyl, 1,2,3-triazol-1-yl, 1,2,4-triazol-1-yl, 1-tetrazolyl, 1-indolinyl, 1-indazolyl, 2-isoindolyl, 1-purinyl, 3-isothiazolyl, 4-isothiazolyl and 5-isothiazolyl. Each of these moieties may be substituted as appropriate.

In R$^6$, an aliphatic heterocyclic moiety in aliphatic heterocyclic carbonyl group is a 5- or 6-membered saturated ring containing from one (1) to four (4) heteroatoms selected from the group consisting of nitrogen, oxygen and sulfur; and including any bicyclic group in which any of the above heterocyclic rings is fused to a benzene ring, C$_3$–C$_8$ cycloalkyl, or another heterocycle; and if chemically feasible, the nitrogen and sulfur atoms may be in the oxidized forms; and substituted by zero (0) to three (3) substituents.

Examples of aliphatic heterocyclic can include piperazinyl group, pyrrolidinyl group, piperidyl group, homopiperidyl group, thiomorpholino group, and morpholino group. Each of these moieties may be substituted as appropriate.

According to the present invention, the term "C$_{1-6}$ alkyl" represents an alkyl group having 1 to 6 carbon atoms. This group may be straight or branched. Illustrative but non-limiting examples of a C$_{1-6}$ alkyl group are methyl, ethyl, n-propyl, isopropyl, n-butyl, iso-butyl, tert-butyl, sec-butyl, n-pentyl, isopentyl and n-hexyl. It is understood that this type of nomenclature extends to terms such as "C$_{1-6}$ methoxy" and therefore encompasses both straight and branced methoxy groups having 1 to 6 carbon atoms.

Also, in the above formula [I] with all substituents as described above, a pharmaceutically acceptable salt thereof is included.

The desired compounds of the present invention have preferred steric configurations. Accordingly, a preferred steric configuration is represented by compounds of the formula [I-1]:

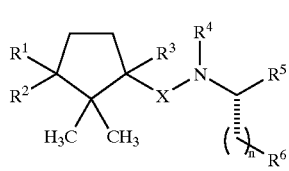

[I-1]

wherein n, R$^1$ through R$^6$ and X are as defined above.

A more preferred steric configuration is represented by compounds according to the formula [I-2]:

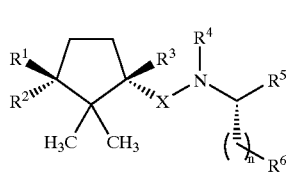

[I-2]

wherein n, R$^1$ through R$^4$, R$^6$ and X are as defined above and R$^5$ can be selected from the following: a —COOH group; a —(C$_{1-6}$ alkylene)COOH group, preferably a —(C$_{1-3}$ alkylene)COOH group; a —(C$_{1-7}$ alkylene)O(C$_{1-6}$ alkyl) group, preferably a —(C$_{1-4}$ alkylene)O(C$_{1-6}$ alkyl) group or a —(C$_{1-7}$ alkylene)O(C$_{1-3}$ alkyl) group, more preferably a —(C$_{1-4}$ alkylene)O(C$_{1-3}$ alkyl) group; a —(C$_{1-7}$ alkylene) OH group, preferably a —(C$_{1-4}$ alkylene)OH group; a —COO(C$_{1-6}$ alkyl) group, preferably a —COO(C$_{1-3}$ alkyl) group; a —CONH(C$_{1-6}$ alkyl) group, preferably a —CONH (C$_{1-3}$ alkyl) group or a —CONH$_2$ group.

In a preferred embodiment of the present invention, R$^6$ can be selected from the following formula:

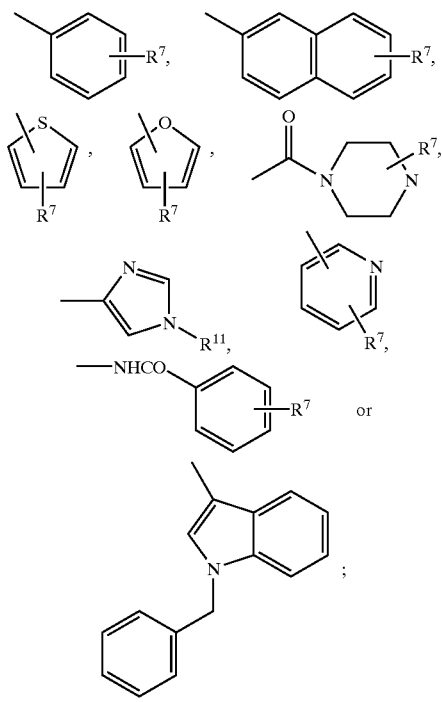

In the above, R$^7$, which occurs one or more times and which may be the same or different in each occurrence, may be selected from the following: a —H group; a —OH group; a —NO$_2$ group; a —NH$_2$ group; a —C$_{1-5}$ alkyl group, preferably a —C$_{1-3}$ alkyl group; a —F group; a —Cl group; a —Br group; a —I group; a —COOH group; a —COO(C$_{1-6}$ alkyl) group, preferably a —COO(C$_{1-3}$ alkyl) group; a —O(C$_1$–C$_8$ alkyl) group, preferably a —O(C$_{1-4}$ alkyl) group; a —CONH(C$_{1-6}$ alkylene)COOH group, preferably a —CONH(C$_{1-3}$ alkylene)COOH group; a —OCH$_2$(C$_{3-7}$ cycloalkyl) group, preferably a —OCH$_2$(C$_{3-6}$ cycloalkyl) group; or a substituent selected from the following formula:

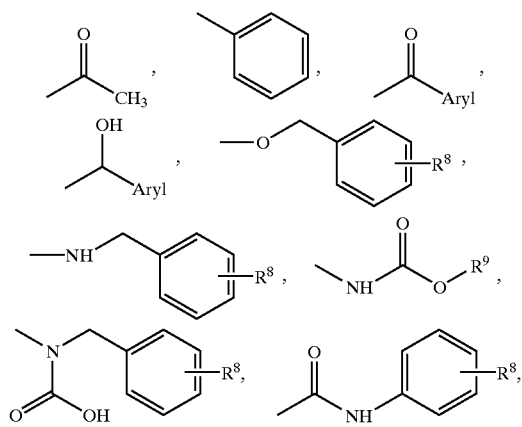

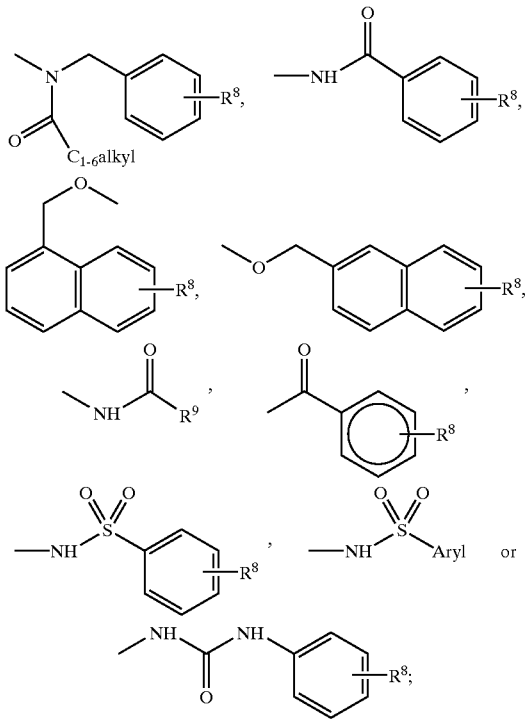

In the above, R$^8$, which occurs one or more times and which may be the same or different in each occurrence, may be selected from the following: a —H group; an —OH group; a —NH$_2$ group; a —NO$_2$ group; a —C$_{1-7}$ alkyl group, preferably a —C$_{1-4}$ alkyl group; a —F group; a —Cl group; a —Br group; a —I group; a —CF$_3$ group; a phenyl group, or a —O(C$_{1-6}$ alkyl) group, preferably a —O(C$_{1-3}$ alkyl) group.

In the above, R$^9$ may be selected from the following: a —H group; a —C$_{1-5}$ alkyl group, preferably a —C$_{1-3}$ alkyl group; a —C$_{3-7}$ cycloalkyl group, preferably a —C$_{3-6}$ cycloalkyl group; a —(C$_{1-6}$alkylene)aryl group, preferably a —(C$_{1-3}$ alkylene)aryl group; an aryl group; or a group selected from the following formula:

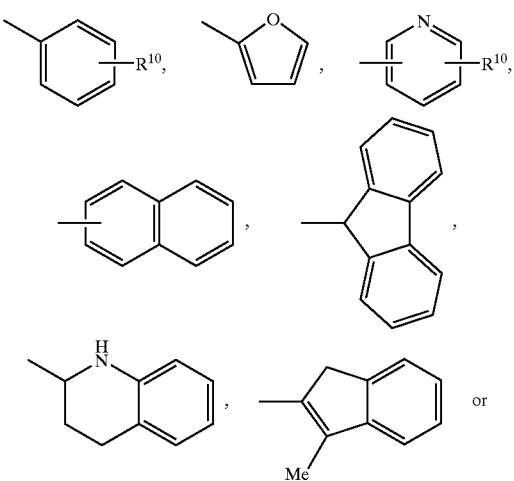

-continued

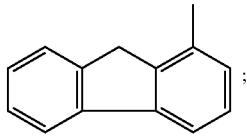

-continued

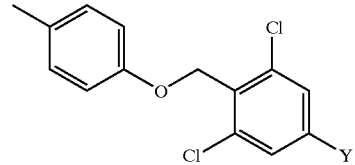

In the above, $R^{10}$, which occurs one or more times and which may be the same or different in each occurrence, may be selected from the following: a —H group; a —F group; a —Cl group; a —Br group; an —I group; a —$NO_2$ group; a —$C_{1-6}$ alkyl group, preferably a —$C_{1-3}$ alkyl group; or a —$O(C_{1-6}$ alkyl) group, preferably a —$O(C_{1-3}$ alkyl) group.

In the above, $R^{11}$ may be selected from the following:

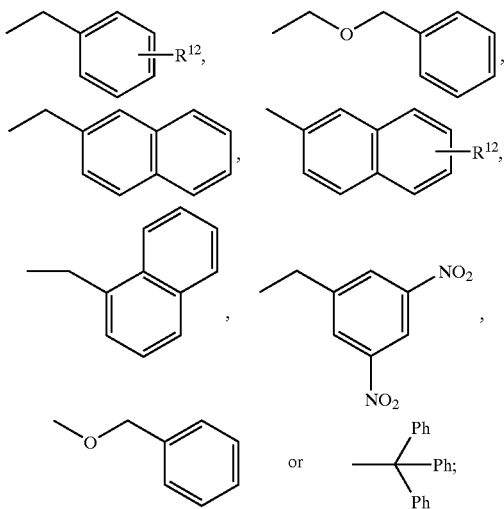

In the above, $R^{12}$, which occurs one or more times and which may be the same or different in each occurrence, may be selected from the following: a —H group; a —$CF_3$ group; a —$OCH_3$ group; a —F group; a —Br group; a —Cl group; or an —I group;

The above embodiments carrying the proviso that when $R^7$ is the formula:

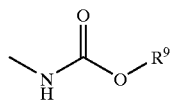

then $R^9$ is other than hydrogen.

In a more preferred embodiment of the present invention, $R^6$ is selected from the following:

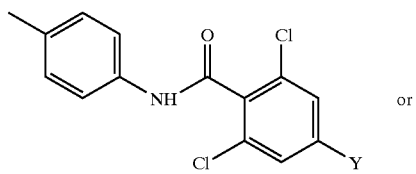

In the above, Y is selected from either a hydrogen atom or a chlorine atom.

In a more preferred embodiment of the present invention, $R^2$ is selected from the following: a —COOH group or an ester or an amide thereof; a —$CONHCH_2COOH$ group; a —$CONHOCH_2Ph$ group; or a —$CONHCH_2CONH_2$ group.

In another preferred embodiment of the present invention, $R^1$ is a —$CH_3$ group, and $R^2$ is a —COOH group; a —$CONHCH_2COOH$ group; a $CONHOCH_2Ph$ group or a —$CONHCH_2CONH_2$ group, and $R^3$ and $R^4$ are hydrogen atoms. Also, X is —CO—, $R^5$ is —COOH, n is 1, and $R^6$ is represented by the following formula

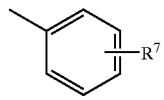

wherein $R^7$ is

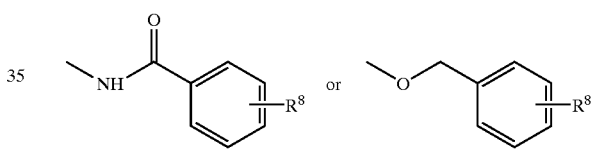

and $R^8$ occurs 2 or 3 times and is a chlorine atom.

Other compounds within the scope of the present invention are compounds of the formula [I-3]:

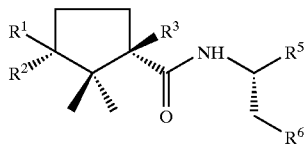

[I-3]

In the above formula [I-3], $R^1$ may be a hydrogen atom or a methyl group. Also in the above formula [I-3], $R^2$ may be selected from the following: a —CN group; a —COOH group; a —$CONH_2$ group; a —CONHOH group; a —CON$(CH_3)_2$ group; a —$CH_2OCH_2COOH$ group; a —CH=CHCCOH group; a —$CONHCH_2COOH$ group; a —$CONH(CH_2)_2COOH$ group; a —$CONCH_2CONH_2$ group; a —$CONH(CH_2)_2CN$ group; a group selected from the following:

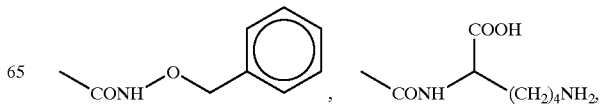

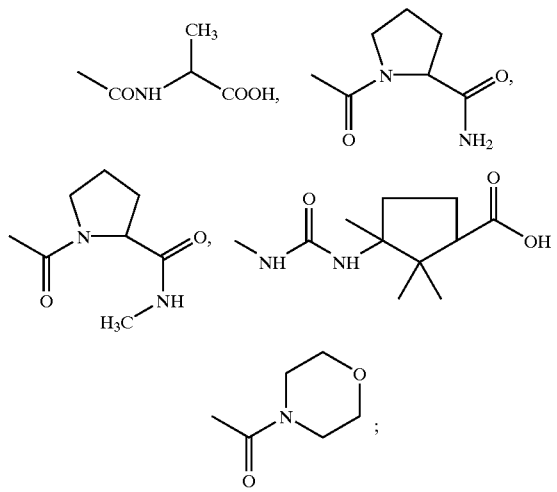

In the above formula [I-3], $R^3$ may be a hydrogen atom or a methyl group and $R^5$ may be a —COOH group or a COOMe group.

In the above formula [I-3], $R^6$ may be selected from the following:

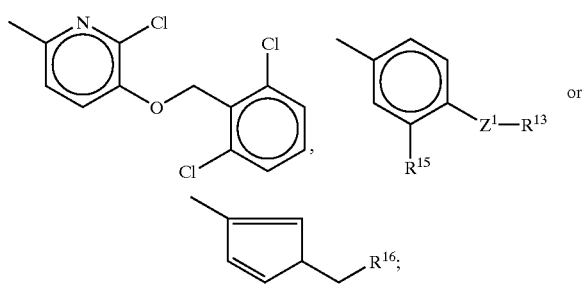

In the above, $Z^1$ may be selected from the following: a —O— group; a —NHCO— group; a —NHCH$_2$— group, a —OCH$_2$— group; a —CONH-group; a —NHSO$_2$— group; a —NHCOCH$_2$— group; or a —N(CH$_3$)CH$_2$— group.

In the above, $R^{13}$ may be selected from the following: a —H group; a -iBuO group; a —CH$_3$ group; a i-Bu group; or a group selected from the following:

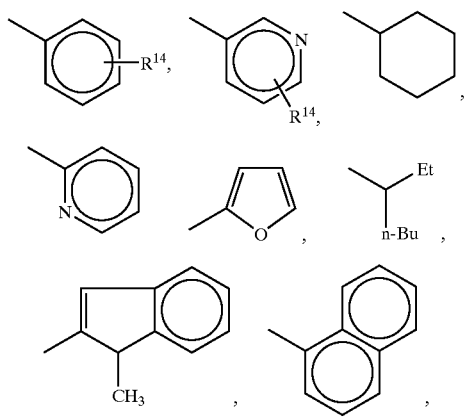

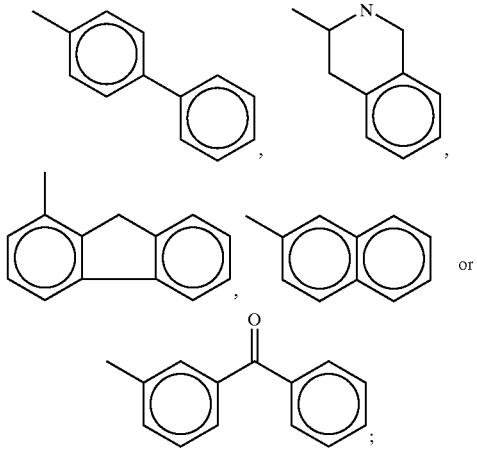

In the above, $R^{14}$, which occurs one or more times and which may be the same or different in each occurence, may be selected from the following: a —H group; a —F group; a —Cl group; a —Br group; an —I group; a —CH$_3$ group; a —OCH$_3$ group; a —CF$_3$ group; a —NO$_2$ group; a —NH$_2$ group; or a -n-C$_7$H$_{15}$ group.

In the above, $R^{15}$ may be selected from the following: a —H group; a —OH group; a —NO$_2$ group; or a group selected from the following:

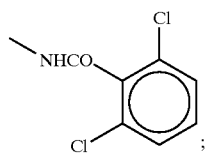

In the above, $R^{16}$ may be selected from the following

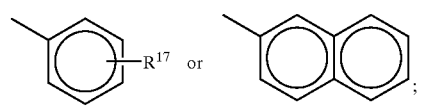

In the above, $R^{17}$, which occurs one or more times and which may be the same of different in each occurrence, may be selected from the following: a —H group; a —Cl group; a —OCH$_3$ group; or a —CF$_3$ group, provided that $R^1$ and $R^3$ must be different.

In a another embodiment of the compounds according to formula [I-3], $R^1$ is a hydrogen atom or a methyl group, and $R^2$ is selected from the following: a —CN group; a —COOH group; a —COOMe group; a —CONH$_2$ group; a —CONHOH group; a —CON(CH$_3$)$_2$ group; a —CH$_2$OCH$_2$COOH group; a —CH=CHCOOH group; a —CONHCH$_2$COOH group; a —CONH (CH$_2$)$_2$COOH group; a —CONHCH$_2$CONH$_2$ group; a —CONH(CH$_2$)$_2$CN group; or a group selected from the following:

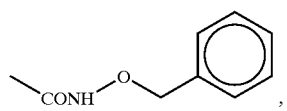

-continued

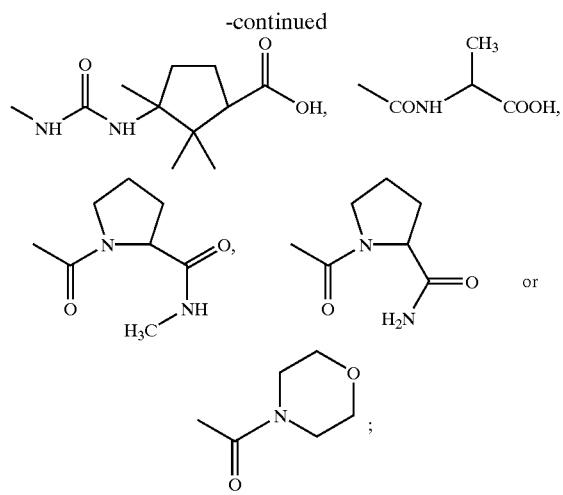

and $R^3$ is a hydrogen atom or a methyl group.

In the another embodiment of formula [I-3], $R^5$ is a —COOH group or a —COOMe group and $R^6$ is selected from the following:

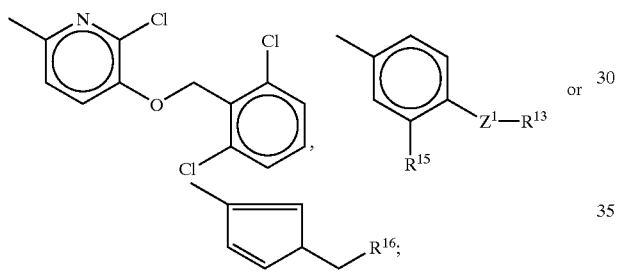

In the above embodiment of formula [I-3], $Z^1$ may be selected from the following: a —O— group; a —NHCO— group; a —NHCH$_2$— group; a —OCH$_2$— group; a —CONH— group; a —NHSO$_2$— group; or a —NHCOCH$_2$— group.

In the above embodiment of formula [I-3], $R^{13}$ may be selected from the following: a —H group; a -iBuO group; a -i-Bu group; or a group selected from the following:

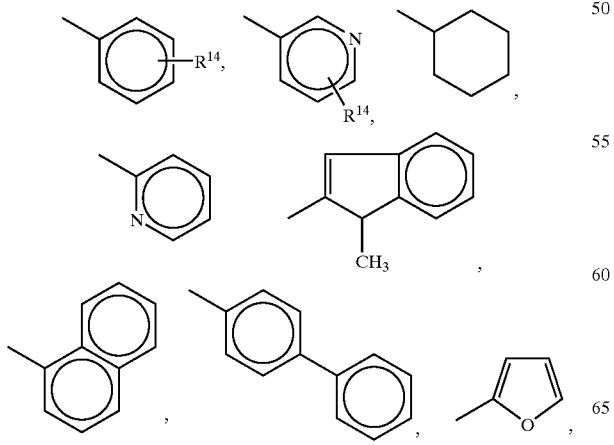

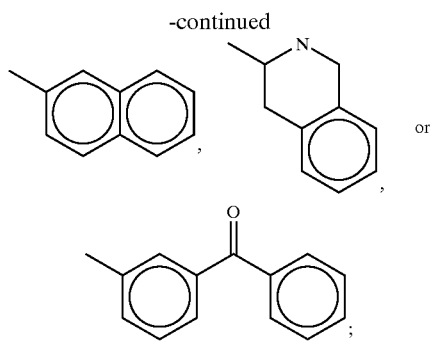

In the above embodiment of formula [I-3], $R^{14}$, which occurs one or more times and which may be the same or different in each occurence, may be selected from the following: a —H. group; a —F group; a —Cl group; a —Br group; an —I group; a —CH$_3$ group; a —OCH$_3$ group; a —CF$_3$ group; a —NO$_2$ group; a —NH$_2$ group; or a -n-C$_7$H$_{15}$ group.

In the above embodiment of formula [I-3], $R^{15}$ may be selected from the following: a —H group; a —OH group; a —NO$_2$ group; or a group selected from the following:

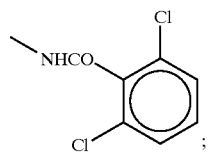

In the above embodiment of formula [I-3], $R^{16}$ may be selected from the following:

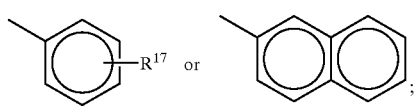

In the above embodiment of formula [I-3], $R^{17}$, which occurs one or more times and which may be the same of different in each occurrence, is a chlorine atom, provided that $R^1$ and $R^3$ must be different.

In another embodiment of formula [I-3], $R^1$ is methyl group and $R^2$ may be selected from the following: a —CN group; a —COOH group; a —CONH$_2$ group; a —CONHOH group; a —CH$_2$O CH$_2$COOH group; a —CH═CHCOOH group; a —CONHCH$_2$COOH group; a —CONH (CH$_2$)$_2$COOH group; a —CONHCH$_2$CONH$_2$ group; a —CONH(CH$_2$)$_2$CN group; or a group selected from the following:

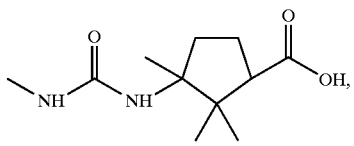

-continued

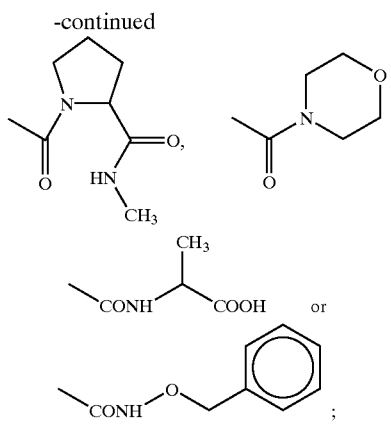

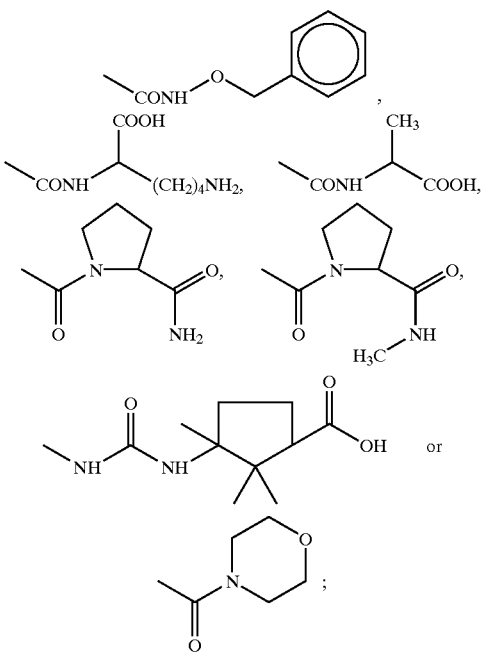

In the above, R₃ is a hydrogen atom, $R^5$ is a —COOH group or a —COOMe group and $R^6$ may be selected from the following:

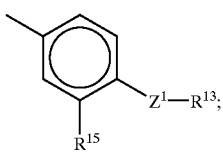

In the above embodiment of formula [I-3], $Z^1$ may be selected from the following: a —NHCO— group; a —OCH₂— group; a —NHCH₂— group; a —CONH— group; or a —NHSO₂— group.

In the above embodiment of formula [I-3], $R^{13}$ may be selected from the following:

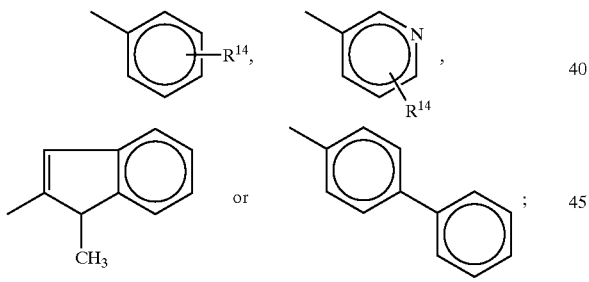

In another embodiment of formula [I-3], $R^{14}$, which occurs one or more times and which may be the same or different in each occurence, may be selected from the following: a —F group; a —Cl group; a —Br group; an —I group; a —CH₃ group; a —OCH₃ group; a —CF₃ group; or a —NO₂ group.

In another embodiment of formula [I-3], $R^{15}$ may be a —H group or a —OH group.

In a another embodiment of formula [I-3], $R^1$ is a hydrogen atom or a methyl group and $R^2$ may be selected from the following: a —CN group; a —COOH group; a —CONH₂ group; a —CONHOH group; a —CONHOCH₃ group; a —CH₂OCH₂COOH group; a —CH=CHCOOH group; a —CONHCH₂COOH group; a —CONH(CH₂)₂COOH group; a —CONHCH₂CONH₂ group; a —CONH(CH₂)₂CN group; or a group selected from the following:

In another embodiment of formula [I-3], $R^3$ is a hydrogen atom or a methyl group, $R^5$ is a —COOH group or a —COOMe group, and $R^6$ may be selected from the following:

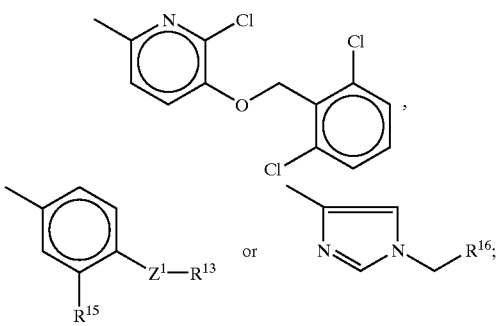

In another embodiment of formula [I-3], $Z^1$ may be selected from the following: a —O— group; a —NHCO— group; a —NHCH₂— group; a —OCH₂— group; a —CONH— group; or a —NHSO₂— group.

In another embodiment of formula [I-3], $R^{13}$ may be selected from the following: a —H group; a -iBuO group; or a group selected from the following:

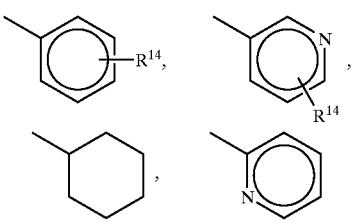

-continued

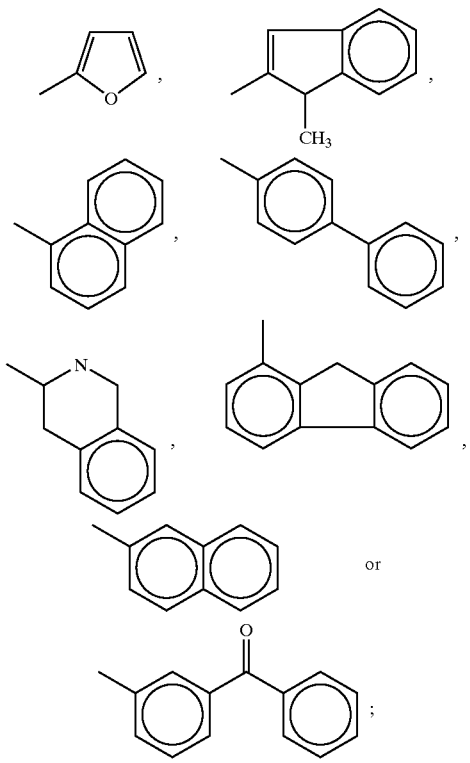

In another embodiment of formula [I-3], $R^{14}$, which occurs one or more times and which may be the same or different in each occurence, may be selected from the following: a —H group; a —OH; a —F group; a —Cl group; a —Br group; an —I group; a —CH$_3$ group; a —OCH$_3$ group; a —CF$_3$ group; a —NO$_2$ group; or a —NH$_2$ group.

In another embodiment of formula [I-3], $R^{15}$ may be selected from the following: a —H group; a —OH group; a —NO$_2$ group; or a group selected from the following:

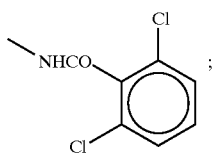

In another embodiment of formula [I-3], $R^{16}$ may be selected from the following:

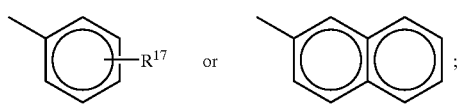

In another embodiment of formula [I-3], $R^{17}$, which occurs one or more times and which may be the same or different in each occurrence, may be a —Cl group or a —CF$_3$ group, provided that $R^1$ and $R^3$ must be different.

In another embodiment of formula [I-3], $R^1$ may be a hydrogen atom or methyl group, $R^2$ may be selected from the following: a —CN group; a —COOH group; a —CONH$_2$ group; a —CONHOH group; a —CH$_2$OCH$_2$COOH group; a —CH=CHCOOH group; a —CONHCH$_2$COOH group; a —CONH(CH$_2$)$_2$COOH group; a —CONHCH$_2$CONH$_2$ group; a —CONH(CH$_2$)$_2$CN group; or a group selected from the following:

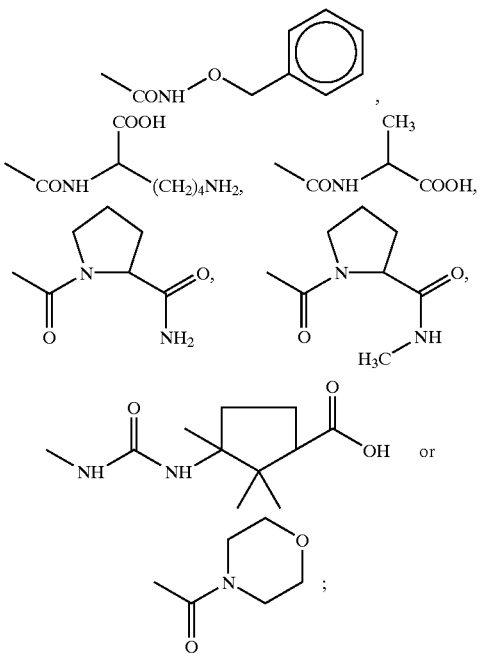

and $R^3$ may be a hydrogen atom or a methyl group.

In another embodiment of formula [I-3], $R^5$ is —COOH group or a —COOMe group and $R^6$ may be selected from the following:

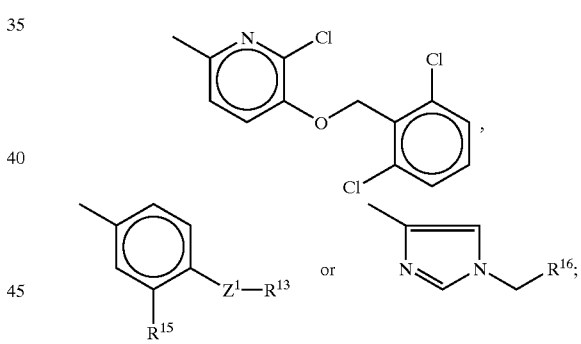

In another embodiment of formula [I-3], $Z^1$ may be selected from the following: a —O— group; a —NHCO— group; a —NHCH$_2$— group; a —OCH$_2$— group; a —CONH— group; or a —NHSO$_2$— group.

In another embodiment of formula [I-3], $R^{13}$ may be a —H group or a group selected from the following:

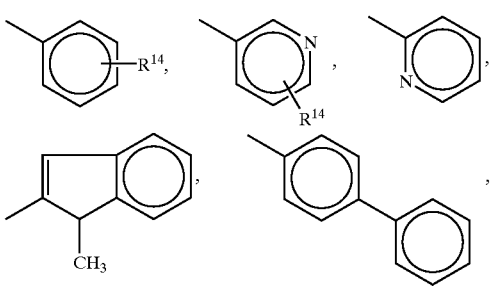

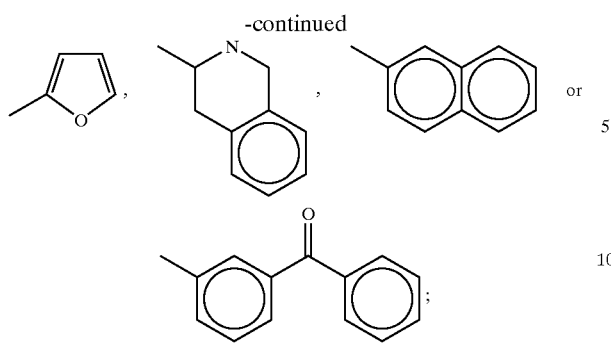

In another embodiment of formula [I-3], $R^{14}$, which occurs one or more times and which may be the same or different in each occurence, may be selected from the following: a —H group; a —F group; a —Cl group; a —Br group; an —I group; a —CH$_3$ group; a —OCH$_3$ group; a —CF$_3$ group; a —NO$_2$ group; or a —NH$_2$ group.

In another embodiment of formula [I-3], $R^{15}$ may be selected from the following: a —H group; a —OH group, a —NO$_2$ group; or a group selected from the following:

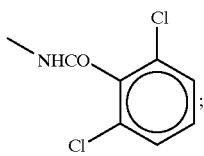

In another embodiment of formula [I-3], $R^{16}$ may be selected from the following:

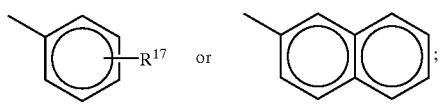

In another embodiment of formula [I-3], $R^{17}$, which occurs one or more themes and which may be the same or different in each occurrence, may be a —H group or a —Cl group, provided that $R^1$ and $R^3$ must be different.

In another embodiment of formula [I-3], $R^1$ is a methyl group, and $R^2$ may be selected from the following: a —CN group; a —COOH group; a —CONH$_2$ group; a —CONHOH group; a —CH$_2$OCH$_2$COOH group; a —CH=CHCOOH group; a —CONHCH$_2$COOH group; a —CONH(CH$_2$)$_2$COOH group; a —CONH(CH$_2$)$_2$CN group; a —CONHCH$_2$CONH$_2$ group; or a group selected from the following:

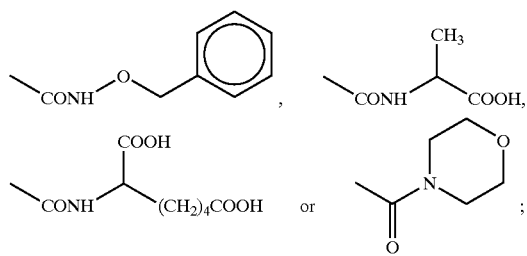

In another embodiment of formula [I-3], $R^3$ is a hydrogen atom, $R^5$ is a —COOH group or a —COOMe group, and $R^6$ may be selected from the following:

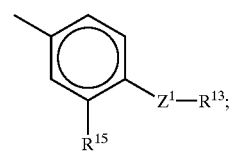

In another embodiment of formula [I-3], $Z^1$ may be selected from the following: a —NHCO— group; a —NHCH$_2$— group; a —NAcCH$_2$— group; a —OCH$_2$— group; or a —CONH— group.

In another embodiment of formula [I-3], $R^{13}$ may be selected from the following:

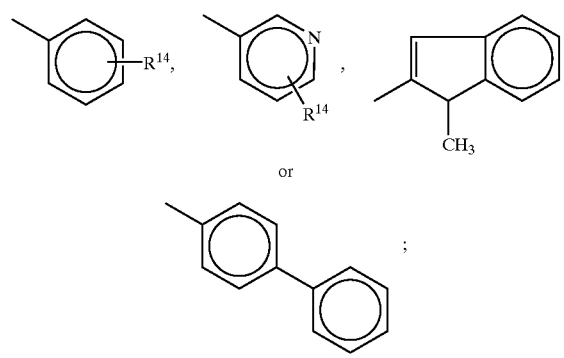

In another embodiment of formula [I-3], $R^{14}$, which occurs one or more times and which may be the same or different in each occurence, may be selected from the following: a —F group; a —Cl group; a —Br group; an —I group; a —OCH$_3$ group; a —CF$_3$ group; or a —NO$_2$ group.

In another embodiment of formula [I-3], $R^{15}$ is a —H group or a —NO$_2$ group.

Preferred compounds according to formula [I] may be selected from the group consisting of (1S-cis)-N-[(3-Carboxy-2,2,3-trimethylcyclopentyl)-carbonyl]-1-[(3,4-dichlorophenyl)methyl]-L-histidine, (1S-cis)-N-[(3-Carboxy-2,2,3-trimethylcyclopentyl)carbonyl]-O-[(2,6-dichlorophenyl)methyl]-L-tyrosine, (1S-cis)-N-[(3-Carboxy-2,2,3-trimethylcyclopentyl)carbonyl]-4-[(2,6-dichlorobenzoyl)amino]-L-phenylalanine, (1S-cis)-N-[(3-Carboxy-2,2,3-trimethylcyclopentyl)carbonyl]-O-[(2,6-dichlorophenyl)methyl]-3-nitro-L-tyrosine, (1S-cis)-N-[(3-Carboxy-2,2,3-trimethylcyclopentyl)carbonyl]-4-[[(2,4,6-trichlorophenyl)carbonyl]-amino]-L-phenylalanine, (1S-cis)-N-[[3-[[(2-Amino-2-oxoethyl)amino]carbonyl]-2,2,3-trimethylcyclopentyl]carbonyl]-4-[(2,6-dichlorobenzoyl)amino]-L-phenylalanine, (1S-cis)-N-[[3-[[(Carboxymethyl)amino]carbonyl]-2,2,3-trimethylcyclopentyl]carbonyl]-4-[(2,6-dichlorobenzoyl)amino]-L-phenylalanine, and (1S-cis)-N-[(3-Cyano-2,2,3-trimethylcyclopentyl)carbonyl]-4-[(2,6-dichlorobenzoyl)amino]-L-phenylalanine.

The desired compounds of the present invention may exist in the form of optical isomers based on asymmetric carbon atoms thereof, and the present invention also includes these optical isomers and mixtures thereof.

In an embodiment of the present invention, the steric configuration of a bond need not be fixed. A bond may be of any acceptable configuration. Further, a compound may be a mixture with several different configurations of the same bond.

The desired compounds of the present invention may be used in the form of an ester or amide thereof. As the ester thereof, there may be mentioned a $C_{1-6}$ alkyl ester, a $C_{2-7}$ alkenyl ester, a $C_{2-7}$ alkynyl ester, a $C_{2-7}$ alkanoyloxy-$C_{1-6}$ alkyl ester, an aryl-$C_{1-6}$ alkyl ester or an aryl ester. As the amide thereof, there may be mentioned an amide (—$CONH_2$), a mono or di N—$C_{1-6}$ alkyl amide, an N—$C_{3-8}$ cycloalkyl amide, an N-aryl amide or an N-aryl-$C_{1-6}$ alkyl amide.

The desired compound of the present invention may be clinically used either in a free form or in the form of pharmaceutically acceptable salts thereof. Pharmaceutically acceptable salts include acid-addition salts with inorganic acid or organic acid (e.g., hydrochloride, sulfate, nitrate, hydrobromide, methanesulfonate, p-toluenesulfonate, acetate), salt with inorganic base, organic base or amino acid (e.g., triethylamine salt, a salt with lysine, an alkali metal salt, an alkali earth metal salt and the like).

The compound may also be formulated into a pharmaceutical composition comprising a therapeutically effective amount of the compound as defined above and a pharmaceutically. acceptable carrier or diluent.

The compound can also be used for treating or preventing $\alpha_4\beta_1$ adhesion mediated conditions in a mammal such as a human. This method may comprise administering to a mammal or a human patient an effective amount of the compound or composition as explained above.

This method can be used to treat such inflammatory conditions as rheumatoid arthritis, asthma, allergy conditions, adult respiratory distress syndrome, AIDS, cardiovascular diseases, thrombosis or harmful platelet aggregation, reocclusion following thrombolysis, allograft rejection, reperfusion injury, psoriasis, eczema, contact dermatitis and other skin inflammatory diseases, osteoporosis, osteoarthritis, atherosclerosis, neoplastic diseases including metastasis of neoplastic or cancerous growth, wound healing enhancement, treatment of certain eye diseases such as detaching retina, Type I diabetes, multiple sclerosis, systemic lupus erythematosus (SLE), inflammatory and immunoinflammatory conditions including ophthalmic inflammatory conditions and inflammatory bowel diseases, ulcerative colitis, atherosclerosis, regional enteritis and other autoimmune diseases.

The desired compound of the present invention or pharmaceutically acceptable salts thereof may be administered either orally or parenterally, and it may be used as a suitable pharmaceutical preparation, for example, a tablet, a granule, a capsule, a powder, an injection, and an inhalation by a conventional process.

The dose of the desired compound of the present invention or a pharmaceutically acceptable salt thereof varies depending on an administration method, age, body weight, and state of a patient, but, in general, the daily dose is preferably about 0.1 to 100 mg/kg/day, particularly preferably 1 to 100 mg/kg/day.

Preferred Routes of Administration for Asthma

It is preferred that the compound of the present invention be administered in the form of an Aerosol. However, other routes of administration include intravenous, oral, intramuscular, and subcutaneous.

In the case of aerosol administration, compositions containing the compounds of the present invention can be prepared to provide for an excellent means for administering in aerosol form for inhalation therapy. Accordingly, the present invention will provide for self-propelling compositions containing the compounds of the present invention.

Propellants employed should be non-toxic and have a vapor pressure suitable for the conditions under which administration occurs. These propellants can be fluorinated or fluorochlorinated lower saturated aliphatic hydrocarbons. The preferred propellants of this type are the halogenated alkanes containing not more than two carbon atoms and at least one fluorine atom. Illustrative of these are trichloromonofluoromethane, dichlorodifluoromethane, monochlorotrifluoromethane, dichloromonofluoromethane and 1,2-dichloro-1,1,2,2-tetrafluoroethane. These compounds are available from E.I. duPont de Nemours and Company under the trade name "Freon". These propellants may be employed singularly or in admixture.

In addition to the propellant, an organic solvent may also be employed. The organic solvent must be non-toxic and without undesirable effects on inhalation in the amount present in the aerosol produced. In addition, the solvent should be substantially anhydrous, completely miscible with the propellant or mixture of propellants employed and have a suitable boiling point. Examples of such solvents included non-toxic aliphatic alcohols such as ethanol; ethers such as ethyl ether and vinyl ether; ketones such as acetone; and suitable halogenated lower alkanes.

In addition to the organic solvent, the composition may also optionally contain a non-toxic hygroscopic glycol. The glycol must be substantially miscible with the organic solvent and the propellant employed. Satisfactory glycols include propylene glycol, triethylene glycol, glycerol, butylene glycol and hexylene glycol.

The above indicated methods of admistration and formulation of aerosol compositions should not be viewed as limiting. The compounds of the present invention can be formulated in anyway deemed suitable to one of ordinary skill in the art so as to obtain the desired effects.

Pharmaceutical Compositions

As indicated previously, the compounds of formula (I) can be formulated into pharmaceutical compositions. In determining when a compound of formula (I) is indicated for the treatment of a given disease, the particular disease in question, its severity, as well as the age, sex, weight, and condition of the subject to be treated, must be taken into consideration and this perusal is to be determined by the skill of the attendant physician.

For medical use, the amount of a compound of Formula (I) required to achieve a therapeutic effect will, of course, vary both with the particular compound, the route of administration, the patient under treatment, and the particular disorder or disease being treated. A suitable daily dose of a compound of Formula (I), or a pharmaceutically acceptable salt thereof, for a mammalian subject suffering from, or likely to suffer from, any condition as described hereinbefore is 0.1 mg to 100 mg of the compound of formula I, per kilogram body weight of the mammalian subject. In the case of systematic administration, the dose may be in the range of 0.5 to 500 mg of the compound per kilogram body weight, the most preferred dosage being 0.5 to 50 mg/kg of mammal body weight administered two to three times daily. In the case of topical administration, e.g., to the skin or eye, a suitable dose may be in the range of 0.1 $\mu$g to 100 $\mu$g of the compound per kilogram, typically about 0.1 $\mu$g/kg.

In the case of oral dosing, a suitable dose of a compound of Formula (I), or a physiologically acceptable salt thereof, may be as specified in the preceding paragraph, but most preferably is from 1 mg to 10 mg of the compound per kilogram, the most preferred dosage being from 1 mg to 5 mg/kg of mammal body weight, for example, from 1 to 2 mg/kg. Most preferably, a unit dosage of an orally administrable composition encompassed by the present invention contains less than about 1.0 g of a formula (I) compound.

It is understood that formulation, both for human and veterinary use, of the present invention may be presented to the mammal by inhalation. To achieve therapeutic effect, the dose may be in the range of 0.5 to 500 mg of the compound, per kg body weight. The most preferred dosage being 0.5 to 50 mg/kg of mammal body weight administered two to three times daily.

It is understood that the ordinarily skilled physician or veterinarian will readily determine and prescribe the effective amount of a compound of Formula I to prevent or arrest the progress of the condition for which treatment is administered. In so proceeding, the physician or veterinarian could employ relatively low doses at first, subsequently increasing the dose until a maximum response is obtained.

The compounds and compositions of the present invention can be administered to patients suffering from a condition listed herein in an amount which is effective to fully or partially alleviate undesired symptoms of the condition. The symptoms may be caused by inappropriate cell adhesion mediated by $\alpha_4\beta_1$ integrins. Such inappropriate cell adhesion would typically be expected to occur as a result of increased VCAM-1 and/or CS-1 expression on the surface of endothelial cells. Increased VCAM-1 and/or CS-1 expression can be due to a normal inflammation response or due to abnormal inflammatory states. In either case, an effective dose of a compound of the invention may reduce the increased cell adhesion due to increased VCAM-1 expression by endothelial cells. Reducing the adhesion observed in the disease state by 50% can be considered an effective reduction in adhesion. More preferably, a reduction in adhesion by 90%, is achieved. Most preferably adhesion mediated by VCAM-1/$\alpha_4\beta_1$ and/or CS-1 interaction is abolished by an effective dose. Clinically, in some instances, effect of the compound can be observed or a decrease in white cell infiltration into tissues or a site of injury. To achieve a therapeutic effect, then, the compounds or compositions of the present invention are administered to provide a dose effective to reduce or eliminate inappropriate cell adhesion or to alleviate undesired symptoms.

While it is possible for an active ingredient to be administered alone, it is preferable to present it as a pharmaceutical formulation comprising a compound of Formula (I) and a pharmaceutically acceptable carrier thereof. Such formulations constitute a further feature of the present invention.

The formulations, both for human and veterinary medical use, of the present invention comprise an active ingredient of Formula (I), in association with a pharmaceutically acceptable carrier thereof and optionally other therapeutic ingredient(s), which are generally known to be effective in treating the disease or condition encountered. The carrier(s) must be "acceptable" in the sense of being compatible with the other ingredients of the formulations and not deleterious to the recipient thereof.

The formulations include those in a form suitable for oral, pulmonary, ophthalmic, rectal, parenteral (including subcutaneous, intramuscular, and intravenous), intra-articular, topical, nasal inhalation (e.g., with an aerosol) or buccal administration. Such formulation are understood to include long-acting formulations known in the art.

The formulations may conveniently be presented in unit dosage form and may be prepared by any of the methods well known in the art of pharmacy. All methods may include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired form.

Formulations of the present invention suitable for oral administration may be in the form of discrete units such as capsules, cachets, tablets, or lozenges, each containing a predetermined amount of the active ingredient in the form of a powder or granules; in the form of a solution or suspension in an aqueous liquid. Formulations for other uses could involve a nonaqueous liquid; in the form of an oil-in-water emulsion or a water-in-oil emulsion; in the form of an aerosol; or in the form of a cream or ointment or impregnated into a transdermal patch for use in administering the active ingredient transdermally, to a patient in need thereof. The active ingredient of the present inventive compositions may also be administered to a patient in need thereof in the form of a bolus, electuary, or paste.

The practitioner is referred to "Remington: The Science and Practice of Pharmacy," 19th Edition, c. 1995 by the Philadelphia College of Pharmacy and Science, as a comprehensive tome on pharmaceutical preparations.

| | Abbreviations |
|---|---|
| $Ac_2O$: | Acetic anhydride |
| AcOEt: | Ethyl acetate |
| BCECF-AM: | 2',7'-bis-(2-carboxyethyl)-5-(and 6-)carboxyfluorescein acetoxymethyl ester |
| BOP-Cl: | Bis (2-oxo-3-oxazolidinyl) phosphinic chloride |
| BOP Reagent: | Benzotriazol-1-yloxy-tris(dimethylamino)-phosphonium hexafluorophosphate |
| DMEM: | Dulbecco's Minimal Eagle's Media |
| DMF: | Dimethyl formamide |
| DIEA: | Diisopropylethylamine |
| EDC: | 1-(3-Dimethylaminopropyl)-3-ethylcarbodiimide hydrochloride |
| Et: | Ethyl |
| EtOH: | Ethanol |
| HATU: | N-[(Dimethylamino)-1H-1,2,3-triazolo[4,5-b]-pyridin-1-ylmethylene]-N-methylmethanaminium hexafluorophosphate N-oxide |
| HBSS: | Hank's Balanced Salt Solution |
| HBTU: | O-Benzotriazol-1-yl-N,N,N',N'-tetramethyluronium hexafluorophosphate |
| HOBT: | 1-Hydroxybenzotriazole |
| HSA: | Human serum albumin |
| LDA: | Lithium diisopropylamide |
| Me: | Methyl |
| meq: | milliequivalent |
| MeOH: | Methanol |
| n-Bu: | n-Butyl |
| NMP: | 1-Methyl-2-pyrrolidinone |
| PBS: | Phosphate buffered saline |
| Pd-C: | Palladium on charcoal |
| Ph: | Phenyl |
| SPDP: | 3-(2-pyridyldithio)propionic acid N-hydroxysuccinimide ester |
| t-Bu: | t-butyl |
| THF: | Tetrahydrofuran |
| TFA: | Trifluoroacetic acid |

According to the present invention, the desired compound [I] can be prepared by the following methods:

Scheme 1

(Method A):

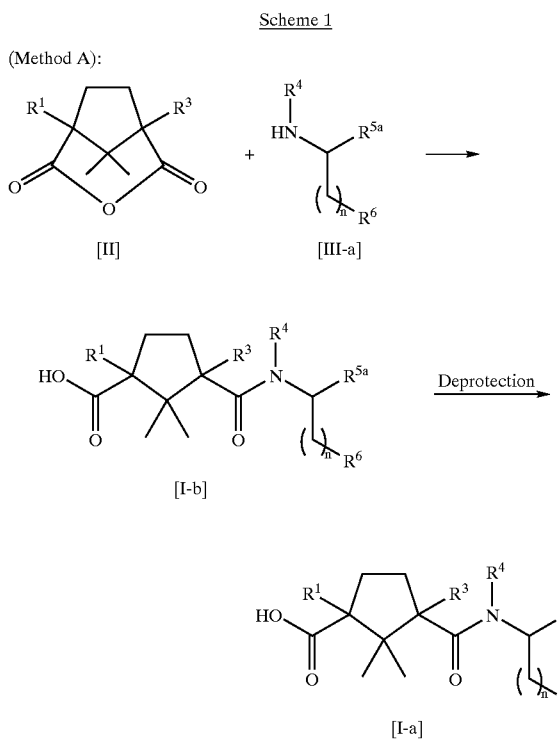

wherein $R^{5a}$ is a group of the formula: —COOR$^{22}$, —($C_{1-6}$ alkylene)COOR$^{22}$, —($C_{1-7}$ alkylene)O($C_{1-6}$ alkyl), —($C_{1-7}$alkylene)OH, —COO($C_{1-6}$ alkyl), —CONH ($C_{1-6}$ alkyl) or —CONH$_2$, $R^{22}$ is a protecting group for the carboxyl group, and the other symbols are the same as defined above.

Method A

The compound of the formula [I] wherein $R^2$ is a group of the formula: —COOH and X is a group of the formula: —CO—, an ester thereof, an amide thereof or a pharmaceutically acceptable salt thereof, i.e., the compound of the formula [I-a]:

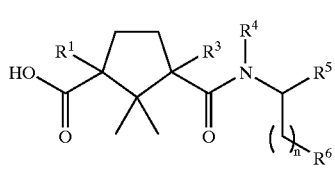

wherein the symbols are the same as defined above, an ester thereof, an amide thereof or a pharmaceutically acceptable salt thereof may be prepared by (1) reacting a compound of the formula [II]:

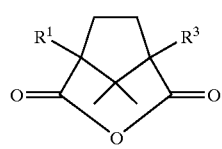

wherein the symbols are the same as defined above, with a compound of the formula [III-a]:

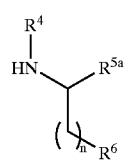

wherein the symbols are the same as defined above, or a salt thereof,
(2) removing the protecting group for the carboxyl group, if desired, and
(3) converting the resulting compound into an ester thereof, an amide thereof or a pharmaceutically acceptable salt thereof by a conventional method, if further desired.

$R^{22}$ can be selected from a conventional protecting group for a carboxyl group, for example, a $C_{1-6}$ alkyl group, a $C_{2-7}$ alkenyl group, a $C_{2-7}$ alkynyl group, a $C_{2-7}$ alkanoyloxy-$C_{1-6}$ alkyl group, an aryl-$C_{1-6}$ alkyl group (e.g., benzyl group) or an aryl group (e.g., phenyl group) and the like.

A salt of the compound [III-a] includes, for example, salt with an inorganic acid (e.g., hydrochloride, sulfate) and salt with an inorganic base (e.g., an alkali metal salt such as sodium salt or potassium salt, an alkali earth metal salt such as magnesium salt or calcium salt).

The reaction of the compound [II] and the compound [III-a] or a salt thereof is carried out in the presence of a base in a suitable solvent or without a solvent. The base can be selected from an organic base (e.g., DIEA, DMAP, Et$_3$N, DBU), an alkali metal hydride (e.g., NaH, LiH), an alkali metal carbonate (e.g., Na$_2$CO$_3$, Na$_2$KO$_3$) an alkali metal hydrogen carbonate (e.g., NaHCO$_3$, KHCO$_3$), an alkali metal amide (e.g., NaNH$_2$), an alkali metal alkoxide (e.g., NaOMe, KOMe), an alkyl-alkali metal (n-BuLi, t-BuLi), an alkali metal hydroxide (e.g., NaOH, KOH), an alkali, earth metal hydroxide (e.g., Ba(OH)$_2$), and the like. The solvent can be selected from any one which does not disturb the reaction, for example, DMF, THF, benzene, toluene, DMSO, CH$_3$CN or a mixture thereof. The reaction is preferably carried out at a temperature from 0° C. to 100° C., more preferably at a temperature from 40° C. to 80° C.

The removal of said protecting group from the products can be carried out by a conventional method, which is selected according to the types of the protecting groups to be removed, for example, hydrolysis, acid treatment, catalytic reduction, and the like.

A more preferred method than method A is:

Scheme 2

(Method B):

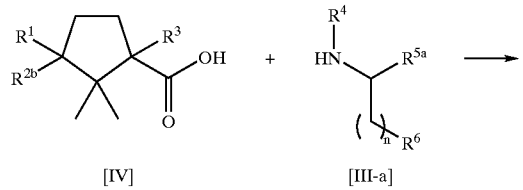

-continued

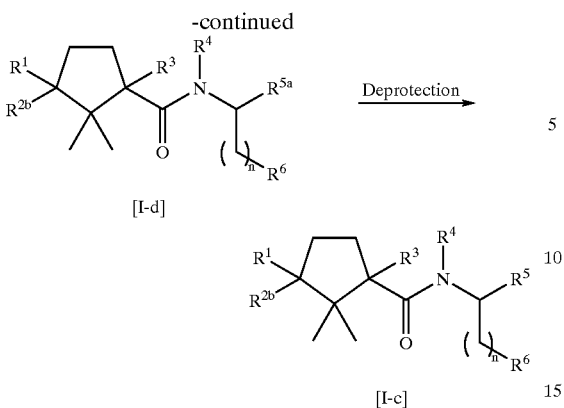

[I-d]

[I-c]

$R^{2a}$ is a group of the formula: —CN, —COOR$^{23}$, —COOH, —(C$_{1-6}$ alkylene)OH, —CH$_2$O(C$_{1-6}$ alkyl), —(C$_{1-6}$ alkylene)COOH, —(C$_{1-6}$ alkylene)COOR$^{23}$, —CH$_2$O(C$_{1-6}$ alkylene)O(C$_{1-6}$ alkyl), —CH$_2$O(C$_{1-6}$ alkylene)COOH, CH$_2$O(C$_{1-6}$ alkylene)COOR$^{23}$, —(C$_{2-7}$ alkenylene)COOH, —(C$_{2-7}$ alkenylene)COOR$^{23}$, —CO(C$_{1-6}$ alkylene)COOH, —CO(C$_{1-6}$ alkylene)COOR$^{23}$, —(C$_{2-7}$ alkenylene)COOH, —CO(C$_{2-7}$ alkenylene) COOR$^{23}$, —CO(C$_{1-6}$ alkylene)O(C$_{1-6}$ alkyl), —CO(C$_{1-6}$ alkylene)CO(C$_{1-6}$ alkyl), —CONH(C$_{1-6}$ alkyl), —CONHO(C$_{1-6}$ alkyl), —CONH(C$_{1-6}$ alkylene)COOH, —CONH(C$_{1-6}$ alkylene)COOR$^{23}$, —CONH(C$_{3-7}$ cycloalkyl), —CONH$_2$, —CONH(C$_{1-6}$ alkylene)CONH$_2$, —CONHOH, —NHCO$_2$CH$_2$Ph, —CONHOCH$_2$Ph, —CONH(C$_{1-6}$alkylene)CN, —COO(CO$_{1-6}$alkyl), —CH$_2$O(CO$_{1-6}$alkylene)CONH$_2$,

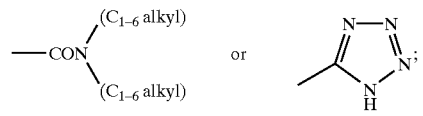

$R^{2b}$ is a group of the formula: —CN, —COOR$^{23}$, —(C$_{1-6}$ alkylene)OH, —CH$_2$O(C$_{1-6}$ alkyl), —(C$_{1-6}$ alkylene)COOR$^{23}$, —CH$_2$O(C$_{1-6}$ alkylene)O(C$_{1-6}$ alkyl), —CH$_2$O(C$_{1-6}$ alkylene)COOR$^{23}$, —(C$_{2-7}$ alkenylene)COOR$^{23}$, —CO(C$_{1-6}$ alkylene)COOR$^{23}$, —CO(C$_{2-7}$ alkenylene) COOR$^{23}$, —CO(C$_{1-6}$ alkylene)O(C$_{1-6}$ alkyl), —CO(C$_{1-6}$ alkylene)CO(C$_{1-6}$ alkyl), —CONH (C$_{1-6}$ alkyl), —CONHO(C$_{1-6}$ alkyl), —CONH (C$_{1-6}$ alkylene) COOR$^{23}$, —CONH(C$_{3-7}$ cycloalkyl), —CONH$_2$, —CONH (C$_{1-6}$ alkylene) CONH$_2$, —CONHOH, —NHCO$_2$CH$_2$Ph, —CONHOCH$_2$Ph, —CONH (C$_{1-6}$alkylene) CN, —COO(C$_{1-6}$alkyl), —CH$_2$O(C$_{1-6}$alkylene)CONH,

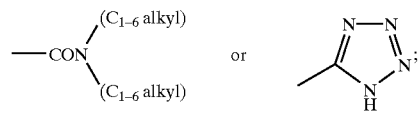

$R^{23}$ is a protecting group for the carboxyl group, and the other symbols are the same as defined above.

Method B

The compound of the formula [I], an ester thereof, an amide thereof or a pharmaceutically acceptable salt thereof, wherein $R^2$ is a group of the formula: —CN, —COOR$^{23}$, —COOH, —(C$_{1-6}$ alkylene)OH, —CH$_2$O(C$_{1-6}$ alkyl), —(C$_{1-6}$ alkylene)COOH, —(C$_{1-6}$ alkylene)COOR$^{23}$, —CH$_2$O(C$_{1-6}$ alkylene)O(C$_{1-6}$ alkyl), —CH$_2$O(C$_{1-6}$ alkylene)COOH, —CH$_2$O(C$_{1-6}$ alkylene)COOR$^{23}$, —(C$_{2-7}$ alkenylene)COOH, —(C$_{2-7}$ alkenylene) COOR$^{23}$, —CO(C$_{1-6}$ alkylene)COOH, —CO(C$_{1-6}$ alkylene)COOR$^{23}$, —CO(C$_{2-7}$ alkenylene)COOH, —CO(C$_{2-7}$ alkenylene)COOR$_{23}$, —CO(C$_{1-6}$ alkylene) O(C$_{1-6}$ alkyl), —CO(C$_{1-6}$ alkylene)CO(C$_{1-6}$ alkyl), —CONH(C$_{1-6}$ alkyl), —CONHO(C$_{1-6}$ alkyl), —CONH(C$_{1-6}$ alkylene)COOH, —CONH(C$_{1-6}$ alkylene)COOR$^{23}$, —CONH(C$_{3-7}$ cycloalkyl), —CONH$_2$, —CONH(C$_{1-6}$ alkylene)CONH$_2$, —CONHOH, —NHCO$_2$CH$_2$Ph, CONHOCH$_2$Ph, —CONH(C$_{1-6}$alkylene)CN, —COO(C$_{1-6}$alkyl), —CH$_2$O(C$_{1-6}$alkylene)CONH$_2$ or

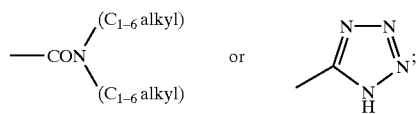

X is a group of the formula: —CO—, i.e., the compound of the formula [I-c]:

[I-c]

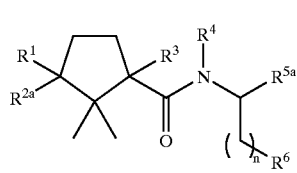

wherein the symbols are the same as defined above, may be prepared by (1) condensing a compound of the formula [IV]:

[IV]

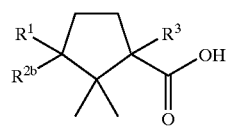

wherein the symbols are the same as defined above, or a salt thereof, with a compound of the formula [III-a]:

[III-a]

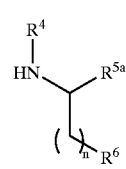

wherein the symbols are the same as defined above, or a salt thereof, (2) removing the protecting group for the carboxyl group and hydroxyl group, if desired, and (3) converting the resulting compound into an ester thereof, an amide thereof or a pharmaceutically acceptable salt thereof by a conventional method, if further desired.

$R^{22}$ and $R^{23}$ are the same or different conventional protecting group for a carboxyl group, for example, a C$_{1-6}$ alkyl group, a C$_{2-7}$ alkenyl group, a C$_{2-7}$ alkynyl group, a C$_{2-7}$ alkanoyloxy-C$_{1-6}$ alkyl group, an aryl-C$_{1-6}$ alkyl group (e.g., benzyl group) or an aryl group (e.g., phenyl group) and the like.

A salt of the compound [III-a] and/or [IV] includes, for example, salt with an inorganic acid (e.g., hydrochloride, sulfate) and salt with an inorganic base (e.g., an alkali metal salt such as sodium, potassium and calcium, an alkali earth metal salt such as barium).

The condensation reaction of the compound [IV] or a salt thereof with the compound [III-a] or a salt thereof is carried out in the presence of a condensing reagent in a suitable solvent or without a solvent. The condensing reagent can be selected from any one which can be used for a conventional peptide synthesis, for example, BOP-Cl, BOP reagent, DCC and WSCI. The solvent can be selected from any one which does not disturb the condensation reaction, for example, $CH_2Cl_2$, DMF or a mixture thereof. The reaction is preferably carried out at a room temperature.

The removal of said protecting group from the products can be carried out by a conventional method, which is selected according to the types of the protecting groups to be removed, for example, hydrolysis, acid treatment, catalytic reduction, and the like.

Scheme 3

(Method C):

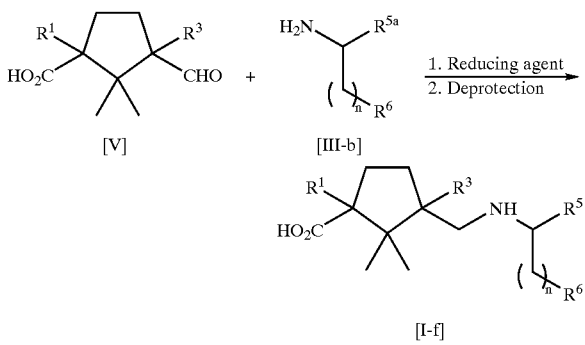

wherein the symbols are the same as defined above.

Method C

The compound of the formula [I] wherein X is a methylene group, an ester thereof, an amide thereof or a pharmaceutically acceptable salt thereof, i.e., the compound of the formula [I-e]:

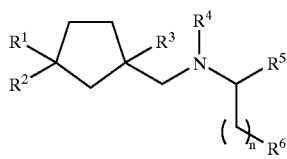

wherein the symbols are the same as defined above, an ester thereof, an amide thereof or a pharmaceutically acceptable salt thereof, may be prepared by
(1) reacting a compound of the formula [V]:

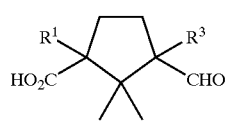

wherein the symbols are the same as defined above, or a salt thereof in the presence of a reducing agent with a compound of the formula [III-b]:

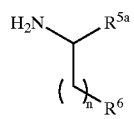

wherein the symbols are the same as defined above,
(2) removing the protecting group for the carboxyl group, if desired, and
(3) converting the resulting compound into an ester thereof, an amide thereof or a pharmaceutically acceptable salt thereof by a conventional method, if further desired.

A salt of the compound [V] and/or [III-b] includes, for example, salt with an inorganic acid (e.g., hydrochloride, sulfate) and salt with an inorganic base (e.g., an alkali metal salt, an alkali earth metal salt).

The reductive alkylation of the compound [V] or a salt thereof with the compound [III-b] or a salt thereof is carried out by a conventional method in the presence of a reducing agent in a suitable solvent or without a solvent. The reducing agent is preferably sodium borohydride, sodium cyanoborohydride, and the like. The solvent can be selected from any one which does not disturb the reaction, for example, alkanol such as methanol, alkanoic acid such as AcOH, THF or a mixture thereof. The reaction is preferably carried out at a temperature from 0° C. to a room temperature.

The reaction of the compound [I-f] or a salt thereof and the compound [VII] is carried out in the presence of an acid acceptor in a suitable solvent or without a solvent. The acid acceptor and the solvent can be selected from the base or the solvent used in Method A. The reaction is preferably carried out at room temperature.

The removal of said protecting group from the products can be carried out by a conventional method, which is selected according to the types of the protecting groups to be removed, for example, hydrolysis, acid treatment, catalytic reduction, and the like.

The desired compound [I] of the present invention can be converted to each other. Such conversion of the present compound [I] into the other compound [I] may be carried out by selecting one of the following procedures from (a) to (e) according to the type of substituent thereof, and if desired, followed by removing the protecting group for the carboxyl group by a conventional method.

Procedure (a)

The compound [I] wherein $R^6$ is an amino-substituted aryl group can be prepared by the reduction of the compound [I] wherein the corresponding $R^6$ is an aralklyoxycarbonyl amino group- or nitro-substituted aryl group. The reduction can be, for example, a catalytic reduction using a palladium catalyst such as palladium on an activated carbon, a platinum catalyst such as platinum oxide, and the like. The catalytic reduction is preferably carried out at a room temperature.

Procedure (b)

The compound [I] wherein $R^2$ is a group of the formula: —$CONH_2$, —$CONH(C_{1-6}$ alkyl); —$CONHO(C_{1-6}$ alkyl), —$CONH(C_{1-6}$ alkylene)$COOR^{23}$, —$CONH(C_{3-7}$ cycloalkyl), —$CONH(C_{1-6}$ alkylene)$CONH_2$, —$CONHOCH_2Ph$, —$CONH(C_{1-6}$ alkylene)CN, $CONHOH$,

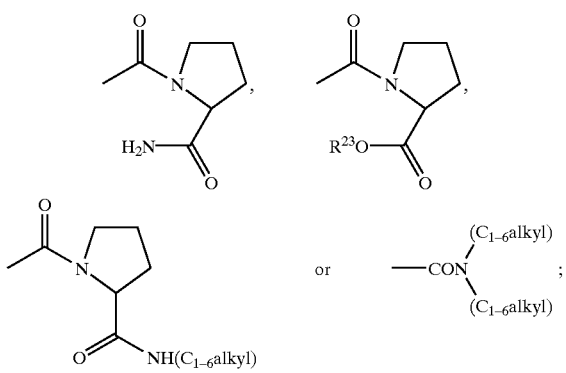

can be prepared by reacting the compound [I] wherein the corresponding $R^2$ is a group of the formula: —COOH with a substituted or unsubstituted amine selected from a group of the formula: $NH_3$, $NH_2(C_{1-6}$ alkyl), $NH_2O(C_{1-6}$ alkyl), $NH_2(C_{1-6}$ alkylene)$COOR^{23}$, $NH_2(C_{3-7}$ cycloalkyl), $NH_2(C_{1-6}$ alkylene)$CONH_2$, $NH_2OH$, $NH_2OCH_2Ph$, $NH_2(C_{1-6}$ alkylene)CN,

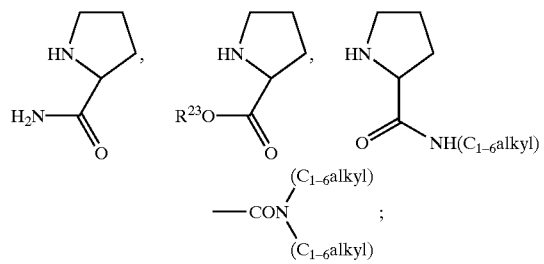

wherein $R^{23}$ is defined as above, in the presence of a condensing reagent (e.g., BOP reagent) which can be used for a conventional peptide synthesis, and removing the protecting group for the carboxyl group, if desired. The reaction is preferably carried out at a temperature from 0° C. to a room temperature.

Procedure (c)

The compound [I] wherein $R^4$ is a $C_{1-6}$ alkyl group can be prepared by reacting the compound [I] wherein the corresponding $R^4$ is a hydrogen atom with a $C_{1-6}$ alkyl halide (e.g., methyl iodide, butyl iodide) in the presence of metal hydride (e.g., NaH). The reaction is preferably carried out at a temperature from 0° C. to room temperature.

Procedure (d)

The compound [I] wherein $R^6$ is a $C_{2-6}$ alkanoylamino-, $C_{3-7}$ cycloalkylcarbonylamino-, aryl $C_{2-7}$ alkanoylamino-, arylcarbonylamino-, $C_{1-5}$ alkyloxycarbonylamino-, $C_{3-7}$ cycloalkyloxycarbonylamino-, aryl $C_{1-6}$ alkyloxycarbonylamino-, arylureido-, or arylsulfonylamino-substituted aryl group can be prepared by reacting the compound [I] wherein the corresponding $R^6$ is an amino aryl group or a ($C_{1-6}$ alkyl)-amino-substituted aryl group with a $C_{2-6}$ alkanoic acid, an anhydride of $C_{2-6}$ alkanoic acid, $C_{2-6}$ alkanoyl halide, $C_{3-7}$ cycloalkanecarboxylic acid, anhydride of $C_{3-7}$ cycloalkanecarboxylic acid, $C_{3-7}$ cycloalkanoyl halide, aryl $C_{2-7}$ alkanoic acid, anhydride of aryl $C_{2-7}$ alkanoic acid, aryl $C_{2-7}$ alkanoyl halide, arylcarboxylic acid, anhydride of arylcarboxylic acid, arylcarbonyl halide, $C_{1-5}$ alkyl halogenoformate, arylisocyanate, or arylsulfonyl halide in the presence or absence of an acid acceptor (e.g., DIEA) and in the presence or absence of a condensing reagent (e.g., BOP-Cl) which can be used for a conventional peptide synthesis. The reaction is preferably carried out at a temperature from 0° C. to a room temperature.

Procedure (e):

(P) = a resin which is used in a conventional solid phase peptide synthesis

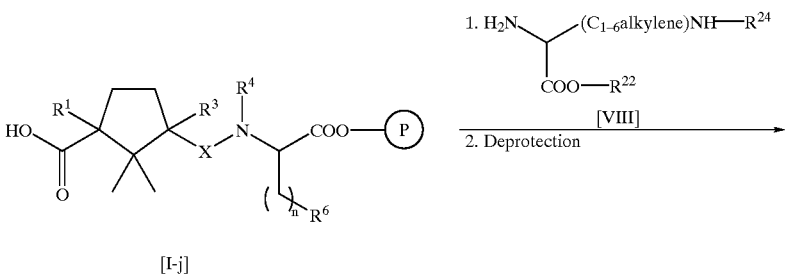

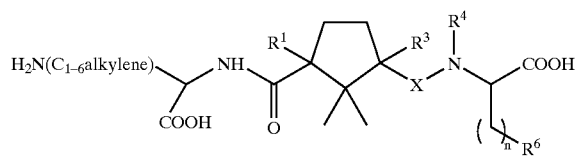

wherein $R^{24}$ is a protecting group for the amino group, and the other symbols are the same as defined above.

The compound of the formula [I-i]:

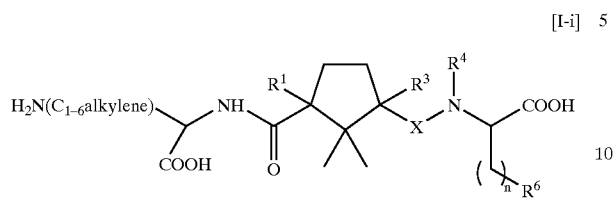

[I-i]

can be prepared by condensing the compound [I] wherein the corresponding $R^2$ is a group of the formula: —COOH with a group of the formula [VIII]:

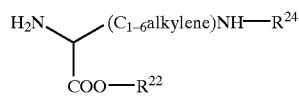

[VIII]

wherein the symbols are the same as defined above, by a conventional solid phase peptide synthesis method also known as Merrifield method (Journal of American Chemical Society 85, 2149–2154 (1963)), followed by the deprotection of amino group and carboxyl group by a conventional method.

$R^{24}$ can be selected from a conventional protecting group for an amino group, for example, tert-butoxy-carbonyl grop (BOC), benzyloxycarbonyl group (Cbz) and the like.

The solvent used for the Procedures (a) to (e) may be selected from any one which does not disturb the procedures, for example, THF, methanol, DMF, $CH_2Cl$, or a mixture thereof.

General Description for Synthesis of Intermediates

The compound [II] may be prepared by reacting a compound of the formula [VI]:

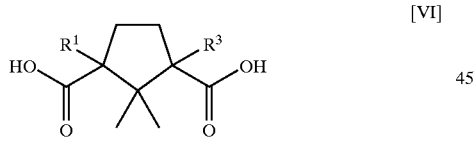

[VI]

wherein the symbols are the same as defined above, in the presence of $C_{1-6}$ alkanoyl halide (e.g., AcCl) and/or $C_{1-6}$ alkanoic anhydride (e.g., $Ac_2O$).

The compound [III-a] may be prepared by a conventional method, which is selected according to the types of the substituents, for example, by the following schemes:

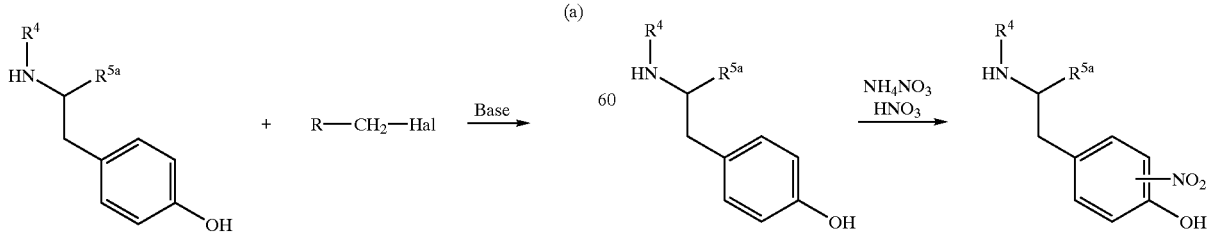

(a)

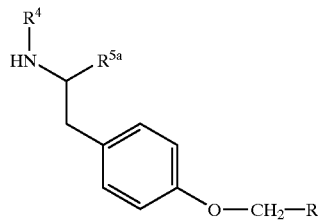

(b)

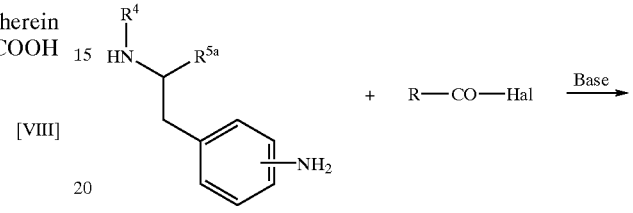

(c)

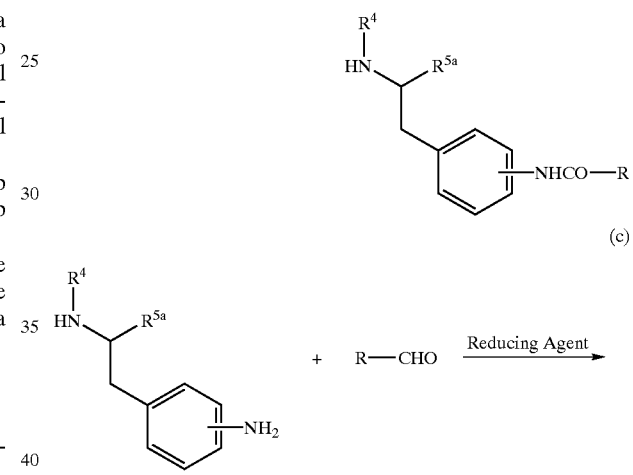

(d)

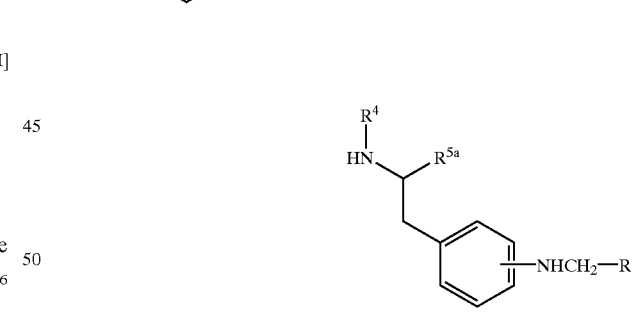

-continued (e)

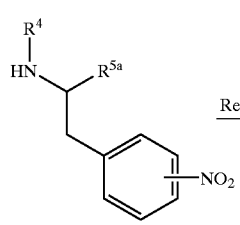 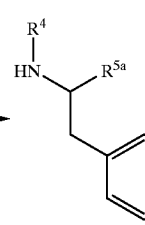

(f)

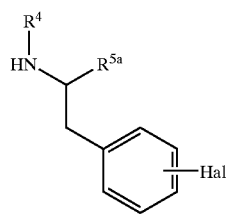

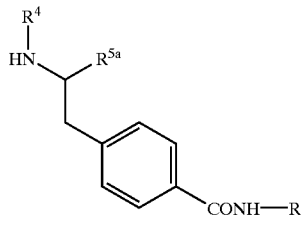

(g)

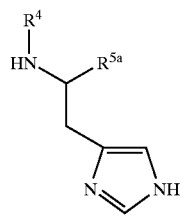

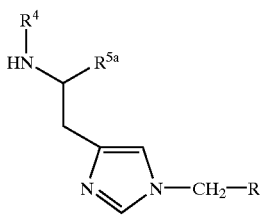

wherein R is (1) a substituted or unsubstituted monocyclic or bicyclic aryl group or (2) a substituted or unsubstituted monocyclic or bicyclic heteroaryl group, Hal is a halogen atom and other symbols are the same as defined above.

The compound [IV] may be prepared as shown in various locations of the present application, for example, in Schemes 7, 8, 9, 10 and 11.

The desired compound [I] of the present invention may also be prepared by the methods as shown in the following Schemes.

Scheme 5a

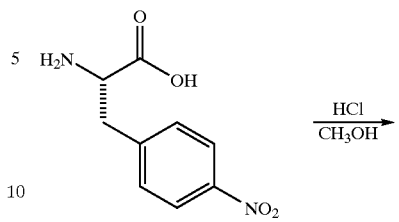

(5a-A)

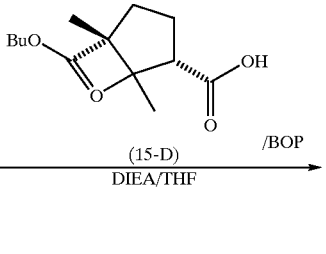
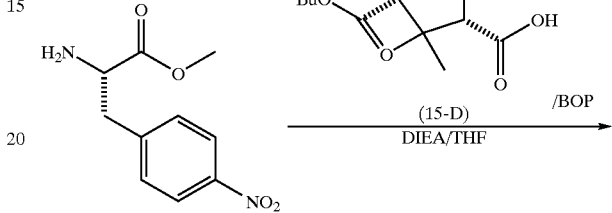

(5a-B)


(5a-C)

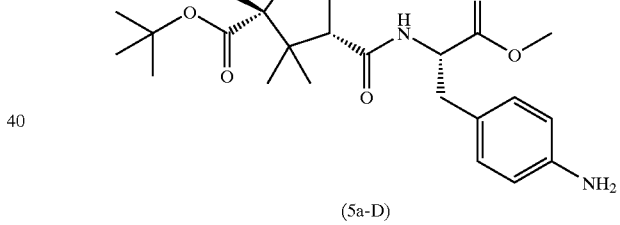

(5a-D)

Commercially available (L)-p-nitroPhe-OH (5a-A) (50.6 g, 240.6 mmol) was dissolved in MeOH (250 mL) and dry HCl was bubbled through the solution for 45 minutes at 0° C. The mixture was refluxed for 15 minutes and allowed to stand overnight. The HCl salt precipitated and the solid material was collected by filtration and washed with $Et_2O$ (3×50 mL). The solid methyl ester (5a-B) thus obtained was pale yellow (55.3 g, 88%): mp=215–218° C. (d).

The HCl salt of (L)-p-nitroPhe-OMe (5a-B) (5.2 g, 19.8 mmol) was dissolved in THF (30 mL) containing DIEA (10.3 mL, 59.4 mmol). To this solution was added (1R-cis)-1,2,2-trimethylcyclopentane-1,3-dicarboxylic acid 1-(1,1-dimethylethyl) ester (15-D) (5.1 g, 19.8 mmol) and BOP reagent (10.6 g, 23.9 mmol) and the solution was stirred under dry $N_2$ for 72 hours. Work-up of the coupling reaction was performed by the addition of 1N HCl (60 mL) and extraction with EtOAc (2×20 mL). The combined organic phase was washed with saturated $NaHCO_3$ (20 mL), then saturated LiCl (15 mL) and dried over $Na_2SO_4$. The solution was filtered, solvent evaporated and the residue chromatographed (SiO$_2$, gradient elution: 100% hexanes→50% EtOAc/hexanes) to provide the fully protected intermediate (1S-cis)-N-[3-[(1,1-dimethylethoxy)-2,2,3-trimethylcyclopentyl]carbonyl]-4-nitro-L-phenylalanine methyl ester (5a-C) (7.1 g, 77%): $^1$H NMR (300 MHz, CDCl$_3$), δ 8.14 (2H), 7.35 (2H), 6.18 (1H), 4.99 (1H), 3.76 (3H), 3.34 (1H), 3.20 (1H), 2.62 (1H), 2.5–2.6 (2H), 2.1–2.2 (1H), 1.6–1.8 (1H), 1.4–1.5 (1H), 1.45 (9H), 1.25 (3H), 1.16 (3H), 0.81 (3H); $^{13}$C NMR (75 MHz, CDCl$_3$), δ 174.57, 172.44, 171.30, 146.69, 144.01, 129.87, 123.31, 79.89, 56.35, 53.98, 52.52, 52.24, 46.10, 37.38, 32.08, 27.72, 22.64, 22.27, 21.62, 20.40; ESMS (m/z) 463 (MH$^+$).

The above compound, (5a-C) (2.7 g, 5.77 mmol), was dissolved in MeOH (40 mL) and degassed with N$_2$. To this solution was added 10% Pd—C (250 mg) and H$_2$ gas was bubbled through the resultant slurry for 15 minutes and the reaction was stirred an additional 3 hours under an atmosphere of H$_2$. The mixture was filtered through celite and the celite washed with CH$_3$OH. The solvent was evaporated to afford Example 56 (5a-D) (2.49 g, 100%): $^1$H NMR (300 MHz, CDCl$_3$), δ 6.88 (2H), 6.64 (2H), 5.71 (1H), 4.82 (1H), 3.72 (3H), 3.0–3.1 (2H), 2.5–2.6 (2H), 2.1–2.2 (1H), 1.6–1.8 (1H), 1.4–1.5 (1H), 1.43 (9H), 1.21 (3H), 1.14 (3H), 0.80 (3H); ESMS (m/z) 433 (MH$^+$).

Scheme 5b

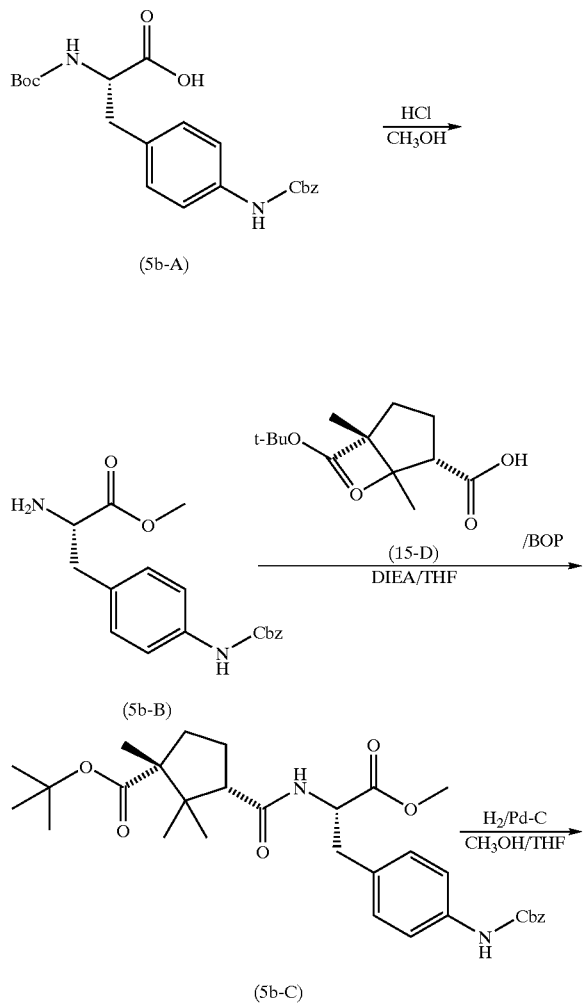

-continued

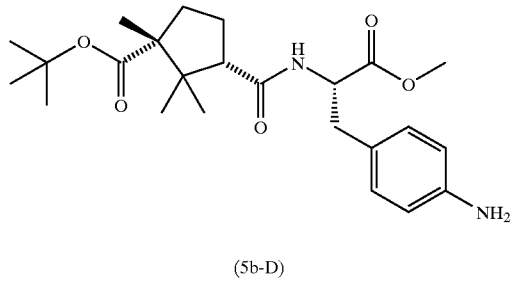

(5b-D)

Commercially available Boc-(L)-Phe(4-N-Cbz)-OH (5b-A) (6.2 g, 14.9 mmol) was dissolved in MeOH (20 mL) and dry HCl was bubbled through the solution for 10 minutes. This mixture was stirred for 1 hour. The solvent was evaporated and the solid material (5b-B) thus obtained was washed with cold Et$_2$O (3×20 mL). This solid material was dissolved in THF (25 mL) containing DIEA (7.8 mL, 44.8 mmol). To this solution was added (15-D) (4.2 g, 16.4 mmol) and BOP reagent (7.9 g, 17.9 mmol) and the solution was stirred under dry N$_2$ overnight. Work-up of the coupling reaction was performed by the addition of 1N HCl (60 mL) and extraction with EtOAc (2×50 mL). The combined organic phase was washed with saturated LiCl (35 mL) and dried over Na$_2$SO$_4$. The solution was filtered, solvent evaporated and the residue chromatographed (SiO$_2$, gradient elution: 100% hexanes→50% EtOAc/hexanes) to provide the fully protected intermediate 4-benzyloxycarbonylamino-N-[[(1S,3R)-3-(tert-butoxycarbonyl)-2,2,3-trimethylcyclopentyl]carbonyl]-L-phenylalanine methyl ester (5b-C) (6.5 g, 77%): $^1$H NMR (300 MHz, CDCl$_3$), δ 7.3–7.4 (6H), 7.17 (1H), 7.01 (2H), 5.80 (1H), 5.17 (2H), 4.86 (1H), 3.70 (3H), 3.06 (2H), 2.5–2.6 (2H), 2.1–2.2 (1H), 1.6–1.8 (1H), 1.4–1.5 (1H), 1.43 (9H), 1.21 (3H), 1.13 (3H), 0.80 (3H); $^{13}$C NMR (75 MHz, CDCl$_3$), δ 174.88, 172.43, 172.06, 153.32, 136.98, 135.95, 130.55, 129.58, 128.46, 128.19, 128.15, 118.71, 80.05, 66.80, 56.54, 54.26, 52.98, 52.17, 46.25, 36.94, 32.21, 27.92, 22.81, 22.32, 21.82, 20.46; ESMS (m/z) 567 (MH$^+$).

The above compound, (5b-C) (5.74 g, 10.13 mmol), was dissolved in MeOH/THF (4:1, 50 mL) and degassed with N$_2$. To this solution was added 10% Pd-C (500 mg) and H$_2$ gas was bubbled through the resultant slurry for 1 hour. The reaction was stirred an additional 3 hours under an atmosphere of H$_2$. The mixture was filtered though celite and the celite washed with CH$_3$OH. The solvent was evaporated to afford Example 56 (5a-D) (4.38 g, 100%): $^1$H NMR (300 MHz, CDCl$_3$), δ 6.90 (2H), 6.68 (2H), 5.73 (1H), 4.82 (1H), 3.72 (3H), 3.0–3.1 (2H), 2.5–2.6 (2H), 2.1–2.2 (1H), 1.6–1.8 (1H), 1.4–1.5 (1H), 1.43 (9H), 1.21 (3H), 1.14 (3H), 0.80 (3H); ESMS (m/z) 433 (MH$^+$).

Scheme 6

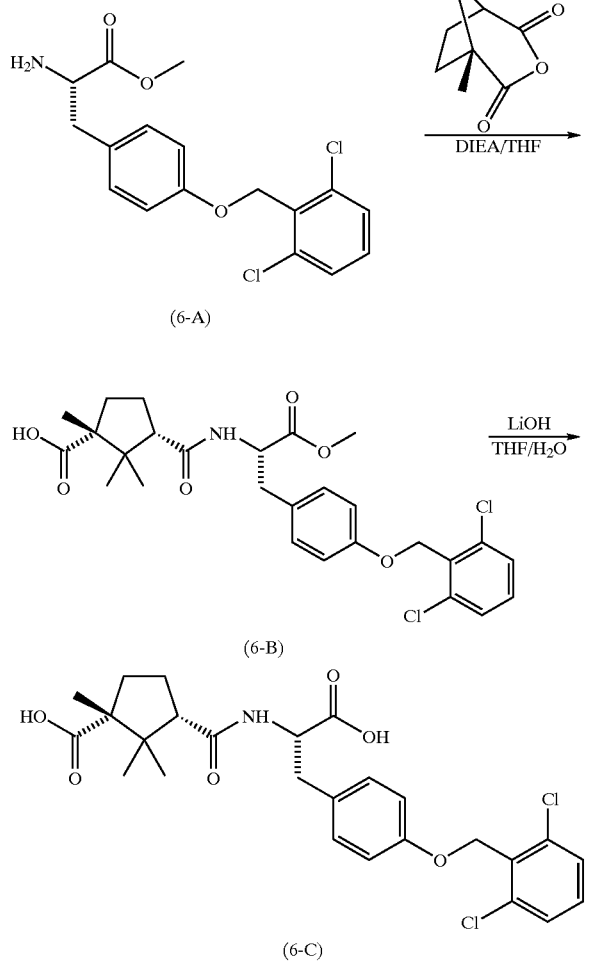

(1R)-Camphoric anhydride (243 mg, 1.33 mmol) was dissolved in THF (10 mL) containing DIEA (1.2 mL, 6.67 mmol). To this solution O-2,6-dichlorobenzyl-L-tyrosine methyl ester (6-A) (618 mg, 1.58 mmol) was added and the solution stirred at 45° C. for 1 h. The reaction was cooled to room temperature and 1 N HCl (20 mL) was added. This was extracted with EtOAc (2×20 mL) and the combined organics were dried ($Na_2SO_4$) filtered, and the solvent removed in vacuo. The residue was chromatographed ($SiO_2$, 10% MeOH in $CH_2Cl_2$) to provide (6-B) (668 mg, 93%) as a colorless oil: $^1$H NMR (300 MHz, $CDCl_3$), (major isomer) δ 7.34 (d, 2H), 7.23 (dd, 1H), 7.04 (d, 2H), 6.9–7.0 (m, 2H), 5.85 (d, 1H), 5.23 (s, 2H), 4.88 (q, 1H), 3.73 (s, 3H), 3.0–3.2 (m, 2H), 2.5–2.6 (m, 2H), 2.2–2.3 (m, 1H), 1.7–1.8 (m, 1H), 1.4–1.5 (m, 1H), 1.23 (s, 3H), 1.22(s, 3H), 0.84(s, 3H); ESMS (m/z) 536 (MH$^+$).

(6-B) (570 mg, 1.06 mmol) was dissolved in THF (2 mL). To this solution LiOH (89 mg, 3.72 mmol) was added in $H_2O$ (2 mL) and the mixture stirred for 12 h at RT. The reaction was acidified with 1 N HCl (10 mL) and then extracted with EtOAc (2×20 mL). The combined organics were dried ($Na_2SO_4$), filtered, and the solvent removed in vacuo to provide Example 12 (6-C) (525 mg, 95%) as a pale yellow foam: $^1$H NMR (300 MHz, Acetone-$d_6$), (major isomer) δ 7.4–7.5 (m, 3H), 7.23 (d, 2H), 6.99 (d, 2H), 5.30 (d, 1H), 5.28 (s, 2H), 4.6–4.7 (m, 1H), 3.13 (dd, 1H), 2.97 (dd, 1H), 2.81 (t, 1H), 2.5–2.6 (m, 1H), 2.0–2.1 (m, 1H), 1.6–1.7 (m, 1H), 1.3–1.4 (m, 1H), 1.27 (s, 3H), 1.19 (s, 3H), 0.80 (s, 3H); $^{13}$C NMR (75 MHz, Acetone-$d_6$), (major isomer) δ 177.79, 173.99, 172.94, 158.53, 137.39, 133.18, 132.01, 131.23, 129.52, 115.24, 65.78, 56.75, 54.47, 53.67, 46.91, 37.19, 33.30, 23.44, 23.01, 22.38, 21.64; ESMS (m/z) 520 (M−H)$^−$.

Scheme 7

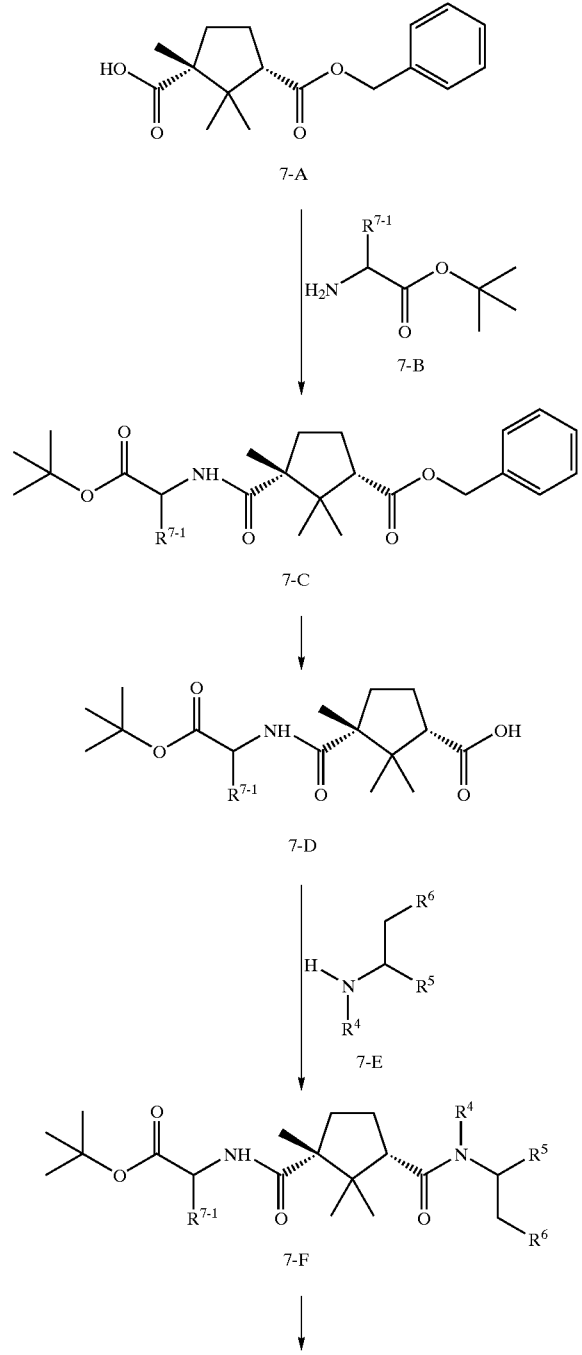

-continued

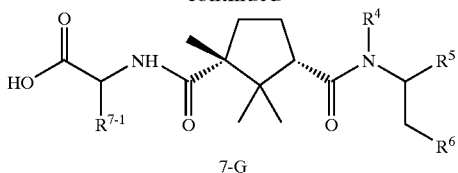

7-G

Preparation 7-A

Scheme 7, 7-A Stereochemistry=1S-cis

Intermediate for Examples 181, 185, and 188

(1R,3S)-Camphoric Acid 1-(1,1-Dimethylethyl)-3-phenylmethyl Ester ($C_{21}H_{30}O_4$)

Benzyl bromide is eluted through neutral alumina (10 mL in a 30 mL sintered glass funnel) to give a colorless liquid (15 mL, 126 mmol) which is added to a stirred solution of (1R,3S)-camphoric acid 1-(1,1-dimethylethyl)ester (15-D) (30 g, 117 mmol), N,N-diisopropylethyl amine (24 mL, 138 mmol), and acetonitrile (90 ml). After seven days, the mixture is filtered to give a white solid (diisopropylethyl amine hydrobromide) and a yellow liquid which is placed in the freezer. After two days, the mixture is filtered (two 50 mL diethyl ether rinses) to give a white solid (24 g, 59% yield).

$^1$H NMR: (300 MHz, CDCl$_3$): δ 7.37–7.29(5H), 5.15 (1H), 5.09(1H), 2.85–2.79(1H), 2.54–2.46(1H), 2.24–2.15 (1H), 1.86–1.74(1H), 1.49–1.36(1H), 1.43(9H), 1.23(,3H), 1.15(3H), 0.78(3H); IR (nujol) 1737, 1724, 1717, 1346, 1272, 1259, 1219, 1210, 1162, 1124, 1116, 1084, 852, 737, 696 cm$^{-1}$; MS (FAB) m/z (rel. intensity) 347 (M+H, 35), 348 (8), 347 (35), 292 (8), 291 (43), 273 (12), 109 (13), 92 (9), 91 (99), 57 (30), 41 (9); HRMS (FAB) calcd for $C_{21}H_{30}O_4$ +H$^+$ 347.2222, found 347.2232; Anal. Calcd for $C_{21}H_{30}O_4$: C, 72.80; H, 8.73; Found: C, 72.79; H, 8.90.

(1R,3S)-Camphoric Acid 3-Phenylmethyl Ester (7-A) ($C_{17}H_{22}O_4$)

To (1R,3S)-camphoric Acid 1-(1,1-Dimethylethyl)-3-phenylmethyl ester (24 g, 69 mmol) is added trifluoroacetic acid (15 mL). After stirring for two days, the solution is evaporated in vacuo to give a pale yellow oil which is dissolved in toluene (250 mL) and shaken with water (6×100 mL). Evaporation of the toluene gave a colorless oil which slowly crystallizes to give 7-A as an oily, white solid (16.4 g, 81% yield).

$^1$H-NMR:(300 MHz, CDCl$_3$): δ 7.38–7.16(5H), 5.17(1H), 5.11(1H), 2.87(1H), 2.60–2.49(1H), 2.30–2.21(1H), 1.91–1.80(1H), 1.57–1.48(1H), 1.27(3H), 1.25(3H), 0.84 (3H); IR (liq.) 3067, 3034, 2972, 2888, 1732, 1696, 1457, 1378, 1285, 1231, 1212, 1166, 1124, 752, 698 cm$^{-1}$; MS (FAB) m/z (rel. intensity) 291 (M+H, 44), 391 (5), 292 (8), 291 (44), 273 (6), 245 (4), 155 (3), 109 (10), 92 (9), 91 (99), 41 (3); HRMS (FAB) m/z calcd for $C_{17}H_{22}O_4$ +H$^+$ 291.1596, found 291.1603; Anal. Calcd for $C_{17}H_{22}O_4$: C, 70.32; H, 7.64; Found: C, 70.21; H, 7.89.

Preparation 7-C-1

Scheme 7, 7-C: wherein $R^{7-1}$=H Stereochemistry= 1S-cis (1R-cis)-N-[[3-[(phenylmethoxy)carbonyl]-1,2,2-trimethylcyclopentyl]carbonyl]glycine (1,1-dimethylethyl) ester (7-C-1) ($C_{23}H_{33}NO_5$)

To (1R,3S)-camphoric acid 3-phenylmethyl ester 7-A (0.736 g, 2.53 mm) in dry DMF (5 mL) is added diisopropylethyl amine (3 mL, 17.2 mmol) and HATU(1.05 g, 2.76 mmol). Thirty minutes later, 7-B ($R^{7-1}$=H) hydrochloride (0.855 g, 5.10 mm) is added. After overnight stirring, the mixture is evaporated to dryness (in vacuo/N$_2$ flow) and then mixed with toluene (50 mL) and THF (50 mL) and washed with water (2×50 mL), 1N HCl (50 mL), and water (4×50 mL). The organic layer is then evaporated to dryness, giving 7-C ($R^{7-1}$=H) as an off-white solid (0.9 g, 90%)

$^1$H NMR(300 MHz, CDCl$_3$) δ 7.37–7.15(5H), 6.05(1H), 5.17–5.08(2H), 3.99–3.82(2H), 2.89–2.83(1H), 2.51–2.40 (1H), 2.29–2.22(1H), 1.94–1.80(1H), 1.59–1.51(1H), 1.47 (9H), 1.31(3H), 1.21(3H), 0.78(3H). MS (ES+) m/z 404.1 (parent).

Preparation 7-D

Scheme 7, 7-D: wherein $R^{7-1}$=H Stereochemistry= 1S-cis (1R-cis)-N-[[3-carboxy-1,2,2-trimethylcyclopentyl]carbonyl]glycine (1,1-dimethylethyl)ester (7-D-1) ($C_{16}H_{27}NO_5$)

Ester 7-C ($R^{7-1}$=H, 0.97 g, 2.4 mmol) in THF (12 mL) and ethanol (6 mL) is shaken with 10%Pd/C (0.115 g) in a Parr bottle under an H$_2$(38 psi) atmosphere. After 8 hours, the bottle is removed from the shaker and filtered through Celite (with 3×30 mL ethanol rinses). The filtrate is evaporated to dryness, giving 7-D ($R^{7-1}$=H) as a thick, colorless oil (0.6 g, 79% yield).

$^1$H NMR(300 MHz, CDCl$_3$) δ 6.13(1H), 4.0–3.84(2H), 2.86–2.80(1H), 2.49–2.39(1H), 2.27–2.17(1H), 1.94–1.80 (1H), 1.60–1.52(1H), 1.46(9H), 1.34(3H), 1.22(3H), 0.88 (3H); IR (liq.) 3385, 2976, 2940, 2887, 1732, 1644, 1528, 1478, 1459, 1405, 1394, 1369, 1277, 1227, 1158 cm$^{-1}$; MS (FAB) m/z (rel. intensity) 314 (M+H, 99), 315 (18), 314 (99), 258 (51), 109 (22), 95 (9), 76 (20), 69 (12), 57 (28), 55 (12), 41 (14). HRMS (FAB) m/z calcd for C16H27NO5 +H1 314.1967, found 314.1974; Anal. Calcd for $C_{16}H_{27}NO5$: C, 61.32; H, 8.68; N, 4.47; Found: C, 61.70; H, 8.86; N, 4.14; Melt Solvate: 3.9% Ethanol.

Preparation 7-F-1

Scheme 7, 7-F: wherein $R^{7-1}$=H, $R^4$=H, $R^5$= CO$_2$CH$_3$ $R^6$=4-[(2,6-Dichlorobenzoyl)amino]phenyl Stereochemistry=(1S-cis)-L (1S-cis)-N-[[3-[[(1,1-dimethylethoxycarbonylmethyl) amino]carbonyl]-2,2,3-trimethylcyclopentyl]carbonyl]-4-[(2,6-dichlorobenzoyl)amino]-L-phenylalanine methyl ester (7-F-1) ($C_{33}H_{41}Cl_2N_3O_7$)

(1R-cis)-N-[[3-carboxy-1,2,2-trimethylcyclopentyl] carbonyl]glycine (1,1-dimethylethyl) ester 7-D ($R^{7-1}$=H, 0.356 g, 1.14 mmol) is dissolved in methylene chloride (6 mL), under N$_2$ in a round bottom flask, and is cooled in an ice water bath. To this stirred solution is added N,N-diisopropylethylamine (1 mL, 5.7 mmol), EDC(0.242 g, 1.26 mmol), HOBt (0.181 g, 1.34 mmol), and 4-N,N- dimethylaminopyridine (0.016 g, 0.13 mmol) followed 30 minutes later by 4-[(2,6-dichlorobenzoyl)amino]-L-phenylalanine methyl ester hydrochloride 7-E-1.HCl (7E: $R^4$=H, $R^5$=$CO_2CH_3$, $R^6$=4-[(2,6-dichlorobenzoyl)amino]phenyl, Stereochemistry=S) (0.487 g, 1.2 mmol). After two days of stirring (the ice bath is allowed to melt), the reaction mixture is evaporated to dryness and then partitioned between THF (100 mL), diethyl ether (50 mL), and water (50 mL). The organic layer is washed with water (3×50 mL), aqueous HCl (0.5N, cold, 3×30 mL), aqueous sodium bicarbonate (1×50 mL), water (3×30 mL, to pH7), and then evaporated to dryness, giving 7-F ($R^{7-1}$=H, $R^4$=H, $R^5$=$CO_2CH_3$, $R^6$=4-[(2,6-Dichlorobenzoyl)amino]phenyl, Stereochemistry=(1S-cis)-L) as a white solid (0.63 g, 80% yield).

$^1$H NMR(300 MHz, $CDCl_3$) δ 7.57(2H), 7.38–7.26(3H), 7.10(2H), 6.07(1H), 5.80(1H), 4.89(1H), 3.97–3.74(2H), 3.21–3.05(2H), 2.58–2.52(1H), 2.45–2.35(1H), 2.30–2.18 (1H), 1.90–1.75(1H), 1.58–1.50(1H), 1.46(9H), 1.30(3H), 1.20(3H), 0.79(3H); IR (nujol) 1739, 1668, 1643, 1609, 1560, 1538, 1516, 1431, 1414, 1327,1288, 1256, 1235, 1195, 1161 $cm^{-1}$; MS (FAB) m/z (rel. intensity) 662 (M+H, 84), 664 (58), 663 (39), 662 (84), 533 (39), 531 (55), 240 (58), 194 (37), 173 (41), 109 (99), 57 (44); HRMS (FAB) m/z calcd for $C_{33}H_{41}Cl_2N_3O_7$ +$H^+$ 662.2399, found 662.2410.

Preparation 7-G-1

Scheme 7, 7-G: wherein $R^{7-1}$=H, $R^4$=H, $R^5$=$CO_2CH_3$ $R^6$=4-[(2,6-Dichlorobenzoyl)amino]-phenyl Stereochemistry=(1S-cis)-L (1S-cis)-N-[[3-[[(Carboxymethyl)amino]carbonyl]-2,2,3-trimethylcyclopentyl]carbonyl]-4-[(2,6-dichlorobenzoyl)amino]-L-phenylalanine methyl ester (7-G-1) ($C_{29}H_{33}Cl_2N_3O_7$)

(1S-cis)-N-[[3-[[(1,1-dimethylethyloxycarbonylmethyl)amino]carbonyl]-2,2,3-trimethylcyclopentyl]carbonyl-4-[(2,6-dichlorobenzoyl)amino]-L-phenylalanine methyl ester 7-F ($R^{7-1}$=H, $R^4$=H, $R^5$=$CO_2CH_3$, $R^6$=4-[(2,6-Dichlorobenzoyl)amino]-phenyl, Stereochemistry=(1S-cis)-L, 0.802 g, 1.21 mmol) is stirred overnight in trifluoroacetic acid (3 mL). The solution is then diluted with toluene (5 mL) and evaporated to dryness in vacuo to give an off white solid which was recrystallized from chloroform/diethyl ether to give 7-G ($R^{7-1}$=H, $R^4$=H, $R^5$=$CO_2CH_3$, $R^6$=4-[(2, 6-Dichlorobenzoyl)amino]-phenyl, Stereochemistry=(1S-cis)-L as a white solid (0.7 g, 90% yield).

$^1$H-NMR: (300 MHz, DMSO-$d_6$): δ 10.68(1H), 7.92(2H), 7.58–7.44(3H), 7.19(2H), 4.53–4.45(1H), 3.75–3.62(2H), 3.58(3H), 3.03–2.85(2H), 2.68–2.62(1H), 2.40–2.28(1H), 1.98–1.81(1H), 1.70–1.50(1H), 1.30–1.25(1H), 1.17(3H), 1.09(3H).

Preparation of Example 181

Scheme 7, 7-G: wherein $R^{7-1}$=H $R^4$=H, $R^5$=$CO_2H$, $R^6$=4-[(2,6-Dichlorobenzoyl)amino]phenyl, Stereochemistry=(1S-cis)-L (1S-cis)-N-[[3-[[(Carboxymethyl)amino]carbonyl]-2,2,3-trimethylcyclopentyl]carbonyl]-4-[(2,6-dichlorobenzoyl)amino]-L-phenylalanine (Example 181) ($C_{28}H_{31}Cl_2N_3O_7$)

(1S-cis)-N-[[3-[[(Carboxymethyl)amino]carbonyl]-2,2,3-trimethylcyclopentenyl]carbonyl]-4-[(2,6-dichlorobenzoyl)amino]-L-phenylalanine methyl ester (7-G-1) (0.7 g, 1.15 mmol) is dissolved in methanol (12 mL). To this is added a mixture of $LiOH.H_2O$ (0.243 g, 5.8 mmol), aqueous $H_2O_2$ (30%, 2 mL), and $H_2O$ (2 mL). After overnight stirring, the reaction mixture is diluted with water (50 mL), and evaporated (room temperature, in vacuo/$N_2$flow) until the methanol is gone. The aqueous solution is then transferred to a separatory funnel and shaken with diethyl ether (2×20 mL). The aqueous layer is then evaporated, to remove residual diethyl ether, and cooled in an ice water bath. The stirred solution is then brought to pH3–4 using aqueous HCl (1N). The resultant precipitate is isolated by suction filtration (with water washes) to give Example 181 as a white solid (0.4 g, 58% yield)

$^1$H-NMR: (300 MHz, DMSO-$d_6$): δ 12.45(1H), 10.6(1H), 7.74(2H), 7.57–7.44(3H), 7.20(2H), 4.48–4.40(1H), 3.65 (2H), 2.94(2H), 2.64(1H), 2.35(1H), 1.90(1H), 1.58(1H), 1.29(1H), 1.18(3H), 1.08(3H), 0.60(3H); IR (nujol) 3124, 3088, 3078, 1738, 1666, 1628, 1612, 1588, 1563, 1552, 1521, 1429, 1334, 1197, 1170 $cm^{-1}$; MS (FAB) m/z (rel. intensity) 592 (M+H, 99), 595 (20), 594 (69), 593 (41), 592 (99), 519 (25), 517 (38), 240 (55), 175 (23), 173 (33), 109 (64); HRMS(FAB) m/z calcd for $C_{28}H_{31}Cl_2N_3O_7$ +$H^+$ 592.1617, found 592.1606; Anal. Calcd for $C_{28}H_{31}Cl_2N_3O_7$: C, 56.76; H, 5.27; N, 7.09; Found: C, 54.92; H, 5.41; N, 6.91; KF Water: 3.05% $H_2O$.

Preparation 7-F-2

Scheme 7, 7-F: wherein wherein $R^{7-1}$=H, $R^4$=H, $R^5$=$CO_2CH_3$, $R^6$=4-[(2,6-Dichlorophenyl)methoxy]-phenyl Stereochemistry=(1S-cis)-L

[1S-cis]-O-[((2,6-Dichlorophenyl)methyl)]-N-[[3-[[(1,1-diemethylethoxy)carbonylmethyl)amino]carbonyl]-2,2,3-trimethylcyclopentyl)carbonyl]-L-tyrosine methyl ester (7-F-2) ($C_{33}H_{42}Cl_2N_2O_7$) is prepared from 7-D ($R^{7-1}$=H and O-[(2,6-dichlorophenyl)methyl]-L-tyrosine methyl ester 7-E-2 (7-E: $R^4$=H, $R^5$=$CO_2CH_3$, $R^6$=4-[(2,6-Dichlorophenyl)methoxy]phenyl, Stereochemistry=S) as taught by Scheme 7.

$^1$H NMR($CDCl_3$) δ 7.39–6.94 (7H), 6.09 (1H), 5.78 (1H), 5.25 (2H), 4.87 (1H), 3.90 (2H), 3.74 (3H), 3.09 (2H), 2.59–2.20 (3H), 1.80 (1H), 1.56 (1H), 1.47 (9H), 1.30 (3H), 1.26 (3H), 0.81 (3H); IR (mull) 3327, 1762, 1741, 1664, 1637, 1538, 1512, 1440, 1241, 1229,1206, 1198, 1174, 1156, 1022 $cm^{-1}$; MS (FAB) m/z (rel. intensity) 649 (M+H, 50), 651 (34), 649 (50), 518 (21), 296 (23), 240 (44), 194 (28), 161 (26), 159 (41), 109 (99), 57 (37).

Preparation 7-G-2

Scheme 7, 7-G: wherein $R^{7-1}$=H, $R^4$=H, $R^5$=$CO_2CH_3$, $R^6$=4-[(2, 6-Dichlorophenyl)methoxy]phenyl Stereochemistry=(1S-cis)-L

[1S-cis]-O-[((2,6-Dichlorophenyl)methyl)]-N-[[3-[[(Carboxymethyl)amino]carbonyl]-2,2,3-trimethylcyclopentyl]carbonyl]-L-tyrosine methyl ester (7-G-2) ($C_{29}H_{34}Cl_2N_2O_7$) is prepared from 7-F-2 as taught by Scheme 7.

$^1$H NMR ($CDCl_3$) δ 8.14 (1H), 7.37–6.93 (7H), 6.51(1H), 6.02 (1H), 5.24 (1H), 4.85 (1H), 4.02 (2H), 3.73 (3H), 3.09 (2H), 2.57 (1H), 2.41 (1H), 2.25 (1H), 1.84 (1H), 1.56 (1H), 1.26 (3H), 1.20(3H), 0.79 (3H); MS(ES+) m/z 592.9.

Preparation of Example 185

Scheme 7, 7-G: wherein $R^{7-1}$=H, $R^4$=H, $R^5$=CO$_2$H, $R^6$=4-[(2,6-Dichlorophenyl)methoxy]phenyl, Stereochemistry=(1S-cis)-L (1S-cis)-N-[[3-[[(Carboxymethyl)amino]carbonyl]-2,2,3-trimethylcyclopentyl]carbonyl]-O-[(2,6-dichlorophenyl)methyl]-L-tyrosine (Example 185) (C$_{28}$H$_{32}$Cl$_2$N$_2$O$_7$) is prepared from 7-G-2 ($R^{7-1}$=H, $R^4$=H, $R^5$=CO$_2$CH$_3$, $R^6$=4-[(2,6-Dichlorophenyl)methoxy]-phenyl, Stereochemistry=S) as taught by Scheme 7.

$^1$H NMR(300 MHz, DMSO-d$_6$) 7.8–6.9(9H), 5.18(2H), 4.42(1H), 3.8–3.6(2H), 3.02 –2.82(2H), 2.65(1H), 2.38(1H), 1.91(1H), 1.58(1H), 1.30(1H), 1.19(3H), 1.10(3H), 0.61 (3H); IR (nujol) 3409, 1733, 1645, 1612, 1585, 1564, 1511, 1439, 1297, 1239, 1197, 1179, 1018, 786, 770 cm$^{-1}$; MS (FAB) m/z (rel. intensity) 579 (M+H, 99), 582 (22), 581 (67), 580 (44), 579 (99), 578 (21), 240 (34), 161 (21), 159 (34), 109 (46), 91(37); HRMS (FAB) m/z calcd for C$_{28}$H$_{32}$Cl$_2$N$_2$O$_7$ +H$^+$ 579.1664, found 579.1667.

Preparation 7-C-2

Scheme 7, 7-C: wherein $R^{7-1}$=CH$_3$
Stereochemistry=[1S-[1α,3α(R*)]]

[1S-[1α,3α(R*)]]-3-[[[1-(1,1-Dimethylethoxycarbonyl)ethyl]amino]carbonyl]-2,2,3-trimethylcyclopentanecarboxylic acid [phenyl(methyl)]ester (7-C-2) (C$_{24}$H$_{35}$NO$_5$) is prepared from 7-A and 7-B. ($R^{7-1}$=CH$_3$, Stereochemistry=S) as taught by Scheme 7.

$^1$H NMR(300 MHz, CDCl$_3$) δ 7.37–7.16 (5H), 6.18 (1H), 5.12 (2H), 4.41 (1H), 2.84 (1H), 2.46 (1H), 2.28 (1H), 1.87(1H), 1.52 (1H), 1.51(9H), 1.35(3H), 1.28(3H), 1.20 (3H), 0.78 (3H). MS(ES+) m/z 455.1

Preparation 7-D-2

Scheme 7, 7-D: wherein wherein $R^{7-1}$=CH$_3$
Stereochemistry=[1S-[1α,3α(R*)]]

[1S-[1α,3α(R*)]]-3-[[[1-(1,1-Dimethylethoxycarbonyl)ethyl]amino]carbonyl]-2,2,3-trimethylcyclopentanecarboxylic acid (7-D-2) (C$_{17}$H$_{29}$NO$_5$) is prepared from 7-C-2 as taught by Scheme 7.

$^1$H NMR(300 MHz, CDCl3) δ 6.28(1H), 4.44(1H), 2.86 (1H); 2.43(1H), 2.23(1H), 1.93(1H), 1.56 (1H), 1.47(9H), 1.36(3H), 1.31(3H), 1.22(3H), 0.90(3H); MS(ES–) m/z 326.1.

Preparation 7-F-3

Scheme 7, 7-F: wherein $R^{7-1}$=CH$_3$, $R^4$=H, $R^5$=CO$_2$CH$_3$, $R^6$=4-[(2, 6-Dichlorophenyl)methoxy]phenyl Stereochemistry=[1S-[1α,3α(R*)]]

[1S-[1α,3α(R*)]]-O-[(2,6-Dichlorophenyl)methyl]-N-[[3-[[[1-(1,1-dimethylethoxycarbonyl)ethyl]amino]carbonyl]-2,2,3-trimethylcyclopentyl]carbonyl]-L-tyrosine methyl ester (7-F-3) (C$_{34}$H$_{44}$Cl$_2$N$_2$O$_7$) is prepared from 7-D-2 and 7-E-2 (7E: $R^4$=H, $R^5$=CO$_2$CH$_3$, $R^6$=4-[(2,6-Dichlorophenyl)methoxy]phenyl) as taught by Scheme 7.

$^1$H NMR(300 MHz, CDCl$_3$) δ7.38–6.93(7H), 6.20 (1H), 5.77(1H), 5.25 (2H), 4.87 (1H), 4.42 (1H), 3.73 (3H), 3.09 (2H), 2.44(2H), 1.76 (2H), 1.52(1H), 1.46 (9H), 1.35(3H), 1.27(3H), 1.20(3H), 0.80(3H). IR (nujol) 1739, 1654, 1612, 1585, 1565, 1511, 1439, 1344, 1300, 1240, 1198, 1177, 1154, 1017, 768 cm$^{-1}$. MS (FARB) m/z (rel. intensity) 663 (M+H, 82), 665 (60), 664 (37), 663 (82), 518 (27), 254 (51), 208 (24), 161 (28), 159 (45), 109 (99), 57 (33).

Preparation 7-G-3

Scheme 7, 7-G: wherein $R^{7-1}$=CH$_3$, $R^4$=H, $R^5$=CO$_2$CH$_3$, $R^6$=4-[(2,6-Dichlorophenyl)methoxy]phenyl Stereochemistry=[1S-[1α,3α(R*)]]-L

[1S-[1α,3α(R*)]]-O-[(2,6-Dichlorophenyl)methyl]-N-[[3-[[(1-Carboxyethyl)amino]carbonyl]-2,2,3-trimethylcyclopentyl]carbonyl]-L-tyrosine methyl ester (7-G-3) (C$_{30}$H$_{36}$Cl$_2$N$_2$O$_7$) is prepared from 7-F-3 as taught by Scheme 7.

$^1$H NMR(300 MHZ, CDCl$_3$) δ 10.55 (1H), 7.38–6.94 (7H). 6.47(1H), 6.12 (1H), 5.25 (2H), 4.87(2H), 4.55(1H), 3.75(3H), 3.10(2H), 2.60 (1H), 2.41 (1H), 2.25 (1H), 1.87 (1H), 1.58 (1H), 1.46(3H), 1.24(3H), 1.21 (3H)., 0.78 (3H); MS(ES+) m/z 606.8

Preparation of Example 188

Scheme 7, 7-G: wherein $R^{7-1}$=CH$_3$, $R^4$=H, $R^5$=CO$_2$H, $R^6$=4-[(2, 6-Dichlorophenyl)methoxy]phenyl, Stereochemistry=[1S-[1α,3α(R*)]

[1S-[1α,3α(R)]]-N-[[3-[[(1-Carboxyethyl)amino]carbonyl]-2,2,3-trimethylcyclopentyl]carbonyl]-O-[(2,6-dichlorophenyl)methyl]-L-tyrosine (C$_{29}$H$_{34}$Cl$_2$N$_2$O$_7$) is prepared from 7-G-3 as taught by Scheme 7.

$^1$H NMR(300 MHz, DMSO-d$_6$ 7.71(1H), 7.54–7.43(3H) 7.28(1H), 7.16(2H), 6.93(2H), 5.16(2H), 4.40(1H), 4.16 (1H), 3.02–2.80(2H), 2.63(1H), 2.35(1H), 1.86(1H), 1.54 (1H), 1.35–1.23(4H), 1.14(3H), 1.08(3H), 0.59(3H); IR (nujol) 3427, 3031, 1731, 1645, 1612, 1585, 1565, 1512, 1439, 1297, 1239, 1230, 1197, 1179, 1017 cm$^{-1}$; MS (FAB) m/z (rel. intensity) 593 (M+H, 99), 596 (22), 595 (69), 594 (43), 593 (99), 592 (17), 504 (22), 254 (63), 161 (44), 159 (40), 109 (72).

Scheme 8

$R^{8-1}$ is defined in the same manner as $R^{7-1}$ to include amino acids included in $R^2$ definition; $R^{8-2}$ is proton or together with $R^{8-1}$ cyclic amino acid.

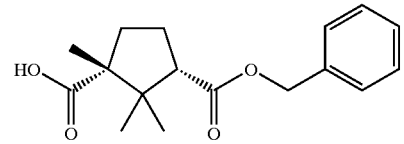

7-A

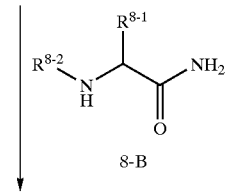

8-B

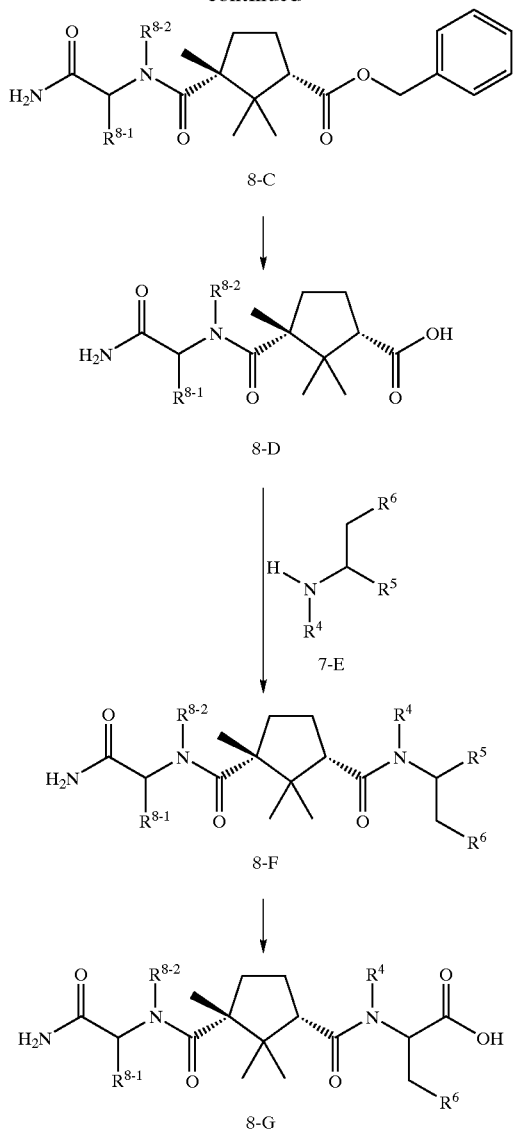

MP: 163–164° C.; $^1$H-NMR (300 MHz, CDCl$_3$): δ 7.25–7.40(5H), 6.36(1H), 6.08(1H), 5.33(3H), 5.15(1H), 5.10(1H), 3.93(2H), 2.85(1H), 2.43(1H), 2.27(1H), 1.40–1.65(2H), 1.30(3H), 1.21(3H), 0.76(3H); IR (nujol) 3383, 3361, 3184, 2924, 1766, 1710, 1684, 1626, 1527, 1402, 1253, 1166, 753 cm$^{-1}$; MS (EI) m/z (rel intensity) 346(M+, 4), 329(2), 273(3), 255(3), 239(3), 211(6), 153(11), 109(17), 91(base); Anal. calcd for C$_{19}$H$_{26}$N$_2$O$_4$: C, 65.88; H, 7.56; N, 8.09; Found: C, 65.94; H, 7.65; N, 8.09.

Preparation 8-D-1

Scheme 8, 8-D: wherein: R$^{8-1}$=H, R$^{8-2}$=H
Stereochemistry=1S-cis (1R-cis)-N-[[3-carboxy-1,2,2-trimethylcyclopentyl]-carbonyl]glycine amide (8-D-1) (C$_{12}$H$_{20}$N$_2$O$_4$)

A solution of 8-C (R$^{8-1=H, R8-2}$=H) (3.46 g, 100 mmol) in THF (225 mL), containing 10% Pd/C (1.14 g), is hydrogenated under 50 psi of hydrogen for 12 hours. The catalyst is removed by filtration through a cake of Celite, the filter cake is rinsed with THF (100 mL), and the combined filtrates are concentrated in vacuo to give the crude product as a white foam. The crude material is recrystallized from hexanes-THF to afford the target compound 8-D (R$^{8-1=H, R8-2}$=H) (2.4 g, 94%) as fine white needles.

MP: 86–87° C.; $^1$H-NMR (300 MHz, DMSO-d$_6$): δ 12.00(1H), 7.28(1H), 7.13(1H), 6.92(1H), 3.56(2H), 2.67 (1H), 2.34(1H), 1.97(1H), 1.72(1H), 1.36 (1H), 1.19(3H), 1.09(3H), 0.68(3H); IR(nujol) 3496, 3391, 3189, 2924, 1729, 1705, 1686, 1623, 1519, 1401, 1280, 1245, 1200, 665 cm$^{-1}$; MS(EI) m/z (rel intensity) 238(2), 221(6), 195(base), 138(26), 109(81), 95(67); Anal. calcd for C$_{12}$H$_{20}$N$_2$O$_4$: C, 56.24; H, 7.86; N, 10.93; Found: C, 55.90; H, 8.05; N, 10.50.

Preparation 8-F-1

Scheme 8, 8-F: wherein R$^{8-1}$=H, R$^{8-2}$=H, R$^4$=H, R$^5$=CO$_2$CH$_3$, R$^6$=4-[(2,6-Dichlorobenzoyl)amino] phenyl, Stereochemistry=(1S-cis)-L (1S-cis)-N-[[3-[[(2-Amino-2-oxoethyl)amino]carbonyl]-2,2,3-trimethylcyclopentyl]carbonyl]-4-[(2,6-dichlorobenzoyl)amino]-L-phenylalanine methyl ester (C$_{29}$H$_{34}$Cl$_2$N$_4$O$_6$)

To 8-D (R$^{8-1}$=H, R$^{8-2}$=H)) (1.03 g, 4 mmol) in dry DMF (25 mL), cooled in a an ice-water bath, is added in order, diisopropylethylamine (2.07 g, 16 mmol, 2.8 mL), 4-(2,6-dichlorobenzamido)-L-phenylalanine methyl ester hydrochloride 7-E-1.HCl (7-E: R$^4$=H, R$^5$=CO$_2$CH$_3$, R$^6$=4-[(2,6-dichlorobenzoyl)amino]phenyl) (1.48 g, 4 mmol), and HATU (1.49 g, 4.2 mmol). The mixture is stirred for 48 hours as the ice melts and the mixture warms to room temperature. The solution is cast into ethyl acetate (1 L) and this solution is washed successively with 1N aq. HCl (1 L), 1N aq. NaOH (1 L), water (4×1 L), and brine (1 L). The organic phase is seperated, dried (Na$_2$SO$_4$), and concentrated in vacuo to give the desired product 8-F (R$^{8-1}$=H, R$^{8-2}$=H, R$^4$=H, R$^5$=CO$_2$CH$_3$, R$^6$=4-[(2,6-dichlorobenzoyl) amino]phenyl) (1.12 g, 42%) as a fine, white powder.

MP: 232–233° C.; $^1$H-NMR (300 MHz, DMSO-d$_6$): δ 10.75(1H), 7.94(1H), 7.45–7.70(5H), 7.35(1H), 7.19(2H), 7.13(1H), 6.92(1H), 4.81(1H), 3.57(3H), 3.55(2H), 2.92 (2H), 2.64(1H), 2.34(1H), 1.88(1H), 1.62(1H), 1.30(1H), 1.16(3H), 1.07(3H), 0.58(3H); IR (nujol): 3344, 3251, 3194, 3126, 3072, 2924, 1743, 1699, 1669, 1652, 1623, 1528, 1432, 1328, 799 cm$^{-1}$; MS (FAB): m/z (rel. intensity) 605(M+2H), base), 531(28), 503(2), 367(7), 349(17), 256

Preparation 8-C-1

Scheme 8, 8-C: wherein: R$^{8-1}$=H, R$^{8-2}$=H
Stereochemistry=1S-cis (1S-cis)-N-[[1-[(phenylmethoxy)carbonyl]-2,2,3-trimethylcyclopentyl]carbonyl]glycine amide (8-C-1) (C$_{19}$H$_{26}$N$_2$O$_4$)

A solution of (1R-cis)-[3-(phenylmethoxy)carbonyl]-1,2,2-trimethylcyclopentanecarboxylic acid (7-A) (1 g, 3.44 mmol) in dry DMF is cooled in an ice water bath and diisopropylethylamine (1.77 g, 13.76 mmol, 2.39 mL), HATU (1.35 g, 3.55 mmol), and 8-B (R$^{8-1}$=H, R$^{8-2}$=H) (0.38 g, 3.44 mmol) are added in order. The mixture is allowed to stir for 48 hours as the ice melts and the solution warms to room temperature. The solution is cast into methylene chloride (0.25 L) and 1N aq. NaOH (0.25 L). The organic phase is separated and washed in order with 1N aq. HCl (0.25 L), water (5×0.25 L), and brine (0.25 L). The organic phase is dried and concentrated in vacuo to give the crude amide as an ivory powder. The crude amide is recrystallized from hexanes-chloroform to furnish the target amide 8-C (R$^{8-1}$=H, R$^{8-2}$=H) as a fine, free flowing, white powder.

(10), 239(66), 194(31), 173(37), 137(12), 109(83); Anal. calcd for $C_{29}H_{34}Cl_2N_4O_6$ –0.3$H_2O$: C, 57.02; H, 5.71; N, 9.17; Found: C, 57.01; H, 5.86; N, 8.89.

Preparation of Example 180

Scheme 8, 8-G: wherein $R^{8-1}$=H, $R^{8-2}$=H, $R^4$=H, $R^5$=$CO_2H$, $R^6$=4-[(2,6-Dichlorobenzoyl)amino] phenyl, Stereochemistry=(1S-cis)-L (1S-cis)-N-[[3-[[(2-Amino-2-oxoethyl)amino]-carbonyl]-2,2,3-trimethylcyclopentyl]carbonyl]-4-](2,6-dichlorobenzoyl)amino]-L-phenylalanine (Example 180) ($C_{28}H_{32}Cl_2N_4O_6$)

To 8-F ($R^{8-1}$=H, $R^{8-2}$=H, $R^4$=H, $R^5$=$CO_2CH_3$, $R^6$=4-[(2,6-dichlorobenzoyl)amino]-phenyl) (1.05 g, 1.7 mmol), dissolved in methanol (30 mL), is added a solution of LiOH. 2$H_2O$ (0.32 g, 7.65 mmol) in water (10 mL), dropwise over 15 minutes. The mixture stirs for 18 hours at room temperature and the pH is then adjusted to ca. 7 by the careful addition of 1N aq. HCl. The majority of the methanol, is removed in vacuo and the pH of the resulting solution is adjusted to ca. 2 with 1N aq. HCl. The resulting flocculent white precipitate is isolated by filtration and dried. The solid is crushed and washed with water (2×10 mL) and dried in vacuo at 50° C. to give 0.97 g (97%) of 8-G ($R^{8-1}$=H, $R^{8-2}$=H, $R^4$=H, $R^5$=$CO_2H$, $R^6$=4-[(2,6-dichlorobenzoyl)amino]-phenyl) as a white, powdery solid.

MP: 203–205° C.; $^1$H NMR (300 MHz, DMSO-$d_6$): 12.51(1H), 10.70(1H), 7.75(1H), 7.45–7.57(3H), 7.33(1H), 7.20(2H), 7.11(1H), 6.92(1H), 4.43(1H), 3.63(1H), 3.47 (2H), 3.30(2H), 3.01(1H), 2.84(1H), 2.31(1H), 1.87(1H), 1.55(1H), 1.31(1H), 1.17(3H), 1.08(3H), 0.59(3H); IR (nujoll): 3511, 3325, 3128, 3082, 2868, 1722, 1697, 1664, 1614, 1555, 1537, 1417, 1337, 1246, 799 cm$^{-1}$; MS (FAB) m/z (rel. intensity) 591(M+H, base), 517(32), 335(26), 239 (32), 173(39), 109(63), 57(80); HRMS (FAB) m/z calcd for $C_{28}H_{32}Cl_2N_4O_6$ +H$^+$ 591.1777, found 591.1747.

Preparation 8-F-2

Scheme 8, 8-F: wherein $R^{8-1}$=H, $R^{8-2}$=H, $R^4$=H, $R^5$=$CO_2CH_3$, $R^6$=4-[(2,6-Dichlorophenyl)methoxy] phenyl Stereochemistry=(1S-cis)-L (1S-cis)-N-[[3-[[(2-Amino-2-oxoethyl)amino]carbonyl]-2,2,3-trimethylcyclopentyl]carbonyl]-O-[(2,6-dichlorophenyl)methyl]-L-tyrosine methyl ester (8-F-2) ($C_{29}H_{35}Cl_2N_3O_6$) is prepared from 8-D ($R^{8-1}$=H, $R^{8-2}$=H) and 7-E-2 ($R^4$=H, $R^5$=$CO_2CH_3$, $R^6$=4-[(2,6-dichlorophenyl)methoxy]phenyl) as taught by Scheme 8.

$^1$H NMR(CDCl$_3$) δ 7.37–6.93 (7H), 6.54 (1H), 6.40 (1H), 5.82 (1H), 5.60(1H), 5.24(2H), 4.85 (1H), 3.93 (2H), 3.73 (3H), 3.09 (2H), 2.54 (1H), 2.40 (1H), 2.23 (1H), 1.78 (1H), 1.52 (1H), 1.27 (3H), 1.20 (3H), 0.78 (3H); MS(ES+) m/z 591.9.

Preparation of Example 187

Scheme 8, 8-G: wherein $R^{8-1}$=H, $R^{8-2}$=H, $R^4$=H, $R^5$=$CO_2H$, $R^6$=4-[(2,6-Dichlorophenyl)methoxy] phenyl Stereochemistry=(1S-cis)-L (1S-cis)-N-[[3-[[(2-amino-2-oxoethyl)amino]carbonyl]-2,2,3-trimethylcyclopentyl]carbonyl]-O-[(2,6-dichlorophenyl)methyl]-L-tyrosine (Example 187) ($C_{28}H_{33}Cl_2N_3O_6$) is prepared from 8-F ($R^{8-1}$=H, $R^{8-2}$=H, $R^4$=H, $R^5$=$CO_2CH_3$, $R^6$=4-[(2,6-dichlorophenyl)methoxy] phenyl) as taught by Scheme 8.

$^1$H NMR(300 MHz, DMSO-$d_6$) 7.74(2H), 7.55–7.40(4H), 7.15(3H), 6.94(3H), 5.16(2H), 4.41(1H), 3.75–3.48(2H), 3.1–2.8(2H), 2.63(1H), 2.33(1H), 1.87(1H), 1.54(1H), 1.32 (1H), 1.17(3H), 1.08(3H), 0.58(3H); MS (FA.B) m/z (rel. intensity) 578 (M+H, 99), 581 (30), 580 (72), 579 (57), 578 (99), 577 (19), 504 (17), 322 (18), 239 (35), 161 (29), 159 (34); HRMS (FAB) m/z calcd for $C_{28}H_{33}Cl_2N_3O_6$ +H$^+$ 578.1824, found 578.1836.

Scheme 9

Example 183

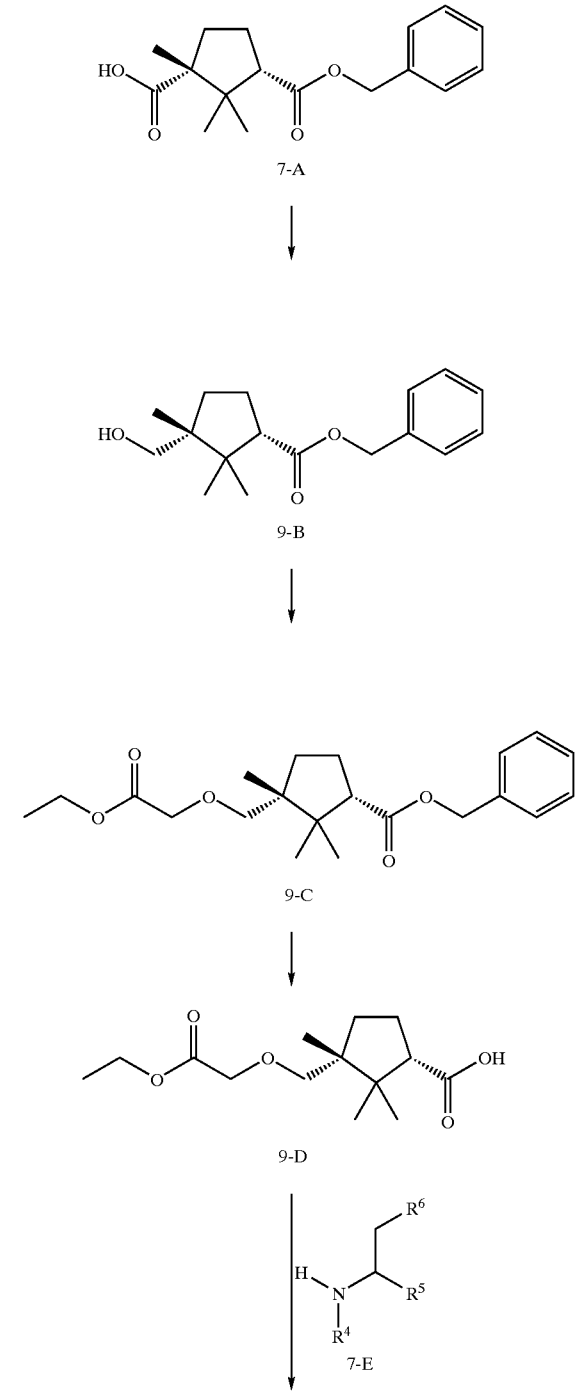

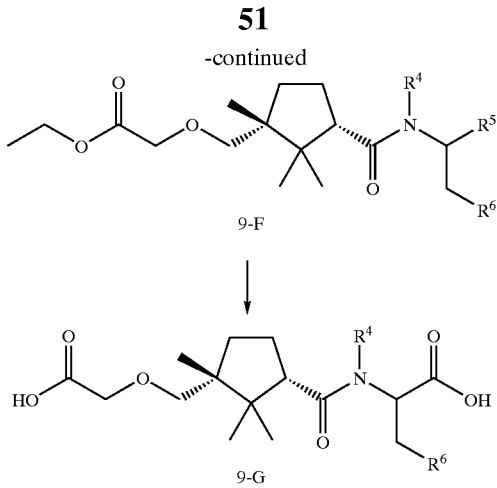

Preparation of Example 183

Scheme 9, 9-G: wherein R⁴=H, R⁶=4-[(2,6-dichlorobenzoyl)amino]phenyl Stereochemistry= (1S-cis)-L (1S-cis)-N-[[3-(carboxymethoxymethyl)-2,2,3-trimethylcyclopentyl]carbonyl]-4-[(2,6-dichlorobenzoyl)amino]-L-phenylalanine (Example 183) 7-A (1.15 g, 3.96 mmol) was dissolved in dry THF (5 mL). The reaction flask was immersed in a −15° C. bath (ethylene glycol/CO₂), then diborane-tetrahydrofuran (1M, 1 equiv, 3.96 mmol, 3.96 mL) was added slowly. The reaction solution was stirred at −15° C. under N₂ during the day, and was equilibrated to room temperature overnight. The reaction solution was treated with potassium carbonate (1.2 g) in H₂O (25 mL). The THF layer was separated and the aqueous phase was extracted with EtOAc (3×20 mL). The organic layers were combined, washed with saturated NaCl (20 mL) and dried (MgSO₄). Solvent was removed in vacuo from the mixture to yield 0.83 g (76%) of 9-B. The crude product was chromatographed, initially using $CH_2Cl_2$, as eluent followed by $CH_2Cl_2$\MeOH (5%) Recovered desired product 9-B (0.76 g, 69%) from column: ¹H NMR (CDCl₃) δ 0.80 (3H), 1.00 (3H), 1.11 (3H), 1.32–1.47 (1H), 1.62–1.91 (2H), 2.09–2.22 (1H), 2.86 (1H), 3.48–3.59 (2H), 5.08–5.18 (2H), 7.28–7.41 (5H).

A solution of benzyl ester 9-B (0.76 g, 2.75 mmol) in $CH_2Cl_2$ (10 mL) was treated at 0° C. and under N₂ with ethyl diazoacetate (5 equiv, 13.75 mmol, 1.4 mL) and a catalytic amount of HBF₄ (0.1 equiv, 0.03 mL). The reaction solution was a stirred under N₂ overnight while the bath temperature equilibrated to room temperature. Solvent was removed under reduced pressure to yield 1.8 g of product. Crude product was subjected to silica gel (35 mm×15.2 cm) flash column chromatography, eluting with 2%-10% EtOAc/hexanes, to provide 0.64 g (64%) of 9-C: ¹H NMR (CDCl₃) δ 0.81 (3H), 1.05 (3H), 1.12 (3H), 1.22–1.31 (3H), 1.32–1.43 (1H), 1.54–1.62 (2H), 1.65–1.92 (2H), 2.08–2.23 (1H), 2.85 (1H), 3.28 (1H), 3.47 (1H), 3.96–4.08 (2H), 4.14–4.25 (2H), 5.07–5.18 (2H), 7.28–7.40 (5H).

Benzyl ester 9-C (0.3 g, 0.83 mmol) was dissolved in absolute EtOH (10 mL). The solution was treated with a catalytic amount of 10% Pd/C (0.2 g) and hydrogenated at 20 psi for 1 h on a Parr hydrogenation apparatus. The suspension was filtered through a Celite cake and washed cake with EtOH. Solvent was removed from the filtrate under reduced pressure to yield 0.19 g (84%) of 9-D: ¹H NMR (CDCl₃) δ 0.90 (3H), 1.06 (3H), 1.16 (3H), 1.19–1.32 (3H), 1.33–1.45 (1H), 1.65–1.92 (2H), 2.03–2.18 (1H) 2.83 (1H), 3.29 (1H). 3.49 (1H), 3.95–4.11 (2H), 4 19 (2H).

Dissolved acid 9-D (0.18 g, 0.66 mmol), HOBT (1.2 equiv, 0.81 mmol, 0.11 g), DMAP (0.11 equiv, 0.074 mmol, 0.009 g), EDCl (1.2 equiv, 0.78 mmol, 0.15 g) and Et₃N (3.8 equiv, 2.5 mmol, 0.35 mL) in $CH_2Cl_2$ (10 mL) at 0° C. The reaction mixture was stirred for several minutes and then 7-E-1 (1.0 equiv, 0.69 mmol, 0.28 g) was added. The mixture was stirred overnight while the bath temperature equilibrated to room temperature. The reaction mixture was concentrated to dryness under reduced pressure. The residue was quenched with acidic H₂O (30 mL) and extracted with CHCl₃ (3×15 mL). The organic layers were combined, washed with saturated NaHCO₃ (30 mL), dried (MgSO₄) and solvent was removed under reduced pressure. Crude product was purified by silica gel (20 mm×22.9 cm) flash chromatography using 90% $CH_2Cl_2$/EtOAc as eluent.

Fractions containing the compound were combined and solvent was removed under reduced pressure. The product was dissolved in $CH_3CN:H_2O$, frozen and lyophilized to yield 0.18 g (44%) of 9-F (where R⁴=H, R⁵=CO₂CH₃ and R⁶=C₆H₄OCH₂C₆H₃Cl₂): ¹H NMR (CDCl₃) δ 0.82 (3H), 1.05 (3H), 1.12 (3H), 1.27 (2H), 1.31–1.43 (1H), 1.59–1.84 (2H), 2.05–2.21 (1H), 2.55 (1H), 3.03–3.23 (2H), 3.30 (1H), 3.47 (1H), 3.74 (3H), 3.93–4.09 (2H), 4.19 (2H), 4.90 (2H), 5.76 (1H), 7.11 (2H), 7.24–7.39 (3H), 7.47 (1H), 7.57 (2H); IR (mineral oil mull) 3292, 3193, 3123, 3064, 3033, 2951, 2922, 2870, 2855, 2854, 1748, 1657, 1656, 1606, 1579, 1562, 1537, 1515, 1461, 1431, 1414, 1376, 1348, 1324, 1271, 1207, 1196, 1153, 1129, 1023, 800, 781 cm⁻¹; MS (FAB) for $C_{31}H_{38}Cl_2N_2O_7$, m/z (relative intensity) 623 (([M+H]⁺, 49), 622 ([M+H]⁺, 29), 621 ([M+H]⁺, 71), 620 (M⁺, 71, 517 (12), 351 (16), 349 (22), 175 (16), 173 (26), 151 (27), 123 (100). Anal. Calcd for $C_{31}H_{38}Cl_2N_2O_7$: C, 59.91;H, 6.16; N, 4.51; Cl, 11.41; Found: C, 59.67;H, 6.09; N, 4.63; Cl, 11.50. Corrected for 0.40% H₂O found by Karl Fischer analysis.

To a solution of methyl ester 9-F (R⁴=H, R⁵=CO₂CH₃, R⁶=C₆H₄OCH₂C₆H₃Cl₂) (0.11 g, 0.18 mmol) in MeOH (5 mL) was added LIOH.H₂O (5 equiv, 0.88 mmol, 0.04 g) in H₂O (1 mL). The reaction solution was allowed to stir for about 2 hrs. The solvent was removed in vacuo. The residue was dissolved in H₂O (30 mL) and acidified with HCl. The resulting precipitate was filtered and washed with H₂O. The precipitate was dissolved in 50% $CH_3CN:H_2O$ (10 mL), was frozen and lyophilized to yield 0.083 g (80%) of Example 183 (9-G: where R⁴=H and R⁶=C₆H₄OCH₂C₆H₃Cl₂): ¹H NMR (MeOD) δ 0.79 (3H), 1.00 (3 H), 1.05 (3H), 1.23–1.41 (1H), 1.60–1.78 (2H) 1.91–2.05 (1H), 2.72 (1H), 2.98 (1H), 3.20 (1H), 3.46 (1H), 3.93–4.08 (2H), 4.66–4.78 (1H), 7.24 (2 H), 7.38–7.51 (3H), 7.57 (2H), 7.73 (1H); IR (mineral oil mull) 3270, 3193, 3123, 3056, 3034, 2954, 2928, 2854, 1731, 1657, 1607, 1562, 1537, 1516, 1461, 1459, 1432, 1414, 1376, 1326, 1272, 1220, 1195, 1126, 800, 781 cm⁻¹; MS (FAB) for $C_{28}H_{32}Cl_2N_2O_7$, m/z (relative intensity) 581 (([M+H]⁺, 51), 580 ([M+H]⁺, 29), 579 ([M+H]⁺, 76), 578 (M⁺, 8), 337 (12), 335 (18), 175 (19), 173 (29), 161 (18), 151 (18), 123 (100). Anal. Calcd for $C_{28}H_{32}Cl_2N_2O_7$: C, 58.04; H, 5.57; N, 4.84; Cl, 12.24; Found: C, 57.87; H, 5.44; N, 4.97; Cl, 12.29. Corrected for 2.17% H₂O found by Karl Fischer analysis.

Scheme 10

$R^{10-1}$ is defined as methyl or $CH_2-OCH_3$.

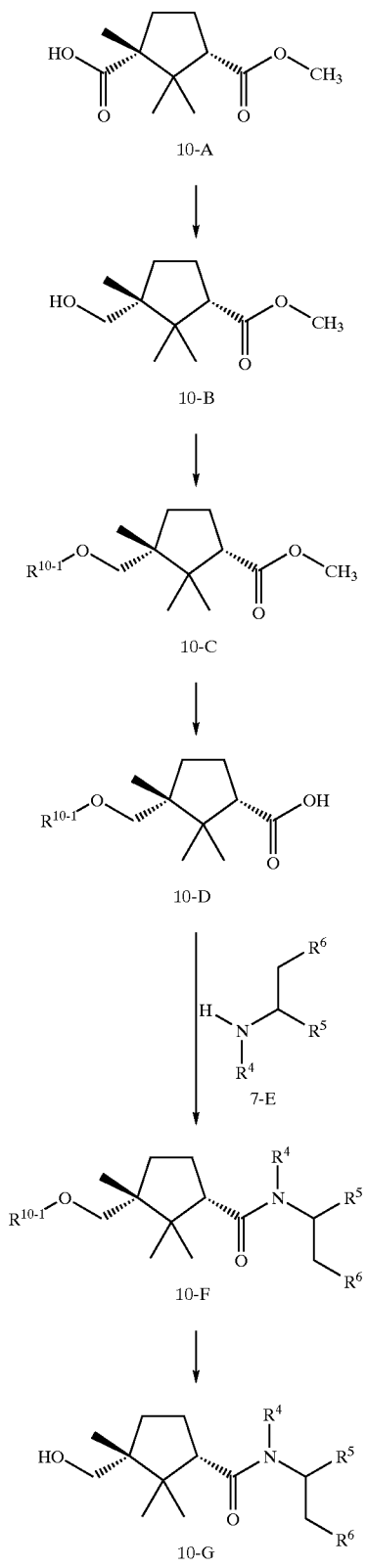

Preparation of Example 192

Scheme 10, 10-G: wherein $R^4$=H, $R^5$=$CO_2$H, $R^6$=4-[(2,6-dichlorophenyl)methoxy]phenyl
Stereochemistry=(1S-cis)-L (1S-cis)-O-[(2,6-Dichlorophenyl)methyl]-N-[(3-hydroxy-2,2,3-trimethylcyclopentyl)carbonyl]-L-tyrosine (Example 192).

Into a 100 mL oven dried round bottom flask was placed (1S-cis)-[3-carboxy-2,2,3trimethyl]cyclopentane carboxylic acid methyl ester (10-A) (5.0 g, 23 mmol, 1 equiv), followed by dry THF (20 mL). The reaction flask was immersed in a −15° C. bath (ethylene glycol/dry ice) and then boron trifluoride-tetrahydrofuran (1 equiv, 1 M, 23 mmol, 23 mL) was slowly added. [Note: observed mild evolution of $H_2$ gas]. The reaction solution was allowed to stir for 24 hrs under $N_2$. The solution was stirred in the −15° C. bath during the day, and the bath was permitted to reach room temperature overnight. Silica gel Thin-layer chromatography, using 1:1 hexanes/ethyl acetate as eluent, showed that the starting material was consumed. Consequently, the reaction solution was quenched with $H_2O$ (100 mL) and then treated with potassium carbonate (6 g). The THF phase was separated while the aqueous phase was extracted with EtOAc (3×80 mL). The organic phases were combined, washed with saturated NaCl (100 mL) and dried ($MgSO_4$). The solvent was removed via rotary evaporator and then by overnight hi vacuum conditions to yield 4.7 g of crude product. Crude product was subjected to a silica gel (35 mm×25.4 cm) flash chromatography column. Elution with 5% EtOAc/hexanes yielded 4.0 g (87%) of 10-B as a clear oil: $^1$H NMR ($CDCl_3$) δ 0.79 (3H), 0.99 (3H), 1.10 (3H), 1.32–1.43 (1H), 1.48 (H), 1.63–1.88 (2H), 2.04–2.15 (1H), 2.8 (1H), 3.52 (2 H), 3.66 (3H); IR (mineral oil mull) 3445, 2968, 2878, 1734, 1719, 1456, 1436, 1372, 1358, 1270, 1218, 1203, 1173, 1031, 1006 $cm^{-1}$; MS (FAB) for $C_{11}H_{20}O_3$, m/z (relative intensity) 202 ([M+2H]+, 11), 201 ([M+H]$^+$, 100), 200 ($M^+$, 0.9), 183 (11), 169 (8), 151 (8), 123 (29). Anal. for $C_{11}H_{20}O_3$: C, 65.97; H, 10.07; Found: C, 65.94; H, 9.91. Corrected for 0.85% $H_2O$ found by Karl Fischer analysis.

(1S-cis)-[3-hydroxymethyl-2,2,3-trimethyl]-cyclopentane carboxylic acid methyl ester 10B (1.5 g, 7.5 mmol) was dissolved in $CH_2Cl_2$ (35 mL). Cooled flask to 0° C., slowly added chloromethyl methyl ether (3.3 equiv, 25 mmol, 1.9 mL) and then added DIEA (5.87 mL, 4.5 equiv, 3.4 mmol). The bath temperature was allowed to equilibrate to room temperature while the reaction mixture was stirred for four days. Solvent was removed via a rotary evaporator. Crude product was dissolved in toluene, the insoluble precipitate was filtered and the concentrated filtrate was chromatographed on silica gel (35 mm×5.2 cm) flash chromatography using 2% EtOAc/hexanes as eluent to yield 1.37 g (75%) of 10-C (where $R^{10-1}$=methoxymethyl): $^1$H NMR ($CDCl_3$) δ 0.80 (3H), 1.02 (3H), 1.12 (3H), 1.34–1.45 (1H), 1.57 (H), 1.67–1.87 (2H), 2.07–2.18 (1H), 2.82 (1H), 3.31 (1H), 3.36 (3H), 3.45 (1H), 3.67 (3H), 4.56–4.61 (2H).

Compound 10-C (1.57 g, 6.4 mmol) was dissolved in THF (20 mL) and treated with $LiOH.H_2O$ (10 equiv, 64 mmol, 2.7 g) in $H_2O$ (30 mL); $H_2O_2$ (6 mL), $H_2O$ (16 mL) and MeOH (16 mL). The mixture was refluxed overnight. The solvent was removed in vacuo, crude residue was quenched with $H_2O$ (35 mL) and the pH was lowered to 5 with 10%, 6N or 12N hydrochloric acid. Extracted aqueous portion with EtOAc (3×20 mL) and then with $CHCl_3$ (3×20 mL). Organic layers were combined, dried ($MgSO_4$) and solvent removed on rotary evaporator.

Crude product was subjected to a silica gel (35 mm×15.2 cm) flash chromatography column using 800 hexanes/EtOAc as eluent to yield 1.1 g (75%) of 10-D (where $R^{10-1}$=methoxy methyl): $^1$H NMR (CDCl$_3$) δ 0.89 (3H), 1.03 (3H), 1.16 (3H), 1.36–1.46, 1.68–1.89, 2.04–2.18 (1H), 2.85 (1H), 3.32 (1H), 3.36 (3H), 3.47 (1H), 4.57–4.62 (2H).

Compound 10-D (0.83 g, 3.6 mmol), HOBT (1.13 equiv, 4.1 mmol, 0.55 g), DMAP (0.11 equiv, 0.4 mmol, 0.048 g), EDCl (1.1 equiv, 4.0 mmol, 0.76 g) and Et$_3$N (3.6 equiv, 13 mmol, 1.8 mL) were mixed in CH$_2$Cl$_2$ (30 mL) at 0° C. The reaction mixture was stirred for several minutes, and then added O-[(2,6-dichlorophenyl)methyl]-L-tyrosine methyl ester hydrochloride 7-E-2.HCl (wherein $R^4$=H, $R^5$=CO$_2$CH$_3$, $R^6$=4-[(2,6-dichlorophenyl)methoxy]phenyl) (1 equiv, 3.6 mmol, 1.4 g). The mixture was stirred overnight while bath temperature equilibrated to room temperature. Reaction mixture was concentrated to dryness under reduced pressure. The residue was quenched with acidic H$_2$O (70 mL), and extracted with CHCl$_3$ (3×35 mL). Organic layers were combined, washed with saturated NaHCO$_3$ (40 mL), dried (MgSO$_4$) and solvent was removed under reduced pressure. Crude product was subjected to a silica gel (35 mm×15.2 cm) flash chromatography column using 10% EtOAc/hexanes as eluent to yield 1.6 g (78%) of 10-F-1 (10-F (where $R^{10-1}$=methoxymethyl, $R^4$=H, $R^5$=CO$_2$CH$_3$ and $R^6$=4-[(2,6-dichlorophenyl)methoxy]phenyl-): $^1$H NMR (CDCl$_3$, 400 MHz) δ 0.82 (3H), 1.03 (3H), 1.11 (3H), 1.33–1.42 (1H), 1.61 (2H), 1.63–1.82 (2H), 2.08–2.21 (1H), 2.56 (1H), 3.03–3.16 (2H), 3.31 (1H), 3.36 (3H), 3.46 (1H), 3.75 (3H), 4.57–4.61 (2H), 4.85–4.93 (1H), 5.26 (2H), 5.72 (1H), 6.96 (2H), 8.6 (2H), 7.22–7.28 (1H), 7.37 (2H); IR (mineral oil mull) 2951, 2879, 1746, 1668, 1657, 1565, 1511, 1468, 1439, 1382, 1371, 1241, 1216, 1197, 1179, 1148, 1108, 1096, 1047, 1019, 780, 768 cm$^{-1}$; MS (FAB) for C$_{29}$H$_{37}$Cl$_2$N$_1$O$_6$, m/z (relative intensity) 568 (([M+H]$^+$, 69), 566 ([M+H]$^+$, 100), 565 (M$^+$, 12), 506 (41), 504 (61), 336 (41), 161 (40), 159 (62), 123 (83), 45 (53). Anal. Calcd for C$_{29}$H$_{37}$Cl$_2$N$_1$O$_6$: C, 61.48; H, 6.58; N, 2.47; Cl, 12.52; Found: C, 61.30; H, 6.55; N, 2.80; Cl, 12.57. Corrected for 0.11% H$_2$O found by Karl Fischer analysis.

Compound 10-F (0.74 g, 1.3 mmol) was dissolved in MeOH (30 mL) and treated with concentrated HCl (5 mL) and stirred at room temperature for 24 hrs. The solvent was removed in vacuo to yield a residue that was taken up in CHCl$_3$ and washed with saturated NaHCO$_3$. [Note: upon treatment with saturated NaHCO$_3$ a precipitate formed which was filtered and washed with CHCl$_3$.] Filtrate volume was reduced in vacuo and subjected to a silica gel (35 mm×16.5 cm) flash chromatography column using 50% hexanes/EtOAc as eluent. Fractions containing pure compound were combined and solvent was removed under reduced pressure. The residue was dissolved in 50% CH$_3$CN:H$_2$O (10 mL), frozen and lyophilized to yield 0.23 g (34%) of 10-G (where $R^4$=H, $R^5$=CO$_2$CH$_3$ and $R^6$=4-[(2,6-dichlorophenyl)methoxy]phenyl-: $^1$H NMR (CDCl$_{13}$, 400 MHz) δ 0.84 (3H), 1.00 (3H), 1.10 (3H), 1.37–1.48 (1H), 1.69–1.82 (2H), 2.09–2.21 (1H), 2.55 (1H), 3.02–3.18 (2H), 3.51–3.59 (2H), 3.75 (3H), 4.84–4.91 (1H), 5.26 (2H), 5.75 (1H), 6.96 (2H), 7.05 (2H), 7.22–7.29 (1H), 7.37 (2H); IR (mineral oil mull) 3428, 3322, 2923, 2870, 2854, 1743, 1654, 1565, 1511, 1466, 1439, 1377, 1298, 1278, 1240, 1197, 1179, 1018, 1003, 780, 768 cm$^{-1}$; MS (FAB) for C$_{27}$H$_{33}$Cl$_2$N$_1$O$_5$, m/z (relative intensity) 524 ([M+H]$^+$, 65), 523 ([M+H]$^+$, 41), 522 ([M+H]$^+$, 100), 521 (M$^+$, 19), 354 (21), 338 (21), 336 (29), 161 (21), 159 (34), 123 (38). Anal. Calcd for C$_{27}$H$_{33}$Cl$_2$N$_1$O$_5$: C, 62.07; H, 6.37; N, 2.68; Cl, 13.57; Found: C, 61.85; H, 6.27; N, 2.85; Cl, 13.50. Corrected for 0.44% H$_2$O found by Karl Fischer analysis.

Compound 10-G (0.19 g, 0.36 mmol) was dissolved in CH$_3$OH (4 mL) and treated with LiOH.H$_2$O (10 equiv, 0.15 g, 3.6 mmol) in H$_2$O (4 mL). Additional MeOH (2 mL) was added to ensure solubility. The solution was stirred for 2 h at room temperature. The solvent was removed under reduced pressure. The residue was dissolved in warm H$_2$O (20 mL) (Note: room temperature H$_2$O caused aqueous solution to gel). The pH of the solution was lowered to 2 with 1.0 N HCl and the resulting precipitate was filtered, washed with H$_2$O and dried to yield 0.17 g (93%) of Example 192 (10-G: where $R^4$=H, $R^5$=CO$_2$H and $R^6$=4-[(2,6-dichlorophenyl)methoxy]phenyl-): unable to determine mp due to compound shrinkage at 80° C.; $^1$H NMR (CDCl$_3$) δ 0.81 (3H), 0.97 (3H), 1.06 (3H), 1.35–1.48 (1H), 1.65–1.88 (2H), 2.03–2.18 (1H), 2.55 (1H), 3.04–3.27 (2H), 3.48–3.58 (2H), 4.81–4.89 (1H), 5.24 (2H), 5.85 (1H), 6.96 (2H), 7.12 (2H), 7.19–7.29 (1H), 7.32–7.38 (2H); IR (mineral oil mull) 3421, 3332, 3058, 3030, 2954, 2920, 2871, 2855, 1729, 1653, 1612, 1585, 1565, 1511, 1466, 1439, 1377, 1299, 1241, 1196, 1179, 1018, 1003, 779, 769 cm$^{-1}$; MS (FAB) for C$_{26}$H$_{31}$Cl$_2$N$_1$O$_5$ m/z (relative intensity) 510 ([M+H]$^+$, 66), 509 ([M+H]$^+$, 37), 508 ([M+H]$^+$, 100), 507 (M$^+$, 15), 340 (12), 324 (15), 322 (22), 161 (23), 159 (36), 123 (45). Anal. Calcd for C$_{26}$H$_{31}$Cl$_2$N$_1$O$_5$: C, 61.42; H, 6.15; N, 2.76; Cl, 13.95; Found: C, 61.33; H, 6.16; N, 2.93; Cl, 13.74. Corrected for 1.61% H$_2$O found by Karl Fischer analysis.

Preparation of Example 198

Scheme 10, 10-F=wherein $R^{10-1}$=methyl, $R^4$=H, $R^5$=CO$_2$H, $R^6$=4-[(2,6-dichlorophenyl)methoxy] phenyl Stereochemistry=(1S-cis)-L (1S-cis)-O-[(2,6-Dichlorophenyl)methyl]-N-[(3-methoxymethyl-2,2,3-trimethylcyclopentyl)carbonyl]-L-tyrosine (Example 198).

Alcohol 10-B (1.0 g, 4.8 mmol), in Et$_2$O (20 mL), was treated with boron trifluoride dimethyl etherate (0.1 equiv, 0.48 mmol, 0.06 mL) and an excess amount of CH$_2$N$_2$Et$_2$O. The reaction mixture was stirred overnight. The mixture was filtered and solvent was removed on rotary evaporator. Crude product was subjected to a silica gel (35 mm×16.5 cm) flash chromatography column using 1% EtOAc/pentane as eluent to yield 0.69 g (67%) of 10C (where $R^{10-1}$=methyl): $^1$H NMR (CDCl$_3$) δ 0.79 (3H), 1.00 (3H), 1.10 (3H), 1.32–1.43 (1H), 1.60–1.89 (2H) 2.04–2.20 (1H), 2.80 (1H), 3.16 (1H), 3.28 (1H), 3.31 (3H), 3.68 (3H).

Ester 10-C (0.37 g, 1.7 mmol) was dissolved in THF (40 mL) and treated with LiOH.H$_2$O (10 equiv, 17 mmol, 0.71 g) in H$_2$O (20 mL), MeOH (10 mL) and H$_2$O$_2$ (10 mL). The mixture was heated at reflux for about 8 h. Solvent was removed via a rotary evaporator. Dissolved residue in H$_2$O (50 mL), lowered pH to 5 with hydrochloric acid, extracted aqueous portion with EtOAc (3×25 mL) followed by CHCl$_3$ (3×25 mL). Organic extracts were combined, dried (MgSO$_4$), and solvent was removed under reduced pressure to yield 0.44 g of 10-D (wherein $R^{10-1}$=Me): $^1$H NMR (CDCl$_3$) δ 0.86 (3H), 1.00 (3H), 1.14 (3H), 1.34–1.44 (1H), 1.62–1.89 (2H), 2.01–2.15 (1H), 2.83 (1H), 3.16 (1H), 3.29 (1H), 3.30 (3H), Compound 10-D (0.25 g, 1.2 mmol), HOBT (1.13 equiv, 1.41 mmol, 0.19 g), DMAP (0.11 equiv, 0.14 mmol, 0.017 g), EDC (1.1 equiv, 1.37 mmol, 0.25 g) and $Et_3N$ (3.6 equiv, 4.49 mmol, 0.6 mL) were mixed in $CH_2Cl_2$ (10 mL) at 0° C. Stirred the reaction mixture for several minutes then added 7-E-2.HCl (0.8 equiv, 1.0 mmol, 0.4 g). The mixture was stirred overnight while the bath temperature equilibrated to room temperature. Concentrated reaction mixture to dryness under reduced pressure. Residue was treated with acidic $H_2O$ (30 mL) and extracted with $CHCl_3$ (3×15 mL). Combined organic layers, washed with saturated $NaHCO_3$ (20 mL), dried ($MgSO_4$) and solvent was removed under reduced pressure. Crude product was purified by silica gel (20mm×16.5 cm) flash chromatography using 10%–15% EtOAc/hexanes as eluent. Fractions containing the compound were combined and solvent was removed under reduced pressure. The residue was dissolved in 50% $CH_2CN:H_2O$ (50 mL), frozen and lyophilized to yield 0.24 g (45%) of 10-F (where $R^{10-1}$=methyl, $R^4$=H, $R^5$=$CO_2CH_3$ and $R^6$=4-[(2,6-dichlorophenyl)methoxy]phenyl-): $^1$H NMR ($CDCl_3$) δ 0.79 (3H), 0.99 (3H), 1.09 (3H), 1.32–1.43 (1H), 1.61 (2H), 1.65–1.85 (2H), 2.08–2.23 (1H), 2.53 (1H), 3.01–3.18 (2H), 3.16 (1H), 3.28 (1H), 3.30 (3H), 3.74 (3H), 4.83–4.91 (1H), 5.25 (2H), 5.74 (1H), 6.96 (2H). 7.05 (2H), 7.23–7.29 (1H), 7.35–7.40 (2H): IR (mineral oil mull) 3317, 2956, 2924, 2871, 2857, 2855, 1745, 1652, 1612, 1565, 1511, 1466, 1439, 1378, 1298, 1278, 1240, 1197, 1178, 1106, 1096, 1017, 1000, 779, 768 cm$^{-1}$; MS (FAB) for $C_{28}H_{35}Cl_2N_1O_5$, m/z (relative intensity) 538 (([M +H]$^+$, 65), 537 ([M +H]$^+$, 40), 536 ([M+H]$^+$, 100), 535 (M$^+$, 16), 338 (16), 336 (24), 161 (18), 159 (28), 123 (69). Anal. Calcd for $C_{28}H_{35}Cl_2N_2O_5$ n$H_2O$: C, 62.69; H, 6.58; N, 2.61; Cl, 13.22; Found: C, 62.44; H, 6.35; N, 2.88; Cl, 13.11. Corrected for 0.37% $H_2O$ found by Karl Fischer analysis.

Ester 10-F (0.27 g, 0.5 mmol) was treated with LiOH.$H_2O$ (10 equiv, 5.0 mmol, 0.21 g) in $H_2O$ (8 mL). The reaction mixture was stirred for 1 h. THF (3 mL) was added to complete dissolution of starting material and MeOH (3 mL) was added to convert reaction mixture to homogeneous solution. The volume was reduced under vacuum. $H_2O$ (40 mL) was added and the mixture was acidified with HCl. The resulting precipitate was filtered, washed with $H_2O$, and dried under house vacuum to yield 0.26 g (99%) of Example 198 (10-F: where $R^{10-1}$=methyl; $R^4$=H; $R^5$=$CO_2H$ and $R^6$=4-[(2,6-dichlorophenyl)methoxy]phenyl stereochemistry=(1S-cis)-L): $^1$H NMR ($CDCl_3$) δ 0.77 (3H), 0.98 (3H), 1.05 (3H), 1.31–1.42 (1H), 1.61–1.85 (2H), 2.01–2.16 (1H), 2.53 (1H), 3.07–3.28 (2H), 3.15 (1H), 3.27 (1H), 3.29 (3H), 4.79–4.87 (1H), 5.24 (2H), 5.77 (1H), 6.97 (2H), 7.12 (2H), 7.21–7.29 (1H), 7.32–7.39 (2H); IR (mineral oil mull) 3424, 3335, 3032, 2955, 2924, 2855, 1734, 1644, 1612, 1586, 1565, 1512, 1466, 1439, 1377, 1299, 1241, 1197, 1179, 1107, 1096, 1018, 873, 779, 769 cm$^{-1}$; MS (FAB) for $C_{27}H_{33}Cl_2N_1O_5$, m/z (relative intensity) 524 (([M+H]$^+$, 62), 523 ([M+H]$^+$, 36), 522 ([M+H]$^+$, 96), 521 (M$^+$, 13), 324 (14), 322 (22), 161 (31), 159 (42), 123 (100). Anal. Calcd for $C_{27}H_{33}Cl_{12}N_1O_5$n$H_2O$: C, 62.07; H, 6.37; N, 2.68; Cl, 13.57; Found: C, 62.04; H, 6.24; N, 2.90; Cl, 13.91. Corrected for 2.18% $H_2O$ found by Karl Fischer analysis.

Preparation of Example 203

Scheme 10, 10-F; where $R^{10-1}$=methoxymethyl; $R^4$=H; $R^5$=$CO_2H$ and $R^6$=4-[(2,6-Dichlorophenyl) methoxy]phenyl-, Stereochemistry=(1S-cis)-L (1S-cis)-O-[(2,6-Dichlorophenyl)methyl]-N-[(3-methoxymethoxymethyl-2,2,3-trimethylcyclopentyl) carbonyl]-L-tyrosine (Example 203)

Compound 10-F-1 (10-F: (where $R^{10-1}$=methoxymethyl, $R^4$=H, $R^5$=$CO_2CH_3$ and $R^6$=4-[(2,6-dichlorophenyl)methoxy]phenyl-) (0.25 g, 0.44 mmol) was dissolved in MeOH (3 mL). Treated the reaction solution with LiOH.$H_2O$ (10 equiv, 4.4 mmol, 0.18 g) in $H_2O$ (5 mL). Additional MeOH (2 mL) was added to ensure solubility. [Note: reaction mixture turned clear within 1 hour of reaction time]. Solution was allowed to stir overnight at room temperature under $N_2$. Solvent volume was reduced on a rotary evaporator, the remaining material was diluted with $H_2O$ (10 mL) and acidified with hydrochloric acid. The resulting precipitate was filtered, washed with $H_2O$ and dried under house vacuum to yield 0.23 g (95%) of Example 203. mp: unable to determine due to compound shrinkage at 60° C.; $^1$H NMR ($CDCl_3$) δ 0.79 (3H), 1.01 (3H), 1.07 (3H), 1.32–1.46 (1H), 1.62–1.84 (2H), 2.01–2.18 (1H), 2.55 (1H), 3.02–3.24 (2H), 3.30 (1H), 3.35 (3H), 3.45 (1H), 4.55–4.61 (2H), 4.81–4.89 (1H), 5.24 (2H), 5.76 (1H), 6.97 (2H), 7.12 (2H), 7.18–7.27 (1H), 7.31–7.37 (2H); IR (mineral oil mull) 2930, 2872, 2855, 1736, 1638, 1612, 1511, 1466, 1439, 1377, 1241, 1196, 1179, 1147, 1108, 1045, 1020 cm$^{-1}$; MS (FAB) for $C_{28}H_{35}Cl_2N_1O_6$n$H_2O$, m/z (relative intensity) 554 (([M+H]$^+$, 67), 552 ([M+H]$^+$, 100), 551 (M$^+$, 16), 492 (38), 490 (56), 322 (33), 161 (40), 159 (64), 123 (73), 45 (61). Anal. Calcd for $C_{28}H_{35}Cl_2N_1O_6$: C, 60.87; H, 6.39; N, 2.54; Cl, 12.83; Found: C, 60.73; H, 6.41; N, 2.69; Cl, 12.86. Corrected for 0.11% $H_2O$ found by Karl Fischer analysis.

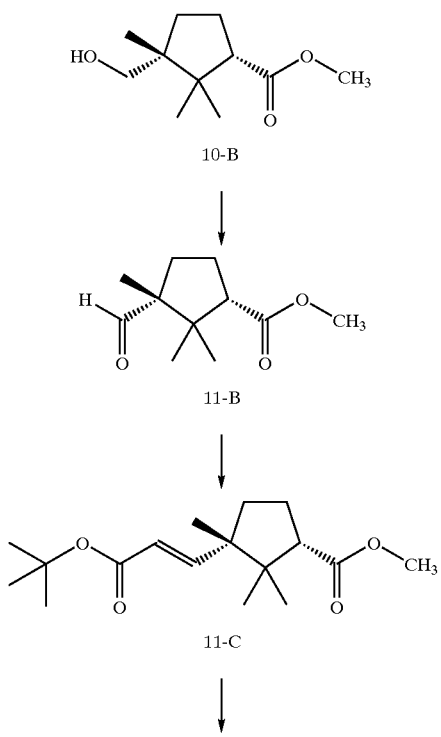

Scheme 11

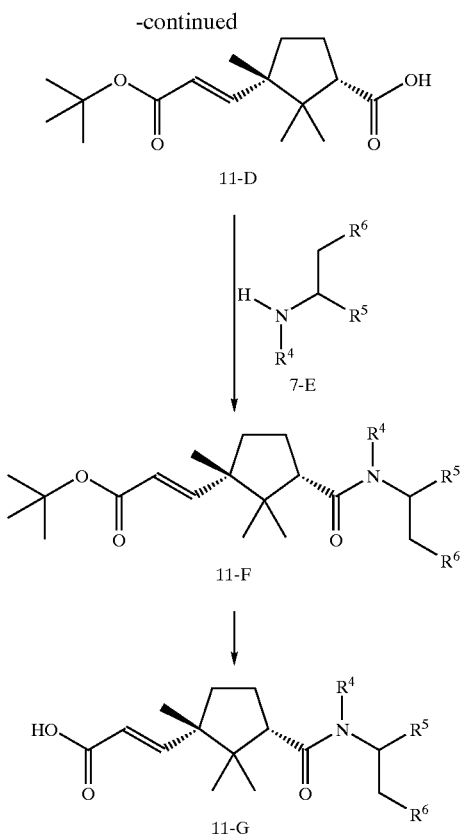

Preparation 11-B

Scheme 11, 11-B Stereochemistry=1S-cis (1S-cis) 3-Formyl-2,2,3-trimethylcyclopentanecarboxylic acid methyl ester (11-B) ($C_{11}H_{20}O_3$)

To a solution of 10-B (2.57 g, 12.8 mmol) in methylene chloride (50 mL) is added a mixture of pyridinium chlorochromate (3.05 g, 14.15 mmol), magnesium sulfate (4 g, 33 mmol), and Celite. After overnight stirring, the mixture is eluted through a short column of silica gel (80 g) using methylene chloride (500 mL) as the eluant. Evaporation in vacuo gives 11-B as a colorless liquid (2.09 g, 82% yield).

$^1$H NMR(CDCl$_3$) δ 9.65(1H), 3.67(3H), 2.81(1H), 2.40 (1H), 2.23 (1H), 1.94(1H), 1.42(1H), 1.16(3H), 1.05 (3H), 0.88 (3H).

Preparation 11-C

Scheme 11, 11-C Stereochemistry=1S-cis, (E)

(1S-cis)-3-[2-[(1,1-dimethylethyoxy)carbonyl]ethenyl]-2,2,3-trimethylcyclopentanecarboxylic acid methyl ester (11-C) ($C_{17}H_{28}O_4$)

To a dry N$_2$ flushed 100 mL flask is added t-butyl diethyl phosphonoacetate (5 mL, 21.3 mmol) and THF (dry, 20 mL). The flask is immersed in an ice water bath and, five minutes later, NaH/oil (60% NaH, 0.5 g, 12.5 mmol) is added in portions. After thirty minutes, 11-B (2.08 g, 10.5 mmol) is mixed with THF (dry, 15 mL) and added via syringe over a five minute period. Four hours later, the still cold solution is diluted with toluene (200 mL), shaken with ice water (4×100 mL), and the organic layer evaporated to dryness in vacuo, giving a colorless oil which is chromatographed on silica gel (80 g) using a gradient from 0 to 4% ethylacetate/hexane. A colorless oil 11-C is obtained (1.99 g, 63% yield).

$^1$H NMR(CDCl$_3$) δ 6.92 (1H), 5.68 (1H), 3.67 (3H), 2.84 (1H), 2.23 (1H), 1.99 (1H), 1.90 (1H), 1.49 (1H), 1.48 (9H), 1.06 (3H), 1.01 (3H), 0.71 (3H); IR (nujol) 1728, 1712, 1651, 1438, 1358, 1316, 1288, 1270, 1228, 1220,1191, 1171, 1151, 1132, 1001 cm$^{-1}$; MS (FAB) m/z (rel. intensity) 297 (M+H, 44), 297 (44), 242 (12), 241 (87), 224 (14), 223 (99), 195 (14), 191 (14), 135 (12), 57 (34), 41 (12); HRMS (FAB) calcd for $C_{17}H_{28}O_4$ +H1 297.2065, found 297.2067; Anal. Calcd for $C_{17}H_{28}O_4$: C, 68.89; H, 9.52; N; Found: C, 69.03; H, 9.18.

Preparation 11-D

Scheme 11, 11-D Stereochemistry=1S-cis, (E)

(1S-cis)-3-[2-[(1,1-dimethylethoxy)carbonyl]ethenyl]-2,2,3-trimethylcyclopentanecarboxylic acid (11-D) ($C_{16}H_{26}O_4$)

A solution of LiOH.H$_2$O (0.65 g, 15.4 mmol) in H$_2$O (15 mL) and aqueous H$_2$O$_2$ (5 mL, 30%) is added to a solution of 11-C (1.52 g, 5.13 mmol) in methanol (30 mL). After stirring for two days, the mixture is diluted with water (100 mL) and evaporated in vacuo until all of the methanol is gone. The aqueous remainder is then shaken with diethyl ether (3×40 mL) and then cooled in an ice water bath and brought to pH 5 using 1N aq. HCl. The resultant white precipitate 11-D is isolated by suction filtration (0.385 g, 26% yield)

$^1$H NMR(CDCl$_3$): δ 6.94(1H), 5.69(1H), 2.88(1H), 2.27–1.84(3H), 1.53(1H), 1.49(9H), 1.11(3H), 1.02(3H) 0.81(3H); IR (nujol) 2729, 2669, 1707, 1647, 1418, 1393, 1316, 1305, 1242, 1154, 999, 976, 960, 944, 856 cm$^{-1}$; MS (FAB) m/z (rel. intensity) 283 (M+H, 34), 566 (13), 283 (34), 228 (13), 227 (99), 210 (13), 209 (96), 191 (14), 181 (14), 57 (51), 41 (16); Anal. Calcd for $C_{16}H_{26}O_4$: C, 68.06; H, 9.28; Found: C, 67.84; H, 9.10.

Preparation 11-F-1

Scheme 11, 11-F: wherein R$^4$=H, R$^5$=CO$_2$CH$_3$ R$^6$= 4-[(2,6-Dichlorobenzoyl)amino]phenyl Stereochemistry=[1S-[1α,3α(E)]]-L

[1S-[1α,3α(E)]]-N-[[3-[2-[(1,1-dimethylethoxy) carbonyl]ethenyl]-2,2,3-trimethylcyclopentyl]carbonyl]-4-[(2,6-dichlorobenzoyl)amino]-L-phenylalanine methyl ester (11-F-1) ($C_{33}H_{38}Cl_2N_2O_6$)

A solution of 11-D (0.45 g, 1.59 mmol) in methylene chloride (15 mL) is cooled in an ice water bath. To this stirred solution were added N,N-diisopropylethyl amine (2 mL, 11.48 mmol), EDC (0.335 g, 1.75 mmol), HOBt (0.25 g, 1.85 mmol), and 4-N,N-dimethylaminopyridine (0.02 g, 0.16 mmol), followed thirty minutes later by the 4-[(2,6-dichlorobenzoyl)amino]-L-phenylalanine methyl ester hydrochloride 7-E-1.HCl (7-E: R$^4$=H, R$^5$=CO$_2$CH$_3$, R$^6$=4-[(2,6-Dichlorobenzoyl)amino]-phenyl) (0.67 g, 1.66 mmol). After two days, the reaction mixture is evaporated to dryness, mixed with toluene (200 mL), and shaken with cold 0.5N aq. HCl (50 mL) followed by water (4×50 mL). The organic layer is then evaporated to dryness in vacuo to give an off-white solid which is recrystallized from ethyl acetate to give a white solid (11-F-1) (0.59 g, 58% yield).

$^1$H NMR(CDCl$_3$) δ 7.84(1H), 7.56(2H), 7.35–7.25(3H), 7.08(2H), 6.90(1H), 5.77(1H), 5.65(1H), 4.87(1H), 3.73 (3H), 3.12(2H), 2.59(1H), 2.21(1H), 2.05(1H), 1.85(1H), 1.49(1H), 1.47(9H), 1.03(3H), 0.99(3H), 0.69(3H); MS(ES+) m/z 631.

Preparation 11-G-1

Scheme 11, 11-G: wherein $R^4$=H, $R^5$=$CO_2CH_3$ $R^6$= 4-[(2,6-Dichlorobenzoyl)amino]-phenyl
Stereochemistry=[1S-[1α,3α(E)]]

[1S-[1α,3α(E)]]-N-[[3-(2-Carboxyethenyl)-2,2,3-trimethylcyclopentyl]carbonyl]-4-[(2,6-dichlorobenzoyl)amino]-L-phenylalanine methyl ester (11-G-1) ($C_{29}H_{30}Cl_2N_2O_6$)

A solution of 11-F-1 (0.5 g, 0.8 mmol) in trifluoroacetic acid (3 mL) is stirred overnight under nitrogen. The solution is then evaporated to dryness in vacuo, diluted with toluene (50 mL) and evaporated to dryness again, giving 11-G-1 as an oil (0.45 g, 97% yield).

$^1$H NMR(300 MHz, DMSO-$d_6$) 10.75(1H), 10.60(1H), 7.96(1H), 7.64–7.44(4H), 7.23–7.14(3H), 6.88(1H), 5.63 (1H), 4.9 (1H), 4.8 (1H), 4.50 (1H), 3.58 (3H), 3.03–2.70 (2H), 2.50(1H), 2.1–1.2(4H), 0.92(3H), 0.83 (3H), 0. 55 (3H).

Preparation of Example 182

Scheme 11, 11-G: wherein $R^4$=H, $R^5$=$CO_2H$ $R^6$=4-[(2,6-Dichlorobenzoyl) amino]-phenyl
Stereochemistry=[1S-[1α,3α(E)]]

[1S-[1α,3α(E)]]-N-[[3-(2-Carboxyethenyl)-2,2,3-trimethylcyclopentyl]carbonyl]-4-[(2,6-dichlorobenzoyl)amino]-L-phenylalanine disodium salt (Example 182) ($C_{28}H_{28}Cl_2Na_2N_2O_6$)

To a solution 11-G-1 (0.45 g, 0.78 mmol) in methanol (5 mL), in a flask cooled in an ice water bath, is added a solution of LiOH.$H_2O$ (0.127 g, 3 mmol) in $H_2O$ (5 mL). After two days, the mixture is diluted with water (50 mL), evaporated in vacuo until the methanol is gone and then cooled to $-10°$ C. and brought to pH 2 using 1N aq. HCl. The resultant white precipitate is isolated by suction filtration to give a white solid which is stirred with saturated aqueous $NaHCO_3$(2 mL) and then transferred to a C-18 reversed phase HPLC column and eluted with a gradient from 0.01%aq $NaHCO_3$ to 10%acetonitrile/0.01%aq $NaHCO_3$. Evaporation is accomplished in vacuo to give Example 182 as a white solid (0.25 g, 51% yield).

$^1$H NMR(300 MHz, DMSO-$d_6$) δ 7.51–7.42(5H), 7.06 (2H), 6.39(1H), 5.49(1H), 4.10(1H), 2.99(1H), 2.86(1H), 2.56(1H), 1.85(2H), 1.61(1H), 1.29(1H), 0.90(3H), 0.85 (3H), 0.51(3H); IR (nujol) 3393, 3257, 3124, 3035, 1654, 1604, 1562, 1544, 1515, 1431, 1398, 1325, 799, 778, 722cm$^{-1}$; MS (FAB) m/z (rel. intensity) 605 (M+H, 44), 629 (5), 627 (14), 608 (8), 607 (30), 606 (14), 605 (44), 585 (14), 583 (21), 73 (45), 23 (99); KF Water: 7.09%.

Scheme 12

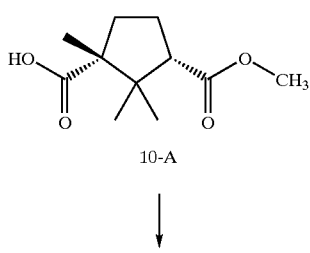

10-A

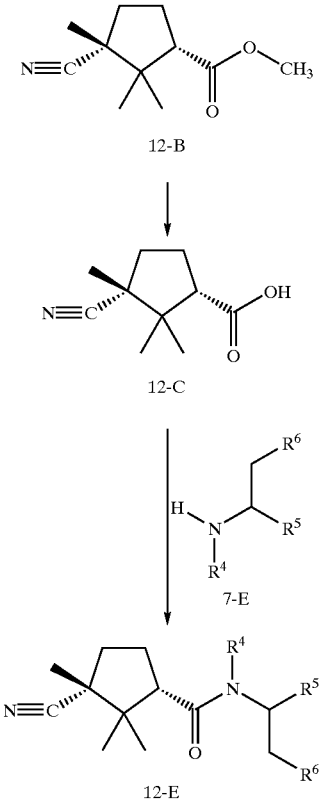

Preparation of Example 184

Scheme 12, 12-E: wherein $R^4$=H, $R^5$=$CO_2H$, $R^6$=4-[(2,6-Dichlorobenzoyl)amino]phenyl
Stereochemistry=(1S-cis)-L (1S-cis)-N-[[3-Cyano-2,2,3-trimethylcyclopentyl]carbonyl]-4-[(2,6-dichlorobenzoyl)amino]-L-phenylalanine Ester 10-A (5.0 g, 23.3 mmol) was dissolved in dry pyridine (100 mL). At 0° C., the reaction solution was treated with methanesulfonyl chloride (MsCl) (1 equiv, 23.3 mmol, 1.8 mL). The mixture was stirred for two days, while the bath temperature equilibrated to room temperature. The reaction mixture was saturated with ammonia (NH$_3$) gas. Excess NH$_3$ was removed via a rotary evaporator. The reaction mixture was treated with MsCl (10 equiv. 18 mL, 0.23 mol) and allowed to stir overnight. Solvent was removed under reduced pressure and resulting crude material was purified by a silica gel (35 mm×15.2 cm) flash column chromatography using 90% hexanes:EtOAc as eluent to yield 3.5 g of 12-B: $^1$H NMR (CDCl$_3$) δ 1.08 (3H), 1.19 (3H), 1.32 (3H), 1.73–2.01 (2H), 2.25–2.41 (2H), 2.71 (1H), 3.70 (3H).

Ester 12-B (0.7 g, 3.6 mmol) was dissolved in THF (20 mL) and treated with LiO.$H_2O$ (10 equiv, 1.5 g, 35.8 mmol) in $H_2O$ (20 mL) and MeOH (10 mL). After 2 h, the solvent was removed in vacuo. The residue was dissolved in acidic $H_2O$ (50 mL), for example 1N HCl, 10%$H_2SO_4$, or 1N AcOH, and was extracted with CHCl$_3$ (3×20 mL) to yield, upon usual work-up, 0.6 g (92%) of 12-C: $^1$H NMR (CDCl$_3$) δ 1.17 (3H), 1.25 (3H), 1.34 (3H), 1.77–2.00 (2H), 2.19–2.41 (2H), 2.69–2.81 (1H).

Acid 12-C (0.6 g, 3.3 mmol), HOBT (1.13 equiv, 0.5 g), DMAP (0.11 equiv, 0.04 g), EDC (1.1 equiv, 0.7 g,), Et$_3$N (3.6 equiv, 1.6 mL) and CH₂Cl₂ (20 mL) were combined and the reaction was stirred for a couple of minutes. Then 7-E-1.HCl (0.75 equiv, 1.0 g) was added and the reaction mixture was stirred overnight at room temperature. The solvent was removed under reduced pressure and the residue was triturated with THF. The precipitate was filtered, dissolved in a mixture of CH₃CN:H₂O, frozen and lyophilized to yield 12-E (where $R^4$=H, $R^5$=CO₂CH3 and $R^6$=4-[(2,6-dichlorobenzoyl)amino]phenyl): mp 170–174° C.; ¹H NMR (MeOD) δ 1.01 (3H), 1.17 (3H), 1.32 (3H), 1.72–1.87 (2H), 2.02–2.32 (2H), 2.67 (1H), 2.97 (1H), 3.18 (1H), 3.71 (3H), 4.73 (1H), 7.22 (2H), 7.38–7.50 (3H), 7.59 (2H); IR (mineral oil mull) 3282, 3252, 3314, 3192, 3125, 3075, 2954, 2925, 2870, 2855, 2235, 1750, 1738, 1653, 1610, 1562, 1541, 1516, 1458, 1431, 1415, 1379, 1332, 1274, 1260, 1243, 1231, 1214, 1195, 799 cm⁻¹; MS (FAB) for $C_{27}H_{29}Cl_2N_3O_4$, m/z (relative intensity) 532 ([M+H]⁺, 68), mp: unable to determine due to compound shrinkage at 50° C.; ¹H NMR (MeOD) δ 1.02 (3H), 1.18 (3H), 1.31 (3H), 1.72–1.87 (2H), 2.01–2.33 (2H), 2.69 (1H), 2.97 (1H), 3.23 (1H), 4.68–4.78 (1H), 7.24 (2H), 7.38–7.49 (3H), 7.58 (2H), 7.96 (1H); IR (mineral oil mull) 3338, 3291, 3260, 3200, 3132, 3079, 3039, 2954, 2914, 2854, 2253, 1746, 1672, 1657, 1611, 1579, 1560, 1544, 1516, 1466, 1457, 1431, 1416, 1397, 1379, 1328, 1282, 1271, 1222, 1210, 1196, 1125, 812, 782, 800 cm⁻¹; MS (FAB) for $C_{26}H_{27}Cl_2N_3O_4$, m/z (relative intensity) 518 ([M+H]⁺, 68), 517 ([M+H]⁺, 35), 516 ([M+H]⁺, 100), 515 (M⁺, 7), 337 (16), 335 (24), 175 (18), 173 (27), 136 (23), 109 (12). Anal. Calcd for $C_{26}H_{27}Cl_2N_3O_4 \cdot nH_2O$: C, 60.47; H, 5.27; N, 8.14; Cl, 13.73; Found: C, 60.33; H, 5.25; N, 8.03; Cl, 13.62. Corrected for 4.58% H₂O found by Karl Fischer analysis Scheme 13

Examples 58, 92 and 93

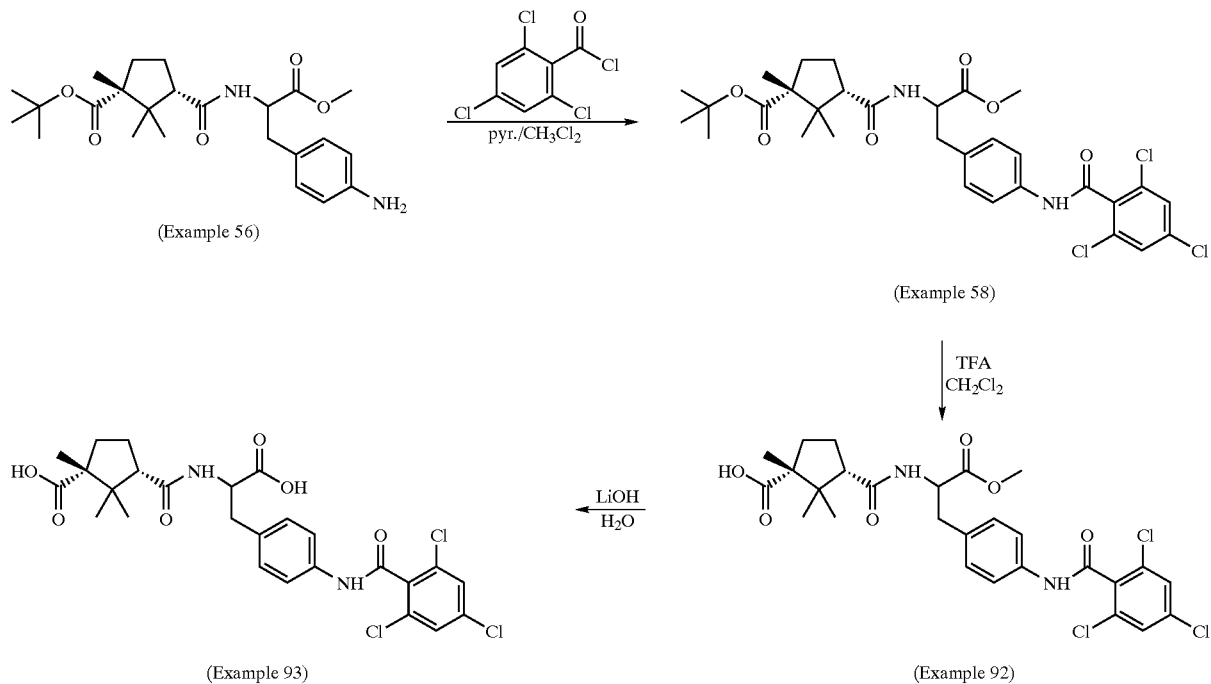

(Example 56)

(Example 58)

(Example 93)

(Example 92)

531 ([M+H]⁺, 35), 530 ([M+H]⁺, 100), 529 (M⁺, 7), 351 (26), 349 (40), 175 (21), 173 (33), 136 (35), 109 (20). Anal. Calcd for $C_{27}H_{29}Cl_2N_3O_4 \cdot nH_2O$: C, 61.14; H, 5.51; N, 7.92; Cl, 13.37; Found: C, 61.32: H. 5.53; N, 7.94; Cl, 13.04. Corrected for 0.66% H₂O found by Karl Fischer analysis.

To a solution of the obtained 12-E (1.0 g, 1.9 mmol), in MeOH (25 mL) was added LiOH.H₂O (5 equiv, 9.4 mmol, 0.4 g) in H₂O (10 mL). The reaction solution was allowed to stir for 4 h. The reaction solution was reduced in vacuo to dryness. The residue was treated with n acidic H₂O (25 mL). The resulting precipitate was filtered and subjected to silica gel (35 mm×15.2 cm) flash chromatography column using CH₃CN spiked with 0.1% acetic acid as an eluent. Fractions containing compound were combined and solvent was removed under reduced pressure. The residue was then dissolved in CH₃CN:H₂O, frozen and lyophilized to yield 0.62 g (63%) of Example 184 (12-E: where $R^4$=H, $R^5$=CO₂H and $R^6$=4-[(2,6-dichlorobenzoyl)amino]phenyl):

The Intermediate amine according to Example 56 (619 mg, 1.43 mmol) was dissolved in CH₂Cl₂ (5 mL) containing pyridine (0.3 mL, 3.58 mmol). To this solution 2,4,6-trichlorobenzoyl chloride (246 mg, 1.58 mmol) was added and the solution stirred at RT for 6 h. The reaction was acidified with 1 N HCl (20 mL) and extracted with CH₂Cl₂ (3×20 mL). The combined organics were dried (Na₂SO₄), filtered, and the solvent removed in vacuo. The residue was chromatographed (SiO₂, gradient elution: 100% hexanes→50% EtOAc/hexanes) to provide Example 58 (866 mg, 95%) as a colorless foam: ¹H NMR (300 MHz, CDCl₃), δ 7.56 (2H) 7.33 (2H), 7.08 (2H), 5.84 (1H), 4.8–4.9 (1H), 3.74 (3H), 3.0–3.2 (3H), 2.4–2.6 (2H), 2.0–2.2 (1H), 1.6–1.8 (1H), 1.43 (9H), 1.21 (3H), 1.14 (3H), 0.76 (3H); ¹³C NMR (75 MHz, CDCl₃) δ 174.92, 172.55, 172.00, 161.81, 136;29, 135.91, 134.46, 133.00, 132.69, 129.75, 128.08, 120.51, 80.19, 56.60, 54.33, 53.04, 52.35, 46.32, 37.14, 32.26, 27.99, 22.90, 22.39, 21.90, 20.50; ESMS (m/z) 639 (MH⁺).

Example 58 (810 mg, 1.27 mmol) was dissolved in CH$_2$Cl$_2$ (5 mL) containing TFA (5 mL). This reaction mixture was stirred for 6 h at RT. Evaporation of the solvent under reduced pressure provided a crude oil. The residue was chromatographed (SiO$_2$, gradient elution: 100% hexanes→50% EtOAc/hexanes) to provide Example 92 (703 mg, 95%) as a colorless foam: $^1$H NMR (300 MHz, Acetone-d$_6$), δ 9.68 (1H), 7.66 (2H), 7.44 (2H), 7.17 (2H), 6.93 (1H), 4.88 (1H), 3.72 (3H), 3.17 (1H), 3.05 (1H), 2.79 (1H); 2.5–2.6 (1H), 2.1–2.2 (1H), 1.7–1.8 (1H), 1.4–1.5 (1H), 1.25 (3H), 1.21 (3H), 0.84 (3H); $^{13}$C NMR (75 MHz, Acetone-d$_6$), δ 176.92, 172.14, 171.14, 160.87, 136.16, 134.58, 134.48, 132.16, 132.12, 128.93, 127.08, 119.23, 59.24, 55.25, 52.60, 51.06, 45.64, 36.03, 31.71, 21.92, 21.63, 20.83, 20.06; ESMS (m/z) 583 (MH$^+$).

Example 92 (684 mg, 1.17 mmol) was dissolved in H$_2$O (8 mL) containing LiOH (127 mg, 5.27 mmol). After 6 h at RT the mixture was acidified with 3 N HCl (3 mL) and the precipitate filtered and washed with cold H$_2$O (3 mL). Drying under high vacuum provided Example 93 (547 mg, 82%) as a colorless solid: $^1$H NMR (300 MHz, Acetone-d$_6$), δ 9.96 (1H), 7.70 (2H), 7.58 (2H), 7.30 (2H), 4.8–4.9 (1H), 3.23 (1H), 3.07 (1H), 2.89 (1H), 2.5–2.6 (1H), 2.0–2.2 (1H), 1.6–1.7 (1H), 1.4–1.5 (1H), 1.26 (3H), 1.19 (3H), 0.81 (3H); $^{13}$C NMR (75 MHz, Acetone-d$_6$), δ 178.52, 174.10, 173.62, 162.22, 138.12, 136.08, 134.47, 133.69, 130.77, 128.90, 120.54, 56.92, 54.56, 53.89, 47.24, 37.48, 33.37, 23.52, 23.04, 22.31, 21.73; ESMS (m/z) 569 ([M-H]$^+$).

Scheme 14

Example 101 and 102.

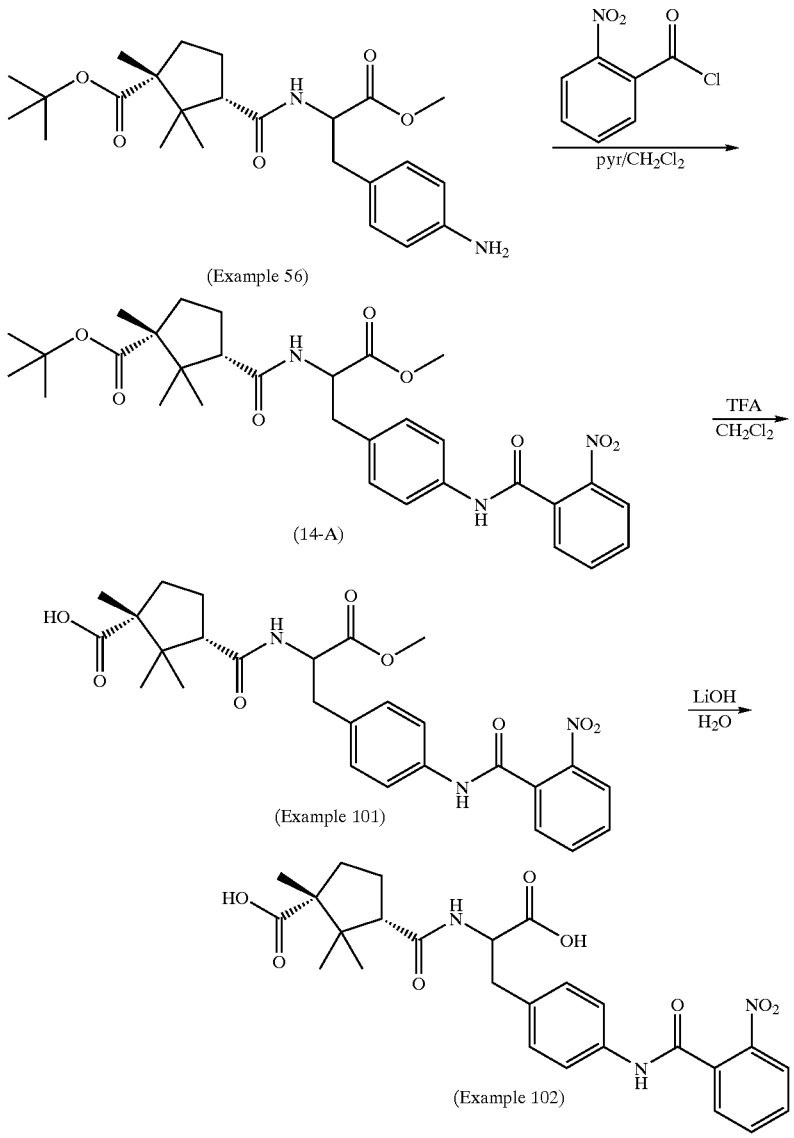

The compound according to Example 56 (810 mg, 1.87 mmol) was dissolved in Pyr/CH$_2$Cl$_2$ (5 mL of each) and O-nitrobenzoyl chloride (383 mg, 2.06 mmol) was added under dry N$_2$. The reaction was stirred for 4 hours at RT. The solvent was evaporated under high vacuum and 1N HCl (20 mL) was added to the residue. This was extracted with CH₂Cl₂ (3×25 mL) and the combined organic phases were dried over Na₂SO₄. The solution was filtered, solvent evaporated and the residue chromatographed (SiO₂, gradient elution: 100% hexanes→50% EtOAc/hexanes) to provide the intermediate (14-A) (808 mg, 74%): ¹H NMR (300 MHz, CDCl₃), δ 8.4–8.6 (1H), 8.03 (1H), 7.6–7.7 (3H), 7.49 (2H), 7.04 (2H), 5.86 (1H), 4.7–4.8 (1H), 3.71 (3H), 3.0–3.2 (2H), 2.4–2.6 (2H), 2.0–2.1 (1H), 1.6–1.7 (1H), 1.4–1.5 (1H), 1.42 (9H), 1.20 (3H), 1.12 (3H), 0.73 (3H); ¹³C NMR (75 MHz, CDCl₃), δ 174.94, 172.61, 171.97, 164.57, 146.15,.136.64, 133.77, 132.76, 132.38, 130.56, 129.62, 128.63, 124.47, 120.56, 80.16, 56.58, 54.23, 53.05, 52.28, 46.31, 37.07, 32.23, 27.96, 22.83, 22.31, 21.85, 20.50; FABMS (m/z) 582 (MH⁺).

The above compound, (14-A) (706 mg, 1.21 mmol), was dissolved in CH₂Cl₂ (5 mL) and TFA (5 mL) was added with stirring at RT. After 4 hours the solvent was evaporated and the residue chromatographed (SiO₂, gradient elution: 100% hexanes→100% EtOAc) to provide the mono methyl ester Example 101 (623 mg, 98%): ¹H NMR (300 MHz, Acetone-d₆), δ 9.79 (1H), 8.11 (1H), 7.7–7.9 (6H), 7.22 (2H), 4.81 (1H), 3.68 (3H), 3.15 (1H), 3.02 (1H), 2.86 (1H), 2.53 (1H), 2.0–2.2 (2H), 1.6–1.8 (1H), 1.43 (1H), 1.26 (3H), 1.20 (3H), 0.81 (3H); ¹³C NMR (75 MHz, Acetone-d₆), δ 177.64, 173.39, 172.92, 165.03, 147.96, 138.68, 134.68, 134.11, 133.81, 131.70, 130.52, 129.97, 125.18, 120.62, 120.54, 56.90, 54.55, 53.88, 52.31, 47.16, 37.56, 33.40, 23.48, 23.00, 22.30, 21.66; ESMS (m/z) 526 (MH⁺).

Example 101 (605 mg, 1.15 mmol) was dissolved in H₂O (5 mL) containing LiOH (138 mg, 5.76 mmol). This was stirred for 4 hours. The solution thus obtained was acidified with 2 N HCl (10 mL) and the precipitate filtered. The filter cake was washed with cold H₂O (3 mL) and then dried under high vacuum to provide Example 102 (539 mg, 92%) as a white amorphous powder: ¹H NMR (300 MHz, DMSO-d₆), δ 10.66 (1H), 8.14 (1H), 7.85 (2H), 7.76 (2H), 7.57 (2H), 7.22 (2H), 4.4–4.5 (1H) 3.02 (1H) 2.88 (1H), 2.70 (1H), 2.3 –2.4 (1H) 1.8–2.0 (1H), 1.5–1.6 (1H), 1.2–1.4 (1H), 1.17 (3H), 1.12 (3H), 0.67 (3H); ¹³C NMR (75 MHz, DMSO-d₆) δ 177.00, 173.17, 172.03, 163.90, 146.50, 137.19, 134.04, 133.35, 132.69, 1.30.92, 129.38, 129.28, 124.23, 119.44, 55.50, 53.59, 51.90, 45.95, 36.10, 32.23, 22.30, 22.23, 21.72, 21.00; ESMS (m/z) 512 (MH⁺).

Preparation 10-A

Scheme 15, 10-A Stereochemistry=(1R-cis)

(1R-cis)-1,2,2-Trimethylcyclopentane-1,3-dicarboxylic acid 3 methyl ester 10-A (C₁₁H₁₈O₄).

To methanol (0.5 L), cooled in an ice-water bath under nitrogen, is added acetyl chloride (50 mL, 0.703 mol) over 30 minutes. After stirring for 30 minutes (1R, 3S)-camphoric acid 15-A (16.g, 0.5 mol) was added in one portion. The camphoric acid dissolves over ca. 10 minutes and the solution was allowed to warm slowly to room temperature and stir for 72 hours. Concentration in vacuo afforded a clear, pale yellow oil which was dissolved in ethyl acetate (0.6 L). The solution was extracted with 0.5N aq. NaOH (4×0.35 L). The combined aqueous phases were washed with pentane (0.35 L) and the pH of the aq. layer was adjusted to ca. 4 with 1N aq. HCl. The aqueous layer was extracted with ether (4×0.35 L) and the combined organic phases were concentrated in vacuo to give a colorless oil which slowly solidified to afford 96 g (90%) of 10-A as a white crystalline solid. An analytical sample can be obtained by recrystallizing 10-A from ether-pentane (1:1) to provide 10-A as clear hexagonal plates.

MP: 76–77° C.; 1H-NMR (CDCl₃) δ 3.69(s, 3H), 2.79(m, 1H), 2.54(m, 1H), 2.20(m, 1H), 1.84(m, 1H), 1.54(m, 1H), 1.45(m, 1H), 1.27(s, 3H), 1.26(s, 3H), 0.86(s, 3H); IR(nujol): 3201, 2925, 1730, 1700, 1237, 1210, 1150, and 1110 cm⁻¹; Anal: Calcd. for C₁₁H₁₈O₄: C, 61.66; H, 8.47; Found: 0,61.63; H, 8,75.

Preparation 15-C

Scheme 15, 15-C Stereochemistry=(1R-cis)

(1R-cis)-1,2,2-Trimethylcyclopentane-1,3-dicarboxylic acid 1 (1,1-dimethylethyl)-3-methyl diester 15-C (C₁₅H₂₆O₄)

To 10-A (25 g, 0.117 mol) in a 500 mL Parr bottle, cooled in a dry ice-iPrOH bath under nitrogen, was condensed isobutylene until the bottle was approximately ½ full. In a separate Erlenmeyer flask, ether (6 mL) was cooled (dry ice-iPrOH bath) and conc. sulfuric acid (3 mL) was added. The mixture was allowed to cool for ca. 5 minutes, then was Scheme 15

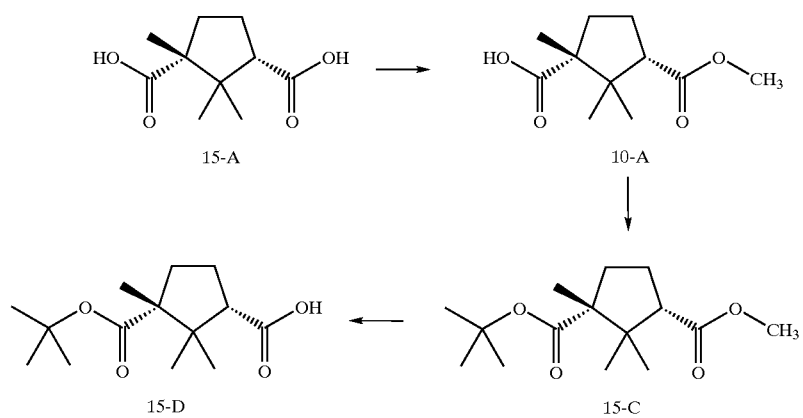

slowly added via disposable pipet to the isobutylene-15-B mixture. The Parr bottle was transferred to the shaker apparatus and shaken for 12 hours (pressure ca. 35 psi at the end of 12 hours). The bottle was surrounded by aluminum foil, dry ice was added to cool the bottle and contents, and the bottle was removed from the shaker when the pressure reading was ca. 0 psi. The isobutylene was condensed from the reaction vessel via a cold finger condenser over ca. 2 hours. The resulting thin oil was dissolved in pentane (0.5 L), the organic phase was washed with water (2×0.25 L), 0.5N aq. NaOH (2×50 mL), and water (2×0.25 L). The organic phase was concentrated in vacuo to provide 15-C as a clear colorless oil which slowly solidified at room temperature. Recrystallization from petroleum ether gave 15-C as a fine white crystalline solid (26.86 g, 89%).

MP: 36–37.6° C.; 1H-NMR: (300MHz, CDCl$_3$): δ 3.68(s, 3H) 2.78(m, 1H), 2.52(m, 1H), 2.16(m, 1H), 1.78(m, 1H), 1.45(m, 1H), 1.45(s, 9H), 1.24(s, 3H), 1.17(s, 3H), 0.81(s, 3H).

Preparation 15-D

Scheme 15, 15-D Stereochemistry=(1R-cis)

(1R-cis)-1,2,2-Trimethylcyclopentane-1,3-dicarboxylic acid 1-(1,1-dimethylethyl) ester 15-D (C$_{14}$H$_{24}$O$_4$)

To 15-C (10.25 g, 0.38 mol) in methanol (0.1 L) was added in order water (0.1 L, see considerable precipitation), LiOH di-hydrate (10 g, 2.38 mol), and 30% aq. hydrogen peroxide (0.1 L). The mixture was warmed in a 90° C. oil bath and allowed to stir for 20 hours. The mixture was cooled to room temperature and concentrated in vacuo to remove methanol and the residual white solid material was removed by filtration. The clear solution was washed with pentane (3×0.15 L), the aqueous layer was cooled in an ice-water bath and carefully acidified to ca. pH 4 with 1N aq. HCl. The resulting white precipitate was isolated by filtration, washed with water (3×0.1 L) and air dried to afford 15-D (9.6 g, 96%) as a fine white solid.

MP: 98–98.6° C.; 1H-NMR: (300MHz, CDCl$_3$): δ 2.82 (1H) 2.50(1H), 2.13(1H), 1.79(1H), 1.46(9H) 1.45(1H), 1.28(3H), 1.18(3H), 0.89(3H); IR(nujol): 3075, 3025, 3006, 1719, 1689, 1270, 1249, 1164, and 851 cm−1; EI/MS: 200(3.8), 183(7.3), 164(7.1), 154(20.3), 136(14.6), 109 (32.8), 57(base); Anal: Calcd. for C$_{14}$H$_{24}$O$_4$-0.18H$_2$O: C, 64.77; H, 9.46; Found: C,64.79; H, 9.44; K.F.-Water: 0.86%.

Scheme 16

Synthesis of Intermediate 16-A

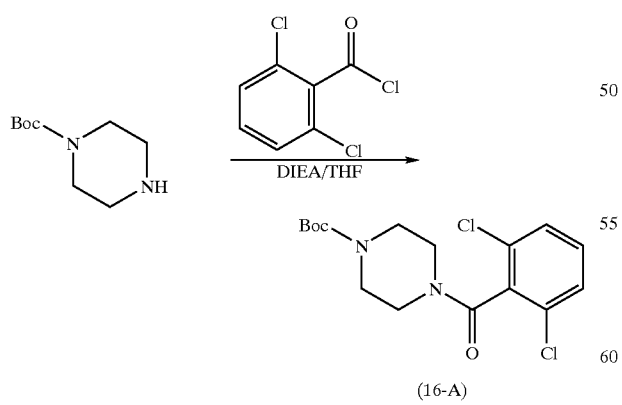

Boc-piperazine (1.9 gm, 10.4 mmol) was dissolved in THF (10 mL) and CH$_2$Cl$_2$ (1 mL) containing DIEA (5.6 mL, 32.2 mmol). To this solution 2,6-dichlorobenzoyl chloride (1.6 mL, 11.4 mmol) was added at 0° C. After stirring the reaction for 1 hour at 0° C., 1N HCl (30 mL) was added. The mixture was extracted with CH$_2$Cl$_2$ (2×20 mL) and the combined organics dried (Na$_2$SO$_4$), filtered and the solvent removed in vacuo. Chromatography of the residue (SiO$_2$, gradient elution, hexanes→30% EtOAc/hexanes) provided Intermediate (16-A) as an off white solid (3.6 gm, 98%): mp=157–159° C.; ESMS (m/z) 359 (MH$^+$).

Scheme 17

Examples 175 and 177

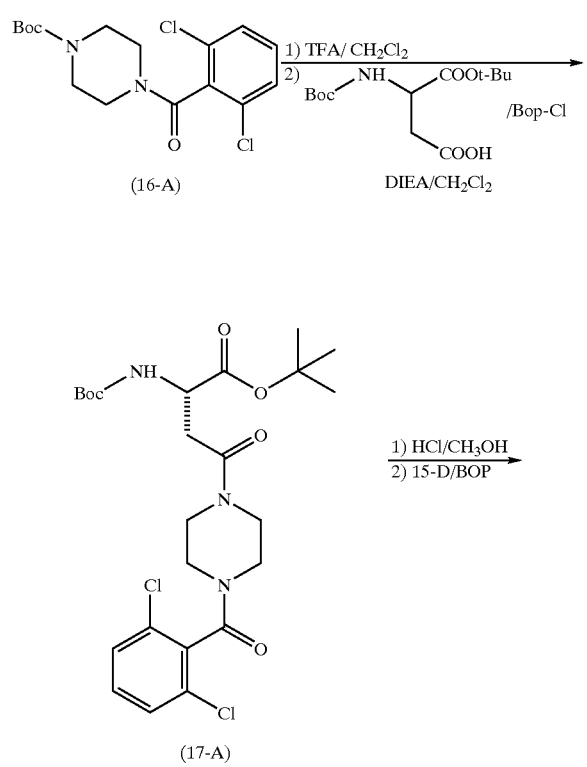

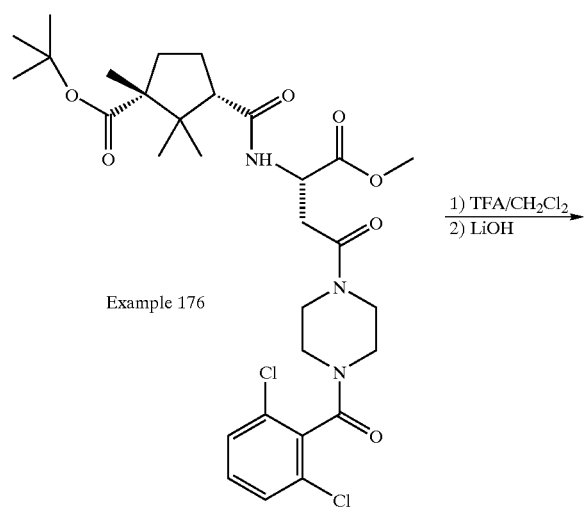

Example 176

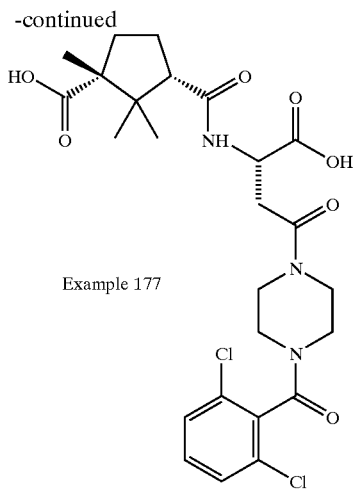

Example 177

Intermediate 16-A (553 mg, 1.54 mmol) was dissolved in CH$_2$Cl$_2$ (5 mL) and treated with TFA (5 mL). After 2 hours the solvent was removed under reduced pressure. The residue was dissolved in CH$_2$Cl$_2$ (20 mL) containing DIEA (0.8 mL, 4.6 mmol). Boc-aspartic acid α t-butyl ester (534 mg, 1.85 mmol) was added with BOP-Cl (470 mg, 1.85 mmol). After stirring at RT for 24 hours the reaction was quenched with 1N HCl (25 mL). The mixture was extracted with CH$_2$Cl$_2$ (3×25 mL). The combined organics were dried (Na$_2$SO$_4$), filtered and the solvent removed in vacuo. The residue was purified by column chromatography (SiO$_2$, gradient elution, hexanes→50% EtOAc/hexanes) to provide the intermediate aspartate (17-A) (405 mg, 50%): ESMS (m/z) 530 (MH$^+$).

To a methanolic solution of the above mentioned intermediate 17-A (0.2 g, 0.378 mmol), HCl gas was bubbled for 5 minutes and the reaction mixture was left to stand overnight at room temperature. The methanol was evaporated and the residual gum was triturated with ether. The resultant solid was washed with ether and dried under high vacuum. The solid was suspended in THF (5 mL), and 17-B (1R, 3S)-1-(tert-butoxycarbonyl)-1,2,2-trimethylcyclopentanecarboxylic acid (102 mg, 0.397 mmol), BOP (176 mg, 0.397 mmol) were,added, followed by DIEA (0.207 mL, 1.19 mmol). The mixture was stirred overnight at room temperature. The solvent was evaporated and the residue was partitioned between 1N HCl (5 mL) and EtOAc (15 mL). The organic layer was separated and washed successively with 1N HCl (5 mL), brine (5 mL), Sat. NaHCO$_3$ (2×5 mL), Sat. LiCl (2×5 mL), and dried over MgSO$_4$. Evaporation of EtOAc produced a colorless solid, which was purified on silica (Chromatotron, hexane:EtOAc (1:1) as eluant) to provide Example 176 (206 mg, 870) as a colorless solid. ESMS: (m/z) 626 (MH$^+$).

Example 176 (0.18 g, 0.287 mmol) was dissolved in CH$_2$Cl$_2$ (1.0 mL) and TFA (1.0 mL). After stirring at room temperature for 1 hr the solvent was evaporated and the resultant gum triturated with ether. The solid was washed with ether and dried under vacuum to provide [1S-[1α(R*),3α]]-α-[[(3-Carboxy-2,2,3-trimethylcyclopentyl)carbonyl]amino]-4-(2,6-dichlorobenzoyl)-γ-oxo-1-piperazinebutanoic acid methyl ester as a colorless solid (0.149 g, 87%). ESMS (m/z) 570 (MH$^+$).

To a solution of the methyl ester obtained above (0.1 g, 0.18 mmol) in THF/CH$_3$OH (5 mL/1 mL) was added an aqueous (1 mL) solution of LiOH mono hydrate (19 mg, 0.378 mmol) and the mixture was stirred at room temperature for 2 h. The organics were evaporated and the residue was taken up in 2 ml of water and acidified with citric acid. The solid was filtered, washed with water and vacuum dried to provide Example 177 (90 mg, 92%). ESMS (m/z) 556 (MH$^+$).

Scheme 18

Examples 178 and 195

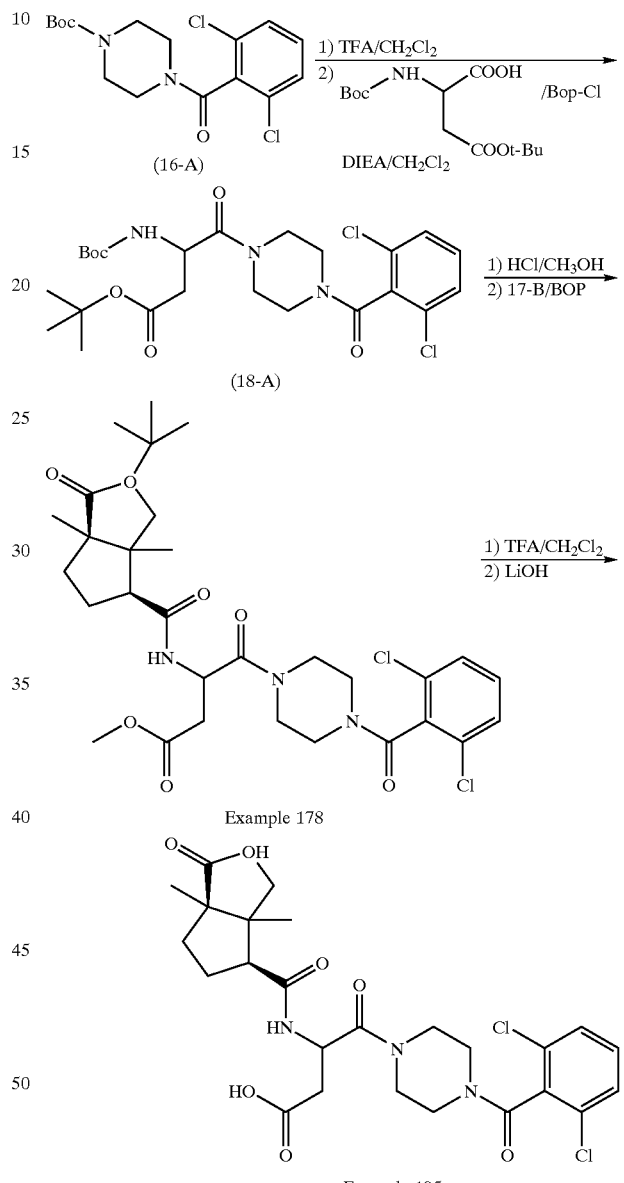

Example 178

Example 195

Intermediate 16-A (593 mg, 1.54 mmol) was dissolved in CH$_2$Cl$_2$ (6 mL) and treated with TFA (6 mL) After 2 hours the solvent was removed under reduced pressure. The residue was dissolved in CH$_2$Cl$_2$ (20 mL) containing DIEA (0.9 mL, 4.95 mmol). Boc-aspartic acid β t-butyl ester (573 mg, 1.98 mmol) was added with BOP-Cl (504 mg, 1.98 mmol). After stirring at RT for 24 hours the reaction was quenched with 1N HCl (15 mL). The mixture was extracted with CH$_2$Cl$_2$ (3×20 mL). The combined organics were dried (Na$_2$SO$_4$), filtered and the solvent removed in vacuo. The residue was purified by column chromatography (SiO$_2$, gradient elution, hexanes→50% EtOAc/hexanes) to provide the intermediate aspartate (18-A) (360 mg, 41%): ESMS (m/z) 530 (MH$^+$).

To a methanolic solution of the above mentioned intermediate (18-A) (0.25 g, 0.47 mmol), HCl gas was bubbled for 5 minutes and the reaction mixture was left to stand overnight at room temperature. The methanol was evaporated and the residual gum was triturated with ether. The resultant solid was washed with ether and dried under high vacuum. The solid was suspended in THF (5 mL), and 15-D (1R,3S)-1-(tert-butoxycarbonyl)-1,2,2-trimethylcyclopentanecarboxylic acid (127 mg, 0.495 mmol), BOP (219 mg, 0.495 mmol) were added, followed by DIEA (0.259 mL, 1.485 mmol). The mixture was stirred overnight at room temperature. The solvent was evaporated and the residue was partitioned between 1N HCl (5 ml) and EtOAc (15 ml). The organic layer was separated and washed successively with 1N HCl (5 ml), brine (5 ml), Sat. NaHCO$_3$ (2×5 ml), Sat. LiCl (2×5 ml), and dried over MgSO$_4$. Evaporation of EtOAc produced a colorless solid, which was purified on silica (Chromatotron, hexane:EtOAc (1:1) as eluant) to provide Example 178 (249 mg, 77%) as a colorless solid. ESMS: (m/z) 626 (MH$^+$).

Example 178 (0.19 g, 0.303 mmol) was dissolved in CH$_2$Cl$_2$ (1.0 mL) and TFA (1.0 mL). After stirring at room temperature for 1 hr the solvent was evaporated and the resultant gum triturated with ether. The solid was washed with ether and dried under vacuum to provide [1S-[1α(R*), 3α]]-β-[[(3-Carboxy-2,2,3-trimethylcyclopentyl)carbonylamino]-4-[2,6-dichlorobenzoyl)-γ-oxo-1-piperazinebutanoic acid methyl ester as a colorless solid (98 mg, 58%). ESMS (m/z) 570 (MH$^+$)

To a solution of the methyl ester obtained above (60 mg, 0.105 mmol) in THF/CH$_3$OH (5 mL/1 mL) was added an aqueous (1 mL) solution of LiOH mono hydrate (9.5 mg, 0.221 mmol) and the mixture was stirred at room temperature for 2 h. The organics were evaporated and the residue was taken up in 2 ml of water and acidified with citric acid. The solid was filtered, washed with water and vacuum dried to provide Example 195 (48 mg, 83%). ESMS (m/z) 556 (MH$^+$).

Scheme 19

Examples 211, 212, 213, 214 and 215

$R^{19-1}$ is defined in the same manner as $R^{7-1}$ to include amino acids included in $R^2$ definition; $R^{19-2}$ is proton or together with $R^{19-1}$ cyclic amino acid; $R^{19-3}$ is $C_{1-6}$ alkyl —NH—, NH$_2$ or $C_{1-6}$alkyl-O— or OH.

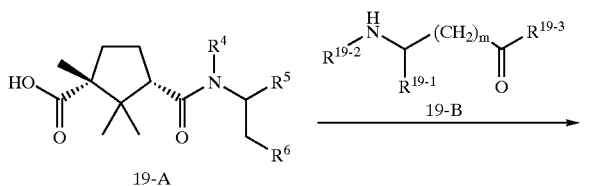

19-A

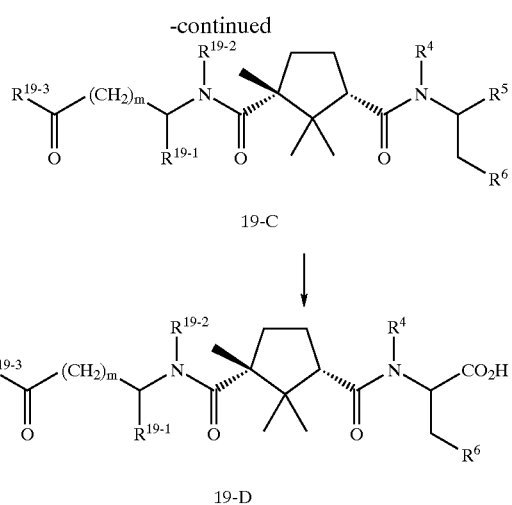

19-C

19-D

Preparation 19-C-1

Scheme 19, 19-C: wherein $R^4$=H, $R^5$=CO$_2$CH$_3$ $R^6$= 4-[(2,6-Dichlorobenzoyl)amino]phenyl, $R^{19-2}$=H, $R^{19-1}$=CH$_3$, $R^{19-3}$=OC(CH$_3$)$_3$, m=0 Stereochemistry=[1S-[1α,3α(S*)]]

[1S-[1α,3α(S*)]]N-3-[[(1-(1,1-dimethylethyoxy)carbonylethyl)amino]carbonyl]-2,2,3-trimethylcyclopentyl)carbonyl-4-(2,6-dichlorobenzoyl)amino]-L-phenylalanine methyl ester (19-C-1) (C$_{34}$H$_{43}$Cl$_2$N$_3$O$_7$)

A solution of (1S-cis)-N-[(3-carboxy-2,2,3-trimethylcyclopentyl)carbonyl]-4-[(2,6-dichlorobenzoyl)amino]-L-phenylalanine methyl ester 19-A-1 (19-A: $R^4$=H, $R^5$=CO$_2$CH$_3$, $R^6$=4-[(2,6-Dichlorobenzoyl)amino]phenyl) (0.468 g, 0.85 mmol), HATU (0.36 g, 0.95 mmol), and diisopropylethyl amine (dry, 2 mL, 11.5 mmol) are stirred together with DMF (dry, 5 mL) in a dry round bottom flask under a nitrogen atmosphere. After 30 minutes, D-alanine tbutyl ester hydrochloride (19-B, ($R^{19-1}$=CH$_3$, $R^{19-2}$=H, $R^{19-3}$=t-BuO, Stereochemistry D) (0.34 g, 1.87 mmol) is added. After three days, the mixture is evaporated to dryness in vacuo to give a yellow oil which is mixed with methylene chloride (100 mL) and shaken with water (5×50 mL). The organic layer is then evaporated to dryness, giving an off-white solid Recrystallization from ethyl acetate/diethyl ether gives 19-C-1, as a white solid (0.428 g, 74% yield).

$^1$H NMR(300 MHz, DMSO-d$_6$) δ 10.70 (1H), 7.90(1H), 7.60–7.18 (8H), 4.48(1H), 4.15(1H), 3.57(3H), 2.95 (2H), 2.75(1H), 2.37(1H), 1.87(1H), 1.55(1H), 1.36(9H), 1.30 (1H), 1.22(3H), 1.18 (3H), 1.09 (3H), 0.57(3H).

Preparation 19-C-2

Scheme 19, 19-C: wherein $R^4$=H, $R^5$=CO$_2$CH$_3$ $R^6$= 4-[(2,6-Dichlorobenzoyl)amino]phenyl $R^{19-2}$=H, $R^{19-1}$=CH$_3$, $R^{19-3}$=OH, m=0 Stereochemistry=[1S-[1α,3α(S*)]]

[1S-[1α,3α(S*)]]-N-[[3-[[(1-Carboxyethyl)amino]carbonyl]-2,2,3-trimethylcyclopentyl]carbonyl]-4-[(2,6-dichlorobenzoyl)amino]-L-phenylalanine methyl ester (19-C-2) (C$_{30}$H$_{35}$Cl$_2$N$_3$O$_7$)

Di-ester 19-C-1 is stirred overnight with trifluoroacetic acid (5 mL) and then the mixture is diluted with toluene (100 mL) followed by evaporation to dryness in vacuo, giving acid 19-C-2 as a pale brown oil (0.34 g, 90% yield).

$^1$H NMR (300 MHz, DMSO-d$_6$) δ 10.70(1H), 7.96 (1H), 7.57–7.10(8H), 4.47 (1H), 4.22 (1H), 3.57(3H), 2.95 (2H), 2.65(1H), 2.37(1H), 1.89(1H), 1.55 (1H), 1.30 (1H), 1.25 (3H), 1.18(3H), 1.09 (3H), 0.57(3H); MS(ES+) m/z 619.8.

Preparation of Example 211

Scheme 19, 19-D: wherein R$^4$=H, R$^6$=4-[(2,6-Dichlorobenzoyl)amino]phenyl R$^{19-2}$=H, R$^{19-1}$=CH$_3$, R$^{19-3}$=OH, m=0 Stereochemistry=[1S-[1α,3α(S*)]]

[1S-[1α,3α(S*)]]-N-[[3-[[(1-Carboxyethyl)amino]carbonyl]-2,2,3-trimethylcyclopentyl]carbonyl]-4-[(2,6-dichlorobenzoyl)amino]-L-phenylalanine Example 211 (C$_{29}$H$_{33}$Cl$_2$N$_3$O$_7$)

A solution of LiOH.H$_2$O (0.15 g, 3.57 mm) in H$_2$O (5 mL) is added to a solution of 19-C-2 in methanol (5 mL). After overnight stirring, the solution is brought to pH7 with 1.2N aq. HCl (2 mL), evaporated in vacuo until the methanol is gone, and shaken with diethyl ether (3×30 mL). The aqueous layer is filtered, cooled in an ice bath and brought to pH2 using 1.2N aq. HCl. The resultant white precipitate is filtered, washed with water (100 mL) and air dried to give Example 211 as a white solid (0.277 g, 78% yield).

$^1$H NMR(DMSO-d$_6$) δ 10.67(1H), 7.76(1H), 7.57–7.44 (5H), 7.31(1H), 7.20(2H), 4.42(1H), 4.22(1H), 3.03–2.82 (2H), 2.64(1H), 2.36(1H), 1.89(1H), 1.54(1H)1.32–1.26 (4H), 1.19(3H), 1.09(3H), 0.58(3H); IR (nujol) 3293, 3261, 3078, 1740, 1672, 1612, 1562, 1551, 1527, 1518, 1429, 1415, 1334, 1276, 1197 cm$^1$; MS (ES−) m/z 606.3, 604.3; KF Water 7.76%.

Preparation 19-C-3

Scheme 19, 19-C: wherein R$^4$=H, R$^5$=CO$_2$CH R$^6$=4-[(2,6-Dichlorobenzoyl)amino]phenyl, R$^{19-2}$, R$^{19-1}$=(CH$_2$)$_3$, R$^{19-3}$=NH2, m=0 Stereochemistry=[1S-[1α,3α(S*)]]

[1S-[1α,3α(S*)]]-N-[3-[[2-(Aminocarbonyl)-1-pyrrolidinyl]carbonyl]-2,2,3-trimethylcyclopentyl]carbonyl-4-[(2,6-dichlorobenzoyl)amino]-L-phenylalanine methyl ester (19-C-3) (C$_{32}$H$_{37}$Cl$_2$N$_4$O$_6$)

In a similar manner to that reported for the synthesis of 19-C-1, 19-A-1 (19-A: R$^4$=H, R$^5$=CO$_2$CH$_3$, R$^6$=4-[(2,6-Dichlorobenzoyl)amino]phenyl)) (0.55 g, 1.00 mmol) is coupled to D-prolineamide (0.39, 2.63 mmol) using HATU (0.40 g, 1.05 mmol) and diisopropylethyl amine (3 mL, 17.2 mmol) in dry DMF. After overnight stirring, the reaction mixture is evaporated to dryness in vacuo, giving a pale yellow oil which is stirred with ethyl acetate (50 mL). A precipitate soon formed and it is isolated by suction filtration to give 19-C-3 as a white solid (0.32 g, 90% yield).

$^1$H NMR(DMSO-d$_6$) δ 10.67 (1H), 7.95(1H), 7.58–7.48 (5H), 7.19(2H), 7.10(1H), 6.65(1H), 4.45(1H), 4.18(1H), 3.70–3.30(1H), 3.57(3H), 2.90(2H), 2.58(1H), 2.28–1.40 (9H), 1.25(3H), 1.12(3H), 0.73(3H).

Preparation of Example 212

Scheme 19, 19-D: wherein R$^4$=H, R$^5$=CO$_2$Li R$^6$=4-[(2,6-Dichlorobenzoyl)amino) phenyl, R$^{19-2}$, R$^{19-1}$=(CH$_2$)$_3$, R$^{19-3}$=(NH$_2$, m=0 Stereochemistry=[1S-[1α,3α(S*)]]

[1S-[1α,3α(S*)]]-N-[3-[[2-(Aminocarbonyl)-1-pyrrolidinyl]carbonyl]-2,2,3-trimethylcyclopentyl]-carbonyl]-4-[(2,6-dichlorobenzoyl)amino]-L-phenylalanine monolithium salt Example 212 (C$_{31}$H$_{35}$Cl$_2$N$_4$O$_6$Li)

A solution of LiOH.H$_2$O (0.2 g, 4.8 mmol) in H$_2$O (4 mL) is added to a stirred solution of the methyl ester 19-C-3 (0.58 g, 0.89 mmol) in methanol (10 mL). After overnight stirring, the mixture is evaporated in vacuo until the methanol is gone. The reaction mixture is then brought to pH 7 with 1N aq. HCl, filtered and the filtrate transferred to a C-18 reversed phase HPLC column and eluted with a 0–10% acetonitrile/water gradient. Evaporation is accomplished in vacuo to give the target compound as a white solid (0.445 g, 78% yield).

$^1$H NMR(300 MHz, DMSO-d$_6$) δ 10.55(1H), 7.56–7.43 (5H) 7.04(3H), 6.79(1H), 6.62(1H), 4.18(1H), 3.92(1H), 3.62(1H) 3.43(1H), 2.96 (2H), 2.44(1H), 2.25–1.5(8H), 1.23 (3H), 1.1(3H), 0.75(3H); IR (nujol) 3392, 3288, 3194, 3124, 3068, 1660, 1604, 1562, 1539, 1515, 1431, 1403, 1325, 799, 686 cm$^{-1}$; MS (FAB) m/z (rel. intensity) 631 (M+H, 1), 659 (29), 653 (24), 643 (26), 639 (34), 637 (50), 279 (33), 133 (26), 109 (61), 70 (35), 23 (99); HRMS (FAB) m/z calcd for C$_{31}$H$_{36}$Cl$_2$N$_4$O$_6$+H$^+$ 631.2090, found 631.2086; KF Water: 9.90%.

Preparation 19-C-4

Scheme 19, 19-C: wherein R$^4$=H, R$^5$=CO$_2$CH$_3$ R$^6$=4-[(2,6-Dichlorobenzoyl)amino]-phenyl, R$^{19-2}$, R$^{19-1}$=(CH$_2$)$_3$, R$^{19-3}$=NH$_2$, m=0 Stereochemistry=[1S-[1α,3α(R*)]]

[1S-[1α,3α(R*)]]-N-[3-[[2-(Aminocarbonyl)-1-pyrrolidinyl]carbonyl]-2,2,3-trimethylcyclopentyl]carbonyl]-4-[(2,6-dichlorobenzoyl) amino]-L-phenyl alanine methyl ester (19-C-4) (C$_{32}$H$_{37}$Cl$_2$N$_4$O$_6$)

In a similar manner to that reported for the synthesis of 19-C-3, 19-A-1 (19-A: R$^4$=H, R$^5$=CO$_2$CH$_3$, R$^6$=4-[(2,6-Dichlorobenzoyl)amino]-phenyl)) (0.50 g, 0.91 mmol) is coupled to L-prolineamide (0.2 g, 1.75 mmol) using HATU (0.41 g, 1.08 mmol) and diisopropylethyl amine (1 mL, 5.74 mmol) in dry DMF (5 mL). After overnight stirring, the mixture is evaporated to dryness in vacuo to give a yellow oil which is shaken with methylene chloride (100 mL) and water (50 mL); this gives a white precipitate which is filtered and the isolated solid is washed with water (3×50 mL). Recrystallization from ethyl acetate gives 19-C-4 as a white solid (0.31 g, 53% yield).

$^1$H NMR(DMSO-d$_6$): δ 10.70(1H), 7.92(1H), 7.50(5H) 7.19(2H), 7.04(1H), 6.74(1H), 4.48(1H), 4.11(1H), 3.58 (3H), 3.47(1H), 2.92(2H), 2.56(1H), 2.35(1H), 2.10–1.45 (8H), 1.24(3H), 1.09(3H), 0.71(3H); MS(ES+, m/z) 644.9.

Preparation of Example 213

Scheme 19, 19-D: wherein R$^4$=H, R$^5$=CO$_2$Na R$^6$=4-[(2,6-Dichlorobenzoyl)amino]-phenyl, R$^{19-2}$, R$^{19-1}$=(CH$_2$)$_3$, R$^{19-3}$=NH$_2$, n=0 Stereochemistry=[1S-[1α(S*),3α(S*)]]

[1S-[1α,3α(R*)]]-N-[3-[[2-(Aminocarbonyl)-1-pyrrolidinyl]carbonyl]-2,2,3-trimethylcyclopentyl]carbonyl]-4-[(2,6-dichlorobenzoyl)amino]-L-phenylalanine monosodium salt Example 213 (C$_{31}$H$_{35}$Cl$_2$N$_4$O$_6$Na)

The ester 19-C-4 (0.258 g., 0.4 mmol) is hydrolyzed in a manner similar to that described above for Example 212. The reaction mixture is then brought to pH 7, filtered and the filtrate transferred to a C-18 reversed phase HPLC column and eluted with a 0–10% acetonitrile/0.1% aqueous Na$_2$CO$_3$ gradient. Evaporation is accomplished in vacuo to give the target compound as a white solid (0.2 g, 76% yield).

¹H NMR (300 MHz, DMSO-d₆): δ 10.57(1H), 7.56–7.44 (4H) 7.02(3H), 6.77(2H), 4.10(1H), 3.91(1H), 3.6(1H), 3.50 (1H), 3.95(1H), 2.44(1H), 2.10–1.50(7H), 1.23(3H), 1.07 (3H), 0.73(3H); IR (nujol) 3392, 3288, 3194, 3124, 3068, 1660, 1604, 1562, 1539, 1515,1431, 1403, 1325, 799, 686 cm⁻¹; MS (FAB) m/z (rel. intensity) 631 (M+H, 1), 659 (29), 653 (24), 643 (26), 639 (34), 637 (50), 279 (33), 133 (26), 109 (61), 70 (35), 23 (99); HRMS (FAB) calcd for $C_{31}H_{36}Cl_2N_4O_6$ +H⁺ 631.2090, found 631.2086; KF Water: 9.90%.

Preparation 19-C-5

Scheme 19, 19-C: wherein R⁴=H, R⁵=CO₂CH₃ R⁶= 4-[(2,6-Dichlorobenzoyl)amino]phenyl, $R^{19-2}$=H, $R^{19-1}$=H, $R^{19-3}$=OCH₃, m=1 Stereochemistry=(1S-cis)-L (1S-cis)-N-[[3-[[[2-(Methyloxycarbonyl)ethyl]amino] carbonyl]-2,2,3-trimethylcyclopentyl]carbonyl]-4-[(2,6-dichlorobenzoyl)amino]-L-phenylalanine methyl ester (19-C-5) ($C_{31}H_{37}Cl_2N_3O_7$)

A solution of 19-A-1 (19-A: R⁴=H, R⁵=CO₂CH₃, R⁶=4-[(2,6-Dichlorobenzoyl)amino]phenyl) (0.6 g, 1.09 mmol), HATU (0.5 g, 1.32 mmol), and diisopropylethyl amine dry, 2 mL, 11.5 mmol) are stirred together with DMF (dry, 5 mL) in a dry round bottom flask under a nitrogen atmosphere. After 30 minutes, β-alanine methyl ester hydrochloride (19-B, $R^{19-1}$=H, $R^{19-2}$=H, $R^{19-3}$=CH₃O) (0.3 g, 2.15 mmol) is added. After 18 hours, the mixture is evaporated to dryness in vacuo to give a yellow oil which is mixed with ehtyl acetate (150 mL) and shaken with water (50 mL). The organic layer is washed with water and brine (2×60 mL, 5:1), satd. aq. NaHCO₃ (50 mL), water and brine (60 mL, 5:1), the organic layer is mixed with pentane (30 mL) and is cooled to −20° C. (3 days). The resulting solid is isolated by filtration, washed with diethyl ether (2×50 mL), and is air dried to give 19-C-5 as a white solid (0.63 g, 91%).

¹H NMR(CDCl₃) δ 7.62(1H), 7.57(2H), 7.32(3H), 7.10 (2H), 6.26 (1H), 5.81 (1H), 4.88 (1H), 3.75 (3H), 3.68 (3H), 3.48 (2H), 3.12 (2H), 2.51 (3H), 2.28 (2H), 1.80 (1H), 1.49 (1H), 1.26(3H), 1.15(3H), 0.74 (3H); MS(ES+) m/z 633.8.

Preparation of Example 214

Scheme 19, 19-D: wherein R⁴=H, R⁶=4-[(2,6-Dichlorobenzoyl)amino]phenyl, $R^{19-2}$=H, $R^{19-1}$=H, $R^{19-3}$=OH, m=1 Stereochemistry=(1S-cis)-L (1S-cis)-N-[[3-[[(2-Carboxyethyl)amino]carbonyl]-2,2,3-trimethylcyclopentyl]carbonyl]-4-[[(2,6-dichlorobenzoyl) amino]-L-phenylalanine (Example 214) ($C_{29}H_{33}Cl_2N_3O_7$)

To a solution of the dimethyl ester 19-C-5 (19-C: R⁴=H, R⁵=CO₂CH₃, R⁶=4-[(2,6-Dichlorobenzoyl)amino]-phenyl, $R^{19-2}$=H, $R^{19-1}$=H, $R^{19-3}$=OCH₃, n=1, Stereochemistry=(1S-cis)-L) (0.52 g, 0.82 mmol) in methanol (10 mL) is added a solution of LiOH.H₂O (0.18 g, 4.29 mmol) in water (4 mL). After overnight stirring, the reaction mixture is brought to pH 8 using 1N aq. HCl and then evaporated to dryness in vacuo. The mixture is chromatographed on a reversed phase (C-18) HPLC column using a gradient (0 to 10% acetonitrile/(3% methanol in H₂O)). The selected eluant is evaporated to dryness and dissolved in water (50 mL), cooled in an ice water bath, and brought to pH3 using 1N aq. HCl. The resultant white precipitate is isolated by suction filtration to give Example 214 as a white solid (0.43 g, 85% yield).

¹H NMR(DMSO-d₆) δ 10.6 (1H), 7.91(1H), 7.55–7.42 (5H) 7.08(2H), 6.78(1H), 4.02 (1H), 3.10 (2H), 2.90 (2H), 2.48(1H), 2.25(1H), 1.93(3H), 1.56(1H), 1.24(1H), 0.99 (3H), 0.93(3H), 0.46(3H); IR (nujol) 3327, 3080, 1726, 1672, 1622, 1614, 1595, 1558, 1515, 1429,1338, 1279, 1262, 1197, 783 cm⁻¹; MS (FAB) m/z (rel. intensity) 606 (M+H, 99), 609 (24), 608 (69), 607 (42), 606 (99), 605 (15), 517 (16), 254 (69), 175 (16), 173 (25), 109 (51); HRMS (FAB) m/z calcd for $C_{29}H_{33}Cl_2N_3O_7$ +H1 606.1774, found 606.1758.

Preparation 19-C-6

Scheme 19, 19-C: wherein R⁴=H, R⁵=CO₂CH₃ R⁶= 4-[(2,6-Dichlorobenzoyl)amino]phenyl, $R^{19-2}$, $R^{19-1}$=(CH₂)₃, $R^{19-3}$=NHCH₃, m=0 Stereochemistry= [1S-[1α,3α(R*)]]

[1S-[1α,3α(R*)]]-4-[(2,6-Dichlorobenzoyl) amino]-N-[3-[[2-[(methylamino)carbonyl]-1-pyrrolidinyl]carbonyl]-2,2,3-trimethylcyclopentyl]carbonyl]-L-phenylalanine methyl ester (19-C-6) ($C_{33}H_{40}Cl_2N_4O_6$)

In a similar manner to that reported for the synthesis of 19-C-l, 19-A-1 (19-A: R⁴=H, R⁵=CO,CH₃, R⁶=4-[(2,6-Dichlorobenzoyl)amino]-phenyl) (0.53 g, 0.96 mmol), HATU (0.4 g, 1.05 mmol), and diisopropylethyl amine (dry, 1.5 mL, 8.6 mmol) are stirred together with DMF (dry, 5 mL) in a dry round bottom flask under a nitrogen atmosphere. After 30 minutes, N-methylprolineamide hydrochloride (19-B: $R^{19-1}$, $R^{19-2}$=CH₂CH₂CH₂, $R^{19-3}$=NHCH₃, n=0, stereochemistry L) (0.5 g, 3.04 mmol) is added. After two days, the mixture is evaporated to dryness in vacuo to give a pale brown oil which is transferred to a silica gel column (20 g) and eluted with a gradient from 0 to 10% methanol/chloroform to give, after solvent evaporation, 19-C-6 as a pale oil (0.55 g, 86%)

¹H NMR(300 MHz, DMSO-d₆) δ 10.68(1H), 7.95(1H), 7.58–7.44(7H), 7.19(2H), 4.48(1H), 4.11(2H), 3.57(3H), 3.06(4H), 2.63(3H), 2.46–1.69(11H), 1.31(3H), 1.12(3H), 0.79(3H).

Preparation of Example 215

Scheme 19, 19-D: wherein R⁴=H, R⁵=CO₂Na R⁶= 4-[(2,6-Dichlorobenzoyl)amino]phenyl, $R^{19-1}$, $R^{19-2}$=CH₂CH₂CH₂, $R^{19-3}$=NHCH₃, m=0 Stereochemistry=[1S-[1α,3α(R*)]]

[1S-[1α,3α(R*)]]-N-[3-[[2-[(Methylamino)carbonyl]-1-pyrrolidinyl]carbonyl]-2,2,3-trimethylcyclopentyl] carbonyl]-4-[(2,6-dichlorobenzoyl)amino]-L-phenylalanine monosodium salt Example 215 ($C_{32}H_{37}Cl_2NaN_4O_6$)

A solution of LiOH.H₂O (0.2 g, 4.8 mmol) in H₂O (6 mL) is added to a stirred solution of the methyl ester 19-C-6 (19-C: R⁴=H, R⁵=CO₂CH₃, R⁶=4-[(2,6-Dichlorobenzoyl) amino]phenyl) (0.53 g, 0.8 mmol) in methanol (10 mL). After overnight stirring, the mixture is diluted with H₂O (50 mL), evaporated in vacuo until the methanol is gone. The reaction mixture is then brought to pH 8 using 1N aq. HCl, filtered, and the filtrate transferred to a C-18 reversed phase HPLC column and eluted with a 10%–18% acetonitrile/ 0.02% aq sodium bicarbonate gradient. The eluant is evaporated to dryness, stirred with isopropanol (3×10 mL) and filtered through a sintered glass funnel. The combined isopropanol filtrates are evaporated to dryness, mixed with water and evaporated to dryness again (2×10 mL H₂O) to give Example 215 as a white solid (0.4 g, 74% yield) ¹H NMR(300 MHz, DMSO-d₆) δ 10.57(1H), 7.51(6H) 7.04 (2H), 6.80(1H), 4.18(1H), 3.90(1H), 3.55(2H), 3.00(2H), 2.53(3H), 2.47(1H), 2.12–1.50(8H), 1.24(3H), 1.09(3H), 0.72(3H).

HRMS (FAB) m/z calcd for $C_{32}H_{37}CL_2N_4O_6Na_1 +H_1$ 667.2066; found 667.2056.

Scheme 20

Example 205

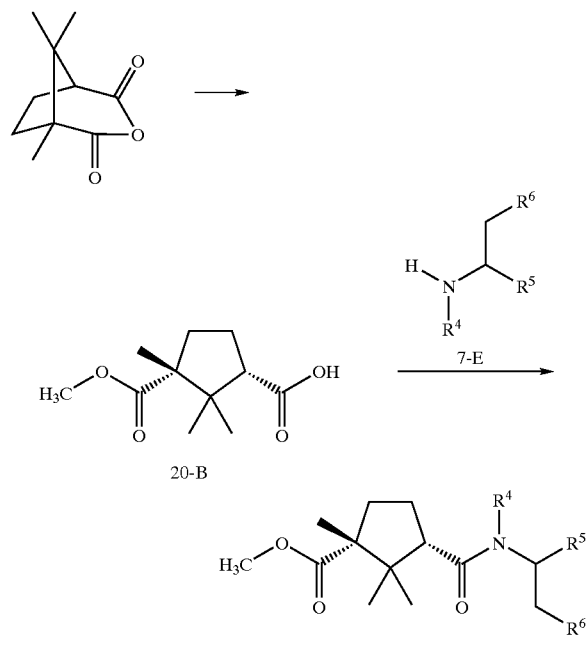

Preparation 20-B

Scheme 20, 20-B (1R-cis)-1,2,2-Trimethylcyclopentane-1,3-dicarboxylic acid 1-methyl ester (20-B)

A solution of (1R)-camphoric anhydride, prepared by the method of Bell, K. H. Aust. J. Chem. 1981, 34 665–670, (5 g, 27.44 mmol) in toluene (400 mL) in a round bottom flask is flushed with $N_2$ and then cooled in a dry ice/ethanol bath. To this cooled solution is added (via dropwise addition) a one molar solution of potassium t-butoxide (30 mL, 30 mmol) over a twenty minute period. After stirring overnight, the room temperature reaction mixture is again cooled on a dry ice/ethanol bath. To the cooled solution is added methyl trifluoromethanesulfonate (3.5 mL, 30.9 mmol). After an additional 12 hours of stirring, the reaction mixture is acidified with trifluoroacetic acid (50 mL, 649 mmol), and is allowed to stir for another 16 hours. The mixture is then diluted with toluene (200 mL), shaken with water (4×120 mL), and evaporated to dryness, giving 20-B as a pale brown solid (2.35 g, 10.97 mmol, 40% yield).

¹H NMR(300 MHz, DMSO-d₆) δ 3.60 (s, 3H), 2.75 (m, 1H) 2.40 (m, 1H), 2.00 (m, 1H), 1.74 (m, 1H), 1.41 (m, 1H), 1.19 (s, 3H), 1.15 (s, 3H), 0.70 (s, 3H).

Preparation 20-D

Scheme 20, 20-D: wherein $R^4$=H, $R^5$=CO₂CH₃ $R^6$= 4-[(2,6-Dichlorophenyl)methoxy]-phenyl Stereochemistry=[1S-cis]-L (1S-cis)-O-[(2,6-Dichlorophenyl)methyl]-N-[[3-(methoxycarbonyl)-2,2,3-trimethylcyclopentyl]carbonyl]-L-tyrosine methyl ester (20-D)

A solution of camphoric acid methyl ester 20-B (0.35 g, 1.63 mmol), EDC (0.35 g, 1.83 mmol), HOBT (0.25 g, 1.85 mmol), 4-dimethylaminopyridine (0.05 g, 0.41 mmol), in methylene chloride (10 mL) is stirred together in a 25 mL, 2-neck flask cooled in an ice water bath. To this mixture is added (2,6-dichlorophenyl)methyl)-L-tyrosine methyl ester hydrochloride (0.65 g, 1.83 mmol), creating a thick, heterogeneous mixture which becomes homogeneous after addition of triethylamine (0.3 mL, 2.15 mmol). After three days, the reaction mixture is diluted with methylene chloride (150 mL) and shaken with water (2×100 mL), aqueous HCl (0.5N, 2×100 mL), water (3×100 mL), aqueous NaHCO₃ (2×100 mL), and water (1×100 mL). The organic layer is then evaporated to dryness, giving 20-D as an off-white foam (0.7 g, 78% yield).

¹H NMR(300 MHz, CDCl₃) δ 7.38(m, 2H), 7.26(m, 1H) 7.05(m, 2H), 6.96(m, 2H), 5.76(m, 1H), 5.25(s, 2H), 4.88(m, 1H), 3.75(s, 3H), 3.67(s, 3H), 3.17–3.03(m, 2H), 2.61–2.50 (m, 2H), 2.26–2.13(m, 1H), 1.84–1.70(m, 1H), 1.54–1.45 (m, 1H), 1.22(s, 3H), 1.19(s, 3H), 0.76(s, 3H).MS(ES+) m/z 549.8

Scheme 21

Example 200

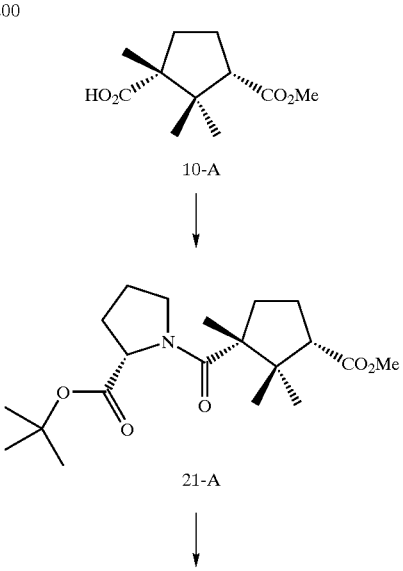

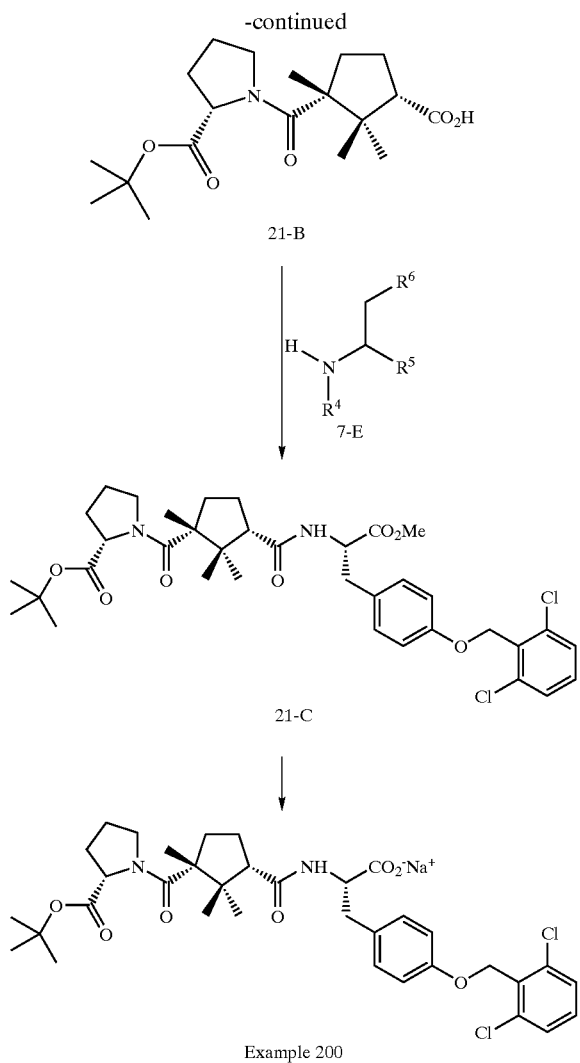

21-B

7-E

21-C

Example 200

(1R-cis)-N-[[3-Methoxycarbonyl-1,2,2-trimethylcyclopentyl] carbonyl-L-proline 1,1-dimethylethyl ester 21-A The camphoric acid mono ester 10-A (1.41 g, 6.58 mmol) in DMF (dry, 5 mL) in a dry flask under $N_2$ is cooled in an ice water bath. Diisopropylethyl amine (4.6 mL, 26.41 mmol) is added followed by HATU (2.6 g, 6.83 mmol). After thirty minutes, L-proline t-butyl ester (1.3 mL, 7.44 mmol) is added. After overnight stirring, the mixture is evaporated to dryness, to give a pale yellow oil. Recrystallization from $CHCl_3$ to give 21-A as a white solid .(1.6 g, 66%. yield). $^1$H NMR(300 MHz, $CDCl_3$) δ 4.32(1H), 3.67(3H), 3.59(2H), 2.71(1H) 2.39(1H), 2.20(2H), 2.10–1.70(5H), 1.43(9H), 1.38(3H), 1.20(3H), 0.93(3H); IR (nujol) 1741, 1733, 1617, 1430, 1396, 1359, 1343, 1218, 1202, 1185, 1174, 1157, 1127, 1014, 771 cm$^{-1}$; MS (FAB) m/z (rel. intensity) 368 (M+H, 99), 369 (22), 368 (99), 312 (15),280 (12), 197 (72), 169 (23), 137 (29), 109 (38), 70 (11), 57 (14). Anal. Calcd for $C_{20}H_{33}NO_5$: C, 65.37; H, 9.05; N, 3.81. Found: C, 65.53; H, 8.88; N, 3.83.

(1R-cis)-[3-Carboxy-1,2,2-trimethylcyclopentyl] carbonyl-L-proline 1,1-dimethylethyl ester 21-B To a solution of the diester 21-A (0.74 g, 2.0 mmol) in methanol (5 mL) is added a solution of $LiOH.H_2O$ (0.15 g, 3.62 mmol) in aq $H_2O_2$ (30%, 2 mL) and water (5 mL). After overnight stirring, the mixture is evaporated until all of the methanol is gone, and then cooled in an ice water bath and brought to pH5 using 1N aq. HCl. The resultant white precipitate is isolated by suction filtration (with water washes, 3×30 mL) to give 21-B as a white solid (0.45 g, 63% yield).

$^1$H NMR(300 MHz, $CDCl_3$) δ 4.34(1H), 3.60(2H), 2.75 (1H) 2.41(1H), 2.18(1H), 2.00–1.70(5H), 1.44(9H), 1.43 (3H), 1.22(3H), 1.02(3H).

[1R-[1α,3α(S*)]]-N-([3-[[[1-Carbomethoxy-2-[4-[(2,6-dichlorophenyl)methoxy]phenyl]ethyl]amino]carbonyl]-1, 2,2-trimethylcyclopentyl]carbonyl]-L-proline 1,1-dimethylethyl ester 21-C A solution of the acid 21-B (0.41 g, 1.16 mmol) in methylene chloride (20 mL) under $N_2$ is cooled in an ice water bath. To this is added diisopropylethyl amine (2 mL), EDC (0.26 g, 1.36 mmol), HOBT (0.19 g, 1.41 mmol) and dimethylaminopyridine (0.02 g, 0.16 mmol). Forty minutes later, 7-E-2 (7-E: $R^4$=H, $R^5$=$CO_2CH_3$, $R^6$=4-[(2,6-Dichlorophenyl)methoxy)phenyl] (0.45 g, 1.27 mmol) is added in one portion. After three days, the mixture is evaporated to dryness, giving a colorless oil which is mixed with THF (100 mL) and water (50 mL) and then shaken sequentially with water (2×50 mL), aq. HCl (0.5N, 4×30 mL), satd. aq. $NaHCO_3$(2×50 mL), and water (2×50 mL). The organic layer is then evaporated to dryness, giving a colorless oil (0.91 g) which is chromatographed on silica gel with 10% methanol/chloroform to give 21-C as a white, foamy solid (0.57 g, 70% yield). #

$^1$H NMR(300 MHz, $CDCl_3$) δ 7.31–6.87(7H), 5.80(1H), 5.18(2H), 4.81(1H), 4.25(1H), 3.67(3H), 3.53(2H), 3.04 (2H), 2.44–1.58(9H), 1.37(9H), 1.33(3H), 1.13(3H), 0.90 (3H). IR (nujol) 1739, 1658, 1622, 1612, 1585, 1511, 1439, 1298, 1241, 1204,1177, 1153, 1122, 1017, 768 cm$^{-1}$; MS (FAB) m/z (rel. intensity) 689 (M+H, 24), 689 (24), 520 (69), 519 (32), 518 (99), 336 (44), 280 (21), 161 (24), 159 (40), 109 (75), 57 (22).

Preparation of Example 200

[1R-[1α,3α(S*)]]-N-[[3-[[[1-Carboxy-2-[4-[(2,6-dichlorophenyl)methoxy]phenyl]ethyl]amino]carbonyl]-1, 2,2-trimethylcyclopentyl]carbonyl]-L-proline 1,1-dimethylethylester, monosodium salt (Example 200)

To a solution of 21-C (0.43 g, 0.62 mmol) in methanol is added a solution of $LiOH.H_2O$ (0.083 g, 1.98 mmol) in aqueous $H_2O_2$ (30%, 3 mL) plus $H_2O$ (3 mL). After overnight stirring, the mixture is diluted with water (50 mL) and evaporated in vacuo until the methanol is gone. The aqueous layer is then washed with diethyl ether (3×30 mL) and brought to pH6 using 1 N aq. HCl. The resultant white precipitate is isolated by suction filtration to give a white solid (0.4 g). This is stirred overnight with $NaHCO_3$ (0.1 g, 1.2 mmol) in $H_2O$ (5 mL). The aqueous solution is brought to pH7–8 using 1 N HCl and then transferred to a C-18.HPLC column and eluted with a gradient of 0–12% acetonitrile/aq. $Na_2CO_3$ (0.02%). Evaporation is accomplished in vacuo to give [1R-[1 α,3α(S*)]]-N-[[3-[[[-Carboxy-2-[4-[(2,6-dichlorophenyl)methoxy]phenyl]ethyl] amino]carbonyl]-1,2,2-trimethylcyclopentyl]carbonyl]-L-proline 1,1-dimethylethylester, monosodium salt as a white solid (0.2 g, 46%)

$^1$H NMR(DMSO-$d_6$) δ 7.55–7.41(3H), 7.01(2H), 6.82 (2H), 6.80(1H), 5.13(2H), 4.08(1H), 3.90(1H), 3.65(1H), 3.40(1H), 3.31(3H), 2.95(2H), 2.44(1H), 2.25–1.5(8H), 1.34 (9H), 1.23(3H), 1.08(3H), 0.76(3H).IR (nujol) 3405, 1735, 1610, 1565, 1511, 1439, 1299, 1240, 1195, 1175, 1153, 1093, 1018, 779, 769 cm−1; MS (FAB) m/z (rel. intensity) 675 (M+H, 0), 720 (27), 701 (25), 700 (67), 699 (39), 698 (99), 336 (32), 280 (23), 159 (20), 109 (53), 23 (28). HRMS (FAB) m/z calcd for $C_{35}H_{44}Cl_2N_2O_7$ +Na 697.2424, found 697.2418.

Scheme 22

Example 216

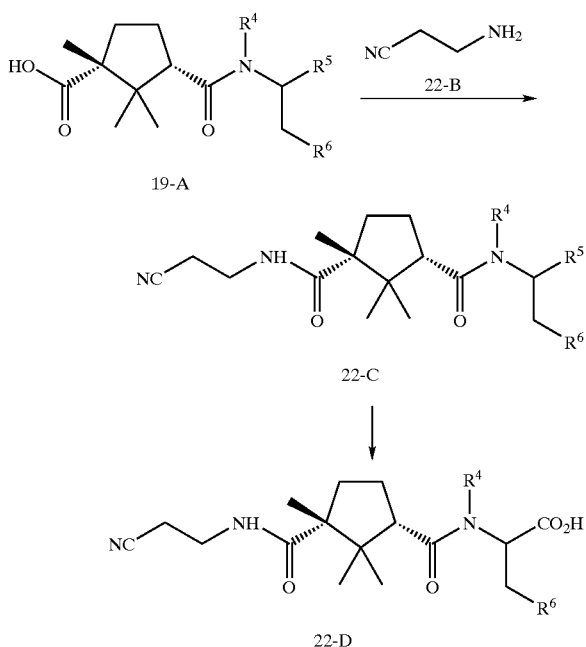

Preparation 22-C-1

Scheme 22, 22-C: wherein $R^4$=H, $R^5$=$CO_2CH_3$ $R^6$= 4-[(2,6-Dichlorobenzoyl)amino]phenyl, Stereochemistry=(1S-cis)-L (1S-cis)-N-[[3-[[(2-Cyanoethyl)amino]carbonyl]-2,2,3-trimethylcyclopentyl]carbonyl]-4-[(2,6-dichlorobenzoyl)amino]-L-phenylalanine methyl ester (22-C-1) ($C_{30}H_{34}Cl_2N_4O_5$)

A solution of 19-A-1 (19-A: $R^4$=H, $R^5$=$CO_2CH_3$, $R^6$=4-[(2,6-Dichlorobenzoyl)amino]phenyl) (0.5 g, 0.91 mmol), HOBT (0.12 g, 0.91 mmol), and DCC (0.18 g, 0.91 mmol are stirred together in $CH_2Cl_2$ (dry, 10 mL) in a dry round bottom flask under a nitrogen atmosphere. After 30 minutes, 2-cyanoethyl amine 22-B (0.064 g, 0.91 mmol) is added. After 24 hours a precipitate is observed and methanol (5 mL) is added to achieve a homogenous solution and an additional portion of 2-cyanoethyl amine 22-B (0.064 g, 0.91 mmol) is added. After an additional 8 days of stirring the solvent is removed in vacuo and the residue is dissolved in THF and purified by chromatography on a column of silica gel to give 22-C-1 (0.42 g, 78%) as a white solid.

$^1$H-NMR (300 MHz, MeOH-$d_4$): δ 7.58(2H), 7.43(3H) 7.22(2H), 5.48(1H), 4.72(1H), 3.69(3H), 3.58(2H), 3.29 (1H), 3.02(1H), 2.65–2.77(3H), 2.40(1H), 2.04(1H), 1.76 (1H), 1.47(1H), 1.27(3H), 1.20(3H), 0.74(3H); Anal. Calcd for $C_{30}H_{34}Cl_2N_4O_7$-0.54$H_2O$: C, 58.95; H, 5.78; N, 9.17; Found: C, 59.04; H, 5.75; N 9.22; KF Water 1.59%.

Preparation of Example 216

Scheme 22, 22-D: wherein $R^4$=H $R^6$=4-[(2,6-Dichlorobenzoyl)amino]phenyl, Stereochemistry= (1S-cis)-L (1S-cis)-N-[[3-[[(2-Cyanoethyl)amino]carbonyl]-2,2,3-trimethylcyclopentyl]carbonyl]-4-[(2,6-dichlorobenzoyl)amino]-L-phenylalanine (Example 216) ($C_{29}H_{32}Cl_2N_4O_5$)

To the L-phenylalanine methyl ester 22-C-1 (22-C: $R^4$=H, $R^5$=$CO_2CH_3$, $R^6$=4-[(2,6-Dichlorobenzoyl)amino]phenyl) (0.16 g, 0.266 mmol), in methanol (10 mL) is added a mixture of LiOH.$H_2O$ (0.056 g, 1.33 mmol), in $H_2O$ (3 mL). The mixture is allowed to stir at room temperature for 2 hours, then the solvent is removed in vacuo. The resulting solid is dissolved in water (10 mL) and the pH is adjusted to ca. 2 with 1N aq. HCl to give a white precipitate. the precipitate is isolated by filtration, washed with water (10 mL) and then dissolved in acetonitrile (25 mL). The organic phase is dried ($Na_2SO_4$) and the solvent is removed in vacuo to give a sticky solid which is dissolved in acetonitrile/water (25 mL, 1:3) and lyophilized to give 0.104 g (67%) of the target compound as a white solid.

$^1$H-NMR (300 MHz, MeOH-$d_4$): δ 7.82(1H), 7.57(2H), 7.46(3H), 7.24(2H), 4.72(1H), 3.40(2H), 3.30(1H), 2.99 (1H), 2.63–2.77(3H), 2.40(1H), 2.03(1H), 1.74(1H), 1.48 (1H), 1.27(3H), 1.20(3H), 0.75(3H); IR(nujol): 3317, 3262, 1762, 1673, 1638, 1608, 1540, 1515, 1432, 1325, 1203, 811, 801, 780 cm$^{-1}$; MS (FAB) m/z (rel. intensity) 587(M$^+$, base), 517(12.4), 335(9.8), 252(8.5), 235(80); Anal. Calcd for $C_{29}H_{32}Cl_2N_4O_7$-2.14$H_2O$: C, 55.64; H, 5.84; N, 8.95; Found: C, 55.74; H, 5.72; N, 8.99; KF Water 6.16%.

Scheme 23

Examples 217, 218 and 219

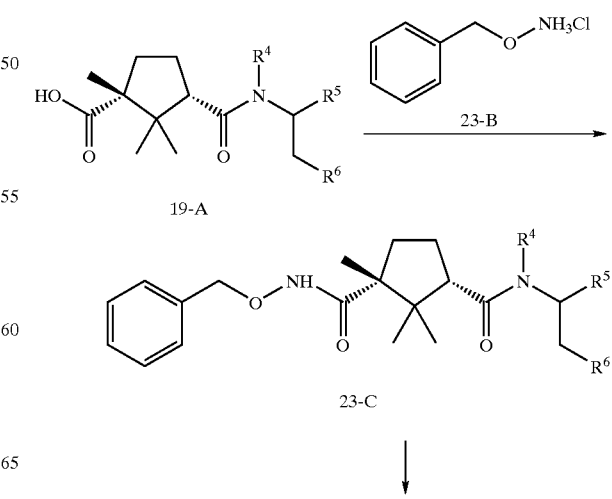

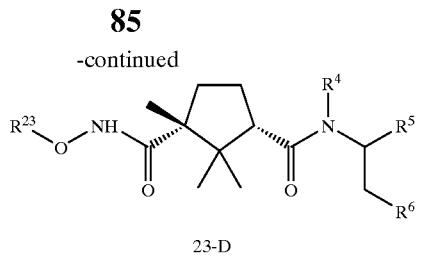

23-D

Preparation 23-C-1

Scheme 23, 23-C: wherein $R^4$=H, $R^5$=$CO_2CH_3$ $R^6$= 4-[(2,6-Dichlorobenzoyl)amino]phenyl, Stereochemistry=(1S-cis)-L (1S-cis)-4-[(2,6-Dichlorobenzoyl)amino]-N-[[2,2,3-trimethyl-3-[[(phenylmethoxy)amino]carbonyl] cyclopentyl]carbonyl]-L-phenylalanine methyl ester (23-C-1) ($C_{34}H_{37}Cl_2N_3O_6$)

A solution of 19-A-1 (19-A: $R^4$=H, $R^5$=$CO_2CH_3$, $R^6$=4-[(2,6-Dichlorobenzoyl)amino]phenyl) (0.5 g, 0.91 mmol), HOBT (0.14 g, 1.04 mmol), EDC (0.19 g, 1.0 mmol), triethylamine (0.46 mL, 3.28 mmol), and DMAP (0.012 g, 0.1 mmol) are stirred together in $CH_2Cl_2$ (dry, 15 mL) in a dry round bottom flask under a nitrogen atmosphere. Stir for 30 minutes at room temperature and benzyloxyamine-HCl 23-B (0.26 g, 1.64 mmol) is added in one portion. The resulting mixture is allowed to stir for 72 hours at room temperature and the solvent is removed in vacuo. The residue is dissolved in $CHCl_3$ (50 mL) and the solution is washed with 1N aq. HCl (50 mL), saturated aq. $NaHCO_3$ (50 mL), and the organic layer is dried ($MgSO_4$). Concentration in vacuo gives the crude product as a sticky oil which is purified by flash chromatography on a column of silica gel (5% MeOH, 95% $CH_2Cl_2$) to give 0.27 g (45%) of 23-C-1 (23-C: $R^4$=H, $R^5$=$CO_2CH_3$, $R^6$=4-[(2,6-Dichlorobenzoyl)amino]phenyl) as a white solid.

$^1$H-NMR (300 MHz, $CDCl_3$): δ 8.13(1H), 7.57(2H) 7.49 (1H), 7.35(6H), 7.10(2H), 5.78(1H), 4.89 (2H), 3.76(3H), 3.14(2H), 2.47(1H), 2.18(2H), 1.30–1.90(4H), 1.27(3H), 1.15(3H), 0.80(3H); Anal. Calcd for $C_{34}H_{37}Cl_2N_3O_6$-0.24$H_2O$: C, 61.97; H, 5.73; N, 6.38; Found: C, 62.02; H, 5.75; N, 6.39; KF Water 0.66%.

Preparation of Example 217

Scheme 23, 23-D: wherein $R^4$=H, $R^5$=$CO_2H$ $R^6$=4-[(2,6-Dichlorobenzoyl)amino]phenyl, $R^{23}$= Phenylmethyl Stereochemistry=(1S-cis)-L (1S-cis)-4-[(2,6-Dichlorobenzoyl)amino]-N-[[2,2,3-trimethyl-3-[[(phenylmethoxy)amino]carbonyl] cyclopentyl]carbonyl-L-phenylalanine (Example 217) ($C_{33}H_{35}Cl_2N_3O_6$)

A solution of 23-C-1 (23-C: $R^4$=H, $R^5$=$CO_2CH_3$, $R^6$=4-[(2,6-Dichlorobenzoyl)amino]phenyl) (0.075 g, 0.11 mmol) in methanol (10 mL) is treated with a solution of LiOH-$H_2O$ (0.024 g, 0.57 mmol) in water (5 mL) over 5 minutes. The mixture is allowed to stir for 4 hours at room temperature, then the solvent is removed in vacuo. The crude residue is dissolved in water (10 mL), is filtered through a sintered glass funnel and then the solution is brought to ca. pH 4 by the addition of 1N aq. HCl. The resulting solid is isolated by suction filtration, washed with water (2×10 mL), and is then dissolved in acetonitrile-water (25 mL, 1:3). The solution is frozen and lyophilized to give Example 217 (23-D: $R^4$=H, $R^5$=$CO_2H$, $R^6$=4-[(2,6-Dichlorobenzoyl)amino]phenyl, $R^{23}$=phenylmethyl) (0.048 g, 68%) as a white solid.

$^1$H-NMR (300 MHz, MeOH-$d_4$): δ7.85(1H), 7.57(2H), 7.32–7.49(8H), 7.24(2H), 4.81(1H), 4.70(1H), 3.21(1H), 2.98(1H), 2.69(1H), 2.24(1H), 1.98(1H), 1.72(1H), 1.40 (1H), 1.25(3H), 1.15 (3H), 0.71(3H); IR(nujol): 3264, 3195, 3063, 3032, 1731, 1658, 1607, 1562, 1538, 1516, 1432, 1326, 1195, 800 $cm^{-1}$; MS (ES+) m/z 640(M+$H^+$); Anal. Calcd for $C_{33}H_{35}Cl_2N_3O_6$-1.19$H_2O$: C, 59.87; H, 5.69; N, 6.35; Found: C, 59.70; H, 5.78; N, 6.37; KF Water 3.24% .

Preparation of Example 218

Scheme 23, 23-D: wherein $R^4$=H, $R^5$=$CO_2CH_3$ $R^6$= 4-[(2,6-Dichlorobenzoyl)amino]phenyl, $R^{23}$=H Stereochemistry=(1S-cis)-L (1S-cis)-4-[(2,6-Dichlorobenzoyl)amino]-N-[[3-[(hydroxyamino)carbonyl]-2,2,3-trimethylcyclopentyl] carbonyl]-L-phenylalanine methyl ester (Example 218) ($C_{27}H_{31}Cl_2N_3O_6$)

A solution of 23-C-1 (23-C: $R^4$=H, $R^5$=$CO_2CH_3$, $R^6$=4-[(2,6-Dichlorobenzoyl)amino]phenyl) (0.7 g, 1.07 mmol) in THF (120 mL) is hydrogenated over Pd(OH)$_2$ (0.42 g) under 46 psi of hydrogen for 2.75 hours. The catalyst is removed by filtration through a pad of Celite®, the filter cake is rinsed with THF (75 mL) and the solvent is removed in vacuo to afford the crude product as a sticky solid. The crude material is purified by flash chromatography on a column of silica gel (EtOAc/HOAc, 99.9:0.1) to give Example 218 (23-D: $R^4$=H, $R^5$=$CO_2CH_3$, $R^6$=4-[(2,6-Dichlorobenzoyl)amino] phenyl, $R^{23}$=H) (0.34 g, 56%) as a white solid.

$^1$H-NMR (300 MHz, MeOH-$d_4$): δ7.58(2H), 7.31–7.49 (3H), 7.22(2H), 4.72(1H), 3.69(3H), 3.18(1H), 2.99(1H), 2.73(1H), 2.29(1H), 2.02(1H), 1.75 (1H), 1.42(1H), 1.27 (3H), 1.18(3H), 0.75(3H); IR(nujol): 3313, 3292, 3245, 3194, 3129, 3073, 1749, 1668, 1653, 1606, 1547, 1517, 1459, 1434; 1336, 1211, 1021, 801, 779 $cm^{-1}$; MS (FAB) m/z (rel. intensity): 564($M^+$+H, 71), 548(3), 531(base), 109(95).

Preparation of Example 219

Scheme 23, 23-D: wherein $R^4$=H, $R^4$=$CO_2H$ $R^6$=4-[(2,6-Dichlorobenzoyl)amino]phenyl, $R^{23}$=H Stereochemistry=(1S-cis)-L (1S-cis)-4-[(2,6-Dichlorobenzoyl)amino]-N-[[3-[(hydroxyamino)carbonyl]-2,2,3-trimethylcyclopentyl] carbonyl]-L-phenylalanine (Example 219) ($C_{26}H_{29}Cl_2N_3O_6$)

A solution of Example 218 (0.14 g, 0.25 mmol) in methanol (8 mL) is treated with a solution of LiOH-$H_2O$ (0.053 g, 1.27 mmol) in water (4 mL) over 15 minutes. The mixture is allowed to stir for 1.5 hours at room temperature, then the solvent is removed in vacuo. The residue is dissolved in water (25 mL), the pH is adjusted to ca. 4 with 1N aq. HCl, and the mixture is extracted with ethyl acetate (3×25 mL). The combined organic extracts are dried ($MgSO_4$), and concentrated in vacuo to give the crude material as a sticky solid. The crude product is dissolved in acetonitrile/water (25 mL, 1:3), and the solution is frozen and lyophylized to provide Example 219 (23-D: $R^4$=H, $R^5$=$CO_2H$, $R^6$=4-[(2,6-Dichlorobenzoyl)amino]-phenyl, $R^{23}$=H) (0.098 g, 71%) as a beige solid.

$^1$H-NMR (300 MHz, MeOH-$d_4$): δ7.57(2H), 7.40–7.47 (3H) 7.24(2H), 4.71(1H), 3.20(1H), 2.99(1H), 2.69(1H), 2.29(1H), 2.03(1H), 1.75(1H), 1.43(1H), 1.28(3H), 1.18

(3H), 0.76(3H); IR(nujol): 3262, 3197, 3127, 3070, 1725, 1657, 1607, 1584, 1562, 1535, 1516, 1432, 1326, 1234, 1194, 800, 781 cm$^{-1}$; MS(FAB) m/z (rel. intensity): 550 (M$^+$+H, 70), 517(75), 198(base); Anal. Calcd for C$_{26}$H$_{29}$Cl$_2$N$_3$O$_6$·0.95H$_2$O: C, 55.02; H, 5.49; N, 7.40; Found: C, 55.29; H, 5.93; N, 7.26; KF Water 3.02%.

Scheme 24

Example 196

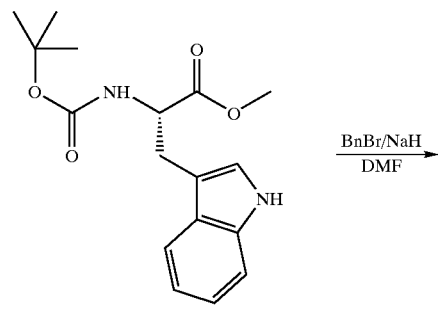

24-A

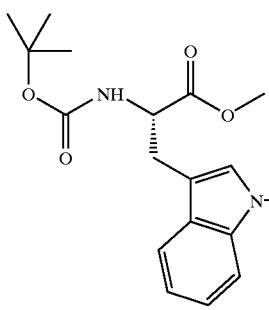

24-B

Boc-Tryptophan-O-methyl ester 24-A (636 mg, 2.00 mmol, 1 eq) was dissolved in dry DMF. To this solution NaH (88 mg, 2.20 mmol, 1.1 eq) was added with evolution of H$_2$. To this mixture benzyl bromide (285 μL, 2.40 mmol, 1.2 eq) was added and the reaction stirred for 3 hours at room temperature. The reaction was quenched with brine (15 mL) and extracted with Et$_2$O (3×15 mL). The combined organics were dried (Na$_2$SO$_4$), filtered and the solvent removed in vacuo. The residue was purified by column chromatography (SiO$_2$, Hexanes to 30%EtOAc/Hexanes gradient elution) to provide 426 mg (52%) of the benzyl indole 24-B.

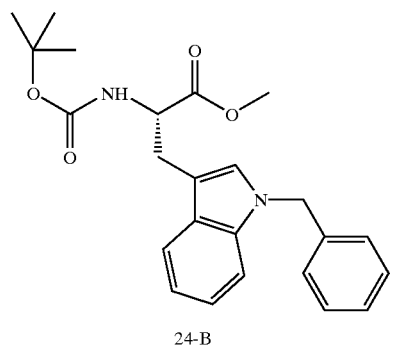

24-B

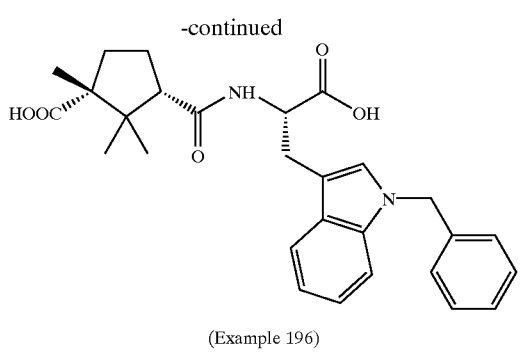

(Example 196)

The final compound Example 196 was produced as described in Example 2. ESMS (m/z): 475 (M−H)$^-$.

Scheme 25

Example 190

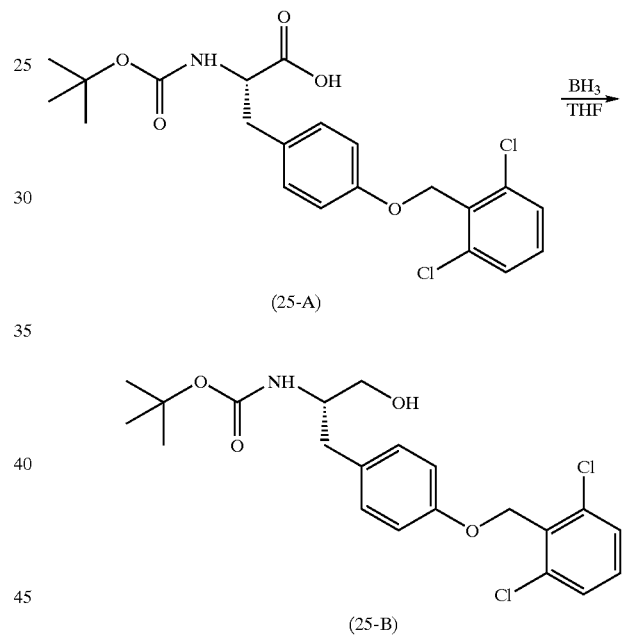

-continued

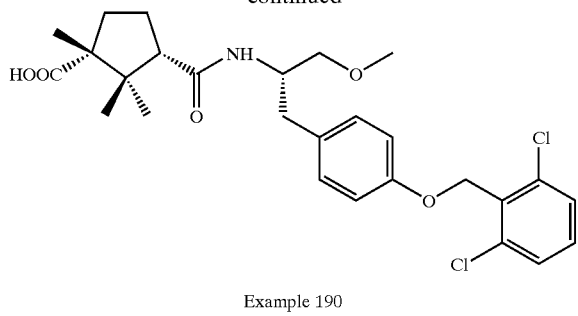

Example 190

The preparation of Example 190 is as follows. Boc Tyr(2,6-dichlorobenzyl)-OH (25-A) (1.31 gm, 2.97 mmol) was dissolved in THF (5 mL) and cooled to −78° C. under dry $N_2$. $BH_3$ THF (5.9 mL, 5.9 mmol, 1N) was added and the reaction warmed slowly to room temperature with stirring for 3 hours. The reaction was cooled to 0° C. and quenched with $H_2O$ (1 mL) and warmed to room temperature. After the addition of 1 N HCl (25 mL), the mixture was extracted with EtOAc (3×25 ml) and the combined organic phases were dried over $Na_2SO_4$. The solution was filtered, solvent evaporated and the residue chromatographed ($SiO_2$, gradient elution: 100% hexanes→50% EtO Ac/hexanes) to provide the intermediate 25-B (665 mg, 53%): ESMS (m/z) 448 (M+Na)⁺.

The above compound, (25-B) (270 mg, 0.634 mmol), was dissolved dry DMF (5 mL) containing methyl iodide (51 µl, 0.824 mmol). To this solution was added NaH (28 mg, 0.697 mmol: in 60% oil) and the mixture was stirred for 5 minutes. The reaction was quenched with the addition of $H_2O$ (1 mL) followed by 1N HCl (10 ml). The mixture was extracted with EtOAc (3×15 mL) and the combined organics were dried over $Na_2SO_4$. The solution was filtered, solvent evaporated and the residue chromatographed ($SiO_2$, gradient elution: 100% hexanes→25% EtOAc/hexanes) to provide intermediate 25-C (130 mg, 47%): ESMS (m/z)462(M+Na)⁺.

25-C (115 mg, 0261 mmol) was dissolved in 3 N HCl/ EtOAc (3 mL) and stirred for 1 h. The solvent was removed under reduced pressure and dried thoroughly under high vacuum. The residue was dissolved in THF (5 mL) and DIEA (228 µL, 1.31 mmol) and (1R)-camphoric anhydride (57 mg, 0.314 mmol) was added. The reaction was warmed to 60° C. with stirring for 48 h. After cooling to room temperature, 1N HCl (15 mL) was added and the mixture extracted with EtOAc (3×15 mL). The combined organics were dried over $Na_2SO_4$, filtered and the solvent removed under reduced pressure. The residue was then chromatographed ($SiO_2$, gradient elution: 100% hexanes→100% EtOAc) to provide Example 190 (113 mg. 83%): ESMS (m/z) 422 (MH⁺).

Scheme 26

Examples 227–229

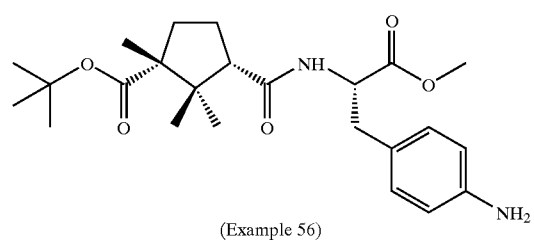

(Example 56)

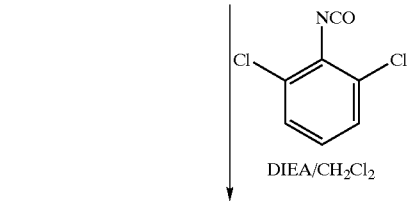

DIEA/CH₂Cl₂

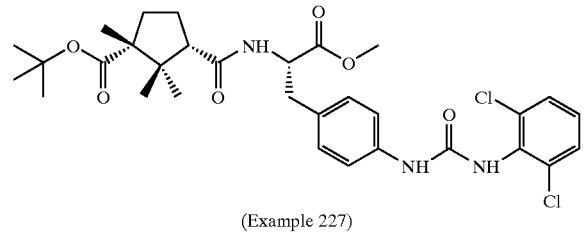

(Example 227)

TFA
CH₂Cl₂

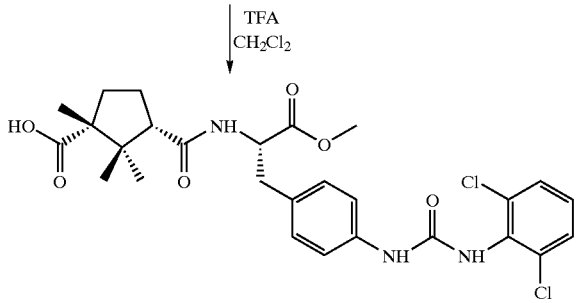

(Example 228)

LiOH

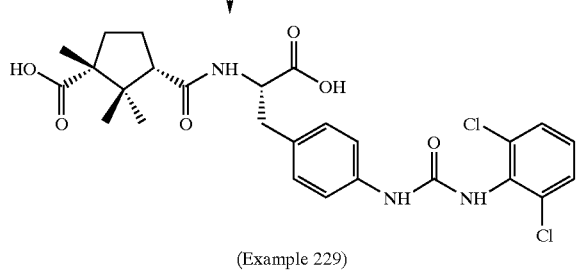

(Example 229)

Example 56 (0.27 gm, 0.62 mmol) was dissolved in $CH_2Cl_2$ (10 mL) and 2,6-dichlorophenylisocyanate (0.18 gm, 0.94 mmol) and DIEA (327 µL, 1.86 mmol) was added and the reaction stirred overnight. After the addition of 1 N HCl (20 mL), the mixture was extracted with EtOAc (3×25 mL) and the combined organic phases were dried over $Na_2SO_4$. The solution was filtered, solvent evaporated and the residue chromatographed (SiO$_2$, gradient elution: 100% hexanes→33% EtOAc/hexanes) to provide Example 227 (310 mg, 82%): ESMS (m/z) 620 (MH$^+$).

Example 227 (250 mg, 0.40 mmol) was dissolved in CH$_2$Cl$_2$ (1.5 mL) and TFA (1.5 mL). After 1 h, the solvent was removed and the residue triturated with Et$_2$O (3×5 mL) to form a gum. The residue was purified by column chromatography (SiO$_2$, gradient elution: 100% hexanes 25% acetone/hexanes) to provide Example 228 (170 mg, 736): ESMS (m/z) 564 (MH$^+$).

Example 228 (130 mg, 0.23 mmol) was dissolved in THF/CH$_3$OH (5 mL/1mL, respectively) and LiOH (22 mg, 0.53 mmol) was added in H$_2$O (1 mL). After 2 h the solvent was evaporated and the residue dissolved in H$_2$O (3 mL). The solution was precipitated with the addition of 1 N HCl (2 mL). The solvent was collected by vacuum filtration and washed with cold H$_2$O (2×2 mL) The solid material was then thoroughly dried under high vacuum to afford Example 229 (80 mg, 64%) as a white solid: ESMS (m/z) 550 (MH$^+$).

Scheme 27 is as follows:

Example 54 (387 mg, 0.704 mmol) and morpholine (0.14 mL, 1.55 mmol) were dissolved in CH$_2$Cl$_2$ (15 mL). This solution was treated with BOP-Cl (215 mg, 0.845 mmol) and stirred under dry N$_2$ at room temperature. After 18 h the reaction was treated with 1 N HCl (10 mL) and extracted with CH$_2$Cl$_2$ (3×15 mL). The combined organics were dried over Na$_2$SO$_4$, filtered and the solvent evaporated. The residue was then purified by column chromatography (SiO$_2$, gradient elution: 100% hexanes→100% EtOAc) to provide Example 226 (160 mg, 37%) as a colorless oil: ESMS (m/z) 618 (M+Na)$^+$.

The methyl ester (Example 226) (160 mg, 0.258 mmol), was dissolved in THF (5 mL) and LiOH (12 mg, 0.52 mmol) was added in H$_2$O (5 mL). After 4 h 1 N HCl (3 mL) was added and the precipitate collected by vacuum filtration washing with cooled H$_2$O (3×3 mL). The product was thoroughly dried under high vacuum to provide Example 225 (148 mg, 95%) as an amorphous powder: ESMS (m/z) 602 (M–H).

Scheme 27

Example 225 and 226

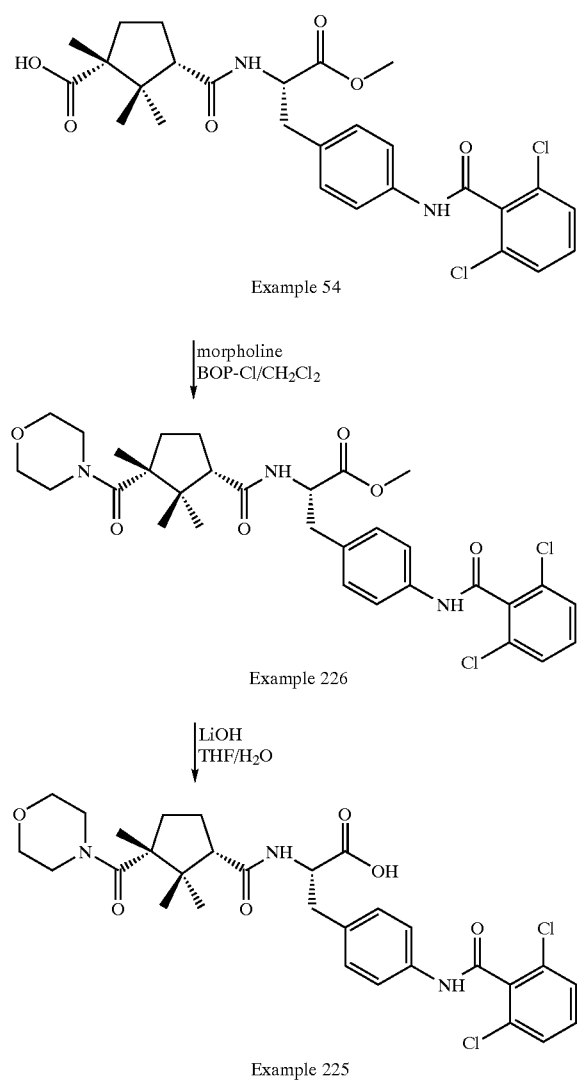

Scheme 28

Example 236

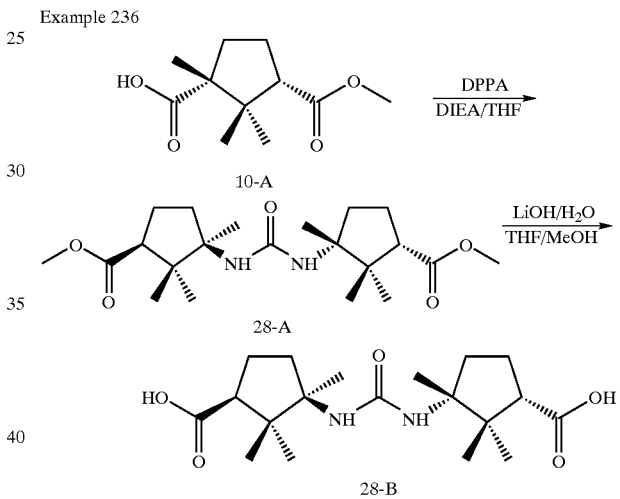

Intermediate Used in Solid Phase Synthesis

Intermediate Urea. Camphoric acid methyl ester (10-A) (2.15 g, 11.65 mmol) was dissolved in THF (25 mL). To this solution was added DPPA (diphenylphosphoryl azide) (3.33 g, 12.1 mmol) and DIEA (1.73 g, 13.4 mmol). The reaction was warmed at 45° C. with stirring. After 2.5 h tert-butyl alcohol was added and heated at 85° C. for an additional 2.5 h. The reaction was worked-up by removing the volatile components under reduced pressure. The residue was then purified by flash chromatography (SiO$_2$, gradient elution: 2% EtOAc/hexanes→20% EtOAc/hexanes) to provide the symmetrical urea diester (28-A) (2.0 g, 43%): ESMS (m/z) 397 (MH$^+$).

The intermediate ester (28-A) (2 g, 5.0 mmol) was dissolved in THF/CH$_3$OH (5 mL/2 mL, respectively) and LiOH (490 mg, 11.6 mmol) was added in H$_2$O (1 mL) After 2 h the solvent was evaporated, and the residue dissolved in H$_2$O (5 mL). The solution was precipitated with the addition of 1 N HCl (15 mL). The solvent was collected by vacuum filtration and washed with cold H$_2$O (2×2 mL). The solid material was then thoroughly dried under high vacuum to afford the intermediate symmetrical urea diacid (28-B) (1.6 g, 89%) as a white solid: ESMS (m/z) 369 (MH$^+$).

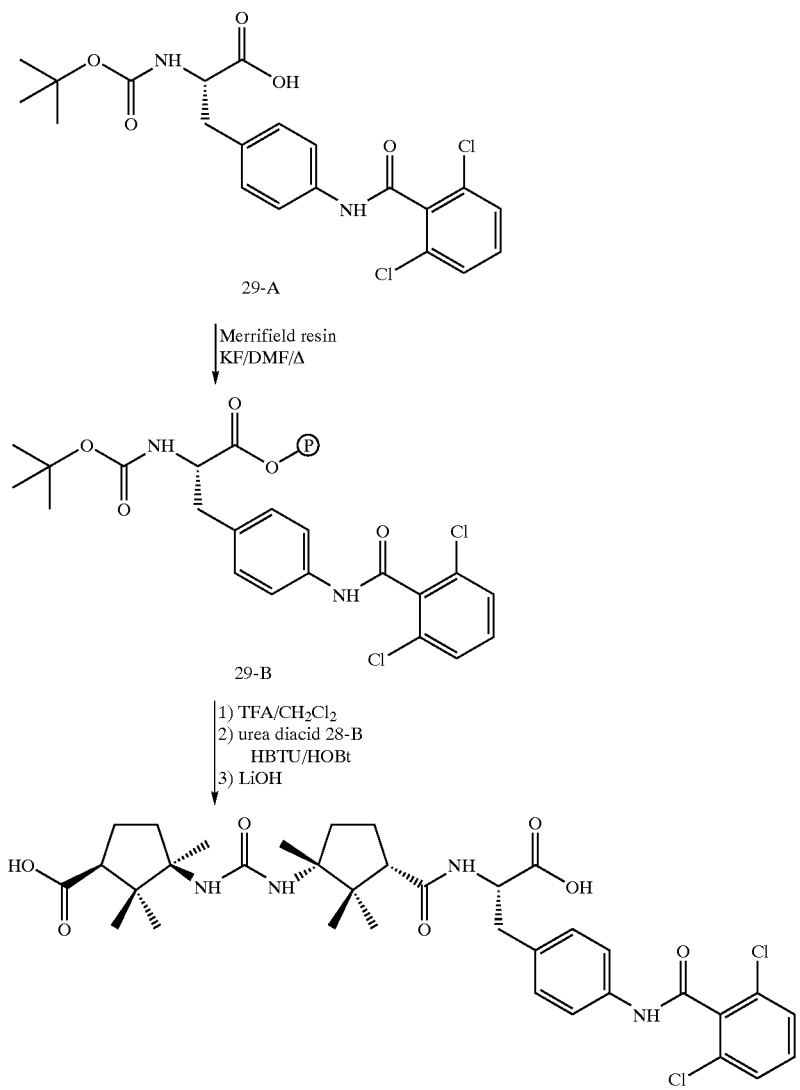

Example 236

To a solution of N-(tert-butoxycarbonyl)-4-(2,6-dichlorobenzamido)-L-phenylalanine (29-A) (9.25 g, 20.3 mmol) in DMF (100 mL) was added Merrifield resin (10.0 g, 10.0 meq/g) and anhydrous potassium fluoride (1.57 g, 20.0 mmol). The reaction mixture was stirred for 1 day at 80° C. and the resulting resin bound amino acid was collected by filtration, washed sequentially with DMF (2×200 mL), 50% aqueous DMF (3×200 mL), $CH_3OH$ (3×300 mL), $CH_2Cl_2$ (3×300 mL) and $CH_3OH$ (3×100 mL) then dried in vacuo to provide the resin bound N-(tert-butoxycarbonyl)-4-(2,6-dichlorobenzamido)-L-phenylalanine (29-B) (0.53 meq/g). Substitution of the Boc (L)Phe[4-(2,6-dichlorobenzamido)]—OH onto the resin was estimated using the picric acid method.

To the obtained resin (29-B) (150 mg, 0.107 mmol) was added 50% $TFA/CH_2Cl_2$ (3 mL) and the mixture was shaken for 30 min. The resin was collected by filtration, washed sequentially with $CH_2Cl_2$ (2×10 mL), $CH_3OH$ (2×10 mL), and $CH_2Cl_2$ (2×10 mL). To the washed resin was added the symmetrical urea diacid (28-B) (118 mg, 0.320 mmol), 0.5 M DMF solution of HBTU-HOBT (0.70 mL, 0.320 mmol), DIEA (0.139 mL, 0.799 mmol) and DMF (3.0 mL) and the mixture was vortexed for 2 hrs. at room temperature. The resin was collected by filtration, washed sequentially with DMF (2×10 mL), $CH_2Cl_2$ (2 10 mL), $CH_3OH$ (2×10 mL), $CH_2Cl_2$ (2×10 mL). To the resin bound substrate was added THF (1.6 mL), $CH_3OH$ (0.5 mL) and 2N LiOH (0.310 mL) and the mixture was shaken for 15 mins. The supernatant was collected by filtration and the resin washed with THF/5% $CH_3OH$ (2×2 mL) and the combined filtrate was evaporated on a Pierce block evaporator. The concentrate was diluted with $H_2O$ (1 mL) and the aqueous solution acidified with 1N HCl (1.5 mL). The precipitate was collected by centrifugation and the solid washed with $H_2O$ (3×3 mL). The solid material was dried under high vacuum to furnish Example 236 (25 mg, 33%): ESMS (m/z) 701 (M–H)⁻.

Scheme 30

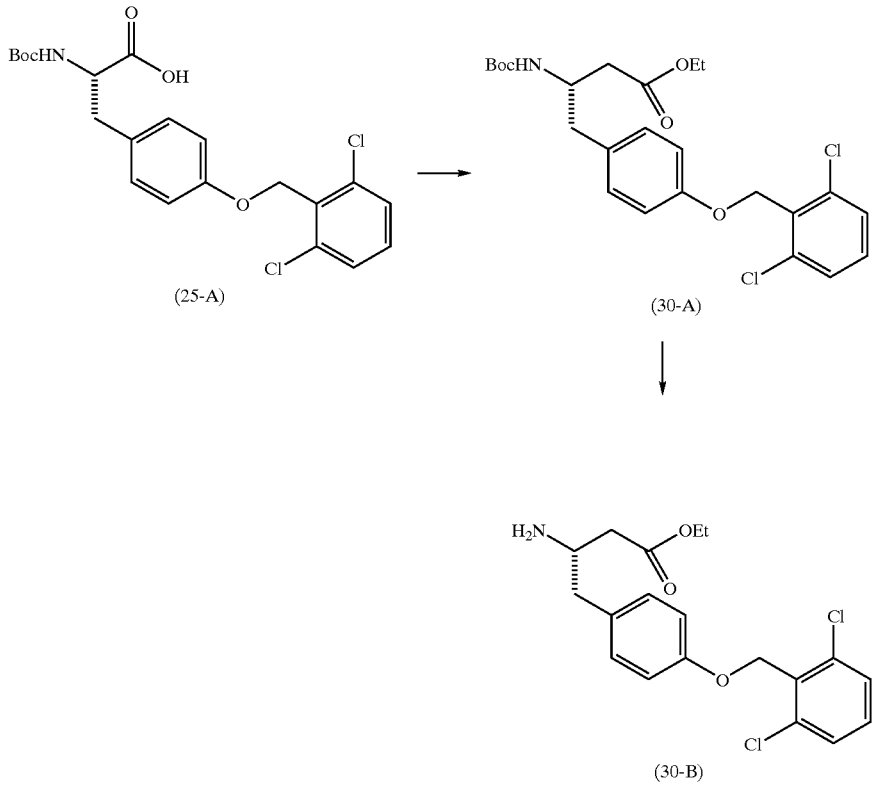

Scheme 2, III-a: wherein $R^4$ H, $R^{5a}$=—CH$_2$CO$_2$Et, $R^6$=4-[(2,6-Dichlorophenyl)methoxy]-phenyl
Stereochemistry=(S)

Intermediate for Examples 201 and 204

(S)-4-[(2,6-Dichlorophenyl)methoxy]-β-[[(1,1-Dimethyl-ethoxy)carbonyl]amino]benzenebutanoic acid ethyl ester (30-A) (C$_{24}$H$_{29}$Cl$_2$NO$_5$)

To a mixture of Boc-O-[(2,6-dichlorophenyl)-methyl]-L-tyrosine (25-A) (5.0 g, 11.36 mmol) and N-methylmorpholine in dry Et$_2$O at −10° C. under Ar is added isobutyl chloroformate (1.49 mL, 11.36 mmol). The reaction is warmed to room temperature, stirred for 1 h, and filtered. The filtrate is reacted at 0° C. with an excess of ethereal CH$_2$N$_2$. The solution is stirred for 1 h at 0° C., and then is concentrated. The residue is dissolved in absolute EtOH, and a solution of C$_6$H$_5$CO$_2$Ag (2.86 g, 12.38 mmol) in Et$_3$N (14 mL) is added slowly. The resulting mixture is stirred for 1 h at room temperature under Ar and filtered. The filtrate is concentrated to a dark brown paste. The product is purified by silica flash chromatography (9:1 and 8:2 hexanes/EtOAc), from which is isolated 2.95 g (6.09 mmol, 54%) of 30-A: TLC R$_f$=0.32 (7:3 hexanes/EtOAc); [α]$_D$ (C=0.9, CHCl$_3$)=−2°; IR (mull) 3360, 2984, 2954, 2925, 2869, 2855, 1721, 1678, 1585, 1524, 1510, 1467, 1447, 1441, 1378, 1373, 1299, 1263, 1251, 1236, 1197, 1177, 1163, 1020, 1016, 783 cm$^{-1}$; $^1$H NMR δ1.27 (3H), 1.41 (9H), 2.38–2.57 (2H), 2.73–2.96 (2H), 4.10–4.20 (3H), 7.22–7.26 (1H), 7.37 (2H); MS (FAB) m/z 482, 426, 382, 364, 348, 338, 319, 294, 268, 216, 159, 133, 116, 107, 57; Anal. C 59.67, H 6.09, Cl 14.59, N 3.03 (calcd C 59.75, H 6.06, Cl 14.70, N 2.90).

(S)-4-[(2,6-Dichlorophenyl)methoxyl]-β-aminobenzenebutanoic acid ethyl ester (C$_{19}$H$_{21}$Cl$_2$NO$_3$). A solution of the Boc-aminoester (30-A) (0.74 g, 1.53 mmol) in 1:1 CH$_2$Cl$_2$/TFA at 0° C. under Ar is stirred for 30 min at 0° C. and for 1.5 h at room temperature. It is concentrated, azeotroped thrice with toluene, and dried to give the aminoester (30-B) as a solid: TLC R$_f$=0.15 (EtOAc); $^1$H NMR (CHCl$_3$) δ1.24 (3H), 2.63–2.73 (2H), 2.77–2.92 (1H), 3.07–3.23 (1H), 3.64–3.82 (1H), 4.15 (2H), 5.23 (2H), 6.97 (2H), 7.13 (2H), 7.16–7.25 (1H), 7.36 (2H), 8.16 (2H); MS (FAB) m/z 382, 365, 348, 294, 268, 224, 159, 133, 116, 70.

Scheme 31

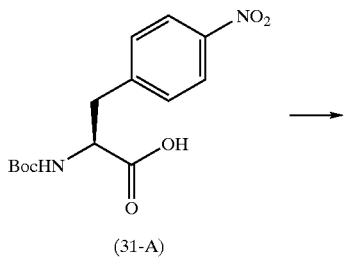

(31-A)

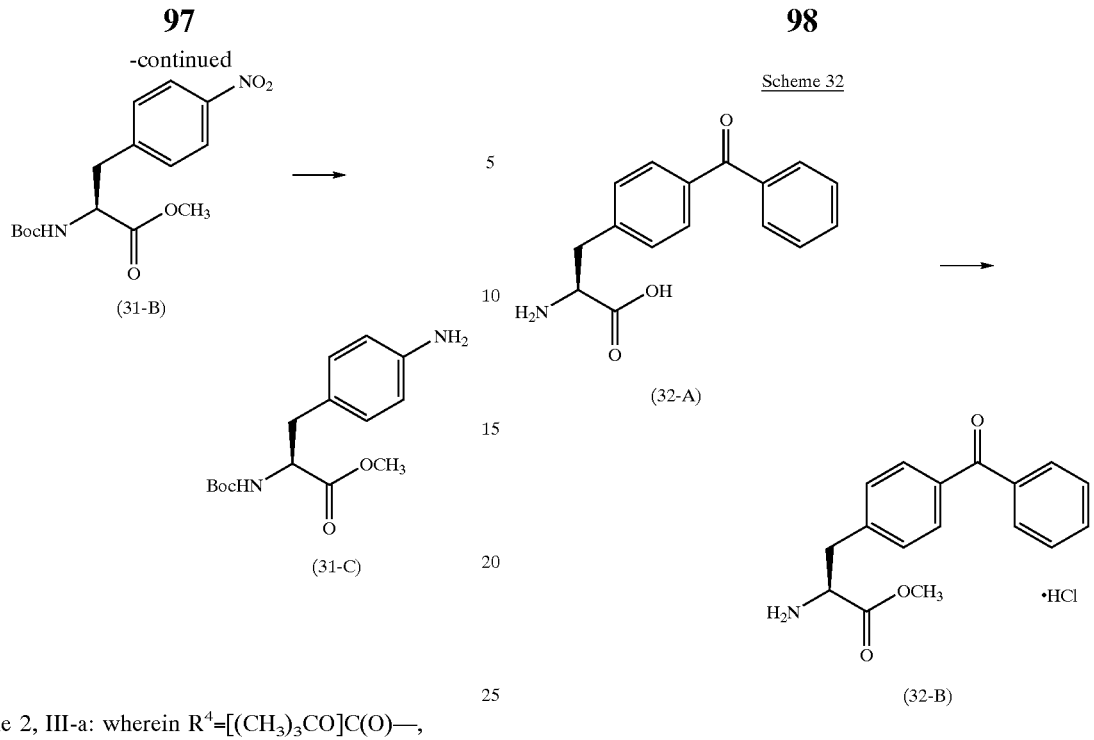

Scheme 2, III-a: wherein R⁴=[(CH₃)₃CO]C(O)—, R⁵ᵃ =—CO₂Me, R⁶=4-aminophenyl-, Stereochemistry=L Intermediate for Examples 208, 209, 210

N-[(1,1-Dimethylethoxy)carbonyl]-4-nitro-L-phenylalanine methyl ester (31-B) ($C_{15}H_{20}N_2O_6$). A solution of N-Boc-4-nitrophenylalanine (31-A) (25.2 g, 81.28 mmol) and DMAP (0.82 g, 6.7 mmol) in dry DMF is cooled to 0° C. under Ar, and treated with MeOH (7.55 mL, 186 mmol) and DCC (18.975 g, 91.04 mmol). The reaction mixture is stirred overnight at room temperature and filtered. The filtrate is washed with satd NaHCO₃ and brine. The aqueous washes are back-extracted with CH₂Cl₂. The organics are dried, filtered and concentrated to a yellow solid. This product is purified by silica flash chromatography (3:1 hexanes/EtOAc) to give 24.6 g (75.85 mmol, 93%) of 31-B: TLC $R_f$=0.36 (7:3 hexanes/EtOAc); ¹H NMR (CHCl₃) δ1.41 (9H), 3.12 (1H), 3.28 (1H), 3.73 (3H), 4.63 (1H), 5.05 (1H), 7.31 (2H), 8.16 (2H); ¹³C NMR δ28.25, 38.38, 52.56, 54.08, 80.35, 123.67, 130.25, 144.03, 147.12, 154.90, 171.64.

4-Amino-N-[(1,1-dimethylethoxy)carbonyl]-L-phenylalanine methyl ester (31-C) ($C_{15}H_{22}N_2O_4$). A solution of the above product (2.87 g, 8.85 mmol) in MeOH is treated at room temperature under N₂ with 10% Pd/C (0.190 g), and hydrogenated at 40 psi for 3.5 h. The reaction mixture is filtered, and the filtrate is concentrated to give (31-C) as a dark foam: TLC $R_f$=0.34 (1:1 EtOAc/hexane); ¹H NMR (CHCl₃) δ 1.42 (9H), 2.97 (2H), 3.48 (2H), 3.70 (3H), 4.51 (1H), 4.93 (1H), 5.05 (1H), 6.61 (2H), 6.90 (2H); MS (EI) m/z 294, 238, 221, 207, 193, 177, 161, 135, 118, 106, 91, 77, 57.

Scheme 2, III-a: Wherein R⁴=H.HCl, R⁵ᵃ =—CO₂CH₃, R⁶=4-benzoylphenyl-, Stereochemistry=L Intermediate to Examples 40, 191 and 197

4-Benzoyl-L-phenylalanine methyl ester, HCl salt (32-B) ($C_{17}H_{17}NO_3$.HCl). To cold MeOH (100 mL) under N₂ is added AcCl (10 mL). The solution is stirred at room temperature for 30 min. 4-Benzoyl-L-phenylalanine (32-A) (0.99 g, 3.7 mmol) is treated with the methanolic HCl solution (60 mL) at room temperature for 26 h. The reaction mixture is concentrated to give 1.05 g of the aminoester.HCl salt (32-B) as a solid: TLC (UV) $R_f$=0.40 (95:5 CHCl₃MeOH); HPLC $t_R$=3.0 min (isocratic 650:350:1 CH₃CN/H₂O/TFA); ¹H NMR (CD₃OD) δ 7.80–7.70 (4H), 7.68–7.60 (1H), 7.55–7.41 (4H), 4.84 (2H), 4.44 (1H), 3.82 (3H), 3.44–3.27 (2H); ¹³C NMR (CD₃OD) δ196.66, 168.86, 139.22, 137.29, 136.91, 132.59, 130.34, 129.62, 129.35, 128.23, 53.56, 52.39, 35.83.

Scheme 33

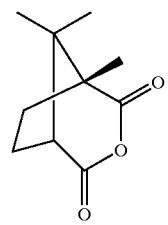

(33-A)

(1S)-1,8,8-Trimethyl-3-oxabicyclo[3.2.1]octane-2,4-dione [(1S)-camphoric anhydride] (33-A) (1S-cis)-1,2,2-Trimethylcyclopentane-1,3-dicarboxylic acid) [(1S,3R)-camphoric acid] (1.0 g, 5 mmol) and acetic anhydride (10 mL) were heated at reflux for 3 h. The reaction was cooled and the solvent was removed on a rotovap (bath temp 60° C.). To the remainder of the material, saturated NaHCO₃ (2 mL) was added. The aqueous portion was extracted with CH$_2$Cl$_2$ (3×5 mL), dried and concentrated in vacuo to 1.08 g. This was triturated with methyl-t-butyl ether to afford after filtering 0.94 g (103%) of (1S)-Camphoric anhydride (33-A): mp 222–223° C.; [α]$_D$+3.8° (c=0.8, toluene); $^1$H NMR (CDCl$_3$) δ 1.01, 1.10 , 1.27 , 1.89–2.35, 2.84; $^{13}$C NMR (CDCl$_3$) ppm 172.7, 170.0, 54.33, 53.8, 43.7, 33.5, 24.5, 20.8, 20.2, 14.1; IR (mineral oil mull) 2925, 1804, 1763, 1180, 1128, 1043, 983, 943 cm$^{-1}$; MS for C$_{10}$H$_{14}$O$_3$, m/z (relative intensity) 169 (1), 138 (37), 123 (17), 110 (16), 95 (100); Anal. Calcd for C$_{10}$H$_{14}$O$_3$: C, 65.92; H, 7.75. Found: C, 65.86; H, 7.74.

Scheme 34

Example 194

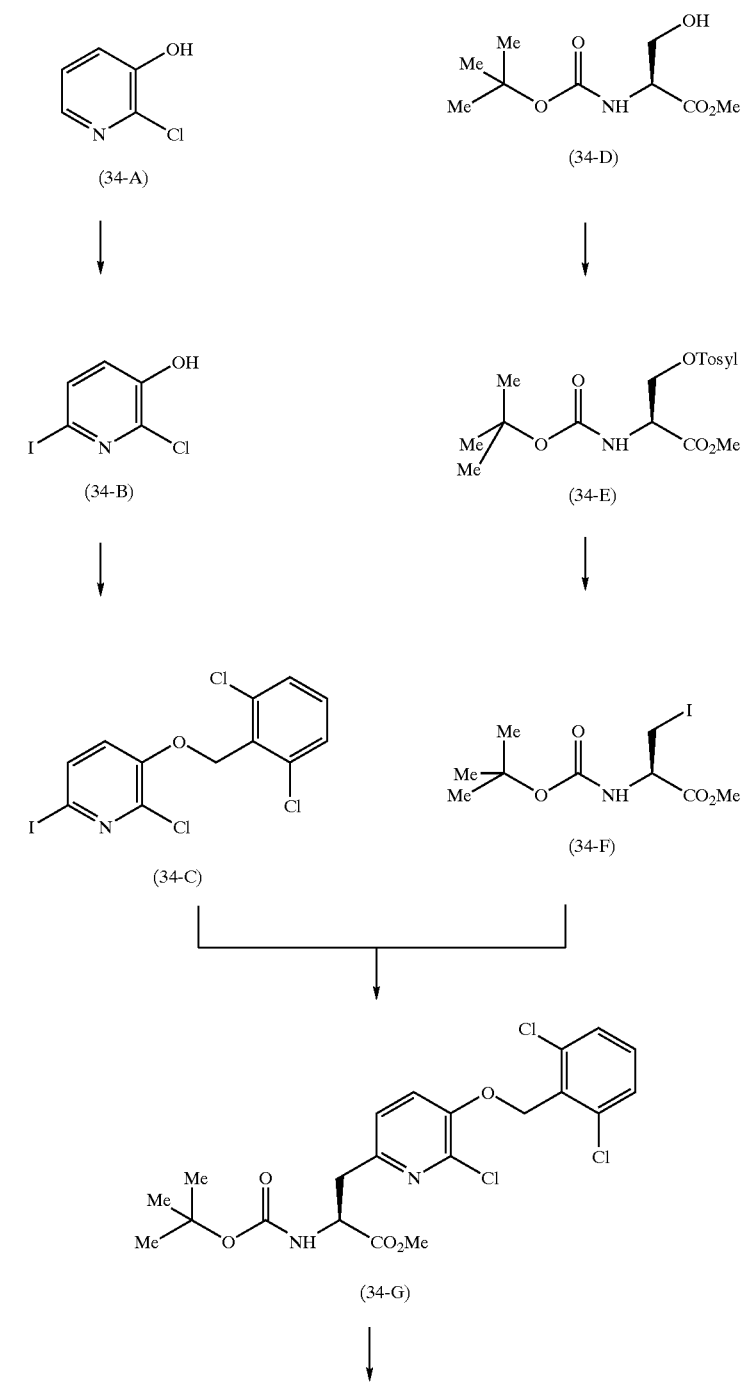

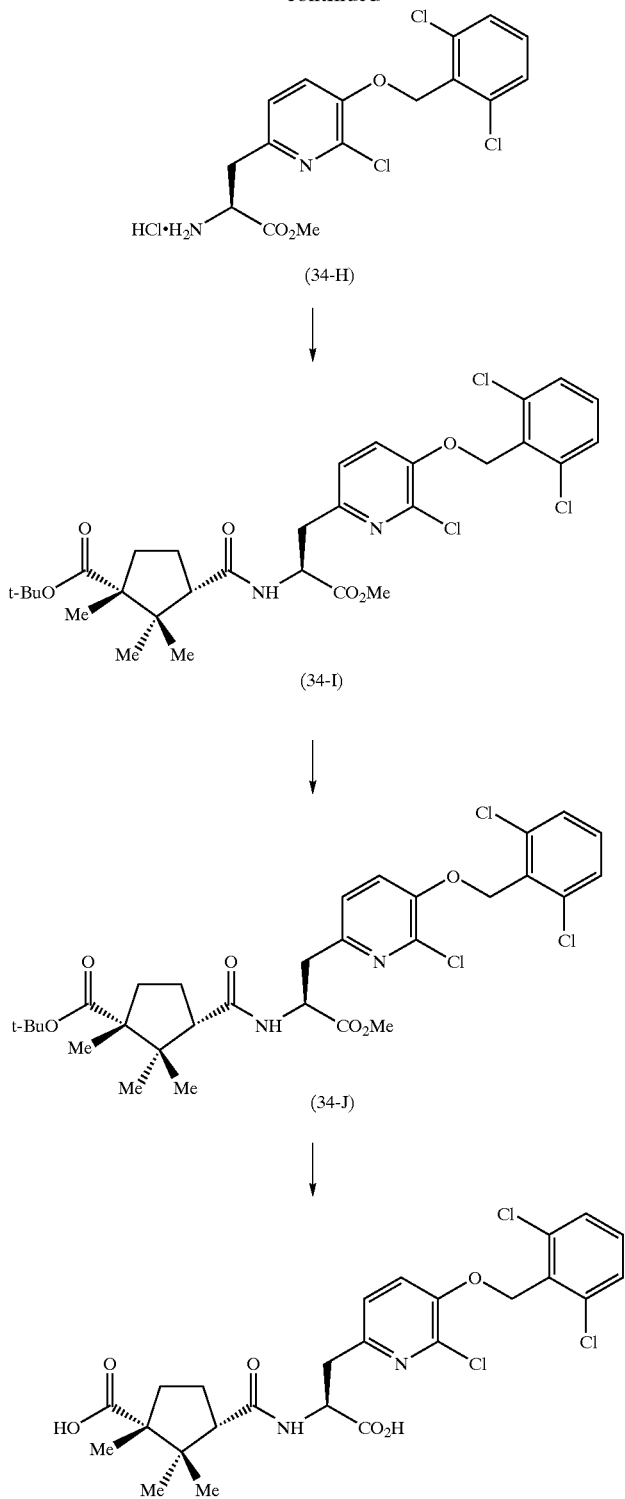

(34-H)

(34-I)

(34-J)

Example 194

Preparation of Intermediate (34-B) (C₅H₃ClINO)

To a solution of 2-chloro-3-hydroxypyridine (34-A) (10.2 g, 78.7 mmol) and K₂CO₃ (38.87 g, 0.27 mol) in H₂O (120 mL) at rt is added I₂ (24.33 g, 95.8 mmol) The solution is stirred at rt for 4 h, and the reaction then is quenched with satd aqueous Na₂S₂O₅·5H₂O. The pH of the reaction mixture is adjusted to pH 2 with 12 M aqueous HCl. The mixture is extracted with EtOAc (3×100 mL), and the combined EtOAc portions dried (MgSO₄), filtered and concentrated to a yellow solid. Recrystallization of this solid from 120:25 heptane/EtOAc (145 mL) gives 11.2 g (43.8 mmol, 56%) of intermediate (34-B): IR 3113, 3068, 3056, 3021, 2991, 2955, 2925, 2871, 2855, 2832, 2808, 2749, 2668, 2601, 2530, 1554, 1457, 1398, 1304, 1289, 1226, 1086, 828, 711, 617 cm$^{-1}$; $^1$H NMR (DMSO-d$_6$) δ7.06 (1H), 7.59 (1H), 11.06 (1H); $^{13}$C NMR (DMSO-d$_6$) δ 101.18, 127.02, 134.98, 138.07, 150.68; Anal. C 23.32, H 1.23, Cl 13.73, N 5.42 (calcd C 23.51, H 1.18, Cl 13.88, N 5.48).

Preparation of Intermediate 34-C' ($C_{12}H_7Cl_3INO$)

To a mixture of (34-B) (5.11 g, 20.0 mmol), Ph$_3$P (5.30 g, 20.0 mmol) and 2,6-dichlorobenzyl alcohol (3.54 g, 20.0 mmol) in dry THF (100 mL) at 0° C. is added dropwise DEAD (3.15 mmol, 20.0 mmol). The reaction mixture is stirred an additional 1.5 h at 0° C. and 1.5 h at rt, and then is concentrated. The reaction product is purified by silica flash chromatography (85:15 hexanes/EtOAc) to give 7.61 g (18.36 mmol, 92%) of (34-C) as a white solid: TLC R$_f$=0.57 (7:3 hexanes/EtOAc); $^1$H NMR (DMSO-d$_6$) δ5.34 (2 H), 7.48 (1H), 7.55–7.63 (3H), 7.85 (1H); MS (ES) m/z 413.8, 327.9, 288.0, 255.9, 183.0, 150.9, 136.9.

Preparation of Intermediate (34-E) ($C_{16}H_{23}NO_7S$)

To a soluition of N-Boc-L-serine methyl ester (34-D) (10.0 g, 45.6 mmol) in anhydrous pyridine (78 mL) at –10° C. under Ar is added TsCl (10.0 g, 52.4 mmol). The reaction mixture is stirred for 3 h at –10° C., and then kept at –15° C. for 66 h. The reaction is quenched with ice, stirred for 2 h, and then extracted with EtOAc (4×300 mL). The combined EtOAc portions are washed with 0.2 M aqueous KHSO$_4$ (3×300 mL), H$_2$O (300 mL), satd aqueous NaHCO$_3$ (300 mL), and H$_2$O (300 mL); and then dried (Na$_2$SO$_4$), filtered and concentrated to a pale yellow-colored oil. The reaction product is purified by silica flash chromatography (3:1 hexanes/EtOAc) to give 13.0 g (34.8 mmol, 76%) of (34-E) as an off-white colored solid: TLC R$_f$=0.25 (7:3 hexanes/EtOAc); IR 3400, 2407, 2313, 2291, 1928, 1741, 1708, 1513, 1350, 1245, 1174, 1159, 1060, 995, 941 cm$^{-1}$; $^1$H NMR (CDCl$_3$) δ1.41 (9H), 2.44 (3H), 3.69 (3H), 4.28 (1H), 4.39 (1H), 4.49 (1H), 5.29 (1H), 7.34 (2H), 7.75 (2H); MS (FAB) m/z 747, 527, 374, 319, 318, 274, 146, 102, 57, 41, 29; Anal. C 51.41, H 6.32, N 3.87, S 8.27 (calcd C 51.46, H 6.21, N 3.75, S 8.59).

Preparation of Intermediate (34-F) ($C_9H_{16}INO_4$)

To a solution of (34-E) (12.82 g, 34.3 mmol) in dry acetone (40 mL), in an amber reaction flask at rt under Ar, is added dropwise a solution of NaI (7.73 g, 51.5 mmol) in dry acetone (40 mL). The reaction mixture is stirred at rt for 42 h, and then is concentrated. The residue is dissolved in CHCl$_3$ (300 mL). This CHCl$_3$ solution is extracted with H$_2$O (2×300 mL), aqueous 1 M Na$_2$S$_2$O$_3$.5H$_2$O (300 mL), and H$_2$O (3×300 mL); and then is dried (Na$_2$SO$_4$), filtered, and concentrated to give a yellow oil. The product is purified by silica flash chromatography (4:1 hexanes/EtOAc) to give 9.49 g (28.8 mmol, 84%) of (34-F) as a white solid: TLC R$_f$=0.52 (7:3 hexanes/EtOAc); $^1$H NMR (CDCl$_3$) δ1.45 (9H), 3.56 (2H), 3.79 (3H), 4.51 (1H); MS (FAB) m/z 330, 274, 230, 211, 170, 146, 102, 57, 41.

Preparation of Intermediate (34-G) ($C_{21}H_{23}Cl_3N_2O_5$).

To a dry amberized reaction flask under Ar, containing activated Zn dust (0.777 g, 11.89 mmol) and (34-F) (3.91 g, 11.9 mmol), is added dry THF (11.8 mL) and CH$_3$C(O)N(Me)$_2$ (11.8 mL). Residual O$_2$ is removed by bubbling Ar through the suspension for 5 min. The reaction mixture is stirred at 65±5° C. for 2 h, and then is cooled to 0° C. The PDCl$_2$[P(Ph)$_3$]$_2$ catalyst (0.41 g) is added, folowed immediately by an O$_2$-free solution of (34-C) (2.46 g, 5.94 mmol) in dry 1:1 THF/CH$_3$C(O)N(Me)$_2$ (17.8 mL). The resulting reaction mixture is stirred at 65±5° C. under Ar for 5 h. It is quenched with satd aqueous NH$_4$Cl (150 mL). The resulting mixture is extracted with EtOAc (3×300 mL). The combined EtOAc portions are washed with brine (300 mL), dried (Na$_2$SO$_4$) filtered and concentrated to a yellow-green colored oil. The product is purified by silica flash chromatography (3:1 hexanes/EtOAc) to give 1.90 g (3.88 mmol, 65%) of (34-G): TLC R$_f$=0.32 (7:3 hexanes/EtOAc); IR 3391, 1734, 1702, 1567, 1561, 1508, 1439, 1287, 1256, 1225, 1214, 1198, 1179, 1167, 1152, 1099, 1087, 1070, 1022, 992, 989, 846, 784, 772, 718 cm$^{-1}$; $^1$H NMR (DMSO-d$_6$) δ1.31 (9H), 2.94–3.03 (2H), 3.60 (3H), 4.32 (1H), 5.30 (2H), 7.28 (2H); 7.45–7.58 (3H), 7.76 (1H); MS (ES) m/z 490.8, 434.8, 388.9.

Preparation of Intermediate (34-H) ($C_{16}H_{15}Cl_3N_2O_3$.HCl)

A solution of (34-G) (1.90 g, 3.88 mmol) in 4 M HCl in 1,4-dioxane (35 mL) is stirred at rt under Ar for 20 h. The reaction mixture is concentrated, diluted with H$_2$O (40 mL), and extracted with Et$_2$O (3×40 mL). The Et$_2$O portions are discarded. The aqueous solution is lyophilized to give 1.39 G (326 mmol, 84%) of (34-H) as a beige-colored solid: $^1$H NMR (DMSO-d$_6$) δ3.27 (2H), 3.72 (3H), 4.37 (1H), 5.32 (2H), 7.37 (1H), 7.48 (1H), 7.58 (1H), 7.81 (1H); 8.62 (3H); $^-$CNMR (DMSO-d$_6$) δ36.29, 51.98, 53.14, 66.74, 123.33, 125.04, 129.38, 131.21, 132.50, 136.63, 138.99, 147.02, 149.88, 169.75.

Preparation of Intermediate (34-I) ($C_{30}H_{37}Cl_3N_2O_6$)

To a reaction mixture containing acid (15-D) (0.513 g, 2.0 mmol), EDC (0.403 g, 2.06 mmol), HOBt (0.284 g, 2.10 mmol), DMAP (0.076 g, 0.62 mmol) and (34-H) (0.878 g, 2.06 mmol) in CH$_2$Cl$_2$ (20.4 mL) at 0° C. is added Et$_3$N (1.02 mL, 7.24 mmol). The mixture is stirred for 2 h at 0° C. and 44 h at rt. It is diluted with CH$_2$Cl$_2$ (200 mL). The CH$_2$Cl$_2$mixture is washed with H$_2$O (3×200 mL), 0.5 M aqueous HCl (2×200 mL), satd aqueous NaHCO$_3$ (2×200 mL), and H$_2$O (2×200 mL). The combined aqueous washes are extracted with one portion of CH$_2$Cl$_2$ (200 mL). The combined CH$_2$Cl$_2$ portions are dried (Na$_2$SO$_4$), filtered, and concnetrated to give a yellow-colored oil. The product is purified by silica flash chromatography (3:2 hexanes/EtOAc) to give 0.919 g (1.46 mmol, 73%) of (34-I): TLC R$_f$=0.15 (7:3 hexanes/EtOAc); $^1$H NMR (CDCl$_3$) δ0.82 (3H), 1.18 (3H), 1.31 (3H), 1.38–1.43 (1H), 1.44 (9H), 1.58–1.81 (1H), 2.14–2.27 (1H), 2.49–2.70 (2H), 3.17 (1H), 3.29 (1H), 3.69 (3H), 4.93 (1H), 5.33 (2H), 7.06 (2H), 7.26–7.39 (4H); $^{13}$C NMR (CDCl$_3$) δ14.19, 20.40, 21.93, 22.19, 22.91, 28.07, 32.36, 37.04, 46.41, 51.76, 52.28, 54.50, 56.78, 60.38, 61.17, 66.73, 80.07, 123.08, 123.23, 128.60, 130.92, 130.96, 137.08, 140.97, 149.43, 149.77, 171.71, 172.70, 175.11.

Preparation of Intermediate (34-J) ($C_{26}H_{29}Cl_3N_2O_6$)

To the solid (34-I) (0.910 g, 1.45 mmol) at 0° C. under Ar is added slowly TFA (9 mL). The resulting solution is stirred for 30 min at 0° C. and 2 h at rt. The reaction mixture is concentrated in vacuo, thrice azeotroped with PhCH$_3$, and dried under vacuum to give (34-J) as an amber-colored foam: TLC $R_f$=0.37 (750:250:5 hexanes/EtOAc/HCO$_2$H); IR 3321, 3061, 1746, 1728, 1696, 1655, 1584, 1565, 1523, 1497, 1440, 1355, 1286, 1209, 1200, 1171, 1119, 1094, 1088, 995, 781, 1769, 731, 717, 695 cm$^{-1}$; $^1$H NMR (CDCl$_3$) δ0.87 (3H) 1.26 (3H), 1.33 (3H), 1.46–1.58 (1H), 1.73–1.87 (1H), 2.14–2.30 (1H), 2.53–2.65 (2H), 2.69 (1H), 3.19 (1H), 3.29 (1H), 3.69 (3H), 4.93 (1H), 5.33 (2H), 7.07 (1H), 7.23–7.40 (4H), 10.8 (1H)

Preparation of Example 194 (C$_{26}$H$_{29}$Cl$_3$N$_2$O$_6$)

To a solution of (34-J) (0.908 g, 1.41 mmol) in THF (28.9 mL) is added a solution of LiOH.H$_2$O (0.291 g, 6.94 mmol) in H$_2$O (14.4 mL). The reaction mixture is stirred for 5 h, and then is diluted with H$_2$O (70 mL) It is cooled to 0° C., acidified with 1 M aqueous HCl, and extracted with EtOAc (3×200 mL). The combined EtOAc portions are washed with brine (200 mL), dried (Na$_2$SO$_4$), filtered and concentrated to a viscous colorless oil. The product is purified by silica flash chromatography (200:50:1 hexanes/EtOAc/HCO$_2$H), azeotroped thrice from PhCH$_3$, dissolved in 1:1 CH$_3$CN/H$_2$O (40 mL), and lyophilized to give 0.752 g (1.35 mmol, 96%) of Example 194 as a white solid: mp 120–122° C.; TLC $R_f$=0.28 (200:1 EtOAc/HCO$_2$H); IR 3323, 3064, 2730, 2668, 1714, 1700, 1648, 1584, 1564, 1522, 1440, 1354, 1284, 1235, 1198, 1162, 1118, 1096, 1089, 995, 862, 828, 780, 769, 716 cm$^{-1}$; $^1$H NMR (DMSO-d$_6$) δ0.63 (3H), 1.09 (3H), 1.12 (3H), 1.24–1.37 (1H), 1.46–1.58 (1H), 1.78–1.94 (1H), 2.27–2.43 (2H), 2.62 (1H), 2.96–3.14 (2H), 3.31 (1H), 4.57 (1H), 5.30 (2H), 7.29 (1H), 7.45–7.58 (3H), 7.75 (1H), 7.85 (1H); MS (EI) m/z 556, 538, 379, 353, 335, 301, 159, 142, 123, 109, 95.

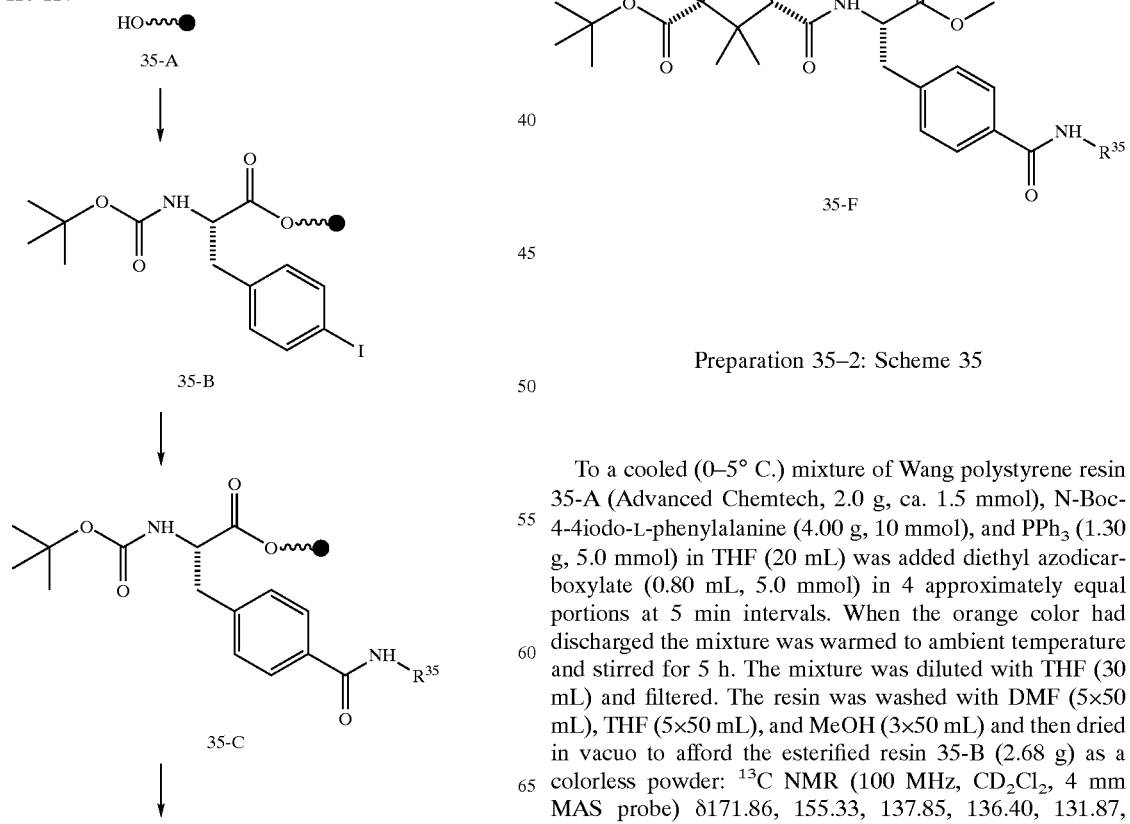

Scheme 35
Examples 220–224

Preparation 35–2: Scheme 35

To a cooled (0–5° C.) mixture of Wang polystyrene resin 35-A (Advanced Chemtech, 2.0 g, ca. 1.5 mmol), N-Boc-4-4iodo-L-phenylalanine (4.00 g, 10 mmol), and PPh$_3$ (1.30 g, 5.0 mmol) in THF (20 mL) was added diethyl azodicarboxylate (0.80 mL, 5.0 mmol) in 4 approximately equal portions at 5 min intervals. When the orange color had discharged the mixture was warmed to ambient temperature and stirred for 5 h. The mixture was diluted with THF (30 mL) and filtered. The resin was washed with DMF (5×50 mL), THF (5×50 mL), and MeOH (3×50 mL) and then dried in vacuo to afford the esterified resin 35-B (2.68 g) as a colorless powder: $^{13}$C NMR (100 MHz, CD$_2$Cl$_2$, 4 mm MAS probe) δ171.86, 155.33, 137.85, 136.40, 131.87, 128.00, 92.74, 80.09, 54.05, 38.05, 28.51.

Preparation 35-C-1: Scheme 35 where $R^{35}$ is 2,4,6-trichlorophenyl.

$N_2$ was bubbled through a mixture of N-Boc-4-iodo-L-phenylalanine functionalized Wang resin (35-B) (500 mg, ca. 0.3 mmol), $PPh_3$ (105 mg, 0.4 mmol), 2,4,6-trichloroaniline (490 mg, 2.5 mmol) and DIEA (1.74 mL, 10 mmol) in NMP (10 mL) for 10 min. $Pd_2dba_3$ (92 mg, 0.1 mmol) was added and the reaction mixture was placed under a CO atmosphere and heated (bath temp. 70° C.) for 18 h. Upon cooling to ambient temperature the mixture was diluted with 3% (w/v) sodium diethyldithiocarbamate in 95:5 NMP:DIEA (10 mL). After an additional 10 min the mixture was filtered and the resin washed with NMP (5×10 mL), THF (3×10 mL), and MeOH (3×10 mL) and dried in vacuo to afford 35-C-1 as a colorless powder.

Preparation 35-D-1: Scheme 35 where $R^{35}$ is 2,4,6-trichlorophenyl.

Resin 35-C-1 was swollen with methylene chloride (0.5 mL) and diluted with 95:5 $TFA:H_2O$ (10 mL). After 90 min the mixture was filtered and the resin washed with TFA (3×5 mL), $CH_2Cl_2$ (3×5 mL) and MeOH (3×5 mL). The combined filtrates were concentrated in vacuo and the residue lyophilized from glacial acetic acid to provide the amino acid 35-D-1 (152 mg, 91%) as a powder which was used without purification: MS (FAB) m/z (rel. intensity) 387 (M+H, 42), 427 (26), 426 (80), 389 (46), 387 (42), 366 (33), 279 (99); 177 (54), 146 (18), 119 (26), 23 (26); HRMS (FAB) calcd for $C_{16}H_{13}Cl_3N_2O_3+H_1$ 387.0070, found 387.0084.

Preparation 35-E-1: Scheme 35 where $R^{35}$ is 2,4,6-trichlorophenyl.

The amino acid 35-D-1 was dissolved in methanolic HCl (20 mL) and heated at 55° C. for 18 h. Concentration in vacuo afforded the methyl ester 35-E-1 which was used without purification: MS (ES+) for $C_{17}H_{15}Cl_3N_2O_3$ m/z 400.9 $(M+H)^+$.

Preparation 35-F-1: Scheme 35 where $R^{35}$ is 2,4,6-trichlorophenyl.

To a cooled (0–5° C.) solution of the methyl ester 35-E-1, 15-D (97 mg, 0.38 mmol), and 1-hydroxy-7-azabenzotriazole (52 mg, 0.38 mmol) in $CH_2Cl_2$/DMF (1:2, 6 mL) was added EDC (73 mg, 0.38 mmol) followed by DIEA (0.23 ml, 1.14 mmol). The solution was gradually allowed to warm to ambient temperature and stirred an additional 16 h. Volatiles were removed in vacuo and the residue partioned between ethyl acetate and 0.25N aq. HCL. The organic layer was washed with saturated aq. $NaHCO_3$ and brine, dried ($MgSO_4$), filtered and concentrated in vacuo. Purification of the residue by flash chromatography using ethyl acetate/$CH_2Cl_2$/hexane (1:1:6) as eluant afforded 35-F-1 (115 mg) as an amorphous powder: $^1$H NMR (300 MHz, $CDCl_3$) δ 7.96 (1H), 7.86 (2H), 7.20 (2H), 5.86 (1H), 4.92 (1H), 3.72 (3H), 3.17 (2H), 2.49 (2H), 2.10 (1H), 1.69 (1H), 1.41 (10H), 1.25 (3H), 1.19 (3H), 0.76 (3H); $^{13}$C NMR (75 MHz, $CDCl_3$) δ174.90, 172.66, 171.88, 165.41, 140.83, 134.42, 133.50, 132.08, 131.27, 129.58, 128.44, 127.97, 80.25, 60.39, 56.64, 54.43, 52.91, 52.47, 46.38, 37.71, 32.33, 28.03, 22.99, 22.51, 21.93, 20.59, 14.17; MS (FAB) m/z (rel. intensity) 639 (M+H, 17), 641 (17), 639 (17), 583 (16), 403 (27), 401 (28), 189 (23), 137 (18), 109 (99), 57 (59), 41 (20); HRMS (FAB) calcd for $C_{31}H_{37}Cl_3N_2O_6+H_1$ 639.1795, found 639.1779.

Preparation of Example 220
(1S-cis)-N-[[(3-Carboxy-2,2,3-trimethylcyclopentyl]carbonyl]-4-[[[(1,1'-biphenyl)-4-yl)amino]-carbonyl]-L-phenylalanine Example 220 was prepared as described in Schemes 35 and 2 starting from 4-aminobiphenyl and 35-B: physical properties as follows: $^1$H NMR (300 MHz, $CD_3OD$) δ7.87 (1H), 7.76 (2H), 7.62 (4H), 7.44 (4H), 7.30 (1H), 4.79 (1H), 3.30 (1H), 3.01 (1H), 2.72 (1H), 2.54 (1H), 2.02 (1H), 1.62 (1H), 1.58 (1H), 1.28 (3H), 1.20 (3H), 0.78 (3H); $^{13}$C NMR (75 MHz, $CD_3OD$) δ179.75, 175.49, 174.98, 168.82, 143.38, 142.03, 139.42, 138.75, 134.74, 130.70, 130.01, 128.86, 128.38, 128.31, 127.87, 122.68, 57.56, 54.69, 47.81, 38.43, 33.87, 23.94, 23.25, 22.57, 21.99; MS (FAB) m/z (rel. intensity) 543 $(M^+, 17)$, 109 (41), 83 (43), 81 (37), 71 (45), 69 (82), 67 (35), 57 (81), 55 (99), 43 (80); HRMS (EI) calcd for $C_{32}H_{34}N_2O_6$ 542.2416, found 542.2429. Anal. Calcd for $C_{32}H_{34}N_2O_6 \cdot 0.5 H_2O$: C, 69.67; H, 6.39; N, 5.08. Found: C, 69.72; H, 6.65; N, 4.75.

Preparation of Example 221
(1S-cis)-[[(3-Carboxy-2,2,3-trimethylcyclopentyl]carbonyl]-4-[[(4-chlorophenyl)amino]-carbonyl]-L-phenylalanine Example 221 was prepared as described in Schemes 35 and 2 starting from 4-chloroaniline and 35-B: physical properties as follows: $^1$H NMR (300 MHz, $CD_3OD$) δ7.85 (2H), 7.68 (2H), 7.40 (2H), 7.36 (2H), 4.82 (1H), 3.29 (1H), 3.05 (1H), 2.81 (1H), 2.54 (1H), 1.96 (1H), 1.70 (1H), 1.24 (1H), 0.91 (3H), 0.86 (3H), 0.77 (3H); $^{13}$C NMR (75 MHz, $CD_3OD$) δ179.74, 175.55, 174.65, 168.73, 143.39, 138.93, 134.55, 130.66, 130.55, 128.86, 123.68, 57.54, 54.62, 47.81, 38.33, 35.92, 33.86, 30.30, 29.00, 26.34, 23.21, 22.51, 21.98, 21.16; HRMS (FAB) calcd for $C_{26}H_{29}ClN_2O_6+H_1$ 501.1792, found 501.1790.

Preparation of Example 222
(1S-cis)-[[(3-Carboxy-2,2,3-trimethylcyclopentyl]carbonyl]-4-[[(2-trifluoromethylphenyl)amino]-carbonyl]-L-phenylalanine Example 222 was prepared as described in Schemes 35 and 2 starting from 2-(triflouromethyl)aniline and 35-B. Physical properties as follows: $^1$H NMR (300 MHz, $CD_3OD$) δ7.86 (2H), 7.66 (4H), 7.40 (2H), 4.78 (1H), 3.30 (1H), 3.10 (1H), 2.72 (1H), 2.49 (1H), 1.98 (1H), 1.62 (1H), 1.48 (1H), 1.28 (3H), 1.20 (3H), 0.78 (3H); $^{13}$C NMR (75 MHz, $CD_3OD$) δ179.70, 175.77, 173.54, 169.59, 143.34, 136.74, 124.18, 133.85, 131.74, 130.73, 128.89, 128.30, 127.13, 123.51, 57.56, 55.05, 62.54, 57.56, 55.05, 54.58, 50.06, 47.80, 38.21, 33.84, 23.89, 23.19, 22.52, 22.30, 21.85; IR (mull) 3302, 1708, 1656, 1613, 1592, 1530, 1508, 1320, 1294, 1260, 1206, 1173, 1123, 1095, 767 cm$^{-1}$; MS (FAB) m/z (rel. intensity) 535 $(M^+, 99)$, 536 (32), 535 (99), 517 (25), 353 (46), 109 (57), 69 (14), 57 (13), 55 (14), 43 (13); HRMS (FAB) m/z calcd for $C_{27}H_{29}F_3N_2O_6+H^1$ 535.2056, found 535.2049. Anal. Calcd for $C_{27}H_{29}F_3N_2O_6 \cdot 0.5 H_2O$: C, 59.66; H, 5.56; N, 5.15. Found: C, 59.75; H, 5.73; N, 4.72.

Preparation of Example 223
(1S-cis)-[[(3-Carboxy-2,2,3-trimethylcyclopentyl]carbonyl]-4-[[(2,4,6-trichlorophenyl)amino]carbonyl]-L-phenylalanine 35-F-1 (110 mg, 0.16 mmol) was deprotected as described in Scheme 2 to afford example 223 (90 mg) as an amorphous powder: $^1$H NMR (300 MHz, $CD_3OD$) δ7.90 (2H), 7.60 (1H), 7.41 (2H), 4.82 (1H), 3.29 (1H), 3.10 (1H), 2.72 (1H), 2.63 (1H), 1.92 (1H), 1.68 (1H), 1.44 (1H), 0.88 (6H), 0.77 (3H); $^{13}$C NMR (75 MHz, $CD_3OD$) δ179.72, 175.52, 174.72, 168.90, 143.97, 136.86, 135.15, 133.59, 133.02, 130.82, 129.66, 129.09, 62.70, 57.53, 54.65, 38.41, 33.85, 23.91, 23.20, 22.53, 21.97; IR (mull) 3263, 3079, 1709, 1657, 1614, 1573, 1556, 1524, 1495, 1287, 1246, 1205, 1190, 869, 857 cm$^{-1}$; MS (ES+) for $C_{26}H_{27}Cl_3N_2O_6$ m/z 568.9 $(M+H)^+$; Anal. Calcd for $C_{26}H_{27}Cl_3N_2O_6$: C, 54.80; H, 4.78; N, 4.92. Found: C, 55.00; H, 5.08; N, 4.64.

Preparation of Example 224

[1S-[α(R*),3α]]-4-[[[(1-Carboxy-3-methylbutyl]-amino]carbonyl]-N-[[(3-carboxy-2,2,3-trimethylcyclopentyl]carbonyl]-L-phenylalanine Example 224 was prepared as described in Schemes 35 and 2 starting from methyl L-leucinate and 35-B: Physical properties as follows: $^1$H NMR (300 MHz, CD$_3$OD) δ7.78 (2H), 7.34 (2H), 4.87 (1H), 4.72 (1H), 3.30 (1H), 3.02 (1H), 2.82 (1H), 2.68 (1H), 1.98 (1H), 1.74 (5H), 1.23 (3H), 0.97 (9H), 0.77 (3H); $^{13}$C NMR (75 MHz, CD$_3$OD) δ179.73, 176.33, 175.23, 174.66, 170.35, 143.05, 133.87, 130.52, 128.72, 62.41, 57.53, 54.63, 52.77, 47.79, 41.51, 38.30, 26.42, 23.90, 23.56, 23.18, 22.51, 21.93; MS (FAB) m/z (rel. intensity) 505 (M$^+$, 99), 506 (27), 505 (99), 487 (20), 109 (29), 71 (20), 69 (34), 57 (34), 55 (33), 43 (36); HRMS (FAB) calcd for C$_{26}$H$_{36}$N$_2$O$_8$+H$_1$ 505.2549, found 505.2570.

Scheme 36

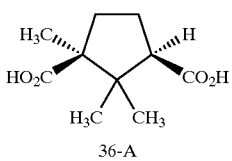

36-A

↓

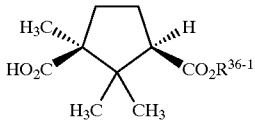

36-B

↓

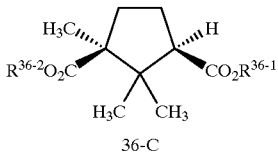

36-C

↓

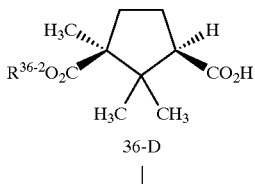

36-D

↓

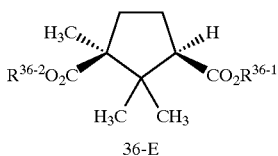

36-E

↙ ↘

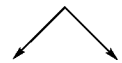

36-F                    36-G

Where R$^{36-1}$ and R$^{36-2}$ are independently defined as —CH$_3$, t-Bu, or —CH$_2$C$_6$H$_5$ and relative configuration is depicted by bold and dotted lines.

Scheme 36 teaches a general method (etherification, epimerization and ester deprotection) for the preparation of selectively protected camphoric acid isomers 36-B, 36-D, 36-G and 36-F.

Scheme 37

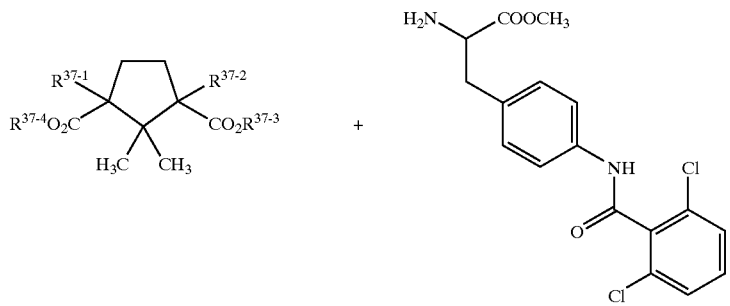

37-A                    37-B

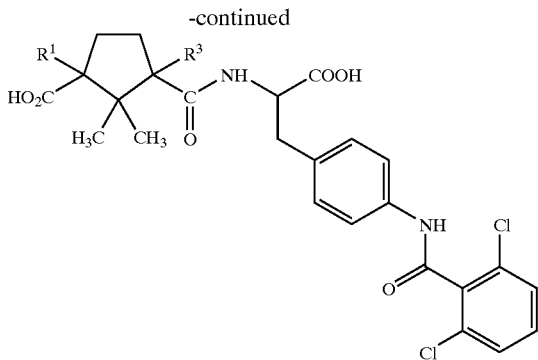

37-C

Where $R^{37-1}$ and $R^{37-2}$ are independently defined as —H or —CH$_3$ and $R^{37-3}$ and $R^{37-4}$ are independently defined as —H, —CH$_3$, t-Bu, or —CH$_2$C$_6$H$_5$.

Scheme 37 teaches methods for the coupling of camphoric acid monoester isomers to isomers of 37-B and ester deprotection for the preparation of isomers of Example 54. 37-C-1 through 37-C-15.

Preparation of Example 237

Scheme 37: 37-C-1 Where $R^3$ is H, $R^1$ is CH$_3$, and the Stereochemistry is (1S-cis) and D-Phenylalanine (1S-cis)-N-[(3-Carboxy-2,2,3-trimethylcyclopentyl) carbonyl]-4-[(2,6-dichlorobenzoyl)amino]-D-phenylalanine (C$_{26}$H$_{28}$Cl$_2$N$_2$O$_6$), 37-C-1 was prepared as follows:

To a solution of (1S-cis)-1,2,2-trimethylcyclopentane-1, 3-dicarboxylic acid 1-(1,1-dimethylethyl)-3-methyl diester (502.7 mg), 15-C, in methylene chloride(8 mL) at 0° C. was added DIEA(1mL), EDC(413.1 mg), HOBT(291.1 mg), and dimethylaminopyridine(26.4 mg). The reaction was stirred at 0° C. for 15 minutes and then 4-[(2,6-dichlorobenzoyl) amino]-D-phenylalanine methyl ester, hydrochloride salt (803 mg), 37-B-2, was added and stirred at ambient temperature for 50 hours. The reaction was diluted with water and extracted with methylene chloride. The extracts concentrated in vacuo and the crude material purified by flash chromatography over silica gel. The crude material was applied to the column by concentrating it on a plug of silica gel and adding this plug to the top of the column. The column was eluted with methanol in methylene chloride to obtain (1S-cis)-N-[[3-[(1,1-Dimethylethoxy)carbonyl]-2,2, 3-trimethylcyclopentyl]carbonyl]-4-[(2,6-dichlorobenzoyl) amino]-D-phenylalanine methyl ester(890 mg). Physical properties as follows: m.p. 265–270° C.; $^1$H NMR (CDCl$_3$) δ7.63 (2H), 7.35 (3H), 7.19 (2H), 4.84 (1H), 3.76 (3H), 3.18 (1H), 3.01 (1H), 2.61 (1H), 2.47 (1H), 2.06 (1H), 1.74 (1H), 1.44 (10H), 1.14 (3H), 1.03 (3H), 0.66 (3H); MS-ESI (m/z): 603 ([M–H$^-$]); MS-ESI (m/z) 605([M+H$^+$]). The deprotection of the carboxylic acids follows that of Examples 53, and 54 to obtain (1S-cis)-N-[(3-Carboxy-2,2,3-trimethylcyclopentyl)carbonyl]-4-[(2,6-dichlorobenzoyl) amino]-D-phenylalanine. Physical properties as follows: m.p. 263–267° C.; $^1$H NMR(300 MHz, DMSO-d$_6$), δ10.6 (1H), 7.83(1H), 7.52(5H), 7.2(2H), 4.45(1H), 3.1(1H), 2.82 (1H), 2.62(1H), 2.3(1H), 1.94(1H), 1.55(1H), 1.3(1H), 1.05 (3H), 0.83(3H), 0.45(3H); MS-ESI (m/z): 533 ([M–H$^-$]); MS-ESI (m/z) 535([M+H$^+$]).

Preparation of Example 238

Scheme 37: 37-C-2 Where $R^3$ is H, $R^1$ is CH$_3$, and the Stereochemistry is (1S-trans) and D-Phenylalanine (1S-trans)-N-[(3-Carboxy-2,2,3-trimethylcyclopentyl) carbonyl]-4-[(2,6-dichlorobenzoyl)amino]-D-phenylalanine (C$_{26}$H$_{28}$Cl$_2$N$_2$O$_6$) 37-C-2 was prepared as follows: The preparation follows that of Preparation 37-C-1. The starting materials are (1S-trans)-1,2,2-trimethylcyclopentane-1,3-dicarboxylic acid 1-(1,1-dimethylethyl)-ester, 36-G-1, and 4-[(2,6-dichlorobenzoyl)amino]-D-phenylalanine methyl ester, hydrochloride salt, 37-B-2. Physical properties as follows: m.p. 158–168° C.; $^1$H NMR(300 MHz, DMSO-d$_6$). δ12.3(1H), 10.5(1H), 7.95(1H), 7.5(5H), 7.19(2H), 4.43 (1H), 3.04(1H), 2.80(1H), 2.66(1H), 1.97(2H), 1.66(1H), 1.42(1H), 0.96(3H), 0.70(3H), 0.44(3H); MS-ESI (m/z): 533 ([M–H$^-$]); MS-ESI (m/z): 535([M+H$^+$]).

Preparation of Example 239

Scheme 37: 37-C-3 Where $R^3$ is H, $R^1$ is CH$_3$, and the Stereochemistry is (1S-trans) and L-Phenylalanine (1S-trans)-N-[(3-Carboxy-2,2,3-trimethylcyclopentyl) carbonyl]-4-[(2,6-dichlorobenzoyl)amino]-L-phenylalanine (C$_{26}$H$_{28}$Cl$_2$N$_2$O$_6$), 37-C-3 was prepared as follows:

The preparation follows that of Preparation 37-C-1. The starting materials are (1S-trans)-1,2,2-trimethylcyclopentane-1,3-dicarboxylic acid 1-(1,1-dimethylethyl)-ester, 36-G-1, and 4-[(2,6-dichlorobenzoyl) amino]-L-phenylalanine methyl ester, hydrochloride salt, 37-B-1. Physical properties as follows: m.p. 172–178° C.; $^1$H NMR(300 MHz, DMSO-d$_6$) δ 10.6(1H), 7.93(1H), 7.5 (5H), 7.19(2H), 4.43(1H) 2.98(1H), 2.86(1H) 2.68(1H), 2.01(2H), 1.89(1H), 1.63(1H), 1.43(1H), 1.02(3H), 0.99 (3H), 0.72(3H); MS-ESI (m/z): 533 ([M–H$^-$]).

Preparation of Example 240

Scheme 37: 37-C-4 Where R $^3$is H, $R^1$ is CH$_3$, and the Stereochemistry is (1R-trans) and L-Phenylalanine (1R-trans)-N-[(3-Carboxy-2,2,3-trimethylcyclopentyl) carbonyl]-4-[(2,6-dichlorobenzoyl)amino]-L-phenylalanine (C$_{26}$H$_{28}$Cl$_2$N$_2$O$_6$), 37-C-4 was prepared as follows: The preparation follows that of Preparation 37-C-1. The starting materials are (1R-trans)-(1,2,2-trimethylcyclopentane-1,3-dicarboxylic acid 1-(1,1-dimethylethyl)-ester, 36-G-2, and 4-[(2,6-dichlorobenzoyl)amino]-L-phenylalanine methyl ester, hydrochloride salt, 37-B-1. Physical properties as follows: m.p. 168–170° C.; $^1$H NMR(300 MHz, DMSO-d$_6$). δ12.3(2H), 10.6(1H), 7.96(1H), 7.51(5H), 7.20(2H), 4.43 (1H), 3.05(1H), 2.80(1H), 1.97(2H), 1.66(1H), 1.42(1H), 0.96(3H), 0.70(3H), 0.44(3H); MS-ESI (m/z): 533 ([M−H$^−$]); MS-ESI (m/z): 535 ([M+H$^+$]).

Preparation of Example 241

Scheme 37: 37-C-5 Where R$^3$ is H, R$^1$ is CH$_3$, and the Stereochemistry is (1R-trans) and D-Phenylalanine (1R-trans)-N-[(3-Carboxy-2,2,3-trimethylcyclopentyl) carbonyl]-4-[(2,6-dichlorobenzoyl) amino]-D-phenylalanine (C$_{26}$H$_{28}$Cl$_2$N$_2$O$_6$) 37-C-5 was prepared as follows: The preparation follows that of Preparation 37-C-1. The starting materials are (1R-trans)-1,2,2-trimethylcyclopentane-1,3-dicarboxylic acid 1-(1,1-dimethylethyl)-ester, 36-G-2, and 4-[(2,6-dichlorobenzoyl)amino]-D-phenylalanine methyl ester, hydrochloride salt, 37-B-2. Physical properties as follows: m.p. 158–165° C.; $^1$H NMR(300 MHz, DMSO-d$_6$). δ 10.6(1H), 7.93(1H), 7.51(5H), 7.19(2H), 4,43(1H), 2.98(1H), 2.86(1H), 2.68 (1H), 2.02(1H), 1.88(1H), 1.62(1H), 1.43(1H), 1.021(3H), 0.99(3H), 0.73 (3H); MS-ESI (m/z): 533 ([M−H$^−$]); MS-ESI (m/z): 535((M+H$^+$]).

Preparation of Example 242

Scheme 37: 37-C-6 Where R$^3$ is H, R$^1$ is CH$_3$, and the Stereochemistry is (1R-cis) and D-Phenylalanine (1R-cis)-N-[(3-Carboxy-2,2,3-trimethylcyclopentyl) carbonyl]-4-[(2,6-dichlorobenzoyl)amino]-D-phenylalanine (C$_{26}$H$_{28}$Cl$_2$N$_2$O$_6$), 37-C-6 was prepared as follows: The preparation follows that of Preparation 37-C-1. The starting materials are (1S-cis)-1,2,2-trimethylcyclopentane-1,3-dicarboxylic acid 1-(1,1-dimethylethyl)-ester, 36-D, and 4-[(2,6-dichlorobenzoyl)amino]-D-phenylalanine methyl ester, hydrochloride salt, 37-B-2. Physical properties as follows: m.p. 166–170° C.; $^1$H NMR(300 MHz, DMSO-d$_6$) δ10.65(1H), 7.81(1H), 7.51(5H), 7.20(2H), 4.44(1H), 2.99 (1H), 2.85(1H), 2.68(1H), 2.34(1H), 1.88(1H), 1.52(1H), 1.30(1H), 1.15(3H), 1.10(3H), 0.65(3H); MS-ESI (m/z): 533 ([M−H$^−$]); MS-ESI (m/z): 535([M+H$^+$]).

Preparation of Example 243

Scheme 37: 37-C-7 Where R$^3$ is H, R$^1$ is CH$_3$, and the Stereochemistry is (1R-cis) and L-Phenylalanine (1R-cis)-N-[(3-Carboxy-2,2,3-trimethylcyclopentyl) carbonyl]-4-[(2,6-dichlorobenzoyl)amino]-L-phenylalanine (C$_{26}$H$_{28}$Cl$_2$N$_2$O$_6$), 37-C-7 was prepared as follows: The preparation follows that of Preparation 37-C-1. The starting materials are (1S-cis)-1,2,2-trimethylcyclopentane-1,3-dicarboxylic acid 1-(1,1-dimethylethyl)-ester, 36-D, and 4-[(2,6-dichlorobenzoyl)amino]-L-phenylalanine methyl ester, hydrochloride salt, 37-B-1. Physical properties as follows: m.p. 171–172° C.; $^1$H NMR(300 MHz, DMSO-d$_6$). δ10.6(1H), 7.82(1H), 7.51(5H), 7.18(2H), 4.45(1H), 3.1 (1H), 2.82(1H), 2.62(1H), 2.32(1H), 1.93(1H), 1.58(1H), 1.34(1H), 1.06(3H), 0.83(3H), 0.45(3H); MS-ESI (m/z): 533 ([M−H$^−$]); MS-ESI (m/z): 535 ([M+H$^+$]).

Preparation of Example 244

Scheme 37: 37-C-8 Where R$^3$ is CH$_3$, R$^1$ is H, and the Stereochemistry is (1S-cis) and L-Phenylalanine (1S-cis)-N-[(3-Carboxy-1,2,2-trimethylcyclopentyl) carbonyl]-4-[(2,6-dichlorobenzoyl)amino]-L-phenylalanine (C$_{26}$H$_{28}$Cl$_2$N$_2$O$_6$), 37-C-8 was prepared as follows: To a solution of (1S-cis)-1,2,2-trimethylcyclopentane-1,3-dicarboxylic acid 3-methyl ester, 36-B(501.3 mg) in DMF(5 mL) and DIEA(3 mL) was added O-(7-Azabenzotriazol-1-yl)-N,N,N', N'-tetramethyluronium hexafluorophosphate (1.0445 g) and the reaction stirred at ambient temperature for 1 hour. To the reaction was added 4-[(2,6-dichlorobenzoyl)amino]-L-phenylalanine methyl ester, hydrochloride salt(1.0093 g), 37-B-1, and the reaction stirred for 3 days. The reaction was then diluted with water and extracted with AcOEt. The concentrated extract was purified by flash chromatography on silica gel eluting with methanol in methylene chloride to obtain (1S-cis)-N-[(3-Methoxycarbonyl)-1,2,2-trimethylcyclopentyl)carbonyl]-4-[(2,6-dichlorobenzoyl)amino]-L-phenylalanine methyl ester (2.272 g). A solution of LiOH(552 mg) in H$_2$O(20 mL) and 4 mL of 30% hydrogen peroxide was added to a solution of the above (1S-cis)-N-[((3-Methoxycarbonyl)-1,2,2-trimethylcyclopentyl)carbonyl]-4-[(2,6-dichlorobenzoyl) amino]-L-phenylalanine methyl ester(C$_{28}$H$_{32}$Cl$_2$N$_2$O$_6$) (2.272 g) in 15 mL of methanol. The solution was stirred for 6 days. The methanol is then removed in vacuo. The aqueous layer is further diluted with water and extracted with diethyl ether and the extract discarded. The aqueous layer is acidified to pH=3–4 with 0.6N HCl resulting in a precipitate. The precipitate is filtered washing with water to obtain (1S-cis)-N-[(3-Carboxy-1,2,2-trimethylcyclopentyl)carbonyl]-4-[(2,6-dichlorobenzoyl)amino]-L-phenylalanine(1.1265 g). Physical properties as follows: m.p. 152–157° C. $^1$H NMR (300 MHz, DMSO-d$_6$). δ12.3(1H), 10.63(1H), 7.50(5H), 7.27(1H), 7.18(2H), 4.45(1H), 2.99(2H), 2.63(1H), 2.25 (1H), 1.93(1H), 1.69(1H), 1.28(1H), 1.16(3H), 1.05(3H), 0.50(3H); MS-ESI (m/z): 533 ([M−H$^−$]); MS-ESI (m/z): 535 ([M+H$^+$]).

Preparation of Example 245

Scheme 37: 37-C-9 Where R$^3$ is CH$_3$, R$^1$ is H, and the Stereochemistry is (1S-cis) and D-Phenylalanine (1S-cis)-N-[(3-Carboxy-1,2,2-trimethylcyclopentyl) carbonyl]-4-[(2,6-dichlorobenzoyl) amino]-D-phenylalanine (C$_{26}$H$_{28}$Cl$_2$N$_2$O$_6$), 37-C-9 was prepared as follows: The preparation follows that of Preparation 37-C-8. The starting materials are (1S-cis)-1,2,2-trimethylcyclopentane-1,3-dicarboxylic acid 3-methyl ester, 36-B, and 4-[(2,6-dichlorobenzoyl)amino]-D-phenylalanine methyl ester, hydrochloride salt, 37-B-2. Physical properties as follows: m.p. 155–163° C.; $^1$H NMR(300 MHz, DMSO-d$_6$). δ12.3(1H), 10.6 (1H), 7.51(5H), 7.29(1H), 7.18(2H), 4.44(1H), 3.07(1H), 2.94(1H), 2.25(1H), 2.62(1H), 1.94 (1H), 1.67(1H), 1.28(1H), 1.04(3H), 0.99(3H), 0.48(3H); MS-ESI (m/z): 533([M−H$^−$]); MS-ESI (m/z): 535([M+H$^+$]).

Preparation of Example 246

Scheme 37: 37-C-10 Where R$^3$ is CH$_3$, R$^1$ is H, and the Stereochemistry is (1S-trans) and D-Phenylalanine (1S-trans)-N-[(3-Carboxy-1,2,2-trimethylcyclopentyl) carbonyl]-4-[(2,6-dichlorobenzoyl)amino]-D-phenylalanine (C$_{26}$H$_{28}$Cl$_2$N$_2$O$_6$), 37-C-10 was prepared as follows: To a solution of (1S-trans)-[3-(Phenylmethoxy)carbonyl]-1,2,2-trimethylcyclopentane-1-carboxylic acid, 36-F-1, (503.7 mg) in DMF(5 mL) and DIEA(3 mL) was added O-(7-Azabenzotriazol-1-yl)-N,N,N',N'-tetramethyluronium hexafluorophosphate(731.7 mg) and the reaction stirred at ambient temperature for 1 hour. To the reaction was added 4-[(2,6-dichlorobenzoyl)amino]-D-phenylalanine methyl ester, hydrochloride salt(698.6 mg), 37-B-2, and the reaction stirred for 5 days. The reaction was then diluted with water and extracted with AcOEt. The concentrated extract was purified by flash chromatography on silica gel eluting with methanol in methylene chloride to obtain (1S-trans)-N-[(3-(Phenylmethoxy)carbonyl)-1,2,2-trimethylcyclopentyl)carbonyl]-4-[(2,6-dichlorobenzoyl)amino]-D-phenylalanine methyl ester(1.1024 g). Physical properties as follows: $^1$H NMR (CDCl$_3$) δ7.82 (1H), 7.58 (2H), 7.28 (8H), 7.05 (2H), 6.07 (1H), 5.06 (2H), 4.74 (1H), 3.66 (3H), 3.07 (3H), 2.05 (3H), 1.53 (1H), 1.21 (3H), 0.90 (3H), 0.75 (3H); MS-ESI (m/z): 637 ([M−H−]); MS-ESI (m/z): 661([M+Na]$^+$).

The product from above was dissolved in THF(10 mL) and 10% palladium on carbon(75 mg) was added and the mixture hydrogenated at atmospheric pressure for 26 hours. The reaction was then filtered and the filtrate concentrated to obtain (1S-trans)-N-[(3-Carboxy-1,2,2-trimethylcyclopentyl)carbonyl]-4-[2,6-dichlorobenzoyl)amino]-D-phenylalanine methyl ester(896.3 mg). Physical properties as follows: MS-ESI (m/z): 547 ([M−H−]); MS-ESI (m/z): 571([M+Na]$^+$) A solution of LiOH(213.2 mg) in H$_2$O(10 mL) and 2 mL of 30% hydrogen peroxide was added to a solution of (1S-trans)-N-[(3-Carboxy-1,2,2-trimethylcyclopentyl)carbonyl]-4-[(2,6-dichlorobenzoyl)amino]-D-phenylalanine methyl ester (896.3 mg) in 10 mL of methanol. The solution was stirred for 26 hours. The methanol is then removed in vacuo. The aqueous layer is further diluted with water and extracted with diethyl ether and the extract discarded. The aqueous layer is acidified to pH=3–4 with 0.6N HCl resulting in a precipitate. The precipitate is filtered washing with water to obtain (1S-trans)-N-[(3-Carboxy-1,2,2-trimethylcyclopentyl)carbonyl]-4-[(2,6-dichlorobenzoyl)amino]-D-phenylalanine (692.2 mg). Physical properties as follows: m.p. 145–150° C.; $^1$H NMR(300 MHz, DMSO-d$_6$). δ12.3(1H), 10.6 (1H), 7.51(5H), 7.29(1H), 7.18(2H), 4.44(1H), 3.07(1H), 2.94 (1H), 2.25(1H), 2.62(1H), 1.94(1H), 1.67(1H), 1.28(1H), 1.04(3H), 0.99(3H), 0.48(3H); MS-ESI (m/z): 533([M−H−]); MS-ESI (m/z): 535([M+H$^+$]).

Preparation of Example 247

Scheme 37: 37-C-11 Where R$^3$ is CH$_3$, R$^1$ is H, and the Stereochemistry is (1S-trans) and L-Phenylalanine (1S-trans)-N-[(3-Carboxy-1,2,2-trimethylcyclopentyl)carbonyl]-4-[(2,6-dichlorobenzoyl) amino]-L-phenylalanine (C$_{26}$H$_{28}$Cl$_2$N$_2$O$_6$), 37-C-12 was prepared as follows: The preparation follows that of Preparation 37-C-10. The starting materials are (1S-trans)-[3-(Phenylmethoxy)carbonyl]-1,2,2-trimethylcyclopentane-1-carboxylic acid, 36-F-1, and 4-[(2,6-dichlorobenzoyl)amino]-L-phenylalanine methyl ester, hydrochloride salt, 37-B-1. Physical properties as follows: m.p. 145–153° C.; $^1$H NMR(300 MHz, DMSO-d$_6$). δ12.3(1H), 10.6 (1H), 7.51(5H), 7.29(1H), 7.18(2H), 4.42 (1H), 3.01(2H), 2.70(1H), 1.88(2H), 1.73(1H), 1.36(1H), 1.04(3H), 0.94(3H), 0.78(3H); MS-ESI (m/z): 533 ([M−H−]); MS-ESI (m/z): 535 ([M+H$^+$]).

Preparation of Example 248

Scheme 37: 37-C-12 Where R$^3$ is CH$_3$, R$^1$ is H, and the Stereochemistry is (1R-cis) and L-Phenylalanine (1R-cis)-N-[(3-Carboxy-1,2,2-trimethylcyclopentyl)carbonyl]-4-[(2,6-dichlorobenzoyl)amino]-L-phenylalanine (C$_{26}$H$_{28}$Cl$_2$N$_2$O$_6$), 37-C-12 was prepared as follows: The preparation follows that of Preparation 37-C-8. The starting materials are: (1R-cis)-1,2,2-trimethylcyclopentane-1,3-dicarboxylic acid 3-methyl ester, 10-A, and 4-[(2,6-dichlorobenzoyl)amino]-L-phenylalanine methyl ester, hydrochloride salt, 37-B-1. Physical properties as follows: m.p. 154–160° C. $^1$H NMR(300 MHz, MeOH-d$_4$). δ7.58 (2H), 7.42 (3H), 7.24(3H) 4.74(1H), 3.3(1H), 3.03(1H), 2.75(1H), 2.41(1H), 2.12(1H), 1.80(1H), 1.43(1H), 1.14 (3H), 1.11(3H), 0.63 (3H); MMS-ESI (m/z): 533 ([M-H-]); MS-ESI (m/z): 535 ([M+H$^+$]).

Preparation of Example 249

Scheme 37: 37-C-13 Where R$^3$ is CH$_3$, R$^1$ is H, and the Stereochemistry is (1R-cis) and D-Phenylalanine (1R-cis)-N-[(3-Carboxy-1,2,2-trimethylcyclopentyl)carbonyl]-4-[(2,6-dichlorobenzoyl)amino]-D-phenylalanine (C$_{26}$H$_{28}$Cl$_2$N$_2$O$_6$), 37-C-13 was prepared as follows: The preparation follows that of Preparation 37-C-8. The starting materials are (1R-cis)-1,2,2-trimethylcyclopentane-1,3-dicarboxylic acid 3-methyl ester, 10-A, and 4-[(2,6-dichlorobenzoyl)amino]-D-phenylalanine methyl ester, hydrochloride salt, 37-B-2. Physical properties as follows: m.p.155–159° C.; $^1$H NMR(300 MHz, DMSO-d$_6$). δ 12.4 (1H), 10.6(1H), 7.51(5H), 7.19(3H), 4.42(1H), 2.99(2H), 2.64(1H), 2.26(1H), 1.94(1H), 1.68(1H), 1.29(1H), 1.17 (3H), 1.05(3H), 0.51(3H); MS-ESI (m/z): 533([M−H−]).

Preparation of Example 250

Scheme 37: 37-C-14 Where R$^3$ is CH$_3$, R$^1$ is H, and the Stereochemistry is (1R-trans) and L-Phenylalanine (1R-trans)-N-[(3-Carboxy-1,2,2-trimethylcyclopentyl)carbonyl]-4-[(2,6-dichlorobenzoyl)amino]-L-phenylalanine (C$_{26}$H$_{28}$Cl$_2$N$_2$O$_6$), 37-C-14 was prepared as follows: The preparation follows that of Preparation 37-C-10. The starting materials are (1R-trans)-[3-(Phenylmethoxy)carbonyl]-1,2,2-trimethylcyclopentane-1-carboxylic acid, 36-F-2, and 4-[(2,6-dichlorobenzoyl)amino]-L-phenylalanine methyl ester, hydrochloride salt, 37-B-1. Physical properties as follows: m.p. 148–155° C.; $^1$H NMR(300 MHz, DMSO-d$_6$). δ 12.3(2H), 10.6 (1H), 7.53(5H), 7.27(1H), 7.21(2H), 4.382 (1H), 3.03(2H), 2.73(1H), 1.92(2H), 1.79(1H), 1.43(1H), 1.04(3H), 0.75(3H), 0.71(3H); MS-ESI (m/z): 533 ([M−H−]); MS-ESI (m/z): 535([M+H$^+$]).

Preparation of Example 251

Scheme 37: 37-C-15 Where R$^3$ is CH$_3$, R$^1$ is H, and the Stereochemistry is (1R-trans) and D-Phenylalanine (1R-trans)-N-[(3-Carboxy-1,2,2-trimethylcyclopentyl)carbonyl]-4-[(2,6-dichlorobenzoyl)amino]-D-phenylalanine (C$_{26}$H$_{28}$Cl$_2$N$_2$O$_6$) 37-C-15 was prepared as follows: The preparation follows that of Preparation 37-C-10. The starting materials are (1R-trans)-[3-(Phenylmethoxy)carbonyl]-

1,2,2-trimethylcyclopentane-1-carboxylic acid, 36-F-2, and 4-[(2,6-dichlorobenzoyl)amino]-D-phenylalanine methyl ester, hydrochloride salt, 37-B-2. Physical properties as follows: m.p. 134–140° C.; $^1$H NMR(300 MHz, DMSO-$d_6$). δ 12.3(1H), 10.6 (1H), 7.50(5H), 7.43(1H), 7.21(2H), 4.43 (1H), 3.03(2H), 2.73(1H), 1.92(2H), 1.78(1H), 1.41(1H), 1.06(3H), 0.96(3H), 0.80(3H); MS-ESI (m/z): 533 ([M−H]$^-$); MS-ESI (m/z): 535([M+H$^+$]).

Preparation of Example 252

The synthesis for Example 252, (1S-cis)-N-[(3-Carboxy-2,2,3-trimethylcyclopentyl)carbonyl]-3-bromo-4-[(2,6-dichlorobenzoyl)amino]-L-phenylalanine ($C_{26}H_{28}Cl_2N_2O_6$), is taught by Scheme 2 (Method B) as follows: To a solution of (1R-cis)-1,2,2-Trimethylcyclopentane-1,3-dicarboxylic acid 1-(1,1-dimethylethyl)ester (153.9 mg), 15-D, in methylene chloride (6 mL) at 0° C. was added DIEA (1mL), EDC(113.2 mg), HOBT (80.3 mg), and dimethylaminopyridine (20.1 mg). The reaction was stirred at 0° C. for 20 minutes and then 3-Bromo-4-[(2,6-dichlorobenzoyl)amino]-L-phenylalanine methyl ester hydrochloride salt (259.4 mg) was added as a solution in methylene chloride (4 mL) and stirred at ambient temperature for 50 hours. The reaction was diluted with water and extracted with methylene chloride. The extracts were washed with 0.5 N HCl, dried over sodium sulfate and concentrated in vacuo. The crude material was purified by flash chromatography over silica gel eluting with AcOEt in hexane to obtain (1S-cis)-N-[[3-[(1,1-Dimethylethoxy)carbonyl]-2,2,3-trimethylcyclopentyl]carbonyl]-3-bromo-4-[(2,6-dichlorobenzoyl)amino]-L-phenylalanine methyl ester (153.8 mg). Physical properties as follows: $^1$H NMR (CDCl$_3$) δ 8.33 (1H), 7.82 (1H), 7.31 (4H), 7.08 (1H), 5.87 (1H), 4.85 (1H), 3.74 (3H), 3.10 (2H), 2.52 (2H), 2.14 (1H), 1.73 (1H), 4.42 (10H), 1.23 (3H), 1.14 (3H), 0.79 (3H). MS-ESI (m/z): 681([M−H]$^-$); MS-ESI (m/z): 683([M+H$^+$]).

The deprotection of the carboxylic acids follows that of Examples 53, and 54 to obtain (1S-cis)-N-[(3-Carboxy-2,2,3-trimethylcyclopentyl)carbonyl]-3-bromo-4-[(2,6-dichlorobenzoyl)amino]-L-phenylalanine. Physical properties as follows: m.p. 150–152° C.; $^1$H NMR (CD$_3$OD) δ 7.95 (1H), 7.67 (1H), 7.57 (1H), 7.45 (3H), 7.35 (1H), 4.73 (1H), 3.25 (1H), 2.99 (1H), 2.75 (1H), 2.52 (1H), 2.00 (1H), 1.70 (1H), 1.44 (1H), 1.24 (3H), 1.21 (3H), 0.79 (3H); MS-ESI (m/z): 611 ([M−H]$^-$); MS-ESI (m/z): 613 ([M+H$^+$]).

Scheme 38
Preparation of Example 253

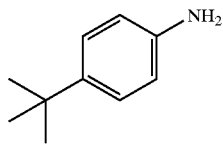

38-A

-continued

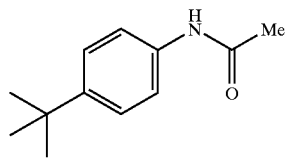

38-B

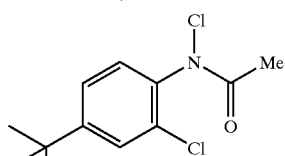

38-C

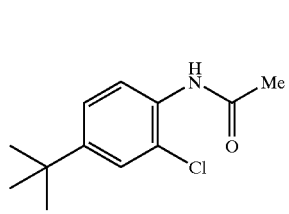

38-D

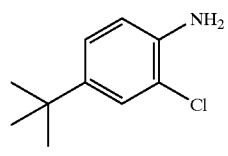

38-E

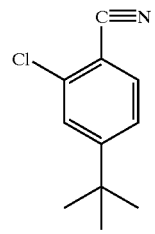

38-F

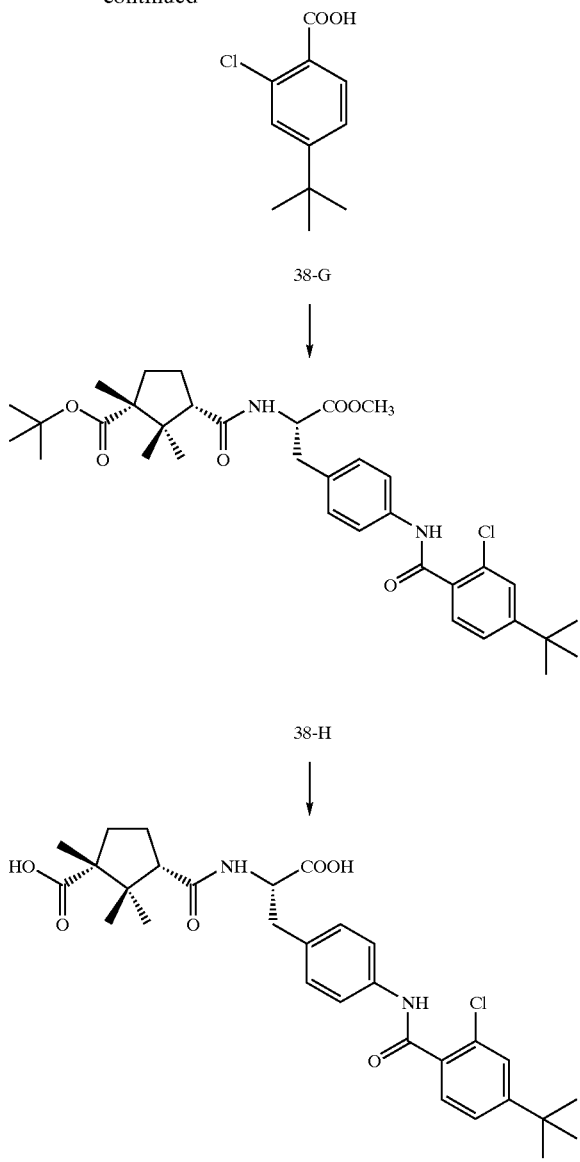

38-G

38-H

Example 253

Preparation of Example 253

(1S-cis)-N-[(3-Carboxy-2,2,3-trimethylcyclopentyl)carbonyl]-4-[(2,6-dichloro-4-[(1,1-dimethyl)ethyl]benzoyl)amino]-L-phenylalanine ($C_{30}H_{37}Cl_1N_2O_6$)

4-[(1,1-Dimethyl)ethyl]acetanilide ($C_{12}H_{17}NO$, 38-B) To a solution of 4-tert-butylaniline 38-A (14.9 g, 99.8 mmol) and pyridine (11 mL, 0.14 mol) in $CH_2Cl_2$ (50 mL), under $N_2$ and at 0° C., is added dropwise acetic anhydride (12 mL, 0.13 mmol). The reaction mixture is stirred at rt for 20 h, and is then quenched with 0.5 M aqueous HCl (100 mL). The reaction mixture is extracted with $CH_2Cl_2$. The combined $CH_2Cl_2$ extracts are washed with 0.5 M NaOH and brine, and then are dried, filtered and concentrated to give 38-B as an orange-colored solid (18.5 g). The solid is recrystallized from MeOH/Heptane to give a white solid (10.3 g, 54%): mp 172–173° C.; TLC (85:15 hexane/acetone) $R_f$=0.19; $^{13}C$ NMR (CD$_3$OD) δ 171.48, 148.15, 137.19, 126.52, 121.03, 35.14, 31.81, 23.74; MS (−ESI) m/z 190.

N,2-Dichloro-4-[(1,1-dimethyl)ethyl]acetanilide ($C_{12}H_{15}Cl_2NO$, 38-C) To a suspension of 38-B (17.5 g, 91.5 mmol) and anhydrous NaOAc (19 g, 0.23 mmol) in HOAc (100 mL) under $N_2$ at 10° C. is added portionwise a solution of $Cl_2$ (7 g) in HOAc (100 ml). Upon complete addition (approximately 15 min) the reaction mixture is allowed to warm to rt and is stirred for 1 h. A second portion of $Cl_2$ (approximately 8 g) in HOAc (100 mL) is added and the resulting mixture is stirred at rt for 4.5 h. Finally, $Cl_2$ gas is bubbled directly into the stirred mixture for 30 min. This mixture is stirred at rt for 17 h. It is concentrated under reduced pressure, chasing the residual HOAc with two portions of toluene. The solid is dissolved in EtOAc. The solution is filtered to give, after evaporation, an orange-colored oil (24.7 g). The oil is purified by silica chromatography (90:10 heptane/EtOAc) to give an orange-colored oil (18.4 g) that is recrystallized from pentane to give 38-C as a white solid (12.8 g, 54%): mp 64–65° C.; TLC (90:10 heptane/EtOAc) $R_f$=0.21; $^{13}C$ NMR (CDCl$_3$) δ 167.84, 155.65, 137.57, 133.57, 130.23, 127.91, 125.61, 35.11, 31.03, 21.52; MS (FAB) m/z 228, 226.

2-Chloro-4-[(1,1-dimethyl)ethyl]acetanilide ($C_{12}H_{16}Cl_1NO$, 38-D). To a solution of 18.6 g (71.5 mmol) of 38-C in absolute EtOH (100 mL) is added 10 M NaOH (7.1 mL). An exothermic reaction ensues. After the temperature had moderated the mixture is heated at reflux for 1 h. The pH of the cooled mixture is adjusted to pH 7–8 with concentrated HCl. The resulting mixture is partially concentrated (to remove EtOH), and then is diluted with $CH_2Cl_2$ and and brine. The $CH_2Cl_2$ layer is separated. The aqueous solution is extracted twice additionally with $CH_2Cl_2$. The combined $CH_2Cl_2$ extracts are dried, filtered and concentrated to brown-colored oil. The oil is purified by silica chromatography (steps of 90:10 and 85:15 heptane/acetone) to give a solid (12.6 g), that is recrystallized from MeOH/pentane to give 38-D (7.49 g, 47%) as a white solid: mp 152–153° C.; TLC (85:15 heptane/acetone) $R_f$=0.33; $^{13}C$ NMR (CDCl$_3$) δ 168.23, 148.25, 131.92, 125.89, 124.70, 122.59, 121.64, 34.49,31.17, 24.70; MS (FAB) m/z 226.0995.

2-Chloro-4-[(1,1-dimethyl)ethyl]aniline($C_{10}H_{14}Cl_1N$,38-E). To a suspension of 38-D (6.0 g, 26 mmol) in EtOH (90 mL) is added 10 N NaOH (10 mL). The resulting mixture is heated at reflux. The suspended solid dissolves gradually. After 17 h at reflux the solution is cooled to 0° C. and is neutralized to pH 7 with concentrated HCl. The mixture is concentrated partially (to remove EtOH). the resulting aqueous mixture is diluted with brine, and is extracted with five portions of $CH_2Cl_2$. The combined $CH_2Cl_2$ extracts are dried, filtered and concentrated to give 38-E as an orange-colored oil (5.5 g): TLC (85:15 heptane/acetone) $R_f$=0.53; $^1H$ NMR (CDCl$_3$) δ 7.25 (1H), 7.09 (1H), 6.72 (1H), 3.82 (2H) 1.27 (9H); MS (+ESI; MeOH) m/z 186, 184.

2-Chloro-4-[(1,1-dimethyl)ethyl]benzonitrile ($C_{11}H_{12}Cl_1N$, 38-F). To a solution of aniline 38-E (5.5 g, 30 mmol) in 10:6 HOAc/H$_2$O (32 mL) is added concentrated H$_2$SO$_4$ (4.7 mL, 85 mmol). The brown-colored solution is cooled to 10° C. and is treated dropwise with a solution of NaNO$_2$ (2.3 g, 33 mmol) in H$_2$O (5 mL). After this addition is complete the reaction mixture is stirred at 10° C. for 1 h, yielding a yellow-colored solution. During this time a solution of KCN (9.8 g, 150 mmole) in H$_2$O (25 mL) is added to a cold (ice bath), mechanically stirred solution of CuSO$_4$.5H$_2$O (9.0 g, 36 mmol) in H$_2$O (25 mL). To this mixture is added NaHCO$_3$ (20 g, 0.24 mmol) and benzene (30 mL), and the entire mixture is heated to 50–55° C. to dissolve all of the solids. The this solution is added dropwise the solution of the diazonium salt over 20 min under N₂ and at 50–55° C. The reaction mixture is kept for 30 min at 50–55° C. for 0.5 h after the addition. The mixture is cooled, and extracted thrice with benzene. The combined benzene extracts are washed with 1N NaOH and brine, and then dried, filtered and concentrated to give a reddish-brown oil (6.8 g). The oil is purified by silica flash chromatography (steps of 95:5 and 90:10 heptane/CH₂Cl₂) to give 38-F (2.4 g, 41%): TLC (75:25 heptane/CH₂C₂) R$_f$=0.31; ¹H NMR (CDCl₃) δ 7.58 (1H), 7.49 (1H), 7.37 (1H), 1.31 (9H); ¹³C NMR (CDCl₃) δ 158.53, 136.59, 133.64, 127.22, 124.49, 116.29, 110.21, 35.49, 30.80.

2-Chloro-4-[(1,1-dimethyl)ethyl]benzoic acid (C₁₁H₁₃ClO₂, 38-G). A solution of 38-F (2.28 g, 11.8 mmol), H₂O (7.4 mL), 10 N NaOH (5.9 mL), and 30% H₂O₂ (6.7 mL) in EtOH (80 mL) is refluxed for 28 h. The solution is cooled to 0° C. and neutralized to pH 7 with concentrated HCl. A solution of NaHSO₃ (7 g), dissolved in the minimal amount of H₂O, is added. The reaction mixture is concentrated partially (to remove most of the EtOH), basified to pH 12 with 1 N NaOH, and extracted twice with CH₂Cl₂. The combined CH₂Cl₂ extracts are discarded. The aqueous solution is acidified with concentrated HCl to pH 3, and then is extracted with CH₂Cl₂. The combined CH₂Cl₂ extracts are dried, filtered and concentrated to give 38-G (2.07 g, 83%) as a white crystalline solid: ¹H NMR 11.62 (1H), 8.02 (1H), 7.51 (1H), 7.39 (1H), 1.36 (9H); ¹³C NMR (CDCl₃) δ 171.17, 158.05, 134.84, 132.58, 128.75, 125.25, 123.96, 35.18, 30.91; MS (+ESI) m/z 237, 235 [M+Na]⁺; MS (-ESI; MeOH) m/z 213, 211.

(1S-cis)-N-[[3-(tert-Butoxycarbonyl)-2,2,3-trimethylcyclopentyl]carbonyl]-4-[(2,6-dichloro-4-tert-butylbenzoyl)amino]-L-phenylalanine methyl ester (C₃₅H₄₇ClN₂O₆, 38-H). A mixture of (1S-cis)-N-[[3-(tert-Butoxycarbonyl)-2,2,3-trimethylcyclopentyl]-carbonyl]-4-nitro-L-phenylalanine methyl ester (406 mg, 0.88 mmol) and 10% Pd/C (39 mg) in 1:1 MeOH:THF (10 mL) is hydrogenated (30 psi H₂) for 1 h. The reaction mixture is filtered and concentrated to give the aniline as a colorless oil. This aniline is coupled directly with acid 15-D (190 mg, 0.89 mmol), as described by the general procedure for the synthesis of intermediates 7-F, to give after silica flash chromatography (steps of 99:1, 98:2, and 98:3 CHCl₃/Acetone) to give 38-H (224 mg, 41%): TLC (95:5 CHCl₃/Acetone) R$_f$=0.52; ¹³C NMR (CDCl₃) δ 175.02, 172.53, 172.14, 164.53, 155.92, 136.86, 132.21, 131.96, 130.38, 130.31, 129.84, 127.48, 124.52,120.26, 80.19, 56.69, 54.44, 53.11, 52.36, 46.39, 37.20, 35.03, 32.36, 31.00, 28.07, 22.98, 22.48, 21.98, 20.61; MS (FAB) m/z 627.3201.

(1S-cis)-N-[(3-Carboxy-2,2,3-trimethylcyclopentyl)carbonyl]-4-[(2,6-dichloro-4-[(1,1-dimethyl)ethyl]benzoyl)amino]-L-phenylalanine (C₃₀H₃₇Cl₁N₂O₆, Example 253). A solution of 38-H (101 mg, 0.16 mmol) in TFA (2 mL) is stirred at rt for 2 h. The solution is diluted with CH₂Cl₂ and concentrated thrice under reduced pressure. The residue is diluted with toluene and again concentrated under reduced pressure to an oil. The oil is dissolved in MeOH (1.0 mL) and then treated with H₂O (0.65 mL) and 1.00 M LiOH (0.35 mL). After 16 h a second portion of 1.00 M LiOH is added and the hydrolysis is allowed to proceed for an additional 4 h. The solution was diluted with H₂O and the pH adjusted to ca. 8–9. The neutralized solution is diluted with MeOH and then concentrated. The aqueous concentrate is diluted with additional H₂O, basified to pH 13 (1N NaOH), and extracted with Et₂O. The Et₂O extract is discarded. The aqueous phase is acidified to pH 2 (conc. HCl) and is extracted with EtOAc.

The combined EtOAc extracts are dried, filtered and concentrated to give Example 253 (93 mg) as a colorless oil: ¹H NMR (CD₃OD) δ 7.61 (2H), 7.55–7.44 (3H), 7.25 (2H), 4.69–4.78 (1H), 3.23 (1H), 3.00 (1H), 2.80–2.70 (1H), 2.60–2.46 (1H), 2.10–1.94 (1H), 1.78–1.61 (1H), 1.52–1.39 (1H), 1.36 (9H); 1.27 (3H), 1.23 (3H), 0.81 (3H); MS (-ESI) m/z 557, 555.

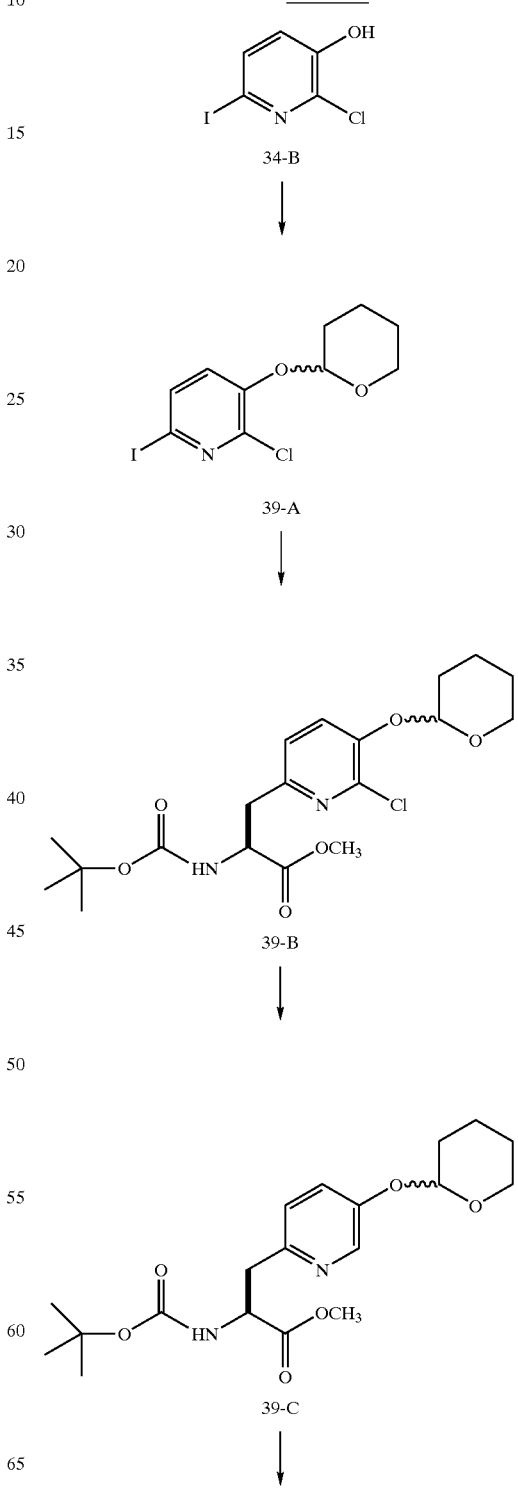

Scheme 39

-continued

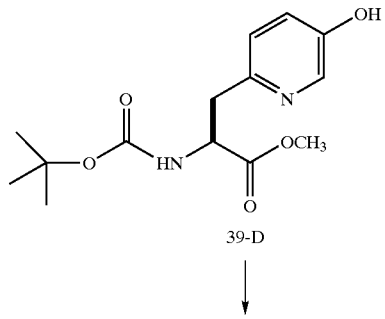
39-D

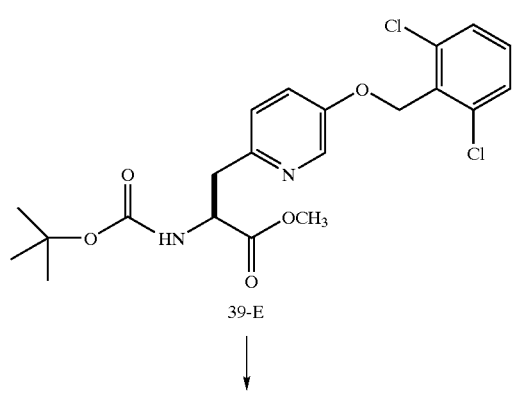
39-E

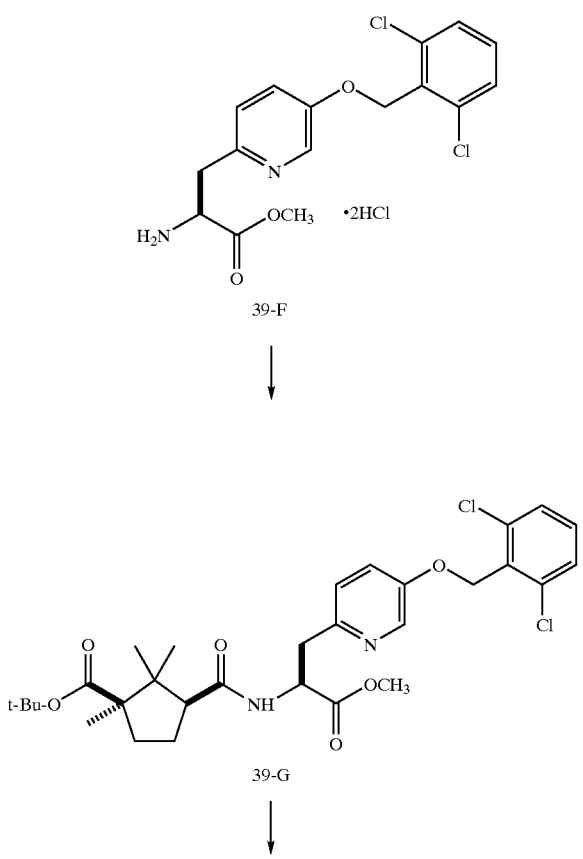

-continued

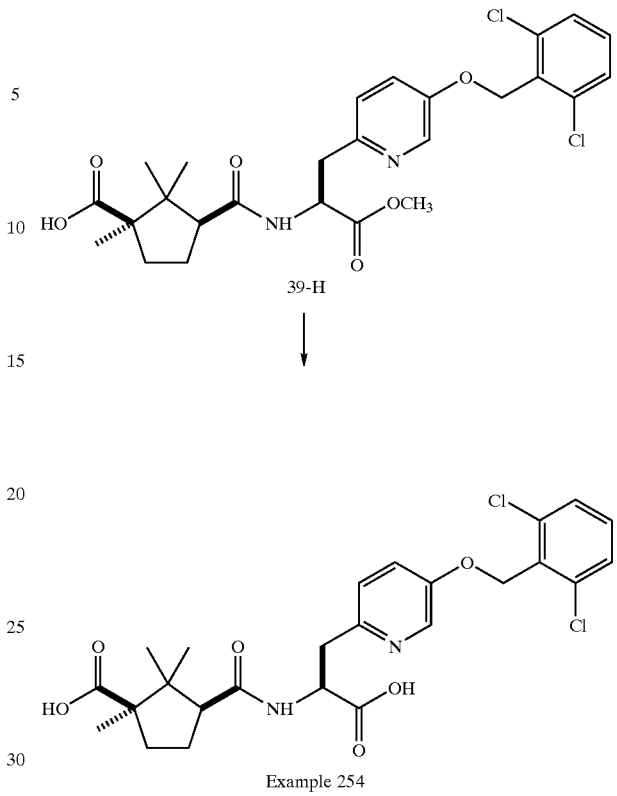

Preparation of Example 254

[1S-[1α(R*),3α]]-α-[[(3-Carboxy-2,2,3-trimethylcyclopentyl)carbonyl]amino]-3-[(2,6-dichlorophenyl)methoxy]-6-pyridinepropanoic acid ($C_{25}H_{28}Cl_2N_2O_6$).

(±)-2-Chloro-3-[(2-tetrahydropyranyl)oxy]-6-iodopyridine ($C_{10}H_{11}ClINO_2$, 39-A): To a solution of chlor-oiodopyridinol 34-B (1.00 g, 3.91 mmol) and dihydropyran (1.0 mL, 10.6 mmol) in $CH_2Cl_2$(10 mL) under Ar at rt is added pyridinium chloride (0.050 g). The reaction mixture is stirred for 72 h. it is diluted with $CH_2Cl_2$, and is washed with satd aq $NaHCO_3$ and brine. The $CH_2Cl_2$ solution is dried, filtered and concentrated to an oil, that is purified by silica flash chromatography (19:1 hexanes/EtOAc) to give 1.06 g (3.12 mmol, 80%) of 39-A: TLC (19:1 hexanes/EtOAc) $R_f$ 0.24; $^1$H NMR ($CDCl_3$, 300 MHz) δ 7.55 (1H), 7.17 (1H) 5.50 (1H), 3.77 (1H), 3.61 (1H), 2.07–1.57 (6H); MS (+ESI) m/z 361.9, 339.9.

(2S)-2-Chloro-α-[[(1,1-dimethylethoxy)carbonyl]amino]-3-[(2-tetrahydropyranyl)-oxy]-6-pyridinepropanoic acid methyl ester ($C_{19}H_{27}ClN_2O_6$, 39-B): To an amberized flask containing Reference Example 57 (1.81 g, 5.52 mmol) and activated Zn dust (0.349 g, 5.51 mmol) under Ar is added THF (2 mL) and 1,2-dibromoethane (0.018 mL, 0.21 mmol). The suspension is brought to reflux for several minutes, cooled to approximately 30° C., and TMSCl (0.17 mL of a 1 M solution in THF) is added. The reaction mixture is stirrred at 40±5° C. for 30 min, cooled in an ice bath, and solid $PdCl_2(PPh_3)_2$ (0.192 g) is added. A degassed solution of the iodide 39-A (0.936 g, 2.76 mmol) in 1:1 THF/ dimethylacetamide (5.6 mL) is added. This reaction mixture is stirred for 4 h at 45±5° C. It is then cooled to 0° C., quenched with satd aq $NH_4Cl$, and extracted with EtOAc. The combined EtOAc portions are washed with satd aq $NH_4Cl$ and brine, and are dried, filtered and concentrated to a green-yellow colored foam. This foam is purified by silica flash chromatography (7:3 hexanes/EtOAc) to give 0.879 g (1.85 mmol, 60%) of 39-B: TLC (7:3 hexanes/EtOAc) $R_f$ 0.21; $^1H$ NMR ($CDCl_3$, 300 MHz) δ 7.39 (1H), 7.00 (1H), 5.46 (1H), 4.61 (1H), 4.13 (1H), 3.80 (3H), 3.62 (1H), 3.20 (1H), 2.13–1.53 (6H), 1.42 (9H); MS (+ESI) m/z 474.0.

(S)-α-[[(1,1-Dimethylethoxy)carbonyl]amino]-3-[(2-tetrahydropyranyl)oxy]-6-pyridinepropanoic acid methyl ester ($C_{19}N_{28}N_2O_6$, 39-C): A suspension of pre-reduced Pd/$CaCO_3$ (3.5 g) and 39-B (1.15 g, 2.77 mmol) in EtOH (40 mL) is hydrogenated (30 psi $H_2$) for 19 h at rt. The mixture is filtered, and the filtrate is evaporated to give a yellow-colored foam that is purified by silica flash chromatography (600:400:1 hexanes/EtOAc/iPrOH) to give 0.367 g (0.96 mmol, 35%) of 39-C: TLC (1:1 hexanes/EtOAc) $R_f$ 0.27; $^1H$ NMR ($CDCl_3$, 300 MHz) δ 8.30 (1H), 7.29 (1H), 7.03 (1H), 5.81 (1H), 5.39 (1H), 4.65 (1H), 3.86 (1H), 3.73 (3H), 3.62 (1H), 3.21 (2H), 1.96–1.53 (6H), 1.42 (9H); MS (+ESI) m/z 381.1.

(S)-α-[[(1,1-Dimethylethoxy)carbonyl]amino]-5-hydroxy-2-pyridinepropanoic acid methyl ester ($C_{14}H_{20}N_2O_5$, 39-D): A solution of 39-C (0.346 g, 0.91 mmol) and pyridinium p-toluenesulfonate (0.031 g, 0.12 mmol) in EtOH (8 mL) is stirred at 55±5° C. for 20 h. The reaction mixture is cooled to rt, and concentrated in vacuo. The residue is taken up in EtOAc (150 mL). This solution is washed with brine, dried, filtered and concentrated to a pale yellow-colored oil that is purified by silica flash chromatography (500:500:1 hexanes/EtOAc/iPrOH). Evaporation of the column fractions gives recovered 39-C (0.27 mmol) and 0.132 g (0.45 mmol, 49%) of 39-D: TLC (1:1 hexanes/EtOAc) $R_f$ 0.18; $^1H$ NMR ($CDCl_3$, 300 MHz) δ 8.13 (1H), 7.13 (1H) 7.03 (1H), 5.71 (1H), 4.65 (1H), 3.70 (3H), 3.20 (2H) 1.39 (9H); MS (+ESI) m/z 297.1.

(S)-5-[(2,6-Dichlorophenyl)methoxy]-α-[[(1,1-dimethylethoxy)carbonyl]amino]-2-pyridinepropanoic acid methyl ester ($C_{21}H_{24}Cl_2N_2O_5$, 39-E): To a solution of 39-D (0.126 g, 0.43 mmol), 2,6-dichlorobenzylalcohol (0.075 g, 0.43 mmol) and $PPh_3$ (0.113 g, 0.43 mmol) in dry THF (4 mL) at 0° C. under Ar is added DEAD (0.068 mL). The reaction mixture is permitted to warm to rt, and is stirred for 18 h. It is concentrated. The residue is purified by silica flash chromatography (700:300:1 hexanes/EtOAc/iPrOH) to give 0.149 g (0.33 mmol, 76%) of 39-E: TLC (7:3 hexanes/EtOAc) $R_f$ 0.34; $^1H$ NMR ($CDCl_3$, 300 MHz) δ 8.31 (1H), 7.37 (2H), 7.25 (2H, 7.08 (1H), 5.81 (1H), 5.29 (2H), 4.65 (1H), 3.70 (3H), 3.24 (2H), 1.63 (1H), 1.43 (9H); $^{13}C$ NMR ($CDCl_3$, 75 MHz) δ 172.47, 155.50, 153.82, 149.71, 137.33, 137.00, 131.51, 130.72, 128.56, 123.99, 122.78, 79.74, 65.64, 53.25, 52.27, 38.43, 28.33; MS (+ESI) m/z 454.9.

(S)-α-Amino-5-[(2,6-dichlorophenyl)methoxyl-2-pyridinepropanoic acid methyl ester dihydrogen chloride salt ($C_{16}H_{16}Cl_2N_2O_3$·2HCl, 39-F): A solution of carbamate 39-E (0.546 g, 1.20 mmol) in 4 M HCl in dioxane (12 mL) is stirred at rt under Ar for 16 h. The reaction mixture is concentrated in vacuo. The residue is dissolved in $H_2O$ (40 mL), and this solution is extracted with $Et_2O$. The aqueous solution is frozen and lyophilized to give 0.485 g (1.13 mmol, 94%) of 39-F as a light yellow-colored solid: $^1H$ NMR ($CD_3SOCD_3$, 300 MHz) δ 8.75 (3H), 8.47 (1H), 7.81 (1H), 7.57 (3H), 7.48 (1H), 5.35 (2H), 4.49 (1H), 3.67 (3H), 3.42 (2H); $^{13}C$ NMR ($CD_3SOCD_3$, 75 MHz) δ 169.42, 154.95, 146.54, 136.57, 134.35, 132.50, 131.30, 129.36, 126.72, 126.52, 66.40, 53.32, 51.79, 34.81.

[1S-[1α(R*),3α]]-3-[(2,6-Dichlorophenyl)methoxy]-α-[[[3-[(1,1-dimethylethoxy)carbonyl]-2,2,3-trimethylcyclopentyl]carbonyl]amino]-6-pyridinepropanoic acid methyl ester ($C_3OH_{38}Cl_2N_2O_6$, 39-G): To a mixture of 15-D (0.141 g, 0.55 mmol), EDC (0.108 g, 0.57 mmol), HOBt (0.079 g, 0.58 mmol), DMAP (0.020 g, 0.16 mmol) and amine 39-F (0.246 g, 0.57 mmol) in $CH_2Cl_2$ (6 mL) at 0° C. under Ar is added $Et_3N$ (0.18 mL, 1.26 mmol). The yellow-colored reaction mixture is stirred at rt for 90 h. It is diluted with $CH_2Cl_2$, and washed with $H_2O$, 0.5 M aq HCl, $H_2O$, satd aq $NaHCO_3$, and $H_2O$. The $CH_2Cl_2$ solution is dried, filtered and concentrated to a pale yellow-colored foam, that is purified by-silica flash chromatography (600:400:1 hexanes/EtOAc.iPrOH) to give 0.195 g (0.33 mmol, 60%) of 39-G: TLC (3:2 hexanes/EtOAc) $R_f$ 0.49; $^1H$ NMR ($CDCl_3$, 300 MHz) δ 8.28 (1H), 7.40–7.28 (4H), 7.13 (1H), 5.31 (2H), 4.92 (1H), 3.68 (3H), 3.33 (1H), 3.25 (1H), 2.65 (1H), 2.53 (1H), 2.21 (1H), 1.67 (1H), 1.44 (9H), 1.31 (3H), 1.18 (3H), 0.83 (3H).

[1S-[1α(R*),3α]]-α-[[(3-Carboxy-2,2,3-trimethylcyclopentyl)carbonyl]amino]-3-[(2,6-dichlorophenyl)methoxy]-6-pyridinepropanoic acid methyl ester ($C_{26}H_{30}Cl_2N_2O_6$, 39-H): A solution of diester 39-G (0.195 g, 0.33 mmol) in TFA (4 mL) under Ar is stirred at 0° C. for 1 h and at rt for 2 h. The solution is concentrated, azeotroped thrice from toluene, and dried under vacuum to give 39-H as a yellow-colored glass: TLC (400:600:5 hexanes/EtOAc/$HCO_2H$) $R_f$ 0.29; $^1H$ NMR ($CDCl_3$, 300 MHz) δ 8.46 (1H), 7.87 (1H), 7.74 (1H), 7.51 (1H), 7.42–7.26 (2H), 5.42 (2H), 5.01 (1H), 3.80 (3H), 3.62 (1H), 3.45 (1H), 2.70 (1H), 2.48 (1H), 1.97 (1H), 1.65 (1H), 1.49 (1H), 1.28 (3H), 1.24 (3H), 0.76 (3H).

[1S-[1α(R*),3α]]-α-[[(3-Carboxy-2,2,3-trimethylcyclopentyl)carbonyl]amino]-3-[(2,6-dichlorophenyl)methoxy]-6-pyridinepropanoic acid ($C_{25}H_{28}Cl_2N_2O_6$, Example 254): A solution of 39-H (0.33 mmol) and LiOHH$_2$O (0.068 g, 1.62 mmol) in 2:1 THF/$H_2O$ (10.5 mL) is stirred under Ar for 5 h at rt. The reaction mixture is diluted with cold $H_2O$, acidified with aq 1 M HCl, and extracted with EtOAc. The combined EtOAc extracts are washed with brine, and are dried, filtered and concentrated to a pale yellow-colored foam that is purified by silica flash chromatography (600:400:2 hexanes/EtOAc/$HCO_2H$). The purified product is azeotroped thrice from toluene to remove $HCO_2H$. It is dissolved in MeCN (10 mL) and the solution is diluted with $H_2O$ (10 mL). The solution is frozen and lyophilized to give, as an beige-colored solid, 0.170 g (0.32 mmol, 98%) of Example 254: mp 118–122° C.; TLC (150:50:1 EtOAc/hexanes/$HCO_2H$) $R_f$ 0.41; $^1H$ NMR ($CD_3SOCD_3$, 300 MHz) δ8.43 (1H), 7.86 (2H), 7.58–7.47 (3H), 7.32 (1H), 5.28 (2H), 4.64 (1H), 3.24–2.99 (2H), 2.61 (1H), 2.32 (1H), 1.83 (1H), 1.51 (1H), 1.30 (1H), 1.12 (3H), 1.09 (3H), 0.63 (3H).

EXAMPLES

Example 1

(1S-cis)-N-[(3-Carboxy-2,2,3-trimethylcyclopentyl)carbonyl]-O-(phenylmethyl)-L-tyrosine methyl ester ($C_{27}H_{33}NO_6$).

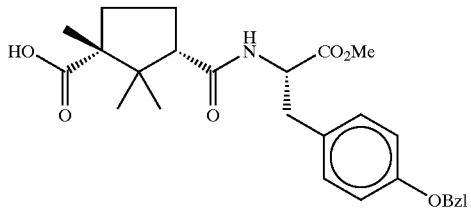

DIEA (0.65 g) was added dropwise to a mixture of (1R)-camphoric anhydride (0.18 g) and O-benzyl-L-tyrosine methyl ester hydrochloride (0.33 g) in DMF (2 ml) at 0° C. The mixture was stirred at 40° C. for 15 hr, cooled, diluted with AcOEt, and acidified with 1N HCl to pH 5. The organic layer was washed with $H_2O$, brine, dried over $Na_2SO_4$, and the solvent was removed in vacuo. The residue was purified by column chromatography on silica gel (eluent; 98:2, $CHCl_3$/MeOH) to give (1S-cis)-N-[(3-Carboxy-2,2,3-trimethylcyclopentyl)carbonyl]-O-(phenylmethyl)-L-tyrosine methyl ester ($C_{27}H_{33}NO_6$) (0.45 g) as a gum. MS(m/z): 468($MH^+$).

Example 2

(1S-cis)-N-[(3-Carboxy-2,2,3-trimethylcyclopentyl)carbonyl]-O-(phenylmethyl)-L-tyrosine ($C_{26}H_{31}NO_6$).

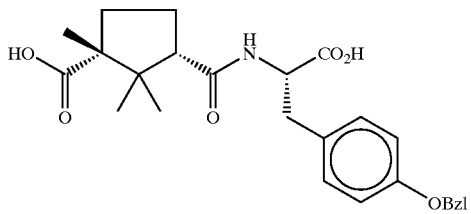

LiOH (72 mg) was added to a mixture of (1S-cis)-N-[(3-Carboxy-2,2,3-trimethylcyclopentyl)carbonyl]-O-(phenylmethyl)-L-tyrosine methyl ester ($C_{27}H_{33}NO_6$) (403 mg), THF (3 ml), and $H_2O$ (3 ml). The mixture was stirred at room temperature for 4 hr, acidified with 1N HCl, and extracted with AcOEt. The extract was dried over $Na_2SO_4$ and the solvent was removed in vacuo to give (1S-cis)-N-[(3-Carboxy-2,2,3-trimethylcyclopentyl)carbonyl]-O-(phenylmethyl)-L-tyrosine (391 mg), mp 146–149° C., MS (m/z): 452 ($[M-H]^-$).

Example 3

(1S-cis)-N-[(3-Carboxy-2,2,3-trimethylcyclopentyl)carbonyl]-1[(3,4-dichlorophenyl)methyl]-L-histidine methyl ester ($C_{24}H_{29}Cl_2N_3O_5$).

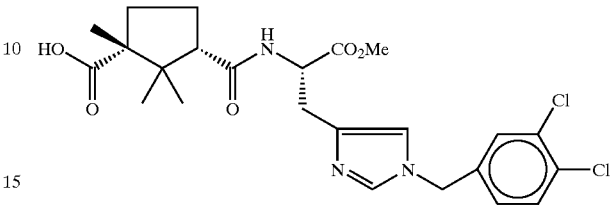

DIEA (4.48 g) was added to a mixture of 1-(3,4-dichlorobenzyl)-L-histidine methyl ester (5.56 g) and (1R)-camphoric anhydride (2.53 g) in DMF (50 ml). The mixture was stirred at 40° C. for 17 hr, cooled, diluted with $H_2O$, acidified with 5% HCl to pH 5, and extracted with $CHCl_3$. The extract was washed with $H_2O$, brine, and dried over $NaSO_4$. The solvent was removed in vacuo and the residue was purified by flash chromatography on silica gel (eluent: 100:1, $CHCl_3$/MeOH), followed by recrystallization from AcOEt/MeOH to give (1S-cis)-N-[(3-Carboxy-2,2,3-trimethylcyclopentyl)carbonyl]-1-[(3,4-dichlorophenyl)methyl]-L-histidine methyl ester (5.90 g), mp 174–175° C. (dec), MS (m/z): 510($MH^+$).

Example 4

(1S-cis)-N-[(3-Carboxy-2,2,3-trimethylcyclopentyl)carbonyl]-1-[(3,4-dichlorophenyl)methyl]-L-histidine ($C_{23}H_{27}Cl_2N_3O_5$).

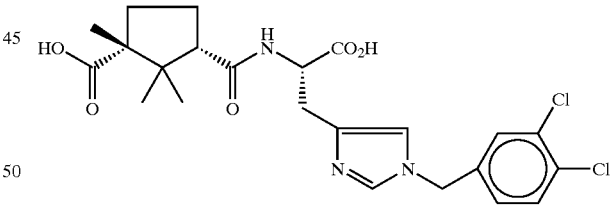

1N NaOH (7.3 ml) was added dropwise to a mixture of (1S-cis)-N-[(3-Carboxy-2,2,3-trimethylcyclopentyl)carbonyl]-1-[(3,4-dichlorophenyl)methyl]-L-histidine methyl ester ($C_{24}H_{29}Cl_2N_3O_5$) (1.50 g) in MeOH (20 ml) at 0° C. The mixture was stirred at room temperature for 15 hr, concentrated in vacuo, diluted with $H_2O$, and acidified with 1N HCl to pH 5–6. The resulting precipitate was collected by filtration, washed with $H_2O$, dried, and recrystallized from DMF/$H_2O$ to give (1S-cis)-N-[(3-Carboxy-2,2,3-trimethylcyclopentyl)carbonyl]-1-[(3,4-dichloro-phenyl)methyl]-L-histidine (0.87 g), mp 148–149° C. (dec), MS (m/z): 496 ($MH^+$).

Example 5

[1S-[1α(R*),3α]]-α-[[(3-Carboxy-2,2,3-trimethylcyclopentyl)carbonyl]amino]-2-naphthalenepropanoic acid phenylmethyl ester ($C_{30}H_{33}NO_5$).

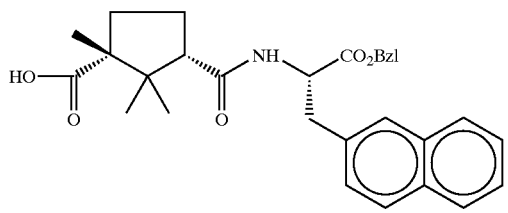

Benzyl (S)-2-amino-3-(2-naphthyl)propionate tosylate (0.20 g) was partitioned between AcOH and sat. $NaHCO_3$. The organic layer was washed with $H_2O$, brine, dried over $Na_2SO_4$, and the solvent was removed in vacuo. DMF (5 ml) and (1R)-camphoric anhydride (0.20 g) were added to the residue. The mixture was stirred at 30–40° C. for 17 hr, cooled, and poured into $H_2O$. The resulting mixture was extracted with AcOH. The extract was washed with $H_2O$, brine, dried over $Na_2SO_4$, and the solvent was removed in vacuo. The residue was purified by column chromatography on silica gel (eluent; 9:1, $CHCl_3$/AcOEt) to give [1S-[1α(R*),3α]]-α-[[(3-Carboxy-2,2,3-trimethylcyclopentyl)carbonyl]amino]-2-naphthalenepropanoic acid phenylmethyl ester (0.51 g) as an oil. MS(m/z): 488($MH^+$).

Example 6

[1S-[1α(R*),3α]]-α-[[(3-Carboxy-2,2,3-trimethylcyclopentyl)carbonyl]amino]-2-naphthalenepropanoic acid ($C_{23}H_{27}NO_5$).

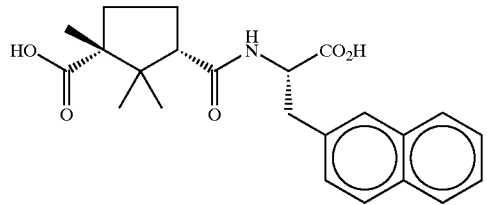

10% Pd—C (0.05 g) was added to a solution of [1S-[1α(R*),3α]]-α-[[(3-Carboxy-2,2,3-trimethylcyclopentyl)carbonyl]amino]-2-naphthalenepropanoic acid phenylmethyl ester ($C_{30}H_{33}NO_5$) (0.20g) in MeOH (10 ml) and the mixture was subjected to hydrogenolysis at a hydrogen pressure of 50 psi. The catalyst was filtered off and the filtrate was evaporated in vacuo to give [1S-[1α(R*),3α]]-α-[[(3-Carboxy-2,2,3-trimethylcyclopentyl)carbonyl]amino]-2-naphthalenepropanoic acid (0.18 g), MS (m/z): 398 ($MH^+$).

Examples 7 through 51 were prepared in a similar manner as described in Examples 1–6, and are shown in Tables 1, 2, and 3.

TABLE 1

Examples 7 through 20:

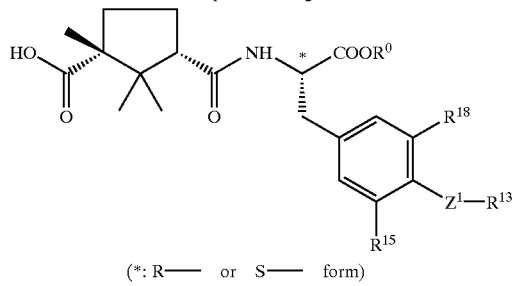

(*: R——— or S——— form)

| Ex. No. | * | $R^0$ | $R^{15}$ | $Z^1$ | $R^{13}$ | $R^{18}$ | physicochemical property |
|---|---|---|---|---|---|---|---|
| 7 | S | H | H | single bond | t-BuO— | H | M.P.: 98–100° C. MS(m/z): 420($MH^+$) |
| 8 | S | $CH_3$ | H | —$OCH_2$— | 1-methylnaphthyl | H | gum MS(m/z): 518($MH^+$) |
| 9 | S | H | H | —$OCH_2$— | 1-methylnaphthyl | H | M.P.: 92–93° C. MS(m/z): 502($[M-H]^-$) |

TABLE 1-continued

Examples 7 through 20:

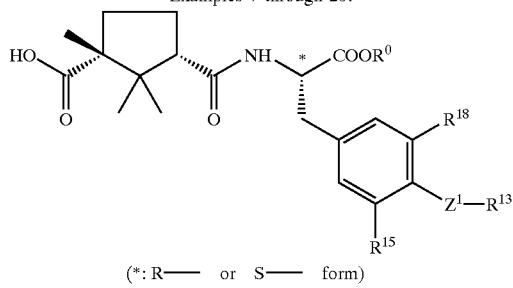

(*: R—— or S—— form)

| Ex. No. | * | R⁰ | R¹⁵ | Z¹ | R¹³ | R¹⁸ | physicochemical property |
|---|---|---|---|---|---|---|---|
| 10 | S | H | H | —OCH$_2$— | 3-methylnaphthalen-2-yl | H | MS(m/z): 504(MH$^+$) |
| 11 | S | CH$_3$ | H | —OCH$_2$— | 2,6-dichloro-3-methylphenyl | H | gum MS(m/z): 536(MH$^+$) |
| 12 | S | H | H | —OCH$_2$— | 2,6-dichloro-3-methylphenyl | H | M.P.: 95–97° C. MS(m/z): 520([M − H]$^-$) |
| 13 | S | H | H | —OCH$_2$— | methylcyclohexyl | H | M.P.: 102–105° C. MS(m/z): 460(MH$^+$) |
| 14 | S | H | H | —OCH$_2$— | Et/n-Bu/isopropyl | H | M.P.: 94–97° C. MS(m/z): 476(MH$^+$) |
| 15 | S | H | I | —OCH$_2$— | 3-bromophenylmethyl | I | M.P.: 210–212° C. (dec.) MS(m/z): 784, 786(MH$^+$) |
| 16 | S | H | H | —OCH$_2$— | 3,4-dichlorophenylmethyl | H | MS(m/z): 520([M − H]$^-$) |
| 17 | S | H | PhCH$_2$O | —OCH$_2$— | Ph | H | MS(m/z): 558([M − H]$^-$) |
| 18 | S | H | H | —OCH$_2$— | biphenyl-4-ylmethyl | H | MS(m/z): 530(MH$^+$) |

TABLE 1-continued

Examples 7 through 20:

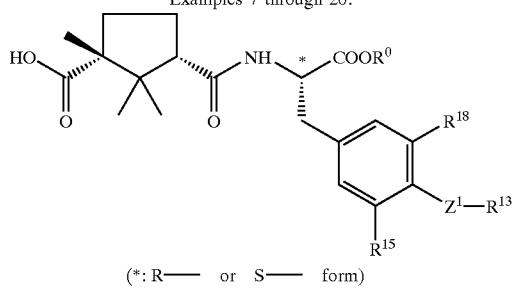

(*: R—— or S—— form)

| Ex. No. | * | R⁰ | R¹⁵ | Z¹ | R¹³ | R¹⁸ | physicochemical property |
|---|---|---|---|---|---|---|---|
| 19 | R | CH₃ | H | —OCH₂— | Ph | H | gum MS(m/z): 468(MH⁺) |
| 20 | R | H | H | —OCH₂— | Ph | H | MS(m/z): 454(MH⁺) |

TABLE 2

Examples 21 through 38:

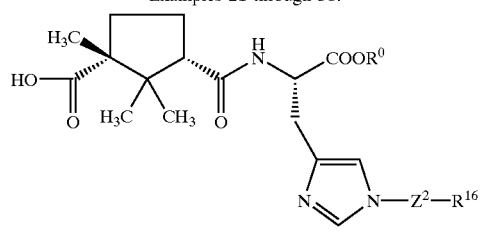

| Ex. No. | R⁰ | Z² | R¹⁶ | physicochemical property |
|---|---|---|---|---|
| 21 | CH₃ | single bond | —C(Ph)₃ | gum MS(m/z): 594(MH⁺) |
| 22 | H | single bond | —C(Ph)₃ | MS(m/z): 580(MH⁺) |
| 23 | CH₃ | CH₂ | 2,4-dichlorophenyl | gum MS(m/z): 510(MH⁺) |
| 24 | H | CH₂ | 2,4-dichlorophenyl | MS(m/z): 496(MH⁺) |
| 25 | CH₃ | CH₂ | 2,6-dichlorophenyl | gum MS(m/z): 510(MH⁺) |

TABLE 2-continued

Examples 21 through 38:

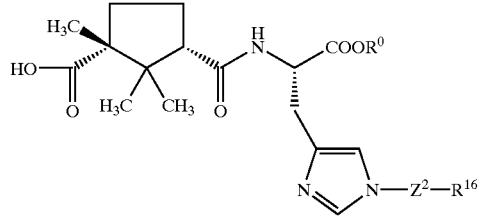

| Ex. No. | R⁰ | Z² | R¹⁶ | physicochemical property |
|---|---|---|---|---|
| 26 | H | CH₂ | 2,6-dichlorophenyl | MS(m/z): 496(MH⁺) |
| 27 | CH₃ | CH₂ | 4-chlorophenyl | gum MS(m/z): 476(MH⁺) |
| 28 | H | CH₂ | 4-chlorophenyl | MS(m/z): 462(MH⁺) |
| 29 | H | CH₂ | Ph | M.P.: 258–259° C. (dec.) MS(m/z): 428(MH⁺) |
| 30 | CH₃ | CH₂ | 4-methoxyphenyl | gum MS(m/z): 472(MH⁺) |
| 31 | H | CH₂ | 4-methoxyphenyl | MS(m/z): 458(MH⁺) |
| 32 | H | CH₂ | PhCH₂O | MS(m/z): 458(MH⁺) |

TABLE 2-continued

Examples 21 through 38:

| Ex. No. | R⁰ | Z² | R¹⁶ | physicochemical property |
|---|---|---|---|---|
| 33 | $CH_3$ | $CH_2$ | 4-F-phenyl | gum MS(m/z): 460(MH⁺) |
| 34 | H | $CH_2$ | 4-F-phenyl | MS(m/z): 446(MH⁺) |
| 35 | $CH_3$ | $CH_2$ | 2-$CF_3$-phenyl | gum MS(m/z): 510(MH⁺) |
| 36 | H | $CH_2$ | 2-$CF_3$-phenyl | MS(m/z): 496(MH⁺) |
| 37 | $CH_3$ | $CH_2$ | 2-naphthyl | gum MS(m/z): 492(MH⁺) |
| 38 | H | $CH_2$ | 2-naphthyl | MS(m/z): 478(MH⁺) |

Example 39

(1S-cis)-N-[(3-Carboxy-2,2,3-trimethylcyclopentyl)carbonyl]-O-[(2,6-dichlorophenyl)methyl]-D-tyrosine ($C_{26}H_{29}Cl_2NO_6$).

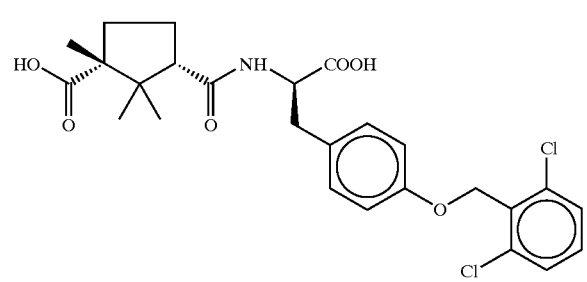

Example 39 is an isomer of Example 12 and is therefore synthesized in a manner similar to that of Example 12.

TABLE 3

Examples 40 through 51:

(*: R—— or S—— form)

| Ex. No. | * | R⁰ | R⁶ | physicochemical property |
|---|---|---|---|---|
| 40 | S | H | Ph-C(O)-(4-phenyl) | MS(m/z): 452(MH⁺) |

TABLE 3-continued
Examples 40 through 51:
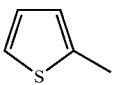
(*: R—— or S—— form)
| Ex. No. | * | R⁰ | R⁶ | physicochemical property |
|---|---|---|---|---|
| 41 | S | H | 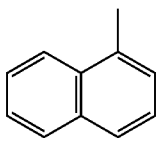 | M.P.: 163–165° C. MS(m/z): 354(MH⁺) |
| 42 | S | H | 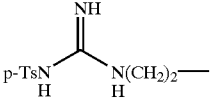 | MS(m/z): 398(MH⁺) |
| 43 | S | H | 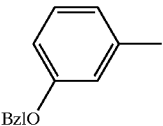 p-TsNH—C(=NH)—N(H)(CH₂)₂— | MS(m/z): 509([M − H⁻]) |
| 44 | S | H | Ph | MS(m/z): 348(MH⁺) |
| 45 | S | CH₃ | 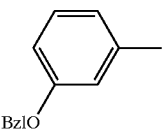 BzlO— | gum MS(m/z): 468(MH⁺) |
| 46 | S | H | 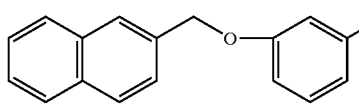 BzlO— | M.P.: 88–90° C. MS(m/z): 452([M − H]⁻) |
| 47 | S | H | 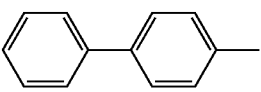 | MS(m/z): 502([M − H]⁻) |
| 48 | S | H | 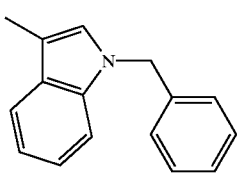 | MS(m/z): 422([M − H]⁻) |
| 49 | S | H | 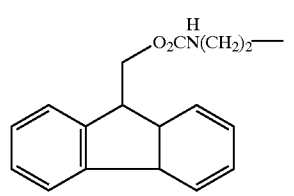 | MS(m/z): 475(M − H]⁻) |
| 50 | S | H | 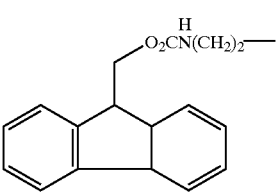 O₂CN(H)(CH₂)₂— | MS(m/z): 537(MH⁺) |

TABLE 3-continued

Examples 40 through 51:

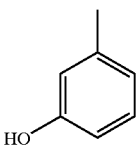

(*: R—— or S—— form)

| Ex. No. | * | R⁰ | R⁶ | physicochemical property |
|---|---|---|---|---|
| 51 | R | H | (3-hydroxyphenyl)methyl | MS(m/z): 364(MH⁺) |

Example 52

(1S-cis)-N-[[3-[(1,1-Dimethylethoxy)carbonyl]-2,2,3-trimethylcyclopentyl]carbonyl]-4-[(2,6-dichlorobenzoyl)amino]-L-phenylalanine methyl ester ($C_{27}H_{30}Cl_2N_2O_6$).

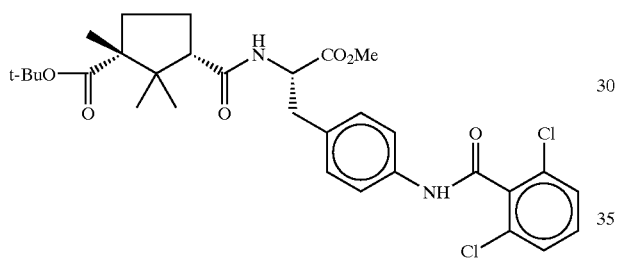

HCl gas was bubbled through a solution of N-(tert-butoxycarbonyl)-4-(2,6-dichlorobenzamido)-L-phenylalanine (800 mg) in MeOH (15 ml) for 5 minutes and the mixture was stirred for 3 hr. at room temperature. Excess HCl was removed by bubbling $N_2$ through the mixture and the solvent was removed in vacuo. The residue was washed with ether and dried. To the resulting solid was added THF (10 ml) containing DIEA (1.3 ml), BOP Reagent (938 mg) and (1S,3R)-3-(tert-butoxycarbonyl)-2,2,3-trimethylcyclopentanecarboxylic acid (480 mg), which was prepared by the saponification of methyl (1S,3R)-3-(tert-butoxycarbonyl)-2,2,3-trimethylcyclopentanecarboxylate derived from methyl (1S,3R)-3-carboxy (or chlorocarbonyl)-2,2,3-trimethylcyclopentanecarboxylate and t-BuOH. The mixture was stirred overnight under $N_2$ and the solvent was removed in vacuo.

1N HCl (10 ml) was added to the residue and the mixture was extracted with AcOEt. The extract was washed with 1N HCl, brine, sat. $NaHCO_3$, brine, sat. LiCl, and brine, dried over $MgSO_4$, and evaporated in vacuo.

The residue was purified by column chromatography on silica gel (eluent; 3:2, Hexane/AcOEt) to give (1S-cis)-N-[[3-[(1,1-Dimethylethoxy)carbonyl]-2,2,3-trimethylcyclopentyl]carbonyl]-4-[(2,6-dichlorobenzoyl)amino]-L-phenylalanine methyl ester ($C_{27}H_{30}Cl_2N_2O_6$) (1.05 g) as a colorless solid.

¹H NMR (300 MHz, CDCl₃), δ 7.58 (2H), 7.3–7.4 (3H), 7.11 (2H), 5.78 (1H), 4.8–5.0 (1H), 3.75 (3H), 3.10 (2H), 2.50 (1H), 2.0–2.2 (1H), 1.6–1.8 (1H), 1.44 (9H), 1.23 (3H), 1.16 (3H), 0.80 (3H); ¹³C NMR (75 MHz, CDCl₃), δ 175.07, 172.59, 172.17, 162.54, 136.32, 132.83, 132.48, 131.11, 130.01, 128.28, 120.56, 80.28, 56.76, 54.53, 53.12, 52.48, 46.46, 37.26, 32.41, 28.14, 23.06, 22.55, 22.06, 20.68; ESMS (m/z) 605 (MH⁺); Anal. Calcd for $C_{31}H_{38}Cl_2N_2O_6 \cdot 1/2$ $H_2O$: C, 60.53; H, 6.35; N, 4.56; Found: C, 60.71; H, 6.31; N, 4.52. MS(m/z): 605 (MH⁺).

Example 53

(1S-cis)-N-[(3-Carboxy-2,2,3-trimethylcyclopentyl)carbonyl]-4-[(2,6-dichlorobenzoyl)amino]-L-phenylalanine methyl ester ($C_{27}H_{30}Cl_2N_2O_6$).

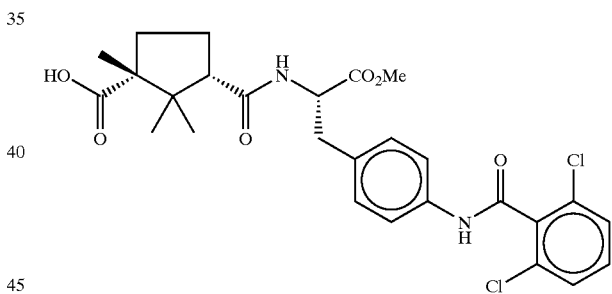

TFA (1.5 ml) was added to a solution of (1S-cis)-N-[[3-[(1,1-Dimethylethoxy)carbonyl]-2,2,3-trimethylcyclopentyl]carbonyl]-4-[(2,6-dichlorobenzoyl)amino]-L-phenylalanine methyl ester ($C_{27}H_{30}Cl_2N_2O_6$) (290 mg) in $CH_2Cl_2$ (1.5 ml) and the mixture was stirred for 3 hr. The solvent was removed in vacuo and the residue was triturated with ether/CHCl₃ to give (1S-cis)-N-[(3-Carboxy-2,2,3-trimethylcyclopentyl)carbonyl]-4-[(2,6-dichlorobenzoyl)amino]-L-phenylalanine methyl ester (180 mg) as a colorless powder.

¹H NMR (300 MHz, Acetone-d₆), δ 9.75 (1H), 7.71 (2H), 7.4–7.6 (3H), 7.25 (2H), 7.12 (1H), 4.7–4.85 (1H), 3.68 (3H), 3.08 (2H), 2.85 (1H), 2.5–2.6 (1H), 1.6–1.8 (1H), 1.4–1.5 (1H), 1.26 (3H), 1.19 (3H), 0.80 (3H); ¹³C NMR (75 MHz, Acetone-d₆), δ 176.29, 172.20, 172.11, 162.00, 137.49, 133.12, 131.85, 131.12, 129.71, 128.16, 119.59, 55.98, 53.63, 52.89, 51.37, 46.14, 36.67, 32.47, 22.57, 22.04, 21.41, 20.74; ESMS (m/z) 549 (MH⁺); Anal. Calcd for $C_{27}H_{30}Cl_2N_2O_6 \cdot 1/2$ $H_2O$: C, 58.02; H, 5.55; N, 5.01; Found: C, 58.70; H, 5.53; N, 5.01. MS(m/z): 549(MH⁺).

Example 54

(1S-cis)-N-[(3-Carboxy-2,2,3-trimethylcyclopentyl)carbonyl]-4-[(2,6-dichlorobenzoyl)amino]-L-phenylalanine ($C_{26}H_{28}Cl_2N_2O_6$).

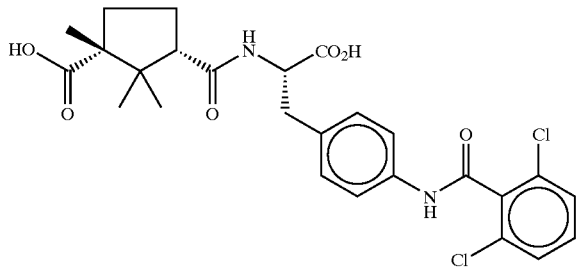

A solution of LiOH (19 mg) in $H_2O$ (1 ml) was added to a solution of (1S-cis)-N-[(3-Carboxy-2,2,3-trimethylcyclopentyl)carbonyl]-4-[(2,6-dichlorobenzoyl)amino]-L-phenylalanine methyl ester ($C_{27}H_{30}Cl_2N_2O_6$) (108 mg) in THF (4 ml)/MeOH (1 ml). The mixture was stirred for 2 hr. acidified with 1N HCl (15 ml), and extracted with AcOEt. The extract was washed with brine, dried over $MgSO_4$, and evaporated in vacuo to give (1S-cis)-N-[(3-Carboxy-2,2,3-trimethylcyclopentyl)carbonyl]-4-[(2,6-dichloro-benzoyl)amino]-L-phenylalanine (80 mg), m.p. 231–233° C.

$^1$H NMR (300 MHz, Acetone-$d_6$). δ 9.72 (1H), 7.71 (2H), 7.47–7.48 (3H), 7.27 (2H), 7.07 (1H), 4.78–4.85 (1H), 3.15 (2H), 2.85 (1H), 2.5–2.6 (1H), 1.6–1.8 (1H), 1.4–1.5 (1H), 1.26 (3H), 1.19 (3H), 0.81 (3H); $^{13}$C NMR (75 MHz, Acetone-$d_6$), δ 177.67, 173.83, 173.62, 163.32, 138.74, 134.64, 133.17, 132.42, 131.10, 129.47, 120.88, 57.29, 54.69, 54.28, 47.47, 37.93, 33.81, 23.91, 23.39, 22.73, 22.08; ESMS (m/z) 535 (MH$^+$), 533 (M–H)$^-$; Anal. Calcd for $C_{26}H_{28}Cl_2N_2O_6$·1/2 $H_2O$: C, 57.46; H, 5.34; N, 5.15; Found: C, 57.48; H, 5.38; N, 5.15. MS(m/z): 533([M–H$^-$]); MS(m/z): 578(MH$^+$)

Example 55

(1S-cis)-N-[[3-[(1,1-Dimethylethoxy)carbonyl]-2,2,3-trimethylcyclopentyl]carbonyl]-O-[(2,6-dichlorophenyl)methyl]-L-tyrosine

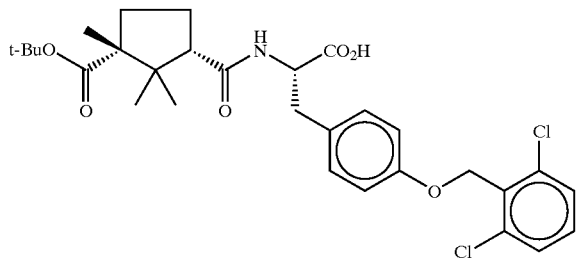

LiOH (177 mg) in $H_2O$ (10 ml) was added to a mixture of (1S-cis)-N-[(3-[(1,1-Dimethylethoxy)carbonyl]-2,2,3-trimethylcyclopentyl)carbonyl]-O-[(2,6-dichlorophenyl)methyl]-L-tyrosine methyl ester (2.18 g) in THF (10 ml)/ MeOH (5 ml) and the mixture was stirred at room temperature for 3 hr, acidified with 1N HCl (20 ml), and extracted with AcOEt. The extract was dried over $Na_2SO_4$ and the solvent was removed in vacuo to give (1S-cis)-N-[(3-[(1,1-Dimethylethoxy)carbonyl]-2,2,3-trimethylcyclopentyl)carbonyl]-O-[(2,6-dichlorophenyl)methyl]-L-tyrosine (2.07 g). MS(m/z): 578(MH$^+$).

Example 56

(1S-cis)-4-Amino-N-[[3-[(1,1-dimethylethoxy)carbonyl]-2,2,3-trimethylcyclopentyl]carbonyl]-L-phenylalanine methyl ester

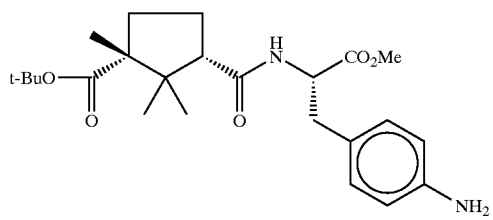

Two methods for the preparation of Example 56 are taught according to Scheme 5a and 5b.

Example 57

(1S-cis)-N-[[3-[(1,1-Dimethylethoxy)carbonyl]-2,2,3-trimethylcyclopentyl]carbonyl]-4-[(2,5-dichlorobenzoyl)amino]-L-phenylalanine methyl ester.

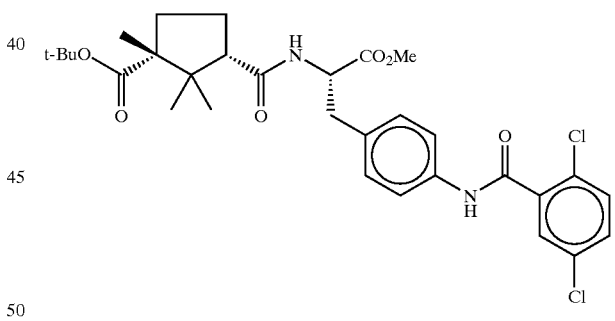

BOP—Cl (425 mg) and 2,5-dichlorobenzoic acid (319 mg) were added to a mixture of (1S-cis)-4-Amino-N-[[3-[(1,1-dimethylethoxy)carbonyl]-2,2,3-trimethylcyclopentyl]carbonyl]-L-phenylalanine methyl ester (433 mg) and DIEA (0.7 ml) in $CH_2Cl_2$ (5 ml). The mixture was stirred for 3 hr. at room temperature, acidified with 1N HCl (50 ml) and extracted with $CH_2Cl_2$. The extract was dried over $Na_2SO_4$ and evaporated in vacuo. The residue was purified by column chromatography on silica gel (eluent; Hexane→50% Hexane/AcOEt) to give (1S-cis)-N-[[3-[(1,1-Dimethylethoxy)carbonyl]-2,2,3-trimethylcyclopentyl]carbonyl]-4-[(2,5-dichlorobenzoyl)amino]-L-phenylalanine methyl ester (804 mg). MS(m/z): 605(MH$^+$).

Example 58

(1S-cis)-N-[[3-[(1,1-Dimethylethoxy)carbonyl]-2,2,3-trimethylcyclopentyl]carbonyl]-4-[(2,4,6-trichlorobenzoyl)amino]-L-phenylalanine methyl ester.

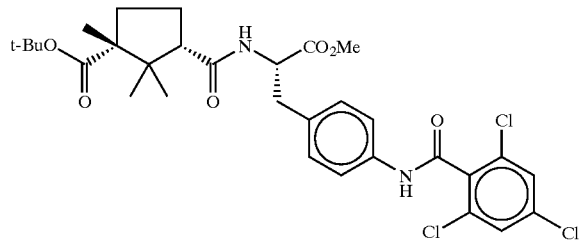

The preparation of Example 58 is taught by Scheme 13.

Example 59

(1S-cis)-4-Acetylamino-N-[[3-[(1,1-dimethylethoxy)carbonyl]-2,2,3-trimethylcyclopentyl]carbonyl]-L-phenylalanine methyl ester.

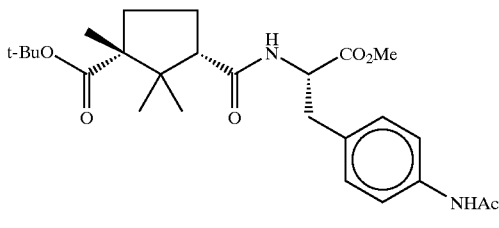

Acetic anhydride (1 ml) was added to a mixture of (1S-cis)-4-Amino-N-[[3-[(1,1-dimethylethoxy)carbonyl]-2,2,3-trimethylcyclopentyl]carbonyl]-L-phenylalanine methyl ester (710 mg) and DIEA (4 ml) in $CH_2Cl_2$ (5 ml). The mixture was stirred for 30 minutes at room temperature and partitioned between sat. $NaHCO_3$ and AcOEt. The organic layer was dried over $Na_2SO_4$ and the solvent was removed in vacuo. The residue was purified by column chromatography on silica gel (eluent; Hexane→EtOH/AcOEt(1:1)) to give (1S-cis)-4-Acetylamino-N-[[3-[(1,1-dimethylethoxy)carbonyl]-2,2,3-trimethylcyclopentyl]carbonyl]-L-phenylalanine methyl ester (669 mg). MS(m/z): 475($MH^+$).

Examples 60–153 were prepared in a similar manner, as described in Examples 52–59, and are shown in Table 4.

TABLE 4

Examples 60 through 153:

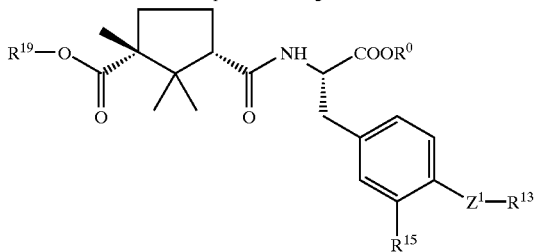

| Ex. No. | $R^{19}$ | $R^0$ | $R^{15}$ | $Z^1$ | $R^{13}$ | physico-chemical property |
|---|---|---|---|---|---|---|
| 60 | H | $CH_3$ | 2,6-dichlorophenyl-CONH— | single bond | OH | gum MS(m/z): 565($MH^+$) |
| 61 | H | H | 2,6-dichlorophenyl-CONH— | single bond | OH | M.P.: 168–171° C. MS(m/z): 549([M − H]⁻) |
| 62 | H | $CH_3$ | $NO_2$ | —$OCH_2$— | 2,6-dichlorophenyl | gum MS(m/z): 581($MH^+$) |

TABLE 4-continued

Examples 60 through 153:

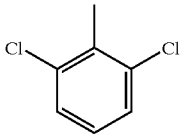

| Ex. No. | $R^{19}$ | $R^0$ | $R^{15}$ | $Z^1$ | $R^{13}$ | physico-chemical property |
|---|---|---|---|---|---|---|
| 63 | H | H | $NO_2$ | —$OCH_2$— | 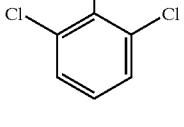 | M.P.: 92–94° C. MS(m/z): 565([M − H]$^-$) |
| 64 | H | $CH_3$ | OH | —$OCH_2$— | 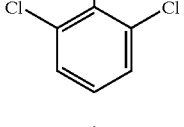 | gum MS(m/z): 552(MH$^+$) |
| 65 | H | H | OH | —$OCH_2$— | 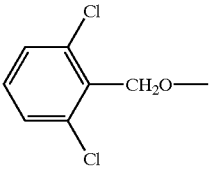 | MS(m/z): 538(MH$^+$) |
| 66 | H | H | 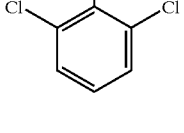 | —$OCH_2$— | 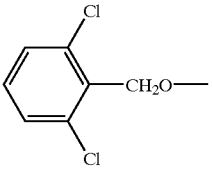 | M.P.: 118–121° C. MS(m/z): 696(MH$^+$) |
| 67 | H | H | 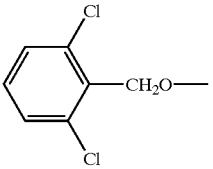 | single bond | OH | M.P.: 236–238° C. MS(m/z): 538(MH$^+$) |
| 68 | H | H | $NO_2$ | single bond | OH | M.P.: 122–125° C. MS(m/z): 407([M − H]$^-$) |
| 69 | H | H | $CH_3CO$ | single bond | OH | M.P.: 105–108° C. MS(m/z): 404([M − H]$^-$) |
| 70 | H | $CH_3$ | 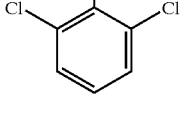 | —$OCH_2$— |  | gum MS(m/z): 710(MH$^+$) |
| 71 | H | $CH_3$ | $NO_2$ | single bond | OH | gum MS(m/z): |

TABLE 4-continued
Examples 60 through 153:
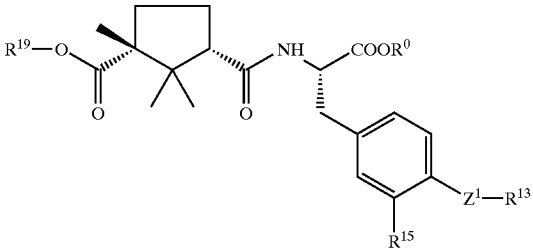
| Ex. No. | $R^{19}$ | $R^0$ | $R^{15}$ | $Z^1$ | $R^{13}$ | physico-chemical property |
|---|---|---|---|---|---|---|
| 72 | H | CH₃ | H | —NHCO— | PhCH₂O | 423(MH⁺) gum MS(m/z): 511(MH⁺) |
| 73 | H | H | H | —NHCO— | PhCH₂O | M.P.: 95–97° C. MS(m/z): 495([M − H]⁻) |
| 74 | H | CH₃ | H | —NHCO— | 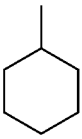 | gum MS(m/z): 487(MH⁺) |
| 75 | H | H | H | —NHCO— | 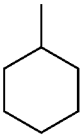 | M.P.: 151–154° C. MS(m/z): 471([M − H]⁻) |
| 76 | H | CH₃ | H | —NHCO— | 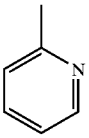 | gum MS(m/z): 482(MH⁺) |
| 77 | H | H | H | —NHCO— | 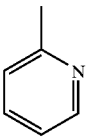 | M.P.: 102–104° C. MS(m/z): 466([M − H]⁻) |
| 78 | H | CH₃ | H | —NHCO— | CH₃ | gum MS(m/z): 419(MH⁺) |
| 79 | H | H | H | —NHCO— | CH₃ | M.P.: 238–240° C. MS(m/z): 403([M − H]⁻) |
| 80 | H | CH₃ | H | —NHCO— | 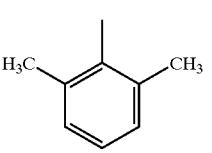 | gum MS(m/z): 509(MH⁺) |

TABLE 4-continued
Examples 60 through 153:
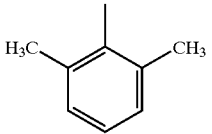
| Ex. No. | $R^{19}$ | $R^0$ | $R^{15}$ | $Z^1$ | $R^{13}$ | physico-chemical property |
|---|---|---|---|---|---|---|
| 81 | H | H | H | —NHCO— | 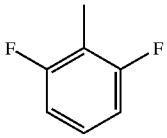 | M.P.: 195–198° C. MS(m/z): 495(MH$^+$); MS(m/z): 493([M − H]$^-$) |
| 82 | H | CH$_3$ | H | —NHCO— | 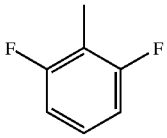 | gum MS(m/z): 517(MH$^+$) |
| 83 | H | H | H | —NHCO— | 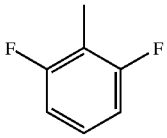 | M.P.: 150–152° C. MS(m/z): 503(MH$^+$) |
| 84 | H | CH$_3$ | H | —NHCO— | Ph | gum MS(m/z): 481(MH$^+$) |
| 85 | H | H | H | —NHCO— | Ph | M.P.: 145–148° C. MS(m/z): 465([M − H]$^-$) |
| 86 | H | CH$_3$ | H | —NHCO— | 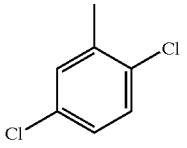 | gum MS(m/z): 549(MH$^+$) |
| 87 | H | H | H | —NHCO— | 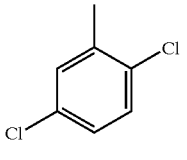 | M.P.: 155–158° C. MS(m/z): 533([M − H]$^-$) |
| 88 | H | CH$_3$ | H | —NHCO— | 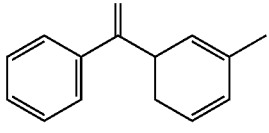 | gum MS(m/z): 585(MH$^+$) |
| 89 | H | H | H | —NHCO— | 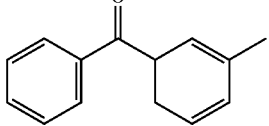 | M.P.: 190—193° C. MS(m/z): 569([[M − H]$^-$) |

TABLE 4-continued
Examples 60 through 153:
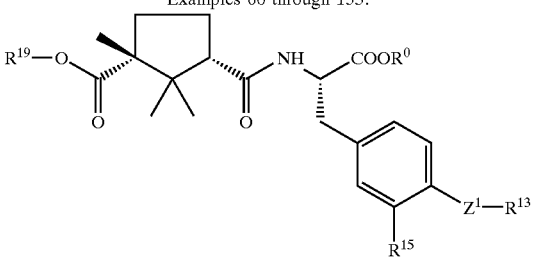
| Ex. No. | $R^{19}$ | $R^0$ | $R^{15}$ | $Z^1$ | $R^{13}$ | physico-chemical property |
|---|---|---|---|---|---|---|
| 90 | H | CH$_3$ | H | —NHCO— | 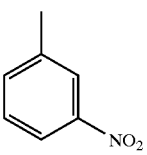 | gum<br>MS(m/z): 526(MH$^+$) |
| 91 | H | H | H | —NHCO— | 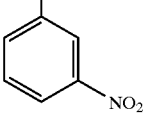 | M.P.: 146–149° C.<br>MS(m/z): 512(MH$^+$) |
| 92 | H | CH$_3$ | H | —NHCO— | 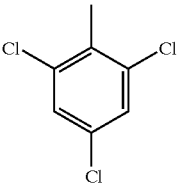 | gum<br>MS(m/z): 583(MH$^+$) |
| 93 | H | H | H | —NHCO— | 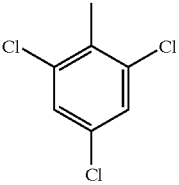 | MS(m/z): 569([M − H]$^-$) |
| 94 | H | CH$_3$ | H | —NHCO— | 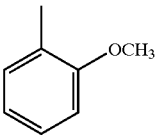 | gum<br>MS(m/z): 511(MH$^+$) |
| 95 | H | H | H | —NHCO— | 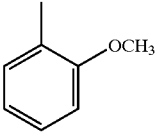 | M.P.: 140–143° C.<br>MS(m/z): 497(MH$^+$) |
| 96 | H | CH$_3$ | H | —NHCO— | 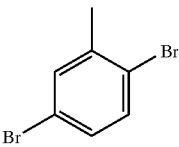 | gum<br>MS(m/z): 637(MH$^+$) |

TABLE 4-continued
Examples 60 through 153:
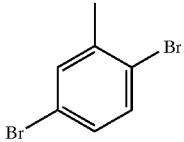
| Ex. No. | $R^{19}$ | $R^0$ | $R^{15}$ | $Z^1$ | $R^{13}$ | physico-chemical property |
|---|---|---|---|---|---|---|
| 97 | H | H | H | —NHCO— | 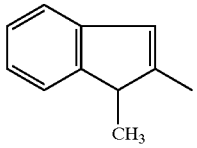 | M.P.: 170–173° C. MS(m/z): 623([M − H]⁻) |
| 98 | t-Bu | CH₃ | H | —NHCO— | 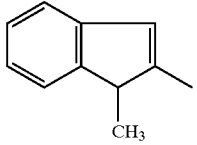 | gum MS(m/z): 589(MH⁺) |
| 99 | H | CH₃ | H | —NHCO— | 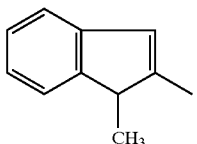 | gum MS(m/z): 533(MH⁺) |
| 100 | H | H | H | —NHCO— | 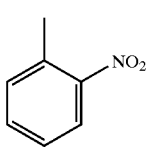 | M.P.: 165° C. (dec.) MS(m/z): 517([M − H]⁻) |
| 101 | H | CH₃ | H | —NHCO— | 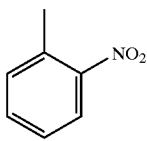 | gum MS(m/z): 526(MH⁺) |
| 102 | H | H | H | —NHCO— | 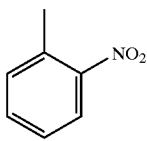 | MS(m/z): 512(MH⁺) |
| 103 | H | CH₃ | H | —NHCO— | 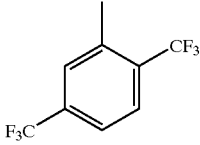 | gum MS(m/z): 617(MH⁺) |

TABLE 4-continued

Examples 60 through 153:

| Ex. No. | R$^{19}$ | R$^0$ | R$^{15}$ | Z$^1$ | R$^{13}$ | physico-chemical property |
|---|---|---|---|---|---|---|
| 104 | H | H | H | —NHCO— | 2-CH$_3$, 3-CF$_3$, 5-CF$_3$ phenyl | M.P.: 148–150° C. MS(m/z): 601([M − H]$^-$) |
| 105 | H | CH$_3$ | H | —NHCO— | 2-Cl, 3-CH$_3$, 6-CH$_3$ phenyl | gum MS(m/z): 529(MH$^+$) |
| 106 | H | H | H | —NHCO— | 2-Cl, 3-CH$_3$, 6-CH$_3$ phenyl | M.P.: 165–168° C. MS(m/z): 513([M − H]$^-$) |
| 107 | H | CH$_3$ | H | —NHCO— | 2-CH$_3$, 3-CF$_3$ phenyl | gum MS(m/z): 549(MH$^+$) |
| 108 | H | H | H | —NHCO— | 2-CH$_3$, 3-CF$_3$ phenyl | M.P.: 180–183° C. MS(m/z): 533([M − H]$^-$) |
| 109 | H | CH$_3$ | H | —NHCO— | 2-CH$_3$, 3-I phenyl | gum MS(m/z): 607(MH$^+$) |
| 110 | H | H | H | —NHCO— | 2-CH$_3$, 3-I phenyl | M.P.: 162–165° C. MS(m/z): 591([M − H]$^-$) |
| 111 | H | CH$_3$ | H | —NHCO— | 2-CH$_3$, 3-Br phenyl | gum MS(m/z): 559, 561(MH$^+$) |

TABLE 4-continued
Examples 60 through 153:
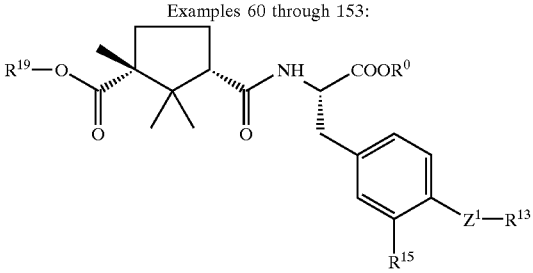
| Ex. No. | $R^{19}$ | $R^0$ | $R^{15}$ | $Z^1$ | $R^{13}$ | physico-chemical property |
|---|---|---|---|---|---|---|
| 112 | H | H | H | —NHCO— | 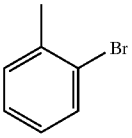 | M.P.: 156–158° C. MS(m/z): 543([M − H]⁻) |
| 113 | H | CH₃ | H | —NHCO— | 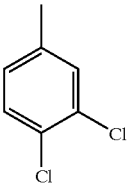 | gum MS(m/z): 549(MH⁺) |
| 114 | H | H | H | —NHCO— | 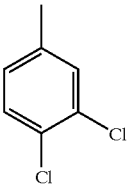 | M.P.: 155–157° C. MS(m/z): 533([M − H]⁻) |
| 115 | H | CH₃ | H | —NHCO— | 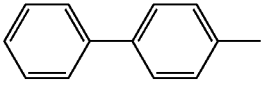 | gum MS(m/z): 557(MH⁺) |
| 116 | H | H | H | —NHCO— | 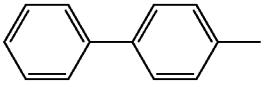 | M.P.: 162–165° C. MS(m/z): 541([M − H]⁻) |
| 117 | H | CH₃ | H | —NHCO— | 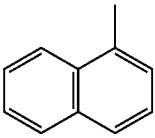 | gum MS(m/z): 531(MH⁺) |
| 118 | H | H | H | —NHCO— | 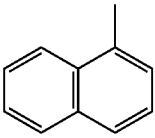 | M.P.: 235–237° C. MS(m/z): 517([M − H]⁻) |
| 119 | H | CH₃ | H | —NHCO— | 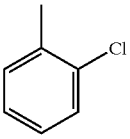 | gum MS(m/z): 515(MH⁺) |

TABLE 4-continued
Examples 60 through 153:
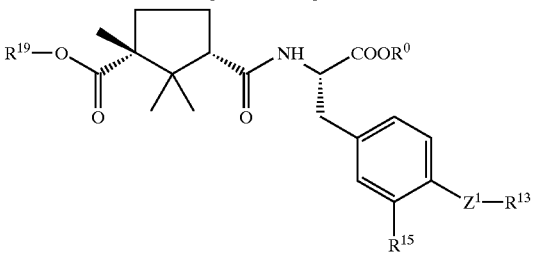
| Ex. No. | $R^{19}$ | $R^0$ | $R^{15}$ | $Z^1$ | $R^{13}$ | physico-chemical property |
|---|---|---|---|---|---|---|
| 120 | H | H | H | —NHCO— | 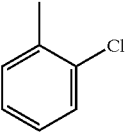 | M.P.: 143–145° C. MS(m/z): 499([M − H]⁻) |
| 121 | H | H | H | —NHCO— | PhCH₂— | M.P.: 240–242° C. MS(m/z): 479([M − H]⁻) |
| 122 | H | H | H | —NHCO— | 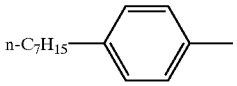 | M.P.: 212–214° C. MS(m/z): 563([M − H]⁻) |
| 123 | H | CH₃ | H | —NHCO— | 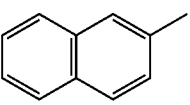 | gum MS(m/z): 531(MH⁺) |
| 124 | H | H | H | —NHCO— | 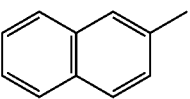 | M.P.: 141–143° C. MS(m/z): 515([M − H]⁻) |
| 125 | H | CH₃ | H | —NHCO— | 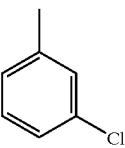 | gum MS(m/z): 515(MH⁺) |
| 126 | H | H | H | —NHCO— | 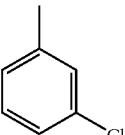 | M.P.: 145–147° C. MS(m/z): 499([M − H]⁻) |
| 127 | H | CH₃ | H | —NHCO— | 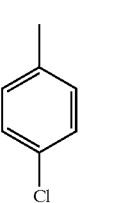 | gum MS(m/z): 515(MH⁺) |

TABLE 4-continued
Examples 60 through 153:
| Ex. No. | $R^{19}$ | $R^0$ | $R^{15}$ | $Z^1$ | $R^{13}$ | physico-chemical property |
|---|---|---|---|---|---|---|
| 128 | H | H | H | —NHCO— | 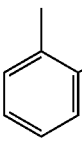 | M.P.: 185–188° C. MS(m/z): 499([M − H]⁻) |
| 129 | t-Bu | CH₃ | H | —NHCO— |  | gum MS(m/z): 553(MH⁺) |
| 130 | H | H | H | —NHCO— |  | M.P.: 158–161° C. MS(m/z): 455([M − H]⁻) |
| 131 | t-Bu | CH₃ | H | —NHCO— |  | gum MS(m/z): 527(MH⁺) |
| 132 | H | H | H | —NHCO— | 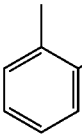 | M.P.: 117–120° C. MS(m/z): 483([M − H]⁻) |
| 133 | H | CH₃ | H | —NHCO— | i-Bu | gum MS(m/z): 461(MH⁺) |
| 134 | H | H | H | —NHCO— | i-Bu | M.P.: 146–148° C. MS(m/z): 445([M − H]⁻) |
| 135 | H | CH₃ | H | —NHCO— | 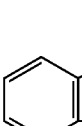 | gum MS(m/z): 569(MH⁺) |
| 136 | H | H | H | —NHCO— | 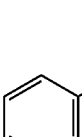 | M.P.: 160–163° C. MS(m/z): 553([M − H]⁻) |

TABLE 4-continued
Examples 60 through 153:
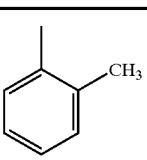
| Ex. No. | $R^{19}$ | $R^0$ | $R^{15}$ | $Z^1$ | $R^{13}$ | physico-chemical property |
|---|---|---|---|---|---|---|
| 137 | H | CH$_3$ | H | —NHCO— | 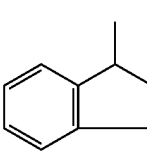 | gum MS(m/z): 495(MH$^+$) |
| 138 | H | CH$_3$ | H | —NHCO— | 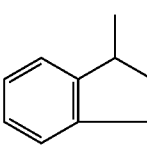 | gum MS(m/z): 569(MH$^+$) |
| 139 | H | H | H | —NHCO— | 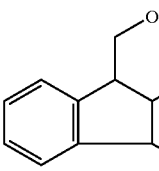 | M.P.: 166–169° C. |
| 140 | H | CH$_3$ | H | —NHCO— | 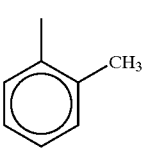 | gum MS(m/z): 599(MH$^+$) |
| 141 | H | H | H | —NHCO— | i-BuO | M.P.: 125–128° C. MS(m/z): 461([M − H]$^-$) |
| 142 | H | H | H | —NHCO— | 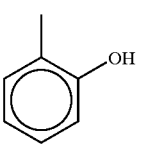 | M.P.: 152–155° C. MS(m/z): 479([M − H]$^-$) |
| 143 | H | H | H | —NHCO— | 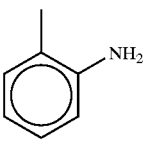 | M.P.: 148–150° C. MS(m/z): 481([M − H]$^-$) |
| 144 | H | H | H | —NHCO— |  | M.P.: 195–198° C. MS(m/z): 480([M − H]$^-$) |

TABLE 4-continued
Examples 60 through 153:
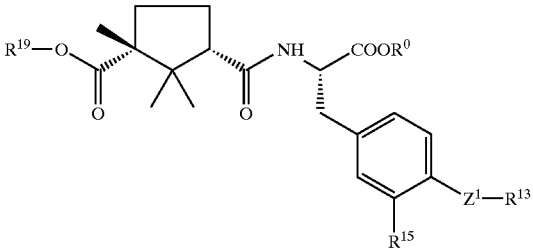
| Ex. No. | $R^{19}$ | $R^0$ | $R^{15}$ | $Z^1$ | $R^{13}$ | physico-chemical property |
|---|---|---|---|---|---|---|
| 145 | H | CH$_3$ | H | —NHCO— | 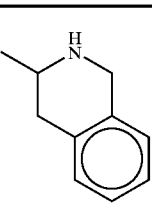 | gum<br>MS(m/z):<br>536(MH$^+$) |
| 146 | H | H | H | —NHCO— | 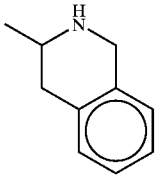 | M.P.: 208–211° C.<br>MS(m/z):<br>520([M − H]$^-$) |
| 147 | H | CH$_3$ | H | —NHSO$_2$— | 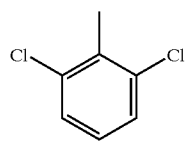 | gum<br>MS(m/z):<br>585(MH$^+$) |
| 148 | H | H | H | —NHSO$_2$— | 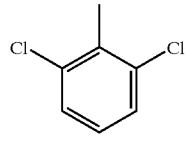 | M.P.: 224–226° C.<br>MS(m/z):<br>569([M − H]$^-$) |
| 149 | H | CH$_3$ | H | —NHSO$_2$— | 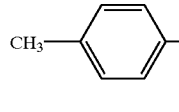 | gum<br>MS(m/z):<br>531(MH$^+$) |
| 150 | H | H | H | —NHSO$_2$— | 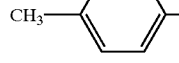 | M.P.: 220–223° C.<br>MS(m/z):<br>515([M − H]$^-$) |
| 151 | H | CH$_3$ | H | —NHCH$_2$— | 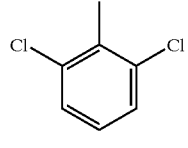 | gum<br>MS(m/z):<br>535(MH$^+$) |

TABLE 4-continued

Examples 60 through 153:

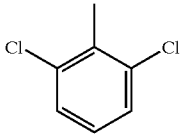

| Ex. No. | $R^{19}$ | $R^0$ | $R^{15}$ | $Z^1$ | $R^{13}$ | physico-chemical property |
|---|---|---|---|---|---|---|
| 152 | H | H | H | —NHCH$_2$- | 2,6-dichlorophenyl | M.P.: 100–103° C. MS(m/z): 519([M − H]$^-$) |
| 153 | H | H | H | —CONH— | 2,6-dichlorophenyl | MS(m/z): 533([M − H]$^-$) |

Example 154

(1S-cis)-N-[[3-(Aminocarbonyl)-2,2,3-trimethylcyclopentyl]carbonyl]-O-[(2,6-dichlorophenyl)methyl]-L-tyrosine methyl ester.

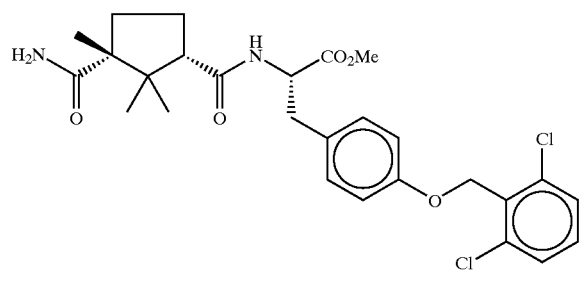

BOP Reagent (674 mg) was added to a mixture of (1S-cis)-N-[(3-Carboxy-2,2,3-trimethylcyclopentyl)carbonyl]-O-[(2,6-dichlorophenyl)methyl]-L-tyrosine methyl ester (743 mg) and aq. NH$_4$OH (0.5 ml) in THF (10 ml). The mixture was stirred for 24 hr. and sat. LiCl (15 ml) was added. The resulting mixture was extracted with AcOEt and the extract was dried over Na$_2$SO$_4$. The solvent was removed in vacuo and the residue was purified by column chromatography on silica gel (eluent; Hexane→90% AcOEt/Hexane) to give (1S-cis)-N-[[3-(Aminocarbonyl)-2,2,3-trimethylcyclopentyl]carbonyl]-O-[(2,6-dichlorophenyl)methyl]-L-tyrosine methyl ester (533 mg). MS(m/z):535(MH$^+$).

Example 155

(1S-cis)-N-[[3-(Aminocarbonyl)-2,2,3-trimethylcyclopentyl]carbonyl]-O-[(2,6-dichlorophenyl)methyl] -L-tyrosine

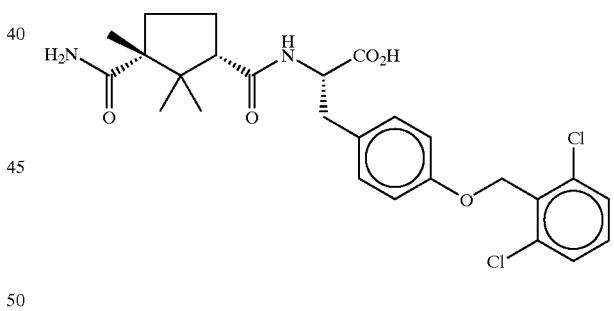

A solution of LiOH (119 mg) in H$_2$O (5 ml) was added to a mixture of (1S-cis)-N-[[3-(Aminocarbonyl)-2,2,3-trimethylcyclopentyl]carbonyl]-O-[(2,6-dichlorophenyl)methyl]-L-tyrosine methyl ester (533 mg) in THF (5 ml)/MeOH (3 ml). The mixture was stirred for 3 hr. at room temperature, acidified with 1N HCl (20 ml), and extracted with AcOEt. The extract was dried over Na$_2$SO$_4$ and evaporated in vacuo to give (1S-cis)-N-[[3-(Aminocarbonyl)-2,2,3-tri-methylcyclopentyl]carbonyl]-O-[(2,6-dichlorophenyl)methyl]-L-tyrosine (466 mg), mp 102–104° C., MS (m/z): 519 ([M–H]$^-$).

Examples 156–166 were prepared in a similar manner, as described in Examples 154 and 155 and are shown in Table 5.

TABLE 5

Examples 156 through 166:

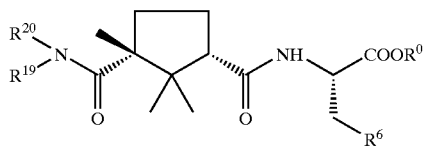

| Ex. No. | $R^{19}$ | $R^{20}$ | $R^0$ | $R^6$ | physicochemical property |
|---|---|---|---|---|---|
| 156 | cyclohexylmethyl | H | H | BzlO-C6H4-CH2- | M.P.: 85–87° C.<br>MS (M/z): 533 ([M − H]$^-$) |
| 157 | Et | H | $CH_3$ | 2,6-Cl2-C6H3-CH2O-C6H4-CH2- | gum<br>MS (m/z): 563 (MH$^+$) |
| 158 | Et | H | H | 2,6-Cl2-C6H3-CH2O-C6H4-CH2- | MS (m/z): 550 (MH$^+$) |
| 159 | Me | H | $CH_3$ | 2,6-Cl2-C6H3-CH2O-C6H4-CH2- | gum; $^1$H NMR<br>(300 MHz, CD$_3$OD),<br>δ7.3–7.4(3H), 7.14(2H), 6.95(2H), 5.22(2H),<br>4.71(1H), 3.69(3H), 3.12(1H), 3.00(1H),<br>2.39(3H), 2.3–2.4(1H), 2.0–2.1(1H),<br>1.7–1.8(1H), 1.4–1.5(1H), 1.27(3H),<br>1.18(3H), 0.73(3H). |
| 160 | Me | H | H | 2,6-Cl2-C6H3-CH2O-C6H4-CH2- | M.P.: 80–83° C.<br>MS (m/z): 533 ([M − H]$^-$) |
| 161 | Me | Me | H | 2,6-Cl2-C6H3-CH2O-C6H4-CH2- | $^1$H NMR (300 MHz, CDCl$_3$),<br>δ 7.3–7.4(3H), 7.16(2H), 7.00(2H), 5.25(2H),<br>4.75(1H), 3.66(3H), 3.22(1H), 3.13(1H),<br>2.5–2.7(1H), 2.1–2.2(1H), 2.05(3H),<br>2.03(3H), 1.7–1.8(1H), 1.4–1.6(1H),<br>1.20(3H), 1.19(3H), 0.73(2H). |
| 162 | MeO | H | $CH_3$ | 2,6-Cl2-C6H3-CH2O-C6H4-CH2- | gum<br>MS (m/z): 565 (MH$^+$) |

TABLE 5-continued

Examples 156 through 166:

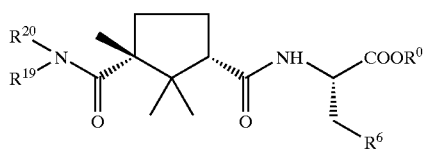

| Ex. No. | $R^{19}$ | $R^{20}$ | $R^0$ | $R^6$ | physicochemical property |
|---|---|---|---|---|---|
| 163 | MeO | H | H | 2,6-dichlorobenzyl-O-(4-methylphenyl) | M.P.: 70–72° C.<br>MS (m/z): 551 ([M – H]$^-$) |
| 164 | Me | H | H | 4-methylimidazolyl-CH$_2$-(3,4-dichlorophenyl) | MS (m/z): 509 (MH$^+$) |
| 165 | Et | H | H | 4-methylimidazolyl-CH$_2$-(3,4-dichlorophenyl) | MS (m/z): 523 (MH$^+$) |
| 166 | H | H | H | 2,6-dichloro-CONH-(4-methylphenyl) | M.P.: 196–198° C.<br>MS (m/z): 532 ([M – H]$^-$) |

Example 167

(1R-cis)-N-[[3-[(1,1-Dimethylethoxy)carbonyl]-1,2,2-trimethylcyclopentyl]carbonyl]-O-(phenylmethyl)-L-tyrosine methyl ester

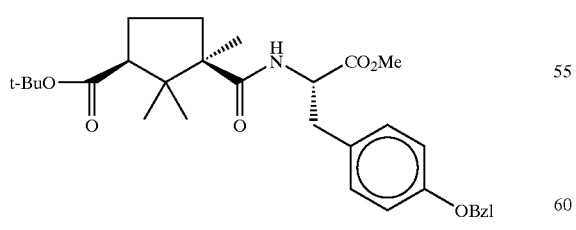

Example 167 was prepared from O-benzyl-L-tyrosine methyl ester hydrochloride and (1R,3S)-3-(tert-butoxycarbonyl)-1,2,2-trimethylcyclopentanecarboxylic acid in a similar manner as described in Example 52. Physicochemical property: gum, MS (m/z):524(MH$^+$).

Example 168

(1R-cis)-N-[(3-Carboxy-1,2,2-trimethylcyclopentyl)carbonyl]-O-(phenylmethyl)-L-tyrosine methyl ester ($C_{27}H_{33}NO_6$).

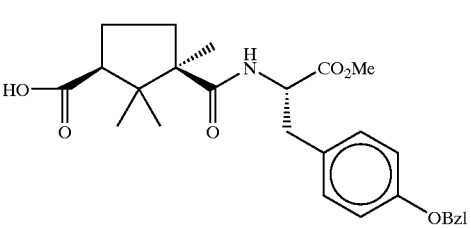

Example 168 was prepared in a similar manner as described in Example 53. Physicochemical property: gum; MS (m/z):468(MH$^+$); MP 191–192° C. (d).

Example 169

(1R-cis)-N-[(3-Carboxy-1,2,2-trimethylcyclopentyl)carbonyl]-O-(phenylmethyl)-L-tyrosine ($C_{26}H_{31}NO_6$).

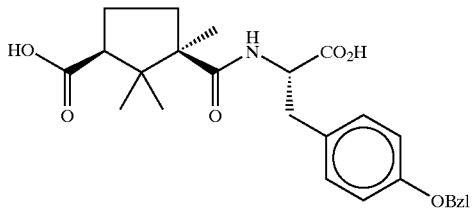

Example 169 was prepared in a similar manner as described in Example 54, MS (m/z):454 (MH$^+$).

Example 170

(1S-cis)-N-[(3-Carboxy-2,2,3-trimethylcyclopentyl)carbonyl]-4-[[N-acetyl-N-[(2,6-dichloro-phenyl)methyl]amino]-L-phenylalanine methyl ester

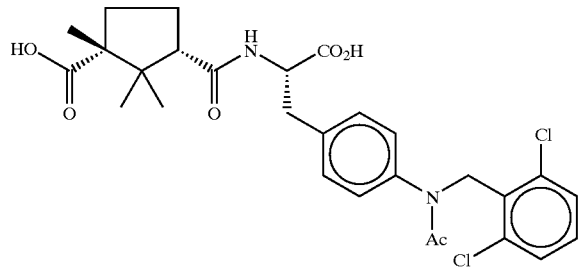

(1S-cis)-N-[[3-[(1,1-Dimethylethoxy)carbonyl]-2,2,3-trimethylcyclopentyl]carbonyl]-4-[N-[(2,6-dichlorophenyl)methyl]amino]-L-phenylalanine methyl ester (0.29 g), which was derived from 4-[[N-(2,6-dichlorophenyl)methyl]amino]-L-phenylalanine methyl ester in a similar manner as described in Example 52, was dissolved in pyridine (3 ml) and Ac$_2$O (2.5 ml) was added. The mixture was stirred overnight, evaporated in vacuo, and extracted with AcOEt. The extract was washed with aq. HCl, brine, sat. NaHCO$_3$, brine, and dried over Na$_2$SO$_4$. The solvent was removed in vacuo to give (1S-cis)-N-[[3-[(1,1-dimethylethoxy)carbonyl]-2,2,3-trimethylcyclopentyl]carbonyl]-4-[(N-acetyl-N-[(2,6-dichlorophenyl)methyl]amino]-L-phenylalanine methyl ester (0.24 g). The obtained diester was treated in a similar manner as described in Examples 53 and 54 to give (1S-cis)-N-[(3-Carboxy-2,2,3-trimethylcyclopentyl)carbonyl]-4-[[N-acetyl-N-[(2,6-dichlorophenyl)methyl]amino]-L-phenylalanine methyl ester as a colorless solid, mp 241–244° C., MS (m/z):561 ([M–H]$^-$).

Example 171

(1S-cis)-N-[(3-Carboxy-2,2,3-trimethylcyclopentyl)methyl]-O-[(2,6-dichlorophenyl)methyl]-L-tyrosine methyl ester ($C_{27}H_{33}Cl_2NO_5$).

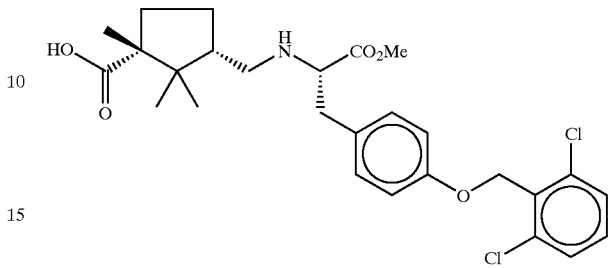

NaCNBH$_3$ (104 mg) was added to a mixture of O-[(2,6-dichlorophenyl)methyl]-L-tyrosine methyl ester (490 mg), (1R,cis)-3-formyl-1,2,2-trimethylcyclopentanecarboxylic acid, (1R,5S)-4-hydroxy-1,8,8-trimethyl-3-oxabicyclo[3,2,1]-octane-2-one (153 mg), AcOH (0.5 ml), and MeOH (25 ml) under argon. The mixture was stirred for 72 hr. at room temperature. The solvent was removed in vacuo and 10% HCl (20 ml) was added. The resulting mixture was stirred for 2 hr. and extracted with AcOEt. The extract was dried over Na$_2$SO$_4$ and evaporated in vacuo. The residue was purified by column chromatography on silica gel (eluent; 10% AcOEt/Hexane) to give (1S-cis)-N-[(3-Carboxy-2,2,3-trimethylcyclopentyl)methyl]-O-[(2,6-dichlorophenyl)methyl]-L-tyrosine methyl ester (75 mg), MS(m/z): 522 (MH$^+$).

Example 172

(1S-cis)-N-[(3-Carboxy-2,2,3-trimethylcyclopentyl)methyl]-O-[(2,6-dichlorophenyl)methyl]-L-tyrosine ($C_{26}H_{31}Cl_2NO_5$).

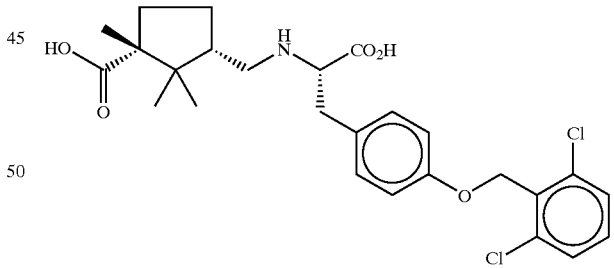

A solution of LiOH (33 mg) in H$_2$O (2 ml) was added to a mixture of (1S-cis)-N-[(3-Carboxy-2,2,3-trimethylcyclopentyl)methyl]-O-[(2,6-dichlorophenyl)methyl]-L-tyrosine methyl ester ($C_{27}H_{33}Cl_2NO_5$) (71 mg) in THF (2 ml). The mixture was stirred for 5 hr. at room temperature, neutralized with 1N HCl, and extracted with AcOEt. The extract was dried over Na$_2$SO$_4$ and evaporated in vacuo to give (1S-cis)-N-[(3-Carboxy-2,2,3-trimethylcyclopentyl)methyl]-O-[(2,6-dichlorophenyl)methyl]-L-tyrosine (40 mg), mp 135–138° C., MS(m/z): 508(MH$^+$).

Example 173

(1S-cis)-N-[(3-Carboxy-2,2,3-trimethylcyclopentyl) carbonyl]-N-methyl-O-(phenylmethyl)-L-tyrosine ($C_{27}H_{33}NO6$).

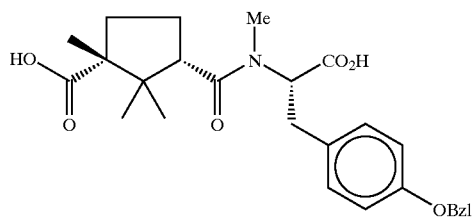

(1S-cis)-N-[(3-Carboxy-2,2,3-trimethylcyclopentyl) carbonyl]-O-(phenylmethyl)-L-tyrosine ($C_{26}H_{31}NO_6$) (52 mg) was added to a suspension of NaH (20.5 mg, 60% in oil) in DMF (5 ml) and the mixture was stirred for 10 min at room temperature. After addition of MeI (43 ml), the mixture was stirred for 14 hr. and quenched with $H_2O$. The resulting mixture was extracted with ether. The extract was evaporated in vacuo and the residue was subjected to saponification using aq. LiOH in THF in a similar manner as described in Example 54. The saponification was carried out for 2 hr. and the mixture was acidified with 1N HCl (10 ml) and extracted with AcOEt. The extract was dried over $Na_2SO_4$, evaporated in vacuo, and the residue was purified by column chromatography on silica gel (eluent; 10% MeOH/$CH_2Cl_2$) to give (1S-cis)-N-[(3-Carboxy-2,2,3-trimethylcyclopentyl)carbonyl]-N-methyl-O-(phenylmethyl)-L-tyrosine (40 mg), MS(m/z): 466 ([M−H]−).

Example 174

(1S-cis)-N-[(3-Carboxy-2,2,3-trimethylcyclopentyl) carbonyl]-O-[(2,6-dichlorophenyl)methyl]-N-methyl-L-tyrosine ($C_{27}H_{31}Cl_2NO6$).

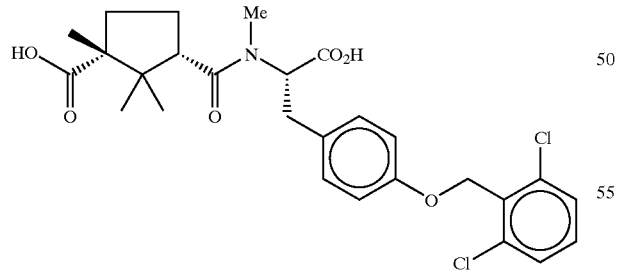

Example 174 was prepared from N-(tert-butoxycarbonyl)-O-[(2,6-dichlorophenyl)methyl]-N-methyl-L-tyrosine and (1S,3R)-3-(tert-butoxycarbonyl)-2,2,3-trimethylcyclopentanecarboxylic acid in a similar manner as described in Example 52, 53 and 54, mp 108–110° C., MS (m/z):536 ($MH^+$).

Example 175

(1S-cis)-N-[(3-Carboxy-2,2,3-trimethylcyclopentyl) carbonyl]-O-[(2,6-dichlorophenyl)methyl]-L-tyrosinamide ($C_{26}H_{30}Cl_2N_2O_5$).

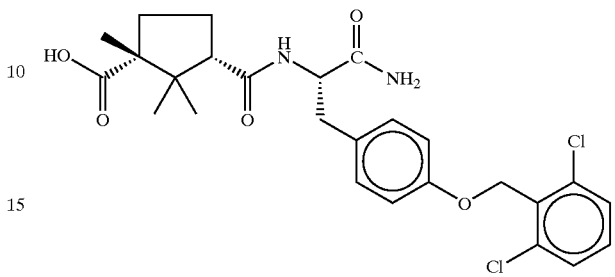

NaCN (10 mg) was added to a solution of (1S-cis)-N-[(3-Carboxy-2,2,3-trimethylcyclopentyl)carbonyl]-O-[2,6-dichlorophenyl)methyl]-L-tyrosine methyl ester (306 mg) in MeOH (10 ml) in a thick walled tube. 15–20 ml of $NH_3$ was condensed into the mixture at −78° C. The tube was sealed and warmed to room temperature. After 48 hr. stirring, the mixture was cooled to −78° C. and the sealed tube was opened. The mixture was warmed to room temperature and excess $NH_3$ was removed by bubbling $N_2$. The solvent was removed in vacuo and the residue was purified by column chromatography on silica gel (eluent; AcOEt→10% MeOH/AcOEt) to give (1S-cis)-N-[(3-Carboxy-2,2,3-trimethylcyclopentyl)carbonyl]-O-[(2,6-dichloro-phenyl)methyl]-L-tyrosinamide (258 mg), mp 120–122° C., MS (m/z): 519 ([M−H]−).

Example 176

[1S-[1α(R*),3α]]-4-(2,6-Dichlorobenzoyl)-α-[[[3-[(1,1-dimethylethoxy)carbonyl]-2,2,3-trimethylcyclopentyl] carbonyl]amino]-γ-oxo-1-piperazinebutanoic acid methyl ester

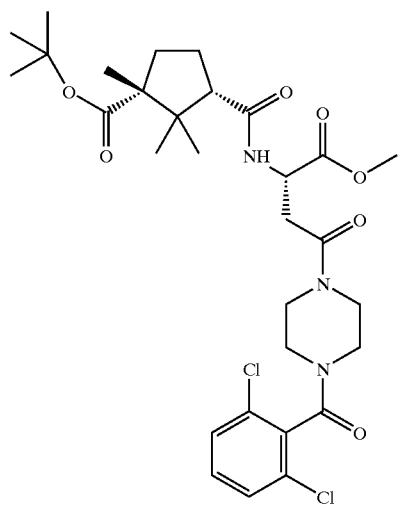

The synthesis of Example 176 is taught by Scheme 17.

Example 177

[1S-[1α(R*),3α]]-α-[[(3-Carboxy-2,2,3-trimethylcyclopentyl)carbonyl]amino]-4-(2,6-dichlorobenzoyl)-γ-oxo-1-piperazinebutanoic acid

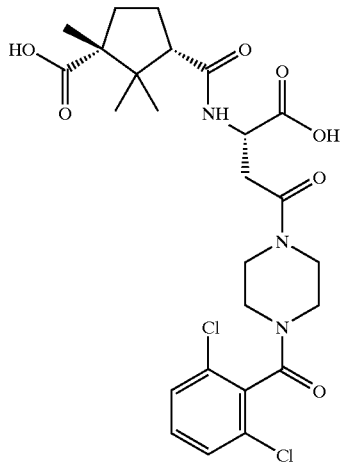

The synthesis of Example 177 is taught by Scheme 17.

Example 178

[1S-[1α(R*),3α]]-4-(2,6-Dichlorobenzoyl)-β-[[[3-[(1,1-dimethylethoxy)carbonyl]-2,2,3-trimethylcyclopentyl]carbonyl]amino]-γ-oxo-1-piperazinebutanoic acid methyl ester

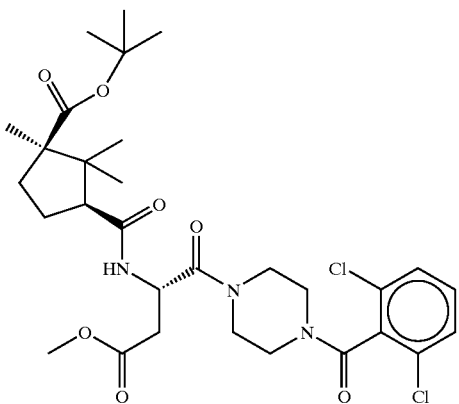

The synthesis of Example 178 is taught by Scheme 18.

Example 179

[1S-[1α,3α(R*)]]-N-[[3-[[(5-Amino-1-carboxypentyl)amino]carbonyl]-2,2,3-trimethylcyclopentyl]carbonyl]-4-[(2,6-dichlorobenzyl)amino]-L-phenylalanine

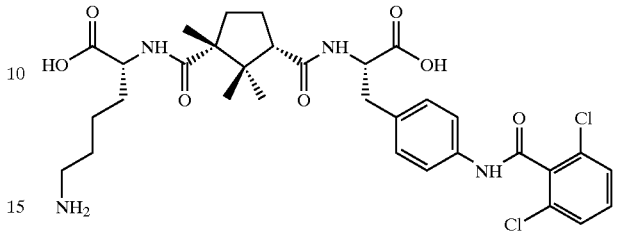

(1) To a solution of N-(tert-butoxycarbonyl)-4-(2,6-dichlorobenzamido)-L-phenylalanine (9.25 g) in DMF (80–100 ml) was added Merrifield resin (10.0 g, 10.0 meq/g, Novabiochem) and anhydrous potassium fluoride (1.57 g). The reaction mixture was stirred for 1 day at 80° C. and the resulting resin bound amino acid derivative was collected by filtration, washed thoroughly with DMF, 50% aqueous DMF, $CH_3OH$, $CH_2Cl_2$, $CH_3OH$, and then dried in vacuo to give the resin bound N-(tert-butoxycarbonyl)-4-(2,6-dichlorobenzamido)-L-phenylalanine (0.53 meq/g). Substitution of the amino acid derivative onto the resin was estimated using the picric acid method.

(2) To the obtained resin (1.0 g, 0.53 meq/g) was added 50% $TFA/CH_2Cl_2$ (10–15 ml) and the mixture was stirred for 30 min. The resin was collected by filtration, washed with $CH_2Cl_2$, $CH_3OH$, and $CH_2Cl_2$. To the resin bound 4-(2,6-dichlorobenzamido)-L-phenylalanine was added a mixture of (1S, 3R)-3-(tert-butoxycarbonyl)-2,2,3-trimethylcyclopentanecarboxylic acid ( 408 mg), 0.5M HBTU-HOBT (3.3 ml) in DMF, DIEA (0.694 ml), DMF (10–15 ml) and the mixture was vortexed for 2 hrs. at room temperature. The resin was collected by filtration, washed with DMF, $CH_2Cl_2$, $CH_3OH$, $CH_2Cl_2$ to give a resin bound (1S-cis)-N-[[3-[(1,1-dimethylethoxy)carbonyl]-2,2,3-trimethylcyclopentyl]carbonyl]-4-[(2,6-dichlorobenzoyl)amino]-L-phenylalanine (0.990 g). To the mixture (3) To the resin (0.390 g, 0.21 meq/g) was added 50% $TFA/CH_2Cl_2$ (4–5 ml) and the mixture was stirred for 2 hrs. The resin was collected by filtration, washed with $CH_2Cl_2$, $CH_3OH$, and $CH_2Cl_2$. To the resin bound (1S-cis)-N-[[3-Carboxy-2,2,3-trimethylcyclopentyl]carbonyl]-4-[(2,6-dichlorobenzoyl)amino]-L-phenylalanine was added a mixture of $N^6$-(tert-butoxycarbonyl)-L-lysine trert-butyl ester (0.210 g), 0.5M HBTU-HOBT (1.5 ml) in DMF, DIEA (0.270 ml) and the mixture was vortexed for 2 hrs. The resin was collected by filtration, washed with DMF, $CH_2Cl_2$, $CH_3OH$, and $CH_2Cl_2$. To the obtained resin was added 50% TFA/CH2Cl2 (4–5 ml) and the mixture was stirred for 30 min. The resin was collected by filtration, washed with $CH_2Cl_2$, $CH_3OH$, and $CH_2Cl_2$. To the resin was added THF (3 ml), $CH_3OH$ (0.9 ml) and 2N LiOH (0.3 ml). The mixture wasd stirred for 15 mins and filtered to a test tube (13×100 mm). The resin was washed with THF/5% $CH_3OH$ and the combined filtrate was evaporated. The residue was dilued with $H_2O$ (1 ml) and acidified with 1N HCl. The precipitate was centrifuged. The supernatant was decanted, and the pellet was washed with H₂O. The residue was lyophilized to give a colorless solid (100 mg).

(4) The solid (80 mg) was purified by a Water Delta Prep 3000 system (Waters, Milford, Mass.) equipped with a reversed phase silica C18 column (4.7 cm×30.0 cm), using a linear gradient of increasing acetonitrile in an aqueous solution of triethylammonium phosphate (TEAP) (prepared by diluting phosphoric acid (25 ml) and triethylamine (50 ml) to 6000 ml of deionized water, pH −5.5). The fractions containing desired compound was desalted with 0.1% acetic acid using the above system. The collected fractions were lyophilized to give [1S-[1α,3α(R*)]-N-[[3-[[(5-Amino-1-carboxypentyl)amino]carbonyl]-2,2,3-trimethyl-cyclopentyl)carbonyl]-4-[(2,6-dichlorobenzoyl)amino]-L-phenylalanine (Example 179) as a colorless solid (10 mg), ESMS:661 (M−H])⁻.

Example 180

(1S-cis)-N-[[3-[[(2-Amino-2-oxoethyl)amino]carbonyl]-2,2,3-trimethylcyclopentyl]carbonyl]-4-[(2,6-dichlorobenzoyl)amino]-L-phenylalanine ($C_{28}H_{32}Cl_2N_4O_6$).

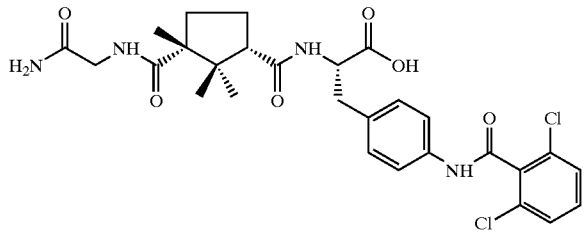

The synthesis of Example 180 is taught by Scheme 8, 8-G: wherein $R^{8-1}$=H, $R^{8-2}$=H, $R^4$=H, $R^6$=4-[(2,6-Dichlorobenzoyl)amino]-phenyl, Stereochemistry=(1S-Cis)-L. Accordingly, the synthesis of (1S-cis)-N-[[3-[[(2-Amino-2-oxoethyl)amino]carbonyl]-2,2,3-trimethylcyclopentyl]carbonyl]-4-[(2,6-dichlorobenzoyl)amino]-L-phenylalanine ($C_{28}H_{32}Cl_2N_4O_6$) is as follows.

To 8-F-1 (8-F: $R^{8-1}$=H, $R^{8-2}$=H, $R^4$=H, $R^5$=CO₂CH₃, $R^6$=4-[(2,6-dichlorobenzoyl)amino]-phenyl, Stereochemistry=(is-cis)-L) (1.05 g, 1.7 mmol), dissolved in methanol (30 mL), is added a solution of LiOH.2H₂O (0.32 g, 7.65 mmol) in water (10 mL), dropwise over 15 minutes. The mixture stirs for 18 hours at room temperature and the pH is then adjusted to ca. 7 by the careful addition of 1N aq. HCl. The majority of the methanol, is removed in vacuo and the pH of the resulting solution is adjusted to ca. 2 with 1N aq. HCl. The resulting flocculent white precipitate is isolated by filtration and dried. The solid is crushed and washed with water (2×10 mL) and dried in vacuo at 50° C. to give 0.97 g (97%) of Example 180 (8-G: $R^{8-1}$=H, $R^{8-2}$=H, $R^4$=H, $R^6$=4-[(2,6-dichlorobenzoyl)amino]-phenyl) as a white, powdery solid.

MP: 203–205° C.; ¹H NMR (300MHz, DMSO-d₆): δ12.51(brs, 1H), 10.70(s, 1H), 7.75(m, 1H), 7.45–7.57(3H), 7.33(m, 1H), 7.20(m, 1H), 7.11(brs, 1H), 6.92(brs, 1H), 4.43(m, 1H), 3.63(m, 1H), 3.47 m, 2H), 3.30(s, 2H), 3.01(m, 1H), 2.84(m, 1H), 2.31(m, 1H), 1.87(m, 1H), 1.55(m, 1H), 1.31(m, 1H), 1.17(s, 3H), 1.08(s, 3H), 0.59(s, 3H); IR (Mull): 3511, 3325, 3128, 3082, 2868, 1722, 1697, 1664, 1614, 1555, 1537, 1417, 1337, 1246, 799; MS (FAB) m/z (rel. intensity) 591(M+H, base), 517(32), 335(26), 239(32), 173(39), 109(63), 57(80); HRMS (FAB) calcd for $C_{28}H_{32}Cl_2N_4O_6$+H⁺591.1777, found 591.1747.

Example 181

(1S-cis)-N-[[3-[[(Carboxymethyl)amino]carbonyl]-2,2,3-trimethylcyclopentyl]carbonyl]-4-[(2,6-dichlorobenzoyl)amino]-L-phenylalanine ($C_{28}H_{31}Cl_2N_3O_7$).

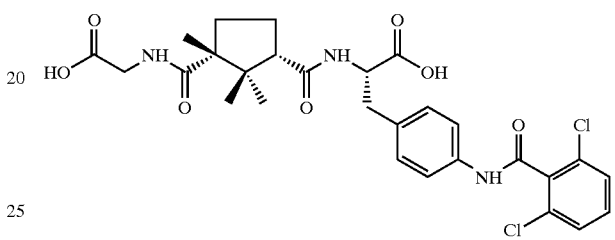

The synthesis of Example 181 is taught by scheme 7, 7-G: wherein $R^{7-1}$=H, $R^4$=H, $R^5$=CO₂H, $R^6$=4-[(2,6-Dichlorobenzoyl)amino]phenyl and Stereochemistry=(1S-cis)-L. Accordingly, (1S-cis)-N-[[3-[[(Carboxymethyl)amino]carbonyl]-2,2,3-trimethylcyclopentyl]carbonyl]-4-[(2,6-dichlorobenzoyl)amino]-L-phenylalanine ($C_{28}H_{31}Cl_2N_3O_7$) is synthesized as follows: (1S-cis)-N-[[3-[[(Carboxymethyl)amino]carbonyl]-2,2,3-trimethylcyclopentyl]carbonyl]-4-[(2,6-dichlorobenzoyl)amino]-L-phenylalanine methyl ester (0.7 g, 1.15 mmol) is dissolved in methanol (12 mL). To this is added a mixture of LiOHH₂O (0.243 g, 5.8 mmol), aqueous H₂O₂ (30%, 2 mL), and H₂O (2 mL). After overnight stirring, the reaction mixture is diluted with water (50 mL), and evaporated (room temperature, in vacuo/N₂ flow) until the methanol is gone. The aqueous solution is then transferred to a separatory funnel and shaken with diethyl ether (2×20 mL). The aqueous layer is then evaporated, to remove residual diethyl ether, and cooled in an ice water bath. The stirred solution is then brought to pH3–4 using aqueous HCl (1N). The resultant precipitate is isolated by suction filtration (with water washes) to give the target compound as a white solid ( 0.4 g, 58% yield) ¹HNMR: (300MHz, DMSO-d₆): δ12.45 (br.s, 1H), 10.6(s, 1H), 7.74(m, 2H), 7.57–7.44(m, 3H), 7.20(m, 2H), 4.48–4.40(m, 1H), 3.65(m, 2H), 2.94(m, 2H), 2.64(m, 1H), 2.35(m, 1H), 1.90(m, 1H), 1.58(m, 1H), 1,29 (m, 1H), 1.18(s, 3H), 1.08(s, 3H), 0.60(s, 3H); IR (mull) 3124, 3088, 3078, 1738, 1666, 1628, 1612, 1588, 1563, 1552, 1521, 1429, 1334, 1197, 1170cm⁻¹; MS (FAB) m/z (rel. intensity) 592 (M+H, 99), 595 (20), 594 (69), 593 (41), 592 (99), 519 (25), 517 (38), 240 (55), 175 (23), 173 (33), 109 (64); HRMS(FAB) m/z calcd for $C_{28}H_{31}Cl_2N_3O_7$+H⁺ 592.1617, found 592.1606; Anal. Calcd for $C_{28}H_{31}Cl_2N_3O_7$: C, 56.76; H, 5.27; N, 7.09; Found: C, 54.92; H, 5.41; N, 6.91; KF Water: 3.05% H₂O.

Example 182

[1S-[1α,3α(E)]]-N-[[3-(2-Carboxyethenyl)-2,2,3-trimethylcyclopentyl]carbonyl]-4-[(2,6-dichlorobenzoyl)amino]-L-phenylalanine disodium salt ($C_{28}H_{28}Cl_2N_2Na_2O_6$).

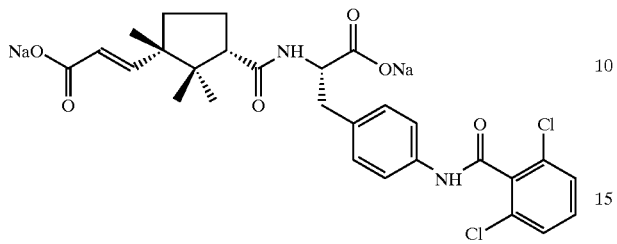

The synthesis of Example 182 is taught by Scheme 11, 11-G: wherein $R^4$=H, $R^5$=$CO_2H$ $R^6$=4-[(2,6-Dichlorobenzoyl)amino]-phenyl and Stereochemistry=[1S-[1α,3α(E)]]-L. Accordingly, [1S-[1α,3α(E)]]-N-[[3-(2-Carboxyethenyl)-2,2,3-trimethylcyclopentyl]carbonyl]-4-[(2,6-dichlorobenzoyl)amino]-L-phenylalanine disodium salt ($C_{28}H_{28}Cl_2Na_2N_2O_6$) of 11-G is synthesized as follows: To a solution of 11-F ($R^4$=H, $R^5$=$CO_2CH_3$, $R^6$=4[(2,6-Dichlorobenzoyl)amino]-phenyl, Stereochemistry=[1S-[1α,3α(E)]]-L) (0.45 g, 0.78 mmol) in methanol (5 mL) in a flask cooled in an ice water bath is added a solution of LiOHH.$_2$O (0.127 g, 3 mmol) in $H_2O$ (5 mL). After two days, the mixture is diluted with water (50 mL), evaporated in vacuo until the methanol is gone and then cooled to −10° C. and brought to pH 2 using 1N HCl. The resultant white precipitate is isolated by suction filtration to give a white solid which is stirred with saturated aqueous $NaHCO_3$(2 mL) and then transferred to a C-18 reversed phase HPLC column and eluted with a gradient from 0.01%aq $NaHCO_3$ to 10%acetonitrile/0.01%aq $NaHCO_3$. Evaporation in vacuo to give Example 182 as a white solid (0.25 g, 51% yield)

$^1$H NMR(300MHz, DMSO-$d_6$) δ7 51–7.42(m, 5H), 7.06 (m, 2H), 6.39(m, 1H), 5.49(m, 1H), 4.10(m, 1H), 2.99(m, 1H), 2.86(m, 1H), 2.56 (m, 1H), 1.85(m, 2H), 1.61 (m, 1H), 1.29(m, 1H), 0.90(s, 3H), 0.85(s, 3H), 0.51(s, 3H); IR (mull) 3393, 3257, 3124, 3035, 1654, 1604, 1562, 1544, 1515, 1431, 1398, 1325, 799, 778, 722cm⁻; MS (FAB) m/z (rel. intensity) 605 (M+H, 44), 629 (9), 627 (14), 608 (8), 607 (30), 606 (14), 605 (44), 585 (14), 583 (21), 73 (45), 23 (99); KF Water: 7.09%H2O.

Example 183

(1S-cis)-N-[[3-[(Carboxymethoxy)methyl]-2,2,3-trimethylcyclopentyl]carbonyl]-4-[(2,6-dichlorobenzoyl)amino]-L-phenylalanine ($C_{28}H_{31}Cl_2N_3O_7$).

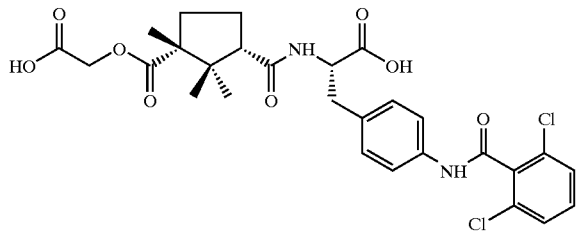

The synthesis of Example 183 is taught by Scheme 9 and by the narrative accompanying Scheme 9.

Example 184

(1S-cis)-N-[(3-Cyano-2,2,3-trimethylcyclopentyl)carbonyl]-4-[(2,6-dichlorobenzoyl)amino]-L-phenylalanine ($C_{26}H_{27}Cl_2N_3O_4$).

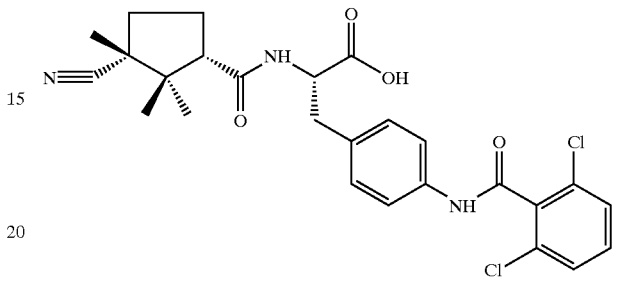

The synthesis of Example 184 is taught by Scheme 12 under the heading Preparation of Example 184.

Example 185

(1S-cis)-N-[3-[[(Carboxymethyl)amino]carbonyl]-2,2,3-trimethylcyclopentyl]carbonyl]-O-((2,6-dichlorophenyl)methyl]-L-tyrosine ($C_{28}H_{32}Cl_2N_2O_7$).

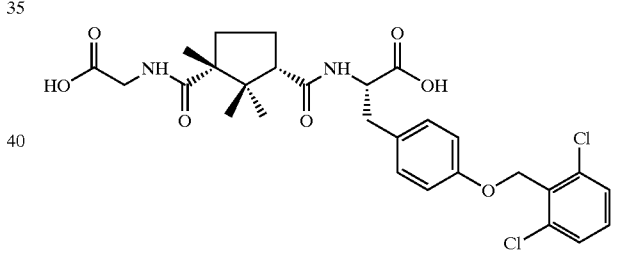

The synthesis of Example 185 is taught by scheme 7, 7-G: wherein $R^{7-1}$=H, $R^4$=H. $R^5$=$CO_2H$, $R^6$=4-[(2,6-Dichlorophenyl)methoxy]-phenyl and Stereochemistry=(1S-cis)-L. Accordingly, (1S-cis)-N-[[3-[[(Carboxymethyl)amino]carbonyl]-2,2,3-trimethylcyclopentyl]carbonyl]-O-[(2,6-dichlorophenyl) methyl]-L- tyrosine ($C_{28}H_{32}Cl_2N_2O_7$) is prepared from 7-G-2 (7-G: $R^{7-1}$=H, $R^4$=H, $R^5$=$CO_2CH_3$, $R^6$=4-[(2,6-Dichlorophenyl)methoxy]phenyl, Stereochemistry=(1S-cis)-L as like as Example 181.

$^1$H NMR(300MHz, DMSO-$d_6$) δ7.8–6.9(m, 9H), 5.18(s, 2H), 4.42 (m, 1H), 3.8–3.6 (m, 2H), 3.02–2.82 (m, 2H), 2.65 (m, 1H), 2.38(m, 1H), 1.91(m, 1H), 1.58(m, 1H), 1.30(m, 1H), 1.19(s, 3H), 1.10(s, 3H), 0.61(s, 3H); IR (mull) 3409, 1733, 1645, 1612, 1585, 1564, 1511, 1439, 1297, 1239, 1197, 1179, 1018, 786, 770cm$^{31}$ $^1$; MS (FAB) m/z (rel. intensity) 579 (M+H, 99), 582 (22), 581 (67), 580 (44), 579 (99), 578 (21), 240 (34), 161 (21), 159 (34), 109 (46), 91 (37); HRMS (FAB) calcd for $C_{28}H_{32}Cl_2N_2O_7$ +H⁺579.1664, found 579.1667.

Example 186

(1R-cis)-N-[(3-Carboxy-1,2,2-trimethylcyclopentyl)carbonyl]-O-(2,6-dichlorophenyl)methyl]-L-tyrosine ($C_{26}H_{29}Cl_2NO_6$).

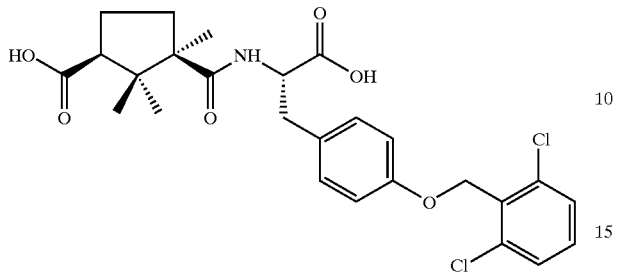

Compound III-a (where $R^4$=H, $R^{5a}$=$CO_2CH_3$, $R^6$=4-[(2,6-dichlorophenyl)methoxy]phenyl, n=1, Stereochemistry S) and (1R)-camphoric anhydride were heated together in diisopropylethyl amine. The crude mixture was concentrated in vacuo to yield crude I-b (where $R^1$=H, $R^3$=$CH_3$, $R^4$=H, $R^{5a}$=$CO_2CH_3$, $R^6$=4-[(2,6-dichlorophenyl)methoxy]phenyl, n=1, Stereochemistry=(1R-cis)-L). I-b was hydrolyzed with LiOH to yield Example 186 (I-a; where $R^1$=H, $R^3$=$CH_3$, $R^4$=H $R^5$=$CO_2$H, and $R^6$=4-[(2,6-dichlorophenyl)methoxy]phenyl, n=1, Stereochemistry (1R-cis)-L): $^{13}$C NMR δ175.9, 175.4, 173.0, 158.6, 137.3, 133.0, 132.0, 131.3, 130.9, 129.7, 115.5, 65.9, 56.5, 54.2, 53.0, 47.0, 36.8, 33.1, 23.2, 22.8, 22.0, 21.0.

Example 187

(1S-cis)-N-[[3-[[(2-Amino-2-oxoethyl) amino]carbonyl]-2,2,3-trimethylcyclopentyl]carbonyl]-O-[(2,6-dichlorophenyl)methyl]-L-tyrosine ($C_{28}H_{33}Cl_2N_3O_6$).

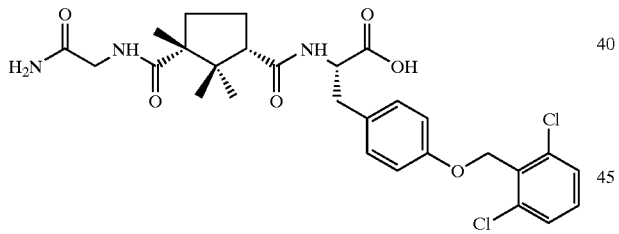

The synthesis of Example 187 is taught by Scheme 8, 8-G: wherein $R^{8-1}$=H, $R^{8-2}$=H, $R^4$=H. $R^6$=4-[(2,6-2,6-Dichlorophenyl)methoxy]-phenyl Stereochemistry=(1s-cis)-L. Accordingly, (1S-cis)-N-[[3-[[(2-Amino-2-oxoethyl)amino]carbonyl]-2,2,3-trimethylcyclopentyl]carbonyl]-O-[(2,6-dichlorophenyl)methyl]-L-tyrosine ($C_{28}H_{33}Cl_2N_3O_6$) is prepared from 8-F-2 ($R^{8-1}$=H, $R^{8-2}$=H, $R^4$=H, $R^5$=$CO_2CH_3$, $R^6$=4-[(2,6-dichlorophenyl)methoxy]-phenyl, Stereochemistry=(1S-cis)-L) as taught by Scheme 8.

$^1$H NMR(300 MHz, DMSO-$d_6$) δ7.74 (m, 2H), 7.55–7.40 (m, 4H), 7.15(m, 3H), 6.94(m, 3H), 5.16(s, 2H), 4.41(m, 1H), 3.75–3.48 (m, 2H), 3.1–2.8 (m, 2H), 2.63 (m, 1H), 2.33 (m, 1H), 1.87 (m, 1H), 1.54 (m, 1H), 1.32 (m, 1H), 1.17(s, 3H), 1.08(s, 3H), 0.58(s, 3H); MS (FAB) m/z (rel. intensity) 578 (M+H, 99), 581 (30), 580 (72), 579 (57), 578 (99), 577 (19), 504 (17), 322 (18), 239 (35), 161 (29), 159 (34); HRMS (FAB) calcd for $C_{28}H_{33}Cl_2N_3O_6$+H$^+$578.1824, found 578.1836.

Example 188

[1S-[1α,3α(R*)]-N-[[3-[[(1-Carboxyethyl)amino]carbonyl]-2,2,3-trimethylcyclopentyl]carbonyl]-O-[(2,6-dichlorophenyl)methyl]-L-tyrosine ($C_{29}H_{34}Cl_2N_2O$ ).

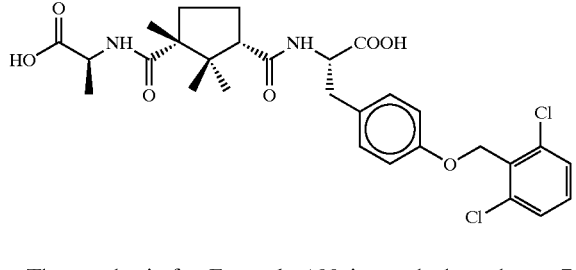

The synthesis for Example 188 is taught by scheme 7, 7-G: wherein $R^{7-1}$=$CH_3$, $R^4$=H, $R^5$=$CO_2$H, $R^6$=4[(2,6-Dichlorophenyl)methoxy]-phenyl and Stereochemistry= [1S-[1α,3α(R*)]-L. Accordingly, [1S-[1α,3α(R*)]]-N-[[3-[[(1-Carboxyethyl)amino]carbonyl]-2,2,3-trimethylcyclopentyl]carbonyl]-O-[(2,6-dichlorophenyl)methyl]-L-tyrosine ($C_{29}H_{34}Cl_2N_2O_7$) is prepared from 7-G-3 as taught by Scheme 7.

$^1$H NMR(300 MHz, DMSO-$d_6$) δ7.71 (m, 1H), 7.54–7.43 (m, 3H), 7.28(m, 1H), 7.16(m, 2H), 6.93(m, 2H), 5.16(s, 2H), 4.40(m, 1H), 4.16(m, 1H), 3.02–2.80(m, 2H), 2.63(m, 1H), 2.35(m, 1H), 1.86(m, 1H), 154(m, 1H), 1.35–1.23(m, 4H), 1.14(s, 3H), 1.08(s, 3H), 0.59(s, 3H); IR (mull) 3427, 3031, 1731, 1645, 1612, 1585, 1565, 1512, 1439, 1297, 1239, 1230, 1197, 1179, 1017 cm$^{-1}$; MS (FAB) m/z (rel. intensity) 593 (M+H, 99), 596 (22), 595 (69), 594 (43), 593 (99), 592 (17), 504 (22), 254 (63), 161 (44), 159 (40), 109 (72).

Example 189

(1R-cis)-N-[(3-Carboxy-2,2,3-trimethylcyclopentyl)carbonyl]-O-[(2,6-dichlorophenyl)methyl]-L-tyrosine ($C_{26}H_{29}Cl_2NO_6$).

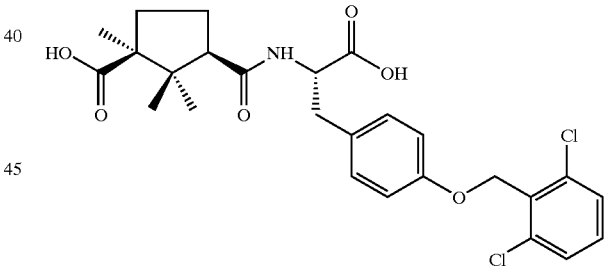

The ester III-a ($R^4$=H, $R^{5a}$=$CO_2CH_3$, $R^6$=4(2,6-dichlorophenyl)methoxy]phenyl, n=1, Stereochemistry=R) (391 mg, 1 mmol), THF (3 mL), and diisopropylethyl amine (880 μL, 5 mmol) were combined. (1S)-Camphoric anhydride (33-A) (182 mg, 1 mmol) was added and the reaction was heated at reflux for 18 h. The reaction mixture was then cooled and concentrated in vacuo. The material was treated with 1 N HCl (1 mL) and extracted with EtOAc (3×5 mL). The organic portion was dried and concentrated in vacuo to yield 590 mg of crude methyl ester I-a as a mixture of regioisomers and diastereomers. Only characteristic and easily discernable protons are listed for the major product (1R-cis)-N-[(3-Carboxy-2,2,3-trimethylcyclopentyl)carbonyl]-O-[(2,6-dichlorophenyl)methyl]-L-tyrosine methyl ester (I-a): $^1$H NMR (CDCl$_3$) δ0.75 (s, H), 1.00 (s, H), 1.19 (s, H), 3.75 (s, H), 4.84–5.00 (m, H), 5.23 (s, H).

The crude methyl ester I-a (560 mg, 1 mmol) was combined with LiOH.H$_2$O (420 mg, 10 mmol) that was dissolved in 6 mL of H$_2$O. After 4.5 h of stirring on the rotovap, 1 N HCl (12 mL) was added to the reaction mixture and a white precipitate was formed. The mixture was extracted with EtOAc (3×20 mL). The organic portion was dried and concentrated in vacuo to afford 480 mg of crude di-acid Example 189. The material was purified by a C$_{18}$ reverse phase chromatography (on the Delta Prep employing a Delta-PAK C$_{18}$, 15 µM particle size column that was conditioned with CH$_3$CN/H$_2$O/TFA (40:60:0.1)). The material was eluted with CH$_3$CN/H$_2$O (38:62) to yield 190 mg (36% overall from anhydride) of Example 189: [α]$_D$–4.5° (c=0.6, EtOH), [α]$_D$–2.8° (c=0.8, EtOH); $^1$H NMR (DMSO-d$_6$) δ0.21 (s), 0.59 (s), 0.86 (s), 1.05–1.18 (m), 1.28–1.45 (m), 1.64–1.82 (m), 2.05–2.20 (m), 2.41 (m), 2.57 (m), 2.87 (m), 4.22–4.32 (m), 4.95 (s), 6.73 (m), 6.97 (m), 7.20–7.30 (m), 7.34 (m), 7.61 (m); $^{13}$C NMR (DMSO-d$_6$) δ176.9 (s), 173.4 (s), 172.0 (s), 157.1 (s), 136.0 (s), 131.8 (s), 131.5 (d), 130.3 (s), 130.1 (d), 128.7 (d), 114.3 (d), 64.9 (t), 55.4 (s), 53.5 (d), 52.2 (d), 45.5 (s), 35.9 (t), 32.3 (t), 22.4 (t), 22.0 (q), 21.5 (q), 20.8 (q); IR (mineral oil mull) 3296, 2925, 1712, 1698, 1651, 1512, 1438, 1242, cm$^{-1}$; MS for C$_{26}$H$_{29}$Cl$_2$NO$_6$, m/z (relative intensity) 523 (M$^+$, 1), 521 (M$^+$, 1), 503 (1), 477 (1), 324 (29), 322 (45), 267 (19), 265 (28), 161 (64), 159 (100). Anal. Calcd for C$_{26}$H$_{29}$Cl$_2$NO$_6$: C, 59.78; H, 5.60; Cl, 13.57, N, 2.68. Found: C, 59.41; H, 5.55; Cl, 13.43, N, 2.52. Corrected for 1.14% H$_2$O found by Karl Fisher analysis.

Example 190

[1S-(1α[(R*),3α]]-N-[[3-Carboxy-2,2,3-trimethylcyclopentyl)carbonyl]-α-methoxymethyl-4-[(2,6-dichlorophenyl)methoxy]benzene-ethanamine

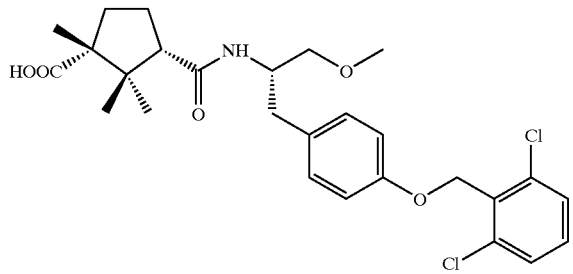

The synthesis of Example 190 is taught by Scheme 25.

Example 191

(1S-cis]-N-[(3-Carboxy-2,2,3-trimethylcyclopentyl)carbonyl]-4(hydroxyphenylmethyl)-L-phenylalanine (C$_{26}$H$_{31}$NO$_6$).

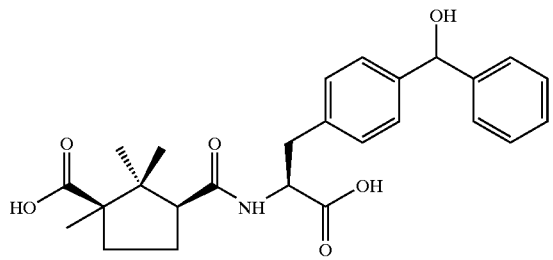

The synthesis of Example 191 is taught by scheme 2, I-c: wherein R$^{2a}$=—CO$_2$H, R$^1$=Me, R$^3$=R$^4$=H, R$^5$=—CO$_2$H, R$^6$=4-(hydroxyphenylmethyl)-phenyl, X=—C(O)— and Stereochemistry=(1S-cis)-L. Accordingly, (1S-cis]-N-[(3-Carboxy-2,2,3-trimethylcyclopentyl)carbonyl]-4-(hydroxyphenylmethyl)-L-phenylalanine (C$_{26}$H$_{31}$NO$_6$) is synthesized as follows: To a solution of Example 40 (0.59 g, 1.3 mmol) in absolute EtOH under N$_2$ at 0° C. is added NaBH$_4$ (100 mg, 2.7 mmol). The reaction mixture is stirred for 17 h at room temperature diluted with H$_2$O, and quenched with 1 N HCl. The solution is treated with satd NH$_4$Cl and adjusted to approximately pH 3 with 1 N HCl. The mixture is extracted with EtOAc. The combined extracts are dried, filtered and concentrated to give a colorless oil (0.60 g). The product is purified by C18 reverse phase chromatography (isocratic 35:65 CH$_3$CN/H$_2$O). The product (0.29 g) is diluted with MeOH/H$_2$O, frozen and lyophilized to give Example 191 as a white powder: TLC R$_f$=0.18 (650:350:1 CHCl$_3$/acetone/HCO$_2$H); HPLC t$_R$=7.3 min (isocratic 650:350:1 CH$_3$CN/H$_2$O/TFA); [α]$_D^{25}$+26° (c 0.48, MeOH); IR (mull) 3327, 1709,, 1653, 1514, 1242, 1207, 1118, 1017, 950, 700 cm$^{-1}$; $^1$H NMR (CD$_3$OD) δ7.37–7.14 (9H), 5.73 (1H), 4.90 (2H), 4.66 (1H), 3.20 (1H), 2.96 (1H), 2.70–2.62 (1H), 2.48 (1H), 1.92 (1H), 1.59 (1H), 1.40 (1H), 1.19 (3H), 1.18 (3H), 0.74 (3H); $^{13}$C NMR (CD$_3$OD) δ178.28, 173.84, 144.56, 142.97, 136.31, 128.84, 127.86, 126.79, 126.33, 126.31, 75.37, 56.00, 53.16, 46.19, 39.04, 36.69, 32.33, 22.43, 21.72, 21.04, 20.43; MS (FAB, HR) m/z 454.2234 (calcd [M+H]$^+$454.2229); MS (FAB) m/z 493, 454, 476, 436, 237, 226, 208, 109; Anal. C 65.54, H 6.74, N 3 .12 (calcd C, 68.86; H, 6.89; N, 3.09.

Example 192

(1S-cis)-N-[[3-(hydroxymethyl)-2,2,3-trimethylcyclopentyl]carbonyl]-O-[(2,6-dichlorophenyl)methyl]-L-tyrosine (C$_{26}$H$_{31}$Cl$_2$NO$_5$).

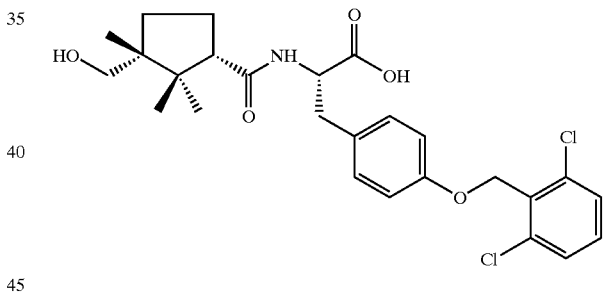

The synthesis of Example 192 is taught by Scheme 10 under the heading Preparation of Example 192.

Example 193

(1R-cis)-N-[(3-Carboxy-1,2,2-trimethylcyclopentyl)carbonyl]-O-(2,6-dichlorophenyl)methyl]-D-tyrosine (C$_{26}$H$_{29}$Cl$_2$NO$_6$).

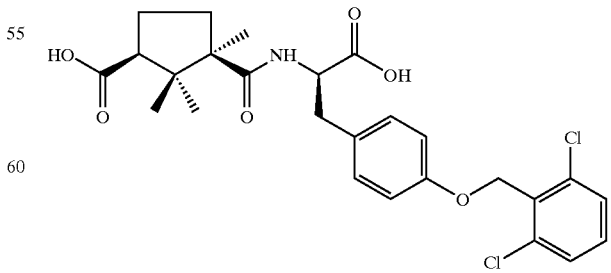

MeOH (10 mL) was cooled to 0° C. and acetyl chloride (2.14 mL, 30 mmol) was added slowly. After 20 min the t-BOC-D-tyrosine derivative III-a (where $R^4$=H, $R^{5a}$=$CO_2CH_3$, $R^6$=4-[(2,6-dichlorophenyl)methoxy]phenyl, n=1, Stereochemistry=R), (2.64 g, 6 mmol) was added. The reaction mixture was stirred at room temperature for 2 h. The mixture was concentrated under vacuum to afford a white solid. The white solid was triturated with $Et_2O$ and filtered. The solid was returned to the flask and was combined with THF (15 mL), diisopropylethyl amine (4.4 mL, 25 mmol), and (1R)-camphoric anhydride (1.0 g, 5 mmol). The reaction mixture was heated at reflux for 18 h. The mixture was then cooled and concentrated in vacuo. The material was treated with 1 N HCl ( 40 mL) and extracted with EtOAc (3×20 mL). The organic portion was dried and concentrated in vacuo to yield 3.30 g of crude methyl ester I-a as a mixture of regioisomers and diastereomers.

The crude methyl ester I-a (2.79 g, 5 mmol) was combined with $LiOH.H_2O$ (2.1 g, 50 mmol) that was dissolved in 30 mL of $H_2O$. After 4.0 h of stirring on the rotovap, 1 N HCl (60 mL) was added to the reaction and a white precipitate formed. The mixture was extracted with EtOAc (3×40 mL). The organic portion was dried and concentrated in vacuo to afford 3.05 g of crude di-acid. The material was chromatographed on 150 g of silica gel eluting with $CHCl_2$/EtOAc/$HCO_2H$ (50:50:0.1) to yield pure (1R-cis)-1N-[(3-Carboxy-1,2,2-trimethylcyclopentyl)carbonyl]-O-(2,6-dichlorophenyl)methyl]-D-tyrosine (Example 193). This material was dissolved in 20 mL of $CH_3CN/H_2O$ (1:1). The mixture was concentrated in vacuo until the liquid appeared milky. The solution was frozen and lyophilized to afford Example 193: $^1H$ NMR (DMSO-$d_6$) δ 0.55 (H), 1.13 (H), 1.25 (H), 1.30–1.45 (1H), 1.68–1.86 (1H), 1.95–2.122 (1H), 2.25–2.41 (1H), 2.73, 2.95–3.20, 4.49–4.62, 5.23, 7.01, 7.25 , 7.30–7.40, 7.45–7.70; $^{13}C$ NMR (DMSO-$d_6$) δ175.3 (s), 174.5 (s), 173.5 (s), 157.3 (s), 136.3 (s), 132.0 (d), 131.7 (s), 130.9 (s), 130.5 (d), 129.0 (d), 114.4 (d), 65.1 (t), 55.3 (s), 53.6 (d), 52.2 (d), 46.3 (s), 35.6 (t), 32.1 (t), 23.2 (q), 22.2 (t), 21.4 (q), 20.6 (q); IR (mineral oil mull) 3436, 2922, 1722, 1707, 1634, 1612, 1512, 1438, 1242, $cm^{-1}$; MS for $C_{26}H_{29}Cl_2NO_6$, m/z (relative intensity) 523 ($M^+$, 0.4), 521 ($M^+$, 0.5), 505 (2), 503 (2), 324 (33), 322 (50), 267 (21), 265 (32), 161 (69), 159 (100). Anal. Calcd for $C_{26}H_{29}Cl_2NO_6$: C, 59.78; H, 5.60; Cl, 13.57, N, 2.68. Found: C, 59.52; H, 5.29; Cl, 13.60, N, 2.52. Corrected for 0.9% $H_2O$ found by Karl Fisher analysis.

Example 194

[1S-[1α(R*),3α]]-α-[[(3-Carboxy-2,2,3-trimethylcyclopentyl)carbonyl]amino]-6-chloro-5-[(2,6-dichlorophenyl)methoxy]-2-pyridinepropanoic acid

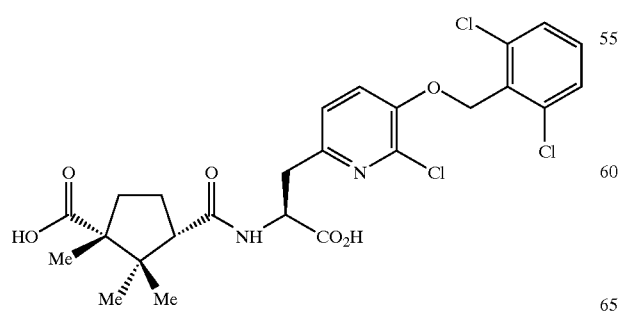

The synthesis of Example 194 is taught by Scheme 34.

Example 195

[1S-[[1α(R*),3α]]-β-[[(3-Carboxy-2,2,3-trimethylcyclopentyl)carbonyl]amino]-4-(2,6-dichlorobenzoyl)-γ-oxo-1-piperazinebutanoic acid

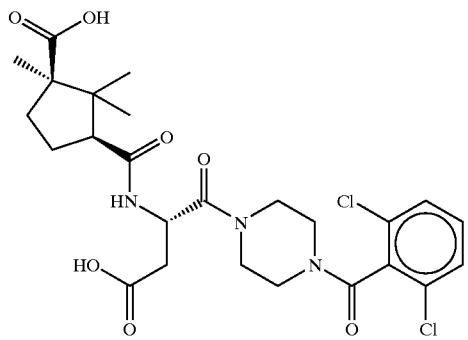

The synthesis of Example 195 is taught by Scheme 18.

Example 196

(1S-cis)-N-[(3-Carboxy-2,2,3-trimethylcyclopentyl)carbonyl]-1-(phenylmethyl)-L-tryptophan ($C_{28}H_{32}N_2O_5$).

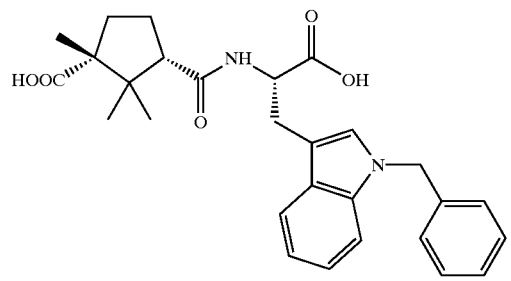

Example 196 was synthesized as described Scheme 24.

Example 197

[1R-cis]-N-[(3-Carboxy-1,2,2-trimethylcyclopentyl)carbonyl]-4-(hydroxyphenylmethyl)-L-phenylalanine ($C_{26}H_{31}NO_6$).

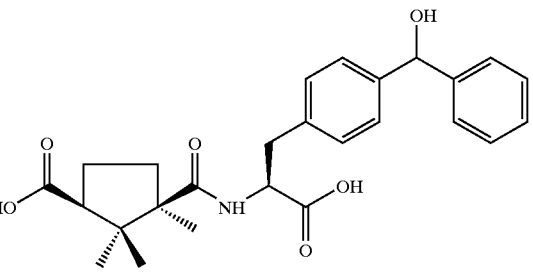

The synthesis of Example 197 is taught by scheme 2, I-c: wherein $R^{2a}$=—$CO_2H$, $R^1$=$R^4$=H, $R^3$=Me, $R^5$=—$CO_2H$, $R^6$=4-(hydroxyphenylmethyl)-phenyl, X=—C(O)— and Stereochemistry=(1R-cis)-L. Accordingly, [1R-cis]-N-[(3-Carboxy-1,2,2-trimethylcyclopentyl)carbonyl]-4-(hydroxyphenylmethyl)-L-phenylalanine ($C_{26}H_{31}NO_6$) is prepared from 32-B and (1R)-camphoric anhydride by the procedures taught by Scheme 2 and by the synthesis of Examples 40, 186, and 191: TLC silica gel $R_f$=0.31 (900:100:1 $CHCl_3$/MeOH/$HCO_2H$); HPLC $t_R$=5.6 min (isocratic 650:350:1 $CH_3CN$/$H_2O$/TFA); $[\alpha]_D^{25}$ +24° (c 0.38, MeOH); UV (MeOH) $\lambda_{max}$ ($\epsilon$) 223 (14200), 254 (425 sh), 258 (493), 263 (481), 268 (364 sh), 272 (257 sh); IR (mull) 3379, 1712, 1642, 1514, 1417, 1377, 1342, 1274, 1179, 1133, 1017, 700 cm$^{-1}$; $^1$H NMR ($CD_3OD$) δ 7.35–7.15 (m 9H), 5.73 (1H), 4.91 (3H), 4.72 (1H), 3.26 (1H), 2.99 (1H), 2.72 (1H), 2.44–2.30 (1H), 2.15–2.00 (1H), 1.82–1.67 (1H), 1.40–1.27 (1H), 1.05 (3H), 1.03 (3H), 0.54 (3H), 0.53 (3H); $^{13}$C NMR ($CD_3OD$) δ 176.29, 176.24, 173.56, 144.56, 143.17, 136.26, 136.23, 128.82, 127.88, 126.85, 126.39, 126.31, 75.33, 55.77, 53.34, 52.47, 46.20, 36.09, 32.03, 22.11, 21.98, 20.17, 20.07; MS (HR FAB) m/z 454.2230 (calcd [M+H]$^+$ 454.2229); MS (FAB) m/z 454, 436, 237, 226, 208, 109; $H_2O$ (Karl Fischer) 1.44%; Anal. C, 67.68; H, 6.98; N, 3.06; (calcd adjusted for $H_2O$: C, 68.86; H, 6.89; N 3.09).

Example 198

(1S-cis)-N-[[(3-methoxymethyl)-2,2,3-trimethylcyclopentyl]carbonyl]-O-[(2,6-dichlorophenyl)methyl]-L-tyrosine ($C_{27}H_{33}Cl_2NO_5$).

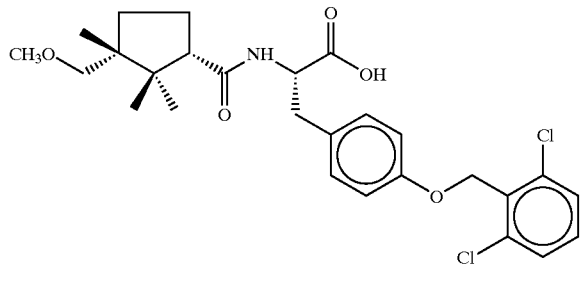

The synthesis of Example 198 is taught by Scheme 10 under the heading Preparation of Example 198.

Example 199

(1R-cis)-N-[(3-Carboxy-2,2,3-trimethylcyclopentyl)carbonyl]-O-[(2,6-dichlorophenyl)methyl]-D-tyrosine ($C_{26}H_{29}Cl_2NO_6$).

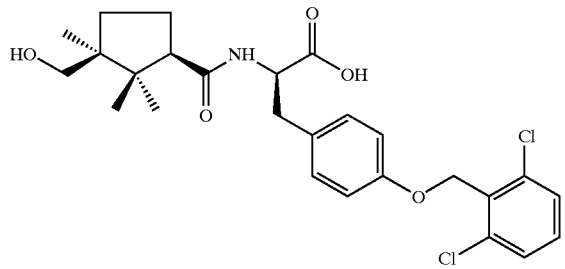

In the same manner as the synthesis of 189, 199 was synthesized and purified (0.5 g, 49% overall yield): $[\alpha]_D$=−31°.

Example 200

[1R-[1α,3α(S*)]]-N-[[3-[[[1-Carboxy-2-[4-[(2,6-dichlorophenyl)methoxy]phenyl]ethyl]amino]carbonyl]-1,2,2-trimethylcyclopentyl]carbonyl]-L-proline 1,1-dimethylethyl ester, monosodium salt ($C_{35}H_{43}Cl_2N_2NaO_7$).

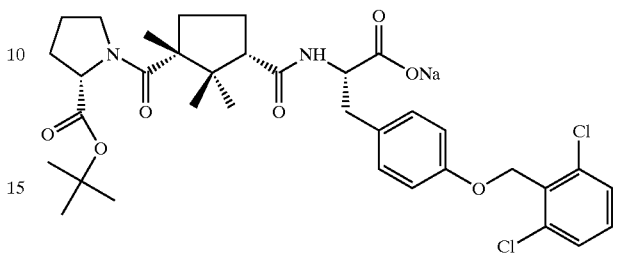

The synthesis of Example 200 is taught by Scheme 21.

Example 201

[1S-[1α(R*),3α]]-β-[[(3-Carboxy-2,2,3-trimethylcyclopentyl)carbonyl]amino]-4-[(2,6-dichlorophenyl)methoxy]-benzenebutanoic acid ($C_{27}H_{31}Cl_2NO_6$).

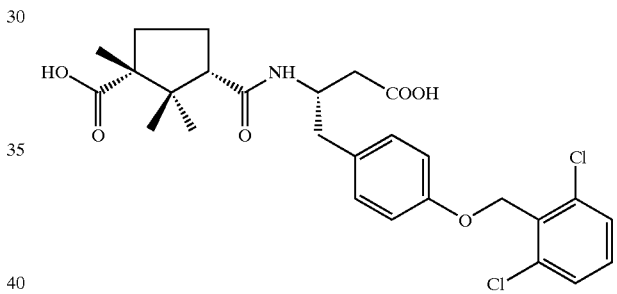

The synthesis of Example 201 is taught by scheme 2, I-c: wherein $R^{2a}$=—$CO_2H$, $R^1$=Me, $R^3$=$R^4$=H, $R^5$=—$CH_2CO_2H$, $R^6$=4-[(2,6-Dichlorophenyl)methoxy]-phenyl-, n=1, Stereochemistry=[1S-[1α(R*),3α]]. Accordingly, [1S-[1α(R*),3α]]-β-[[(3-Carboxy-2,2,3-trimethylcyclopentyl)carbonyl]amino]-4-[(2,6-dichlorophenyl)methoxy]-benzenebutanoic acid ($C_{27}H_{31}Cl_2NO_6$) is prepared from 30-B and 15-D as taught by Scheme 2: TLC: $R_f$=0.22 (50:50:0.2 hexanes/EtOAc/$HCO_2H$); $[\alpha]_D$=+3 (MeOH); IR 3320, 3057, 3026, 2953, 2924, 2868, 2855, 1703, 1641, 1612, 1585, 1565, 1511, 1465, 1439, 1403, 1378, 1297, 1283, 1241, 1197, 1179, 1158, 1017, 768 cm$^{-1}$; $^1$H NMR δ 0.71 (3H), 1.22 (3H), 1.23 (3H), 1.41–1.53 (1H), 1.67–1.86 (1H), 2.26–2.60 (4H), 2.71–2.87 (2H), 2.96–3.08 (1H), 4.46–4.62 (1H); 5.26 (2H), 5.43 (1H), 6.98 (2H), 7.13 (2H), 7.23–7.28 (1H), 7.37 (2H); $^{13}$C NMR 67 20.22, 21.66, 22.29, 22.91, 31.91, 37.19, 39.64, 46.44, 48.57, 54.26, 56.48, 65.14, 115.09, 128.37, 129.62, 130.23, 130.33, 131.98, 136.90, 157.72, 171.75, 178.54, 182.19; MS (FAB) m/z 536, 495, 464, 449, 431, 418, 386, 353, 336, 287, 236; $H_2O$ (Karl Fischer) 0.70%; Anal. C, 60.08; H, 5.86; Cl, 13.05; N, 2.70 (calcd corrected for $H_2O$: C 60.03; H, 5.86; Cl, 13.13; N, 2.59).

Example 202

(1S-cis) -1-[(3,4-Dichlorophenyl)methyl]-N-[[3-[(1,1-dimethylethoxy)carbonyl]-2,2,3-trimethylcyclopentyl]carbonyl]-L-histidine ($C_{27}H_{35}Cl_2N_3O_5$).

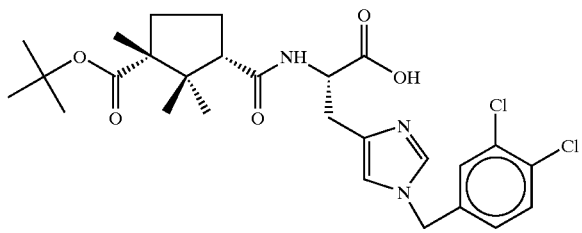

To (1S-cis)-N-[[3-[(1,1-dimethylethoxy)carbonyl]-2,2,3-trimethylcyclopentyl]carbonyl]-1-[(3,4-dichlorophenyl)methyl]-L-histidine methyl ester (0.5 g, 0.88 mmol) in $H_2O$ (10 mL) was added $LiOH \cdot H_2O$ (10 equiv, 8.8 mmol, 0.37 g) in cold $H_2O$ (10 mL). Stirred reaction overnight. Lowered pH of reaction solution to 5 with 1N HCl. Filtered resulting precipitate, washed precipitate with $H_2O$ and dried precipitate under hi vacuum conditions to yield 0.46 g (95%) of (1S-cis)-1-[(3,4-Dichlorophenyl)methyl]-N-[[3-[(1,1-dimethylethoxy)carbonyl]-2,2,3-trimethylcyclopentyl]carbonyl]-L-histidine Example 202 (I-c; where $R^{2a}$=(1,1-dimethylethoxy)carbonyl, $R^1$=$CH_3$, $R^3$=H $R^4$=H, $R^5$=$CO_2H$, and $R^6$=1-(3,4-dichlorophenyl)methyl]-4-imidazolyl, n=1, Stereochemistry=(1S-cis)-L): mp 234–235° C.

Example 203

(1S-cis)-N-[[(3-Methoxymethoxymethyl)-2,2,3-trimethylcyclopentyl]carbonyl]-O-[(2,6-dichlorophenyl)methyl]-L-tyrosine ($C_{27}H_{33}Cl_2NO_5$).

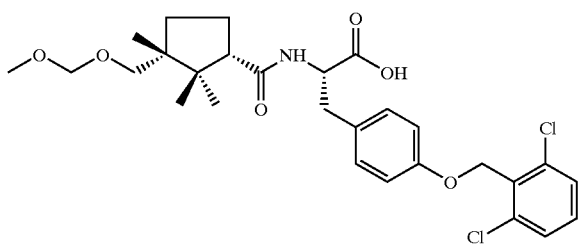

The synthesis of Example 203 is taught by Scheme 10 under the heading Preparation of Example 203.

Example 204

[1R-[1α(S*),3α]]-β-[[(3-Carboxy-1,2,2-trimethylcyclopentyl)carbonyl]amino]-4-[(2,6-dichlorophenyl)methoxy]-benzenebutanoic acid ($C_{27}H_{31}Cl_2NO_6$).

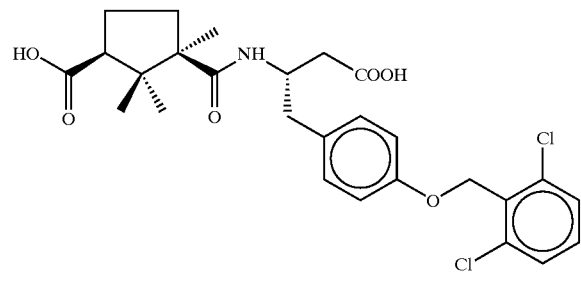

The synthesis of Example 204 is taught by scheme 2, I-c: wherein $R^{2a}$=—$CO_2H$, $R^1$=$R^4$=H, $R^3$=Me, $R^5$=—$CH_2CO_2H$, $R^6$=4-[(2,6-Dichlorophenyl)methoxy]phenyl-, n=1, Stereochemistry=[1R-[1α(S*),3α]]. Accordingly, [1R-[1α(S*),3α]]-β-[[(3-Carboxy-1,2,2-trimethylcyclopentyl)carbonyl]amino]-4-[(2,6-dichlorophenyl)methoxy]benzenebutanoic acid ($C_{27}H_{31}Cl_2NO_6$) is obtained from 30-B and (1S)-camphoric anhydride (33-A) by the procedures taught by Scheme 1: mp 106–108° C.; TLC $R_f$=0.24 (250:250:1 hexanes/EtOAc/$HCO_2H$); $[\alpha]_D$=+13 (MeOH); IR 3144, 3057, 3030, 2954, 2924, 2870, 2855, 1706, 1627, 1612, 1585, 1565, 1511, 1466, 1439, 1377, 1299, 1241, 1197, 1178, 1017, 1000, 778, 768 cm$^{-1}$; $^1$H NMR δ0.70 (3H) 1.16 (3H), 1.16 (3H), 1.30 (3H), 1.43–1.61 (1H) 1.77–1.97 (1H), 2.09–2.32 (2H), 2.36–2.49 (1H), 2.57–2.68 (1H), 2.69–2.83 (2H), 2.90–3.02 (1H), 4.44–4.59 (1H), 5.25 (2H), 5.73 (1H), 6.97 (2H), 7.11 (2H), 7.22–7.26 (3H), 7.37 (2H); $^{13}$C NMR δ20.88, 21.16, 22.04, 23.15, 32.57, 37.76, 39.59, 47.39, 48.16, 52.44, 55.73, 65.17, 86.13, 115.02, 128.37, 129.56, 130.34, 132.00, 136.89, 157.72, 174.53, 178.42, 181.12; MS (FAB) m/z 536, 518, 490, 378, 354, 336, 294, 159, 137, 109, 88, 69, 55; $H_2O$ (Karl Fischer) 0.52%; Anal. C, 60.07; H, 5.84; Cl, 13.03; N, 2.71; (calcd corrected for $H_2O$: C, 60.14; H, 5.85; Cl 13.15; N 2.60).

Example 205

(1S-cis)-O-[(2,6-Dichlorophenyl)methyl]-N-[[3-(methoxycarbonyl)-2,2,3-trimethylcyclopentyl]carbonyl]-L-tyrosine ($C_{27}H_{31}Cl_2NO_6$).

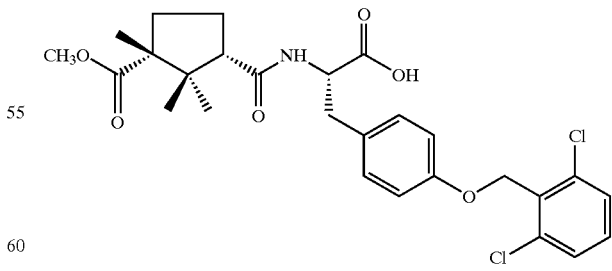

Example 205 is taught by Scheme 20, 20-D: wherein $R^4$=H, $R^5$=$CO_2H$, $R^6$=4-[(2,6-Dichlorophenyl)methoxy]-phenyl and Stereochemistry=[1S-cis]-L.

To a solution of the diester 20-D ($R^4$=H, $R^5$=$CO_2CH_3$; $R^6$=4-[(2,6-Dichlorophenyl)methoxy]phenyl, Stereochemistry=(1S-cis)-L (0.32 g, 0.58 mmol) in methanol (5 mL) is added a solution of LiOH.H₂O (0.31 g, 7.4 mmol) in H₂O (5 mL). After overnight stirring, the mixture is diluted with water (50 mL) and evaporated in vacuo until the methanol is gone. The aqueous solution is cooled in an ice bath and brought to pH4 using 1N HCl, resulting in a white precipitate which is chromatographed on silica gel (10% methanol/chloroform) to give a white solid (0.25 g, 80% yield).

¹H NMR(D₆DMSO) 7.85(m, 1H), 7.58–7.44(m, 3H), 7.19(m, 2H), 6.96(m, 2H), 5.18(s, 2H), 4.43(m, 1H), 3.59(s, 3H), 3.03–2.81(m, 2H), 2.69(m, 1H), 2.40(m, 1H), 1.91(m, 1H), 1.56(m, 1H), 1.39(m, 1H), 1.16(s, 3H), 1.31(s, 3H), 0.59(s, 3H); IR (mull) 1727, 1639, 1612, 1585, 1565, 1511, 1439, 1298, 1241, 1197, 1179, 1160, 1119, 779, 768; MS (FAB) m/z (rel. intensity) 536 (M+H, 99), 538 (66), 537 (39), 536 (99), 322 (22), 197 (27), 169 (21), 159 (29), 137 (31), 109 (66), 107 (22).

Example 206

(1S-cis)-4-[(2,6-Dichlorobenzoyl)amino]-N-[[2,2,3-trimethyl-3-[[(phenylmethoxy)amino]-carbonyl]cyclopentyl]carbonyl]-L-phenylalanine methyl ester ($C_{34}H_{37}Cl_2N_3O_6$).

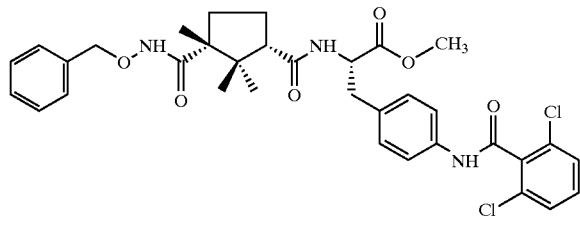

The synthesis of Example 206 is taught by Scheme 23 under the heading Preparation 23-C.

Example 207

(1S-cis)-N-[[3-[[(2-Cyanoethyl)amino]carbonyl]-2,2,3-trimethylcyclopentyl]carbonyl]-4-[(2,6-dichlorobenzoyl)amino]-L-phenylalanine methyl ester

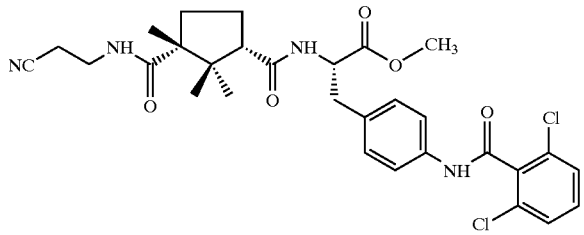

The synthesis of Example 207 is taught by Scheme 22 under the heading Preparation of 22-C.

Example 208

(1S-cis)-N-[(3-Carboxy-2,2,3-trimethylcyclopentyl)carbonyl]-4-[[(2-chloro-3-pyridinyl)carbonyl]amino]-L-phenylalanine ($C_{25}H_{28}ClN_3O_6$).

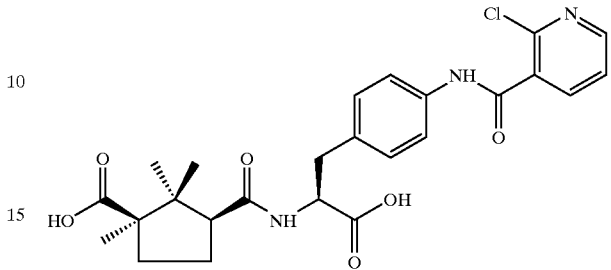

The synthesis of Example 208 is taught by Scheme 2, I-c: wherein $R^{2a}$=—CO₂H, $R^1$=Me, $R^3$=$R^4$=H, $R^5$=—CO₂H, $R^6$=4-[[(2-chloro-3-pyridyl)carbonyl]amino]phenyl, n=1, Stereochemistry=(1S-cis)-L. Accordingly, (1S-cis)-N-[(3-Carboxy-2,2,3-trimethylcyclopentyl)carbonyl]-4-[[(2-chloro-3-pyridinyl)carbonyl]amino]-L-phenylalanine ($C_{25}H_{28}ClN_3O_6$) is prepared from 31-C, 15-D and 2-chloro-3-nicotinic acid by the procedures taught by Scheme 2: mp 172–174° C.; TLC silica gel $R_f$=0.17 (750:250:3 EtOAc/hexanes/HCO₂H); IR (mineral oil mull) 3410, 3289, 3193, 3124, 3050, 2955, 2924, 2868, 2855, 1714, 1655, 1606, 1582, 1537, 1516, 1461, 1415, 1401, 1377, 1329, 1279, 1257, 1242, 1207, 1187, 1152 cm⁻¹; ¹H NMR δ 0.80 (3H), 1.13–1.28 (1H), 1.16 (3H), 1.19 (3H), 1.38–1.50 (1H), 1.67–1.83 (1H), 2.08–2.23 (1H), 2.45–2.58 (2H), 3.04–3.24 (2H), 4.75–4.87 (1H), 5.96 (1H), 7.12 (2H), 7.32 (1H), 7.56 (2H), 7.96 (1H), 8.43 (1H), 9.32 (1H); MS (FAB) m/z 504, 502, 484, 468, 456, 371, 320, 302, 274, 140, 109; Anal. C, 57.54; H, 5.84; Cl, 6.79; N, 8.05; (calcd corrected for H₂O: C, 57.55; H, 5.83; Cl, 6.79; N, 8.08).

Example 209

(1S-cis)-N-[(3-Carboxy-2,2,3-trimethylcyclopentyl)carbonyl]-4-[[(2,6-dichloro-3-pyridinyl)carbonyl]amino]-L-phenylalanine ($C_{25}H_{27}Cl_2N_3O_6$).

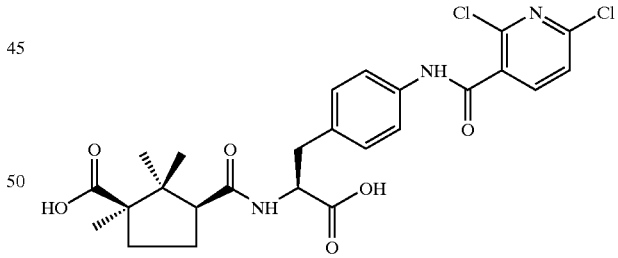

The synthesis of Example 209 is taught by Scheme 2, I-c: wherein $R^{2a}$=—CO₂H, $R^1$=Me, $R^3$=$R^4$=H, $R^5$=—CO₂H, $R^6$=4-[[(2,6-dichloro-3-pyridyl)carbonyl]amino]phenyl, n=1, Stereochemistry=(1S-cis)-L. Accordingly, (1S-cis)-N-[(3-Carboxy-2,2,3-trimethylcyclopentyl)carbonyl]-4-[[(2,6-dichloro-3-pyridinyl)carbonyl]amino]-L-phenylalanine ($C_{25}H_{27}Cl_2N_3O_6$) is prepared from 31-C, 15-D and 2,6-dichloro-3-nicotinic acid as taught by Scheme 2 and by the synthesis of Example 208: mp 246–247° C.; TLC silica gel $R_f$=0.28 (750:250:2 EtOAc/hexanes/HCO₂H); IR (mineral oil mull) 3292, 3196, 3125, 3059, 2954, 2923, 2855, 1712, 1656, 1607, 1575, 1544, 1515, 1461, 1426, 1414, 1377, 1343, 1329, 1272, 1244, 1206, 1186, 1160, 1144 cm⁻¹; ¹H NMR δ0.65 (3H), 1.10 (3H), 1.15 (3H), 1.24–1.37 (1H), 1.43–1.62 (1H), 1.83–1.97 (1H), 2.26–2.45 (1H), 2.67 (1H), 2.82–3.04 (2H), 3.30 (3H), 4.38–4.49 (1H), 7.21 (2H), 7.55 (2H), 7.71 (1H), 7.80 (1H), 8.14 (1H), 10.63 (1H); MS (FAB) m/z 538, 536, 538, 518, 490, 371, 354, 336, 281, 200, 174, 137, 109.

Example 210

(1S-cis)-N-[(3-Carboxy-2,2,3-5 trimethylcyclopentyl)carbonyl]-4-[[(2-methoxy-6-chloropyridin-3-yl)carbonyl]-amino]-L-phenylalanine

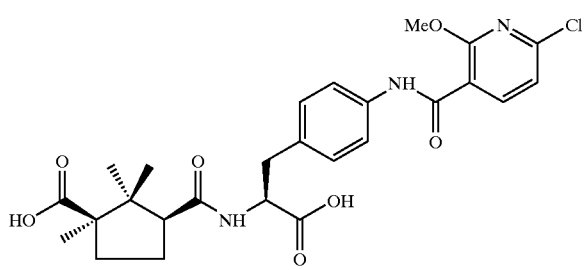

The synthesis of Example 210 is taught by Scheme 2, I-c: wherein $R^{2a}$=—$CO_2H$, $R^1$=Me, $R^3$=R=H, $R^5$=—$CO_2H$, $R^6$=4-[[(6-chloro-2-methoxy-3-pyridyl)carbonyl]amino] phenyl, n=1, Stereochemistry=(1S-cis)-L. Accordingly, Example 210 is synthesized as follows:

A solution of the dimethyl ester of Example 209 (0.098 g, 0.18 mmol) in 4:1 THF/MeOH is reacted at room temperature under Ar with an aqueous solution of LiOH.H₂O (0.042 g, 1.0 mmol). The reaction mixture is stirred for 2.5 h. It is diluted with H₂O, acidified with aq HCl, and extracted with EtOAc. The combined extracts are washed with brine, dried, filtered and concentrated to an oil that is purified by silica gel flash chromatography (650:350:4 EtOAc/hexanes/HCO₂H). The product is azeotroped thrice from toluene, diluted with CH₃CN/H₂O, and lyophilized to give 0.043 g (0.081 mmol, 45%) of Example 210 as a white solid: mp 128–131° C.; TLC silica gel R$_f$=0.13 (500:500:2 EtOAc/hexanes/HCO₂H); ¹H NMR δ 0.64 (3H), 1.10 (3H), 1.15 (3H), 1.23–1.38 (1H), 1.44–1.53 (m, 1H), 1.78–1.97 (m, 1H), 2.66 (t, 2H, J=9.4), 2.78–3.07 (m, 2H), 3.67–3.84 (1H), 3.96 (3H), 4.37–4.46 (1 H), 7.19 (2H), 7.57 (2H), 7.78 (2H), 8.05 (1H), 10.18 (1H); MS (FAB) m/z 534, 532, 514, 486, 371, 360, 350, 332, 304, 275, 190, 127, 109.

Example 211

(1S-[1α,3α(R*)]]-N-[[[3-[[(1-Carboxyethyl)amino]carbonyl]-2,2,3-trimethylcyclopentyl]carbonyl]-4-[(2,6-dichlorobenzoyl)amino]-L-phenylalanine

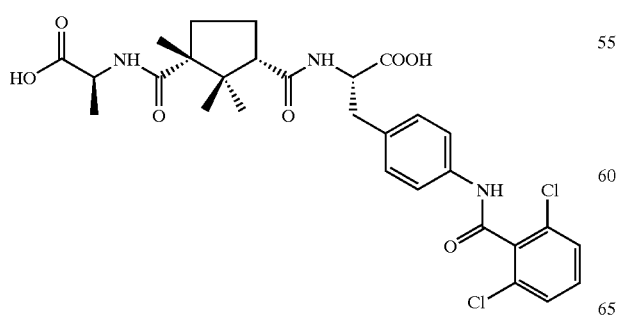

The synthesis of Example 211 is taught by Scheme 19 under the heading Preparation of Example 211.

Example 212

[1S-[1α,3α(S*)]]-N-[3-[[2-(Aminocarbonyl)-1-pyrrolidinyl]carbonyl]-2,2,3-trimethylcyclopentyl]carbonyl]-4-[(2,6-dichlorobenzoyl)amino]-L-phenylalanine monolithium salt

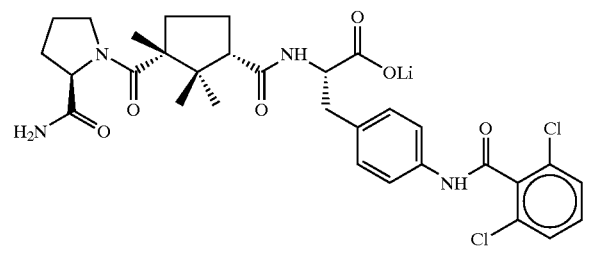

The synthesis of Example 212 is taught by Scheme 19 under the heading Preparation of Example 212.

Example 213

[1S-[1α,3α(R*)]]-N-[3-[[2-(Aminocarbonyl)-1-pyrrolidinyl]carbonyl]-2,2,3-trimethylcyclopentyl]carbonyl]-4-[(2,6-dichlorobenzoyl)amino]-L-phenylalanine monosodium salt

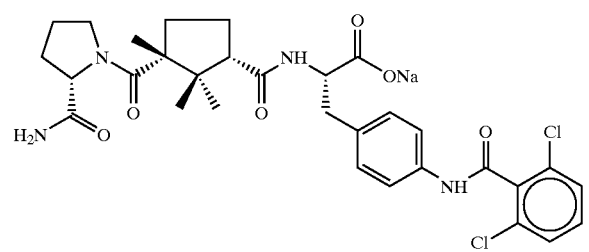

The synthesis of Example 213 is taught by Scheme 19 under the heading Preparation of Example 213.

Example 214

(1S-cis)-N-[[3-[[(2-Carboxyethyl)amino]carbonyl]-2,2,3-trimethylcyclopentyl]carbonyl]-4-[(2,6-dichlorobenzoyl)amino]-L-phenylalanine ($C_{29}H_{33}Cl_2N_3O_7$).

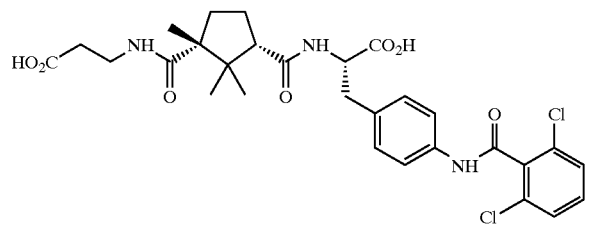

The synthesis for Example 214 is taught by Scheme 19 under the heading Preparation of Example 214.

Example 215

[1S-[1α,3α(R*)]3-N-[3-[[2-[(Methylamino)carbonyl]-1-5 pyrrolidinyl]carbonyl]-2,2,3-trimethylcyclopentyl]carbonyl]-4-[(2,6-dichlorobenzoyl)amino]-L-phenylalanine monosodium salt

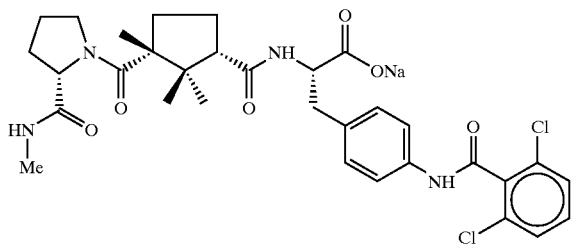

The synthesis for Example 215 is taught by Scheme 19 under the heading Preparation of Example 215.

Example 216

(1S-cis)-N-[[3-[[(2-Cyanoethyl)amino]carbonyl]-2,2,3-trimethylcyclopentyl]carbonyl]-4-[(2,6-dichlorobenzoyl)amino]-L-phenylalanine

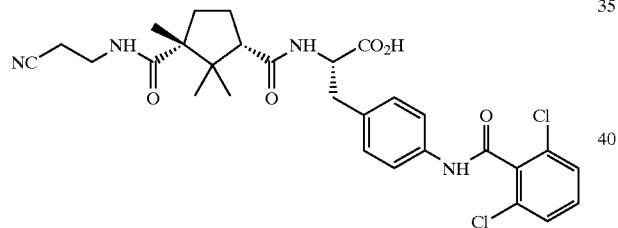

The synthesis of Example 216 is taught by Scheme 22 under the heading Preparation of Example 216.

Example 217

(1S-cis)-4-[(2,6-Dichlorobenzoyl)amino]-N-[[2,2,3-trimethyl-3-[[(phenylmethoxy)amino]-carbonyl]cyclopentyl]carbonyl]-L-phenylalanine ($C_{33}H_{35}Cl_2N_3O_6$).

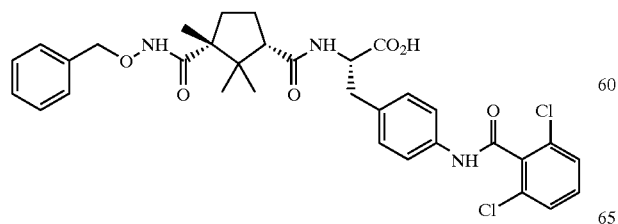

The synthesis for Example 217 is taught by Scheme 23 under the heading Preparation of Example 217.

Example 218

(1S-cis)-4-[(2,6-Dichlorobenzoyl)amino]-N-[[3-[(hydroxyamino)carbonyl]-2,2,3-trimethylcyclopentyl]carbonyl]-L-phenylalanine methyl ester.

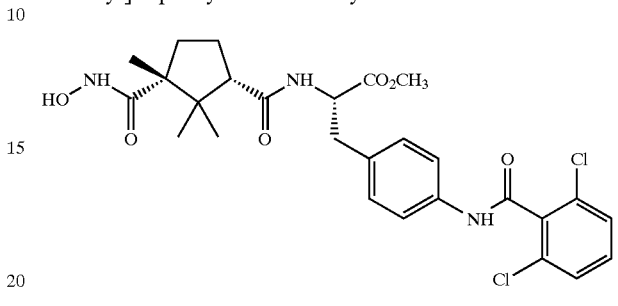

The synthesis for Example 218 is taught by Scheme 23 under the heading Preparation of Example 218.

Example 219

(1S-cis)-4-[(2,6-Dichlorobenzoyl)amino]-N-[[3-[(hydroxyamino)carbonyl]-2,2,3-trimethylcyclopentyl]carbonyl]-L-phenylalanine

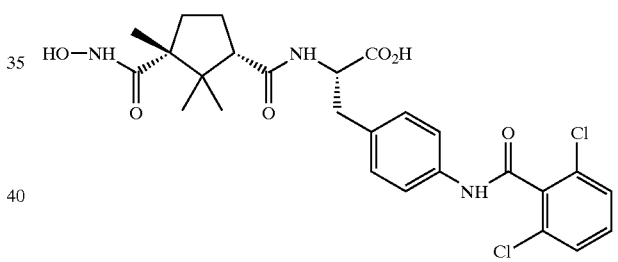

The synthesis for Example 219 is taught by Scheme 22 under the heading Preparation of Example 219.

Example 220

(1S-cis)-N-[[(3-Carboxy-2,2,3-trimethylcyclopentyl]carbonyl]4-[[[(1,1'-biphenyl)-4-yl]amino]-carbonyl]-L-phenylalanine

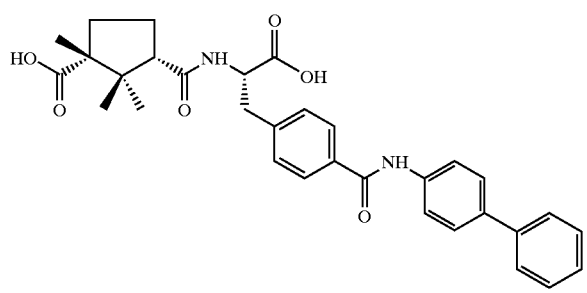

The synthesis for Example 220 is taught by Schemes 35 and 2 under the heading Preparation of Example 220.

Example 221

(1S-cis)-[[(3-Carboxy-2,2,3-trimethylcyclopentyl]carbonyl]-4-[[(4-chlorophenyl)amino]carbonyl]-L-phenylalanine

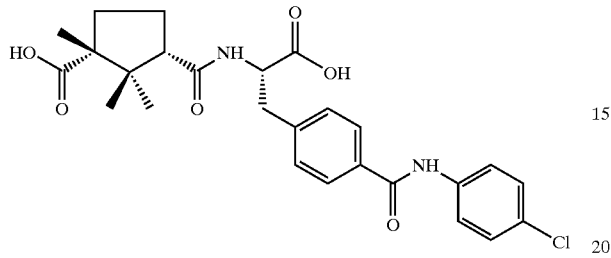

The synthesis for Example 221 is taught by Schemes 35 and 2 under the heading Preparation of Example 221.

Example 222

(1S-cis)-[[(3-Carboxy-2,2,3-trimethylcyclopentyl]carbonyl]-4-[[(2-trifluoromethylphenyl)amino]carbonyl]-L-phenylalanine

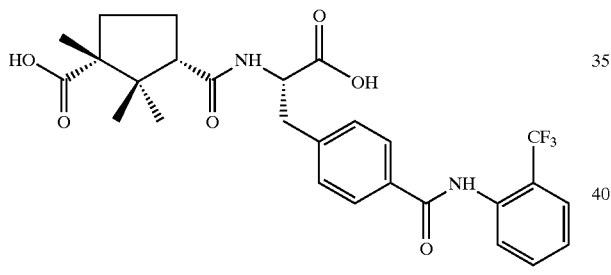

The synthesis for Example 222 is taught by Schemes 35 and 2 under the heading Preparation of Example 222.

Example 223

(1S-cis)-[[(3-Carboxy-2,2,3-trimethylcyclopentyl]carbonyl]-4-[[(2,4,6-trichlorophenyl)amino]-carbonyl]-L-phenylalanine

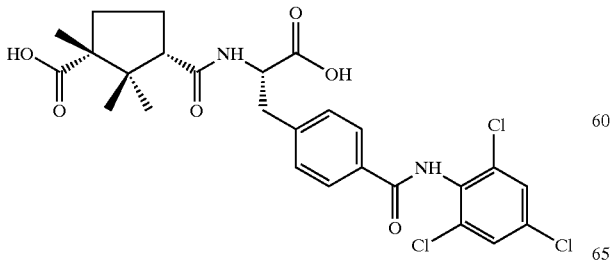

The synthesis for Example 223 is taught by Schemes 35 and 2 under the heading Preparation of Example 223.

Example 224

[1S-[1α(R*),3α]]-4-[[[(1-Carboxy-3-methylbutyl]amino]carbonyl]-N-[[(3-carboxy-2,2,3-trimethylcyclopentyl]-carbonyl]-L-phenylalanine

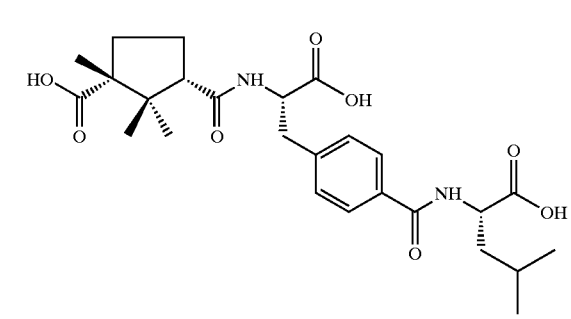

The synthesis for Example 224 is taught by Schemes 35 and 2 under the heading Preparation of Example 224.

Example 225

(1S-cis)-4-[(2,6-Dichlorobenzoyl)amino]-N-[[2,2,3-trimethyl-3-[(4-morpholinyl)carbonyl]-cyclopentyl]carbonyl]-L-phenylalanine

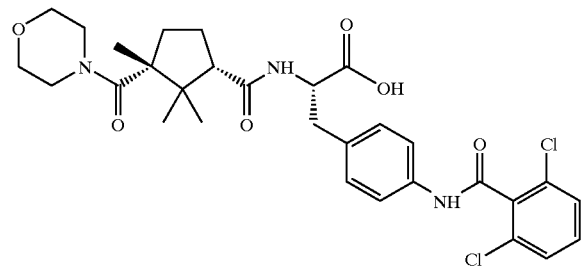

The preparation of Example 225 is taught by Scheme 27.

Example 226

(1S-cis)-4-[(2,6-Dichlorobenzoyl)amino]-N-[[2,2,3-trimethyl-3-[(4-morpholinyl)carbonyl]cyclopentyl]carbonyl]-L-phenylalanine methyl ester

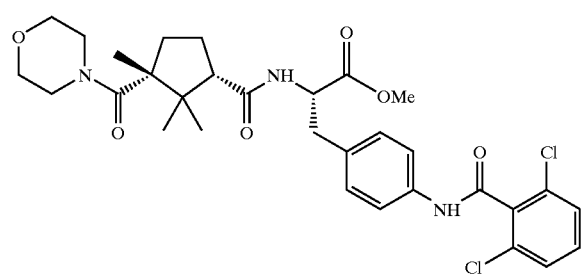

The preparation of Example 226 is taught by Scheme 27.

Example 227

(1S-cis)-N-[[3-[(1,1-Dimethylethoxy)carbonyl]-2,2,3-trimethylcyclopentyl]carbonyl]-4-[[[(2,6-dichlorophenyl)amino]carbonyl]amino]-L-phenylalanine methyl ester

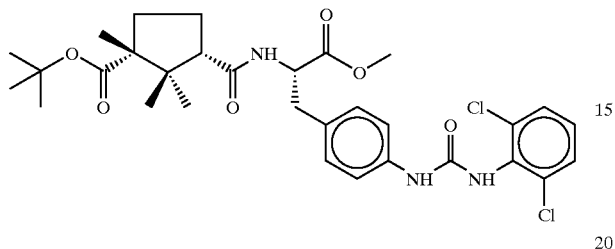

The synthesis of Example 227 is taught by Scheme 26.

Example 228

(1S-cis)-N-[(3-Carboxy-2,2,3-trimethylcyclopentyl)carbonyl]-4-[[[(2,6-dichlorophenyl)amino]carbonyl]amino]-L-phenylalanine methyl ester

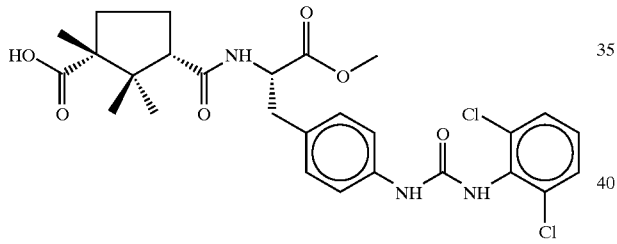

The synthesis of Example 228 is taught by Scheme 26.

Example 229

(1S-cis)-N-[(3-Carboxy-2,2,3-trimethylcyclopentyl)carbonyl]-4-[[[(2,6-dichlorophenyl)amino]carbonyl]amino]-L-phenylalanine

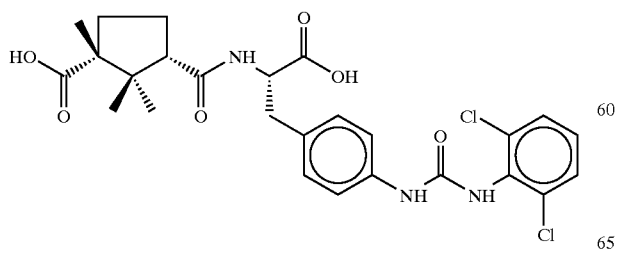

The synthesis of Example 229 is taught by Scheme 26.

Example 230

(1S-cis)-N-[[3-[(1,1-Dimethylethoxy)carbonyl]-2,2,3-trimethylcyclopentyl]carbonyl]-4-[(2-chloro-5-trifluoromethylbenzoyl)amino]-L-phenylalanine methyl ester

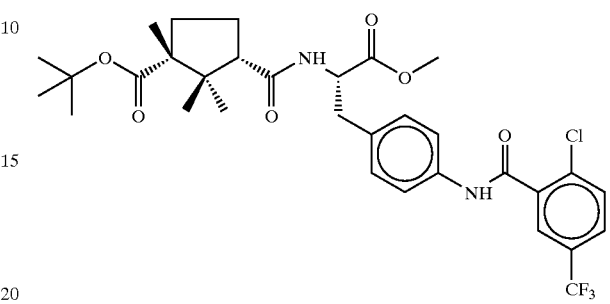

Example is 230 synthesized in the same manner as Example 54.

Example 231

(1S-cis)-N-[(3-Carboxy-2,2,3-trimethylcyclopentyl)carbonyl]-4-[(2-chloro-5-trifluoromethylbenzoyl)amino]-L-phenylalanine methyl ester

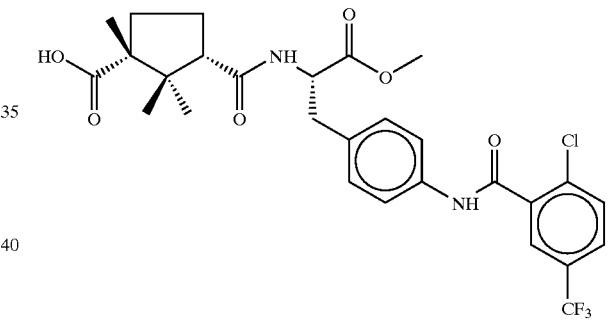

Example 231 is synthesized in the same manner as Example 54.

Example 232

(1S-cis)-N-[(3-Carboxy-2,2,3-trimethylcyclopentyl)carbonyl]-4-[(2-chloro-5-trifluoromethylbenzoyl)amino]-L-phenylalanine

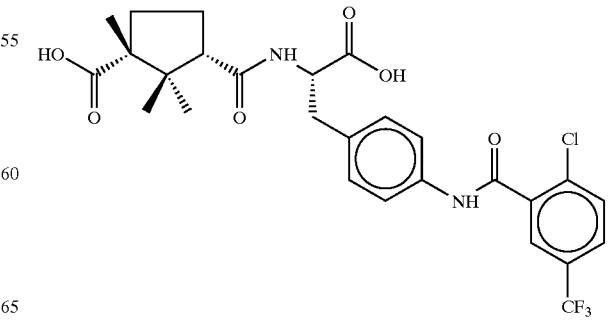

Example 232

Example 232 is synthesized in the same manner as Example 54.

Example 233

(1S-cis)-N-[[3-[[(2-Amino-2-oxoethyl)amino]carbonyl]-2,2,3-trimethylcyclopentyl]carbonyl]-4-[(2,6-dichlorobenzoyl)amino]-L-phenylalanine methyl ester

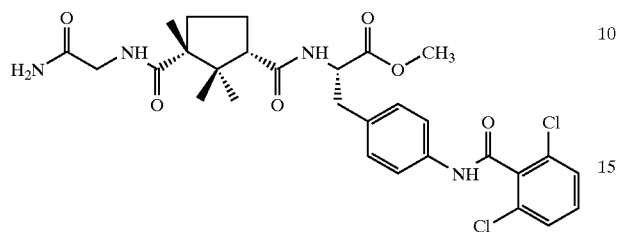

The synthesis for Example 233 is taught by Scheme 8 under the heading Preparation of 8-F.

Example 234

[1S-[1α(R*),3α]]-2-[[[3-Carboxy-2,2,3-trimethylcyclopentyl]carbonyl]amino]-6-[(2,6-dichlorobenzoyl)amino]hexanoic acid

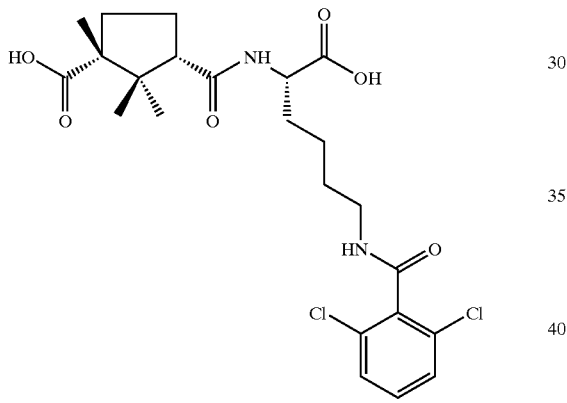

Example 234% as prepared according to Scheme 2. Physical properties as follows: $^1$H NMR (300 MHz, CD$_3$OD) δ 7.36 (3H), 4.29 (1H), 3.24 (2H), 2.71 (1H), 2.45 (1H), 2.04 (1H), 1.71 (8H), 1.23 (3H), 1.13 (3H), 0.75 (3H); $^{13}$C NMR (75 MHz, CD$_3$OD) δ 176.74, 173.06, 164.47, 137.20, 131.64, 130.84, 128.05, 55.91, 52.87, 46.16, 38.50, 32.31, 30.44, 28.43, 22.64, 22.32, 21.92, 21.07, 20.57; MS (FAB) m/z (rel. intensity) 501 (M$^+$, 22), 504 (20), 503 (32), 502 (26), 501 (22), 109 (17), 73 (99), 69 (25) 57 (27), 55 (23); MS (ES−) for C$_{23}$H$_{30}$Cl$_2$N$_2$O$_6$ m/z 499.3 (M−H)$^-$; Anal. Calcd for C$_{23}$H$_{30}$Cl$_2$N$_2$O$_6$ . 0.25H$_2$O: C, 54.60; H, 6.07; N, 5.53; Found: C, 54.58; H, 6.14; N, 5.45.

Example 235

[1S-[1α(R*),3α]]-2-([[3-Carboxy-2,2,3-trimethylcyclopentyl]carbonyl]amino]-5-[(2,6-dichlorobenzoyl)amino]pentanoic acid

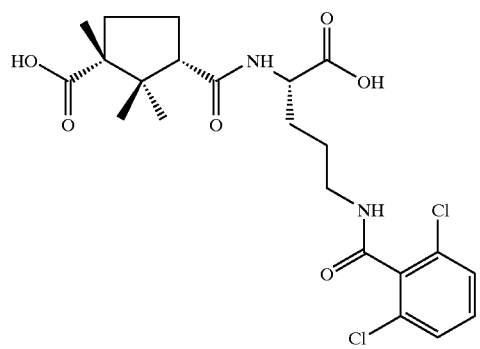

Example 235% as prepared according to Scheme 2. Physical properties as follows: $^1$H NMR (300 MHz, CD$_3$OD) δ7.38 (3H), 4.41 (1H), 3.40 (2H), 2.83 (1H), 2.53 (1H), 2.08 (1H), 1.79 (3H), 1.47 (1H), 1.30 (3H), 1.24 (3H), 0.83 (3H); $^{13}$C NMR (75 MHz, CD$_3$OD) δ 178.23, 174.24, 173.83, 165.84, 136.07, 131.79, 130.67, 127.80, 56.06, 52.92, 52.10, 38.84, 32.35, 28.57, 25.43, 22.33, 21.61, 20.95, 20.50; MS (FAB) m/z (rel. intensity) 487 (M$^+$, 99), 490 (14), 489 (67), 488 (25), 487 (99), 305 (19), 242 (16), 175 (12), 173 (18); Anal. Calcd for C$_{22}$H$_{28}$Cl$_2$N$_2$O$_6$: C, 54.22; H, 5.79; N, 5.75. Found: C, 53.91; H, 5.93; N, 5.43.

Example 236

[1S-[1α,3α(1S*,3R*)]]-N-[[3-[[[(3-Carboxy-1,2,2-trimethylcyclopentyl)amino]carbonyl]amino]-2,2,3-trimethylcyclopentyl]carbonyl]-4-[(2,6-dichlorobenzoyl)-amino]-L-phenylalanine

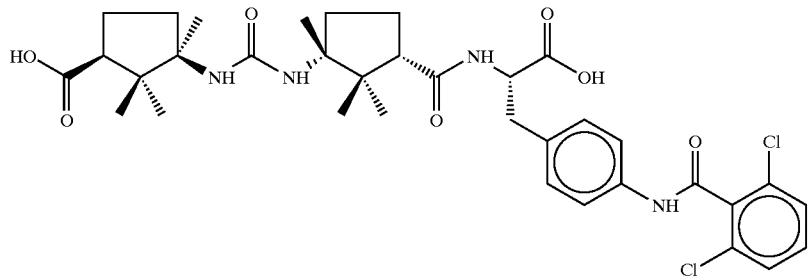

The synthesis of Example 236 is taught by Schemes 28 and 29.

Example 237

(1S-cis)-N-[(3-Carboxy-2,2,3-trimethylcyclopentyl)carbonyl]-4-[(2,6-dichlorobenzoyl)amino]-D-phenylalanine ($C_{26}H_{28}Cl_2N_2O_6$)

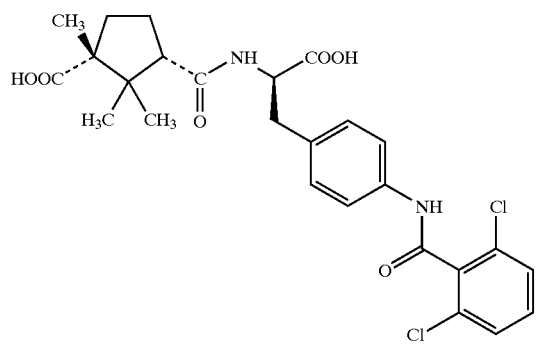

The synthesis for Example 237 is taught by Scheme 37 under the heading Preparation of Example 237.

Example 238

(1S-trans)-N-[(3-Carboxy-2,2,3-trimethylcyclopentyl)carbonyl]-4-[(2,6-dichlorobenzoyl)amino]-D-phenylalanine ($C_{26}H_{28}Cl_2N_2O_6$)

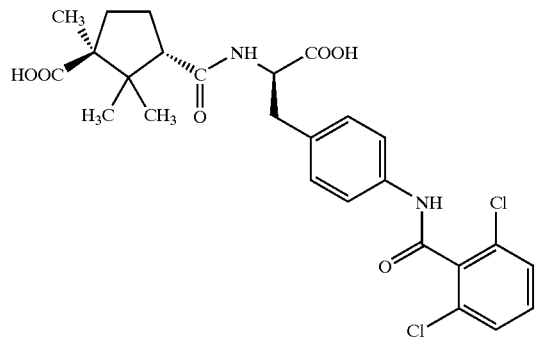

The synthesis for Example 238 is taught by Scheme 37 under the heading Preparation of Example 238.

Example 239

(1S-trans)-N-[(3-Carboxy-2,2,3-trimethylcyclopentyl)carbonyl]-4-(2,6-dichlorobenzoyl)amino]-L-phenylalanine ($C_{26}H_2Cl_2N_2O_6$)

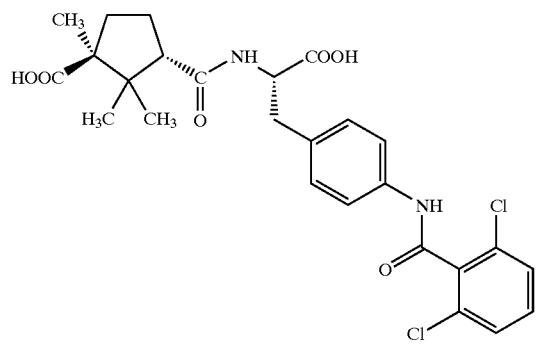

The synthesis for Example 239 is taught by Scheme 37 under the heading Preparation of Example 239.

Example 240

(1R-trans)-N-[(3-Carboxy-2,2,3-trimethylcyclopentyl)carbonyl]-4-[(2,6-dichlorobenzoyl)amino]-L-phenylalanine ($C_{26}H_{28}Cl_2N_2O_6$)

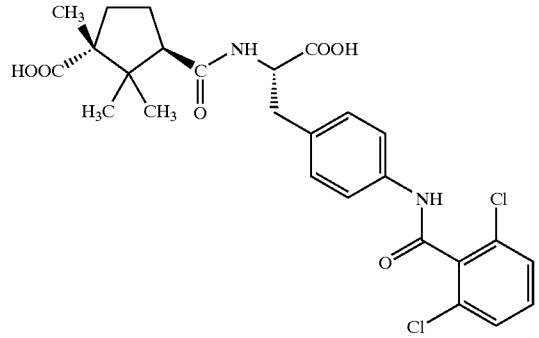

The synthesis of Example 240 is taught by Scheme 37 under the heading Preparation of Example 240.

Example 241

(1R-trans)-N-[(3-Carboxy-2,2,3-trimethylcyclopentyl)carbonyl]-4-[(2,6-dichlorobenzoyl)amino]-D-phenylalanine ($C_{26}H_{28}Cl_2N_2O_6$)

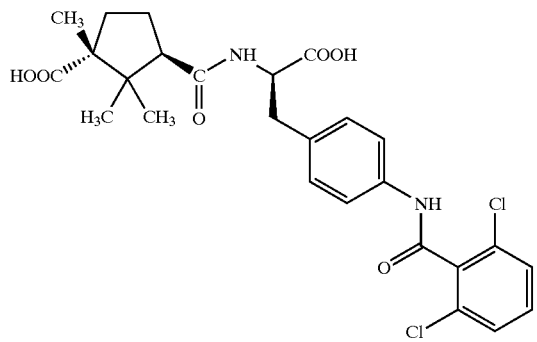

The synthesis of Example 241 is taught by Scheme 37 under the heading Preparation of Example 241.

Example 242

(1R-cis)-N-[(3-Carboxy-2,2,3-trimethylcyclopentyl)carbonyl]-4-[(2,6-dichlorobenzoyl)amino]-D-phenylalanine ($C_{26}H_{28}Cl_2N_2O_6$)

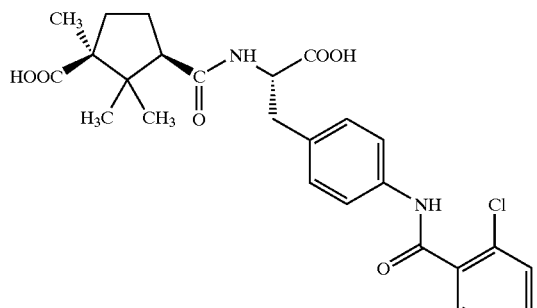

The synthesis of Example 242 is taught by Scheme 37 under the heading Preparation of Example 242.

Example 243

(1R-cis)-N-[(3-Carboxy-2,2,3-trimethylcyclopentyl)carbonyl]-4-[(2,6-dichlorobenzoyl)amino]-L-phenylalanine ($C_{26}H_{28}Cl_2N_2O_6$)

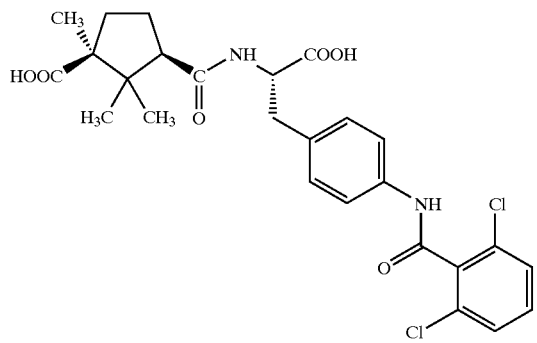

The synthesis of Example 243 is taught by Scheme 37 under the heading Preparation of Example 243.

Example 244

(1S-cis)-N-[(3-Carboxy-1,2,2-trimethylcyclopentyl)carbonyl]-4-[(2,6-dichlorobenzoyl)amino]-L-phenylalanine ($C_{26}H_{28}Cl_2N_2O_6$)

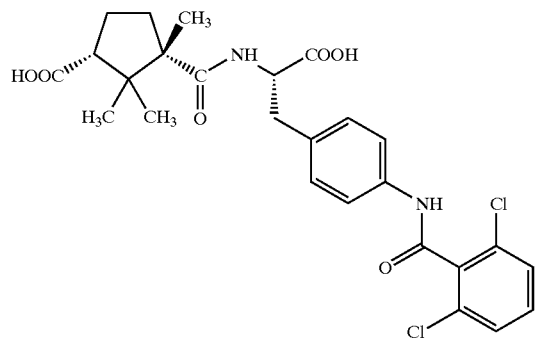

The synthesis of Example 244 is taught by Scheme 37 under the heading Preparation of Example 244.

Example 245

(1S-cis)-N-[(3-Carboxy-1,2,2-trimethylcyclopentyl)carbonyl]-4-[(2,6-dichlorobenzoyl)amino]-D-phenylalanine ($C_{26}H_{28}Cl_2N_2O_6$)

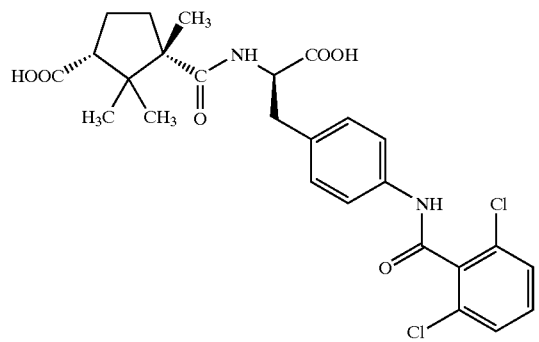

The synthesis of Example 245 is taught by Scheme 37 under the heading Preparation of Example 245.

Example 246

(1S-trans)-N-[(3-Carboxy-1,2,2-trimethylcyclopentyl)carbonyl]-4-[(2,6-dichlorobenzoyl)amino]-D-phenylalanine ($C_{26}H_{28}Cl_2N_2O_6$)

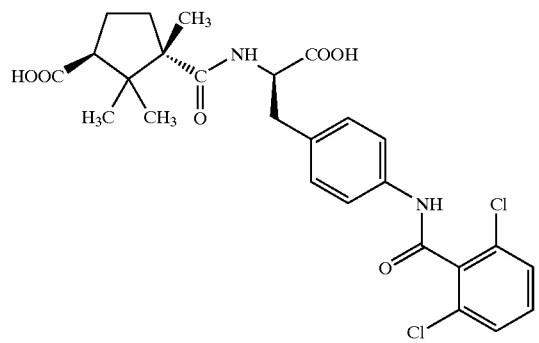

The synthesis of Example 246 is taught by Scheme 37 under the heading Preparation of Example 246.

Example 247

(1S-trans)-N-[(3-Carboxy-1,2,2-trimethylcyclopentyl)carbonyl]1-4-[(2,6-dichlorobenzoyl)amino]-L-phenylalanine ($C_{26}H_{28}Cl_2N_2O_6$)

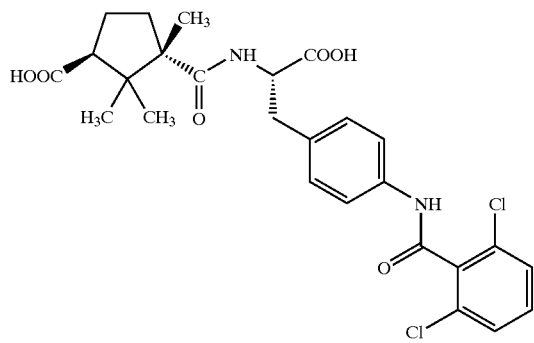

The synthesis of Example 247 is taught by Scheme 37 under the heading Preparation of Example 247.

Example 248

(1R-cis)-N-[(3-Carboxy-1,2,2-trimethylcyclopentyl)carbonyl]-4-[(2,6-dichlorobenzoyl)amino]-L-phenylalanine ($C_{26}H_{28}Cl_2N_2O_6$)

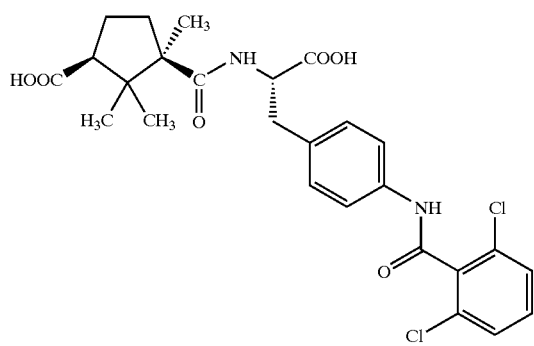

The synthesis of Example 248 is taught by Scheme 37 under the heading Preparation of Example 248.

Example 249

(1R-cis)-N-[(3-Carboxy-1,2,2-trimethylcyclopentyl)carbonyl]-4-[(2,6-dichlorobenzoyl)amino]-D-phenylalanine ($C_{26}H_{28}Cl_2N_2O_6$)

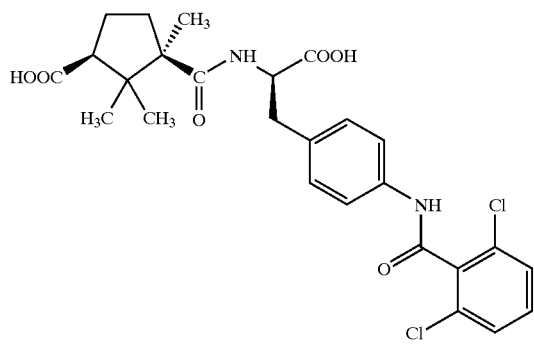

The synthesis of Example 249 is taught by Scheme 37 under the heading Preparation of Example 249.

Example 250

(1R-trans)-N-[(3-Carboxy-1,2,2-trimethylcyclopentyl)carbonyl]-4-[(2,6-dichlorobenzoyl)amino]-L-phenylalanine ($C_{26}H_{28}Cl_2N_2O_6$)

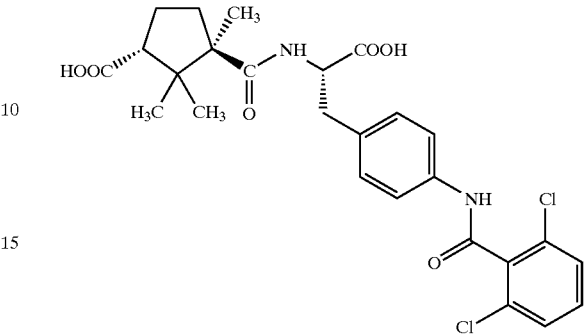

The synthesis of Example 250 is taught by Scheme 37 under the heading Preparation of Example 250.

Example 251

(1R-trans)-N-[(3-Carboxy-1,2,2-trimethylcyclopentyl)carbonyl]-4-[(2,6-dichlorobenzoyl)amino]-D-phenylalanine ($C_{26}H_{28}Cl_2N_2O_6$)

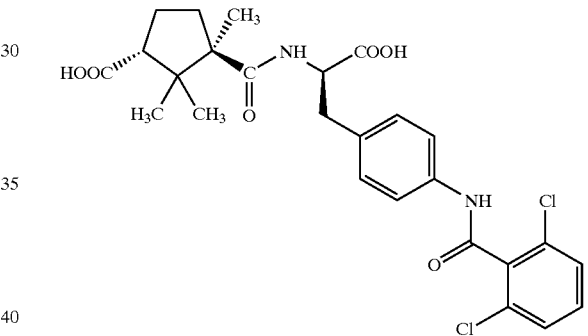

The synthesis of Example 251 is taught by Scheme 37 under the heading Preparation of Example 251.

Example 252

(1S-cis)-N-[(3-Carboxy-2,2,3-trimethylcyclopentyl)carbonyl]-3-bromo-4-[(2,6-dichlorobenzoyl)amino]-L-phenylalanine ($C_{26}H_{28}Cl_2N_2O_6$)

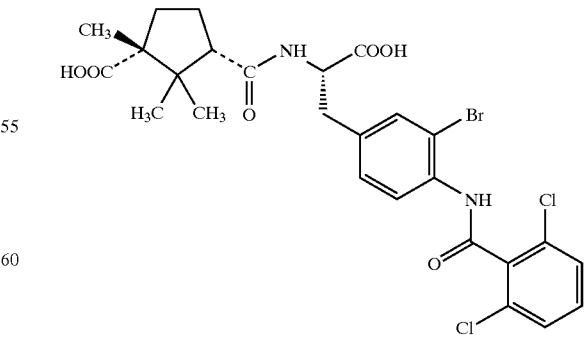

The synthesis for Example 252 is taught by Scheme 2 (Method B) and is explained under the heading Preparation of Example 252.

Example 253

(1S-cis)-N-[(3-Carboxy-2,2,3-trimethylcyclopentyl)carbonyl]-4-[[2-chloro-4-[(1,1-dimethyl)ethyl]benzoyl]amino]-L-phenylalanine (C$_{30}$H$_{37}$Cl$_1$N$_2$O$_6$)

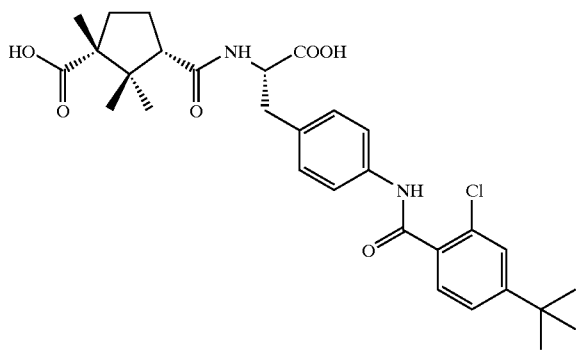

The synthesis of Example 253 is taught by Scheme 38 under the heading Preparation of Example 253.

Example 254

[1S-[1α(R*),3α]]-α-[[(3-Carboxy-2,2,3-trimethylcyclopentyl)carbonyl]amino]-3-[(2,6-dichlorophenyl)methoxy]-6-pyridinepropanoic acid (C$_{25}$H$_{28}$Cl$_2$N$_2$O$_6$)

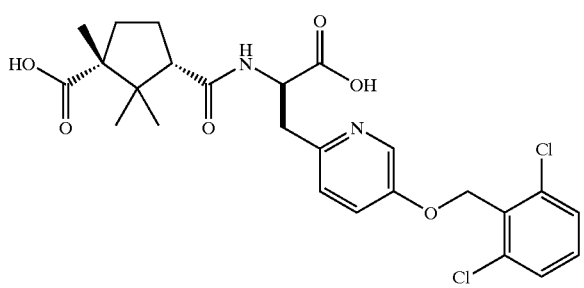

The synthesis of Example 254 is taught by Scheme 39 under the heading Preparation of Example 254.

REFERENCE EXAMPLES

R. Examples

R. Example 1

(1R)-1,8,8-Trimethyl-3-oxabicyclo[3.2.1]octane-2,4-dione[(1R)-camphoric anhydride]

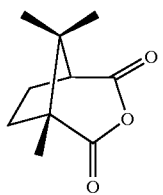

Method A: A mixture of (1R-cis)-1,2,2-Trimethylcyclopentane-1,3-dicarboxylic acid) [(1R,3S)-camphoric acid] (40.0 g), AcCl (23.5 g), and Ac$_2$O (81.6 g) was heated under reflux for 3 hr. The mixture was concentrated in vacuo, dissolved in CHCl$_3$, washed with sat. NaHCO$_3$, brine, and dried over Na$_2$SO$_4$. The solvent was removed in vacuo and the residue was triturated with i-Pr$_2$O to give (1R)-1,8,8-Trimethyl-3-oxabicyclo[3.2.1]octane-2,4-dione [(1R)-camphoric anhydride (34.0 g) as crystals.

Method B: DIEA (8.0 g) was added to a suspension of (1R,3S)-camphoric acid (5.0 g) and BOP Reagent (11.1 g) in THF (50 ml) at room temperature. The mixture was stirred for 4 hr. and the solvent was removed in vacuo. The residue was extracted with AcOEt and the extract was washed with 5% HCl, sat. NaHCO$_3$, and sat. LiCl, and dried over Na$_2$SO$_4$. The solvent was removed in vacuo and the residue was purified by flash chromatography on silica gel (eluent; CHCl$_3$) to give (1R)-camphoric anhydride (4.1 g) as a colorless powder.

R. Example 2

(1R-cis)-1,2,2-Trimethylcyclopentane-1,3-dicarboxylic acid 3-(1,1-dimethylethyl)ester.

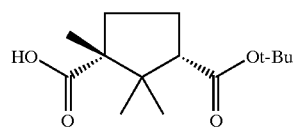

To a solution of (1R)-camphoric anhydride (0.18 g) in THF (2 ml) was added 1M t-BuOK in THF (1 ml) at −78° C. under N$_2$ and the mixture was stirred for 10 hr. at the same temperature. The mixture was concentrated in vacuo, dissolved in H$_2$O, and extracted with AcOEt. The aqueous layer was acidified with 1N HCl to pH 3 and extracted with CH$_2$Cl$_2$. The extract was washed with brine and dried over Na$_2$SO$_4$. The solvent was removed in vacuo to give (1R-cis)-1,2,2-Trimethylcyclopentane-1,3-dicarboxylic acid 3-dimethylethyl ester (0.24 g).

R. Example 3

(1R-cis)-3-Formyl-1,2,2-trimethylcyclopentanecarboxylic acid.

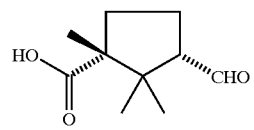

A mixture of (1R)-camphoric anhydride (1.76 g), N,O-dimethylhydroxylamine hydrochloride (1.13 g), DIEA (8.4 ml) in THF (15 ml) was heated for 3 hr. at 85° C. in a sealed tube. After cooling, the tube was opened and 1N HCl (75 ml) was added. The resulting mixture was extracted with AcOEt. The extract was dried over Na$_2$SO$_4$ and the solvent was removed in vacuo. The residue was purified by column chromatography on silica gel to give (1R,3S)-3-(N-methoxy-N-methylcarbamoyl)-1,2,2-trimethylcyclopentanecarboxylic acid (800 mg)

To a solution of the obtained compound (215 mg) in THF (5 ml) was added a 1M solution of LiAlH$_4$ in THF (1.5 ml) at −78° C. The mixture was stirred for 1 hr. at −78° C., warmed to 0° C. and quenched with 1N HCl. The resulting mixture was extracted with AcOEt. The extract was dried over Na$_2$SO$_4$ and the solvent was removed in vacuo to give a 3:1 mixture of (1R-cis)-3-Formyl-1,2,2-trimethylcyclopentanecarboxylic acid (aldehyde form) and (1R,5S)-4-hydroxy-1,8,8-trimethyl-3-oxabicyclo[3.2.1]- octane-2-one (acetal form) (153 mg). Both forms are exchangeable with each other in solution.

R. Example 4

O-(Cyclohexylmethyl)-L-tyrosine methyl ester, hydrochloride salt.

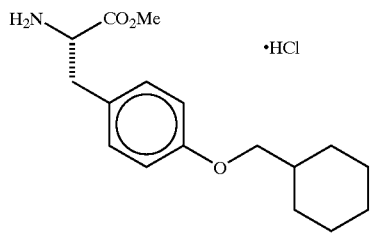

To a mixture of N-(tert-butoxycarbonyl)-L-tyrosine methyl ester (356 mg), $K_2CO_3$ (830 mg), n-$Bu_4NI$ (89 mg) in DMF (5 ml) was added cyclohexylmethyl bromide (202 μl) and the mixture was stirred for 1 day at room temperature. After addition of brine (40 ml), the resulting mixture was extracted with AcOEt. The extract was dried over $Na_2SO_4$ and the solvent was removed in vacuo. The residue was purified by column chromatography on silica gel (eluent; 9:1, Hexane/AcOEt→1:1, Hexane/AcOEt) to give N-(tert-butoxycarbonyl)-O-cyclohexylmethyl-L-tyrosine methyl ester (470 mg). The obtained compound (347 mg) was dissolved in 3N HCl/AcOEt (5 ml) and the mixture was stirred overnight. The solvent and excess HCl was removed in vacuo to give O-(Cyclohexylmethyl)-L-tyrosine methyl ester, hydrochloride salt.

R. Example 5

1-[(2,4-Dichlorophenyl)methyl]-L-histidine methyl ester, dihydrochloride salt.

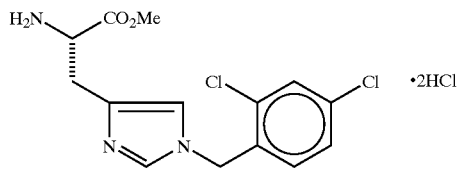

N-(tert-butoxycarbonyl)-L-histidine methyl ester (1.0 g) was added to a solution of 2,4-dichlorobenzyl chloride (0.73 g) and $Et_3N$ (0.27 g) in benzene (10 ml) and the mixture was heated under reflux for 1 hr. The mixture was cooled and the precipitate was removed by filtration. The filtrate was washed with $H_2O$, dried over $Na_2SO_4$, and the solvent was removed in vacuo. The residue was purified by column chromatography on silica gel (eluent; 95:5, $CHCl_3$/MeOH) to give N-(tert-butoxycarbonyl)-1-[(2,4-dichlorophenyl) methyl]-L-histidine methyl ester. The obtained compound was treated in a similar manner as described in R. Example 4 to give 1-[(2,4-Dichlorophenyl)methyl]-L-histidine methyl ester, dihydrochloride salt.

R. Example 6

1-[(2,6-Dichlorophenyl)methyl]-L-histidine methyl ester, dihydrochloride salt.

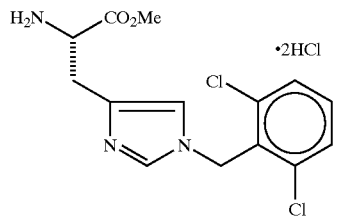

L-histidine (3.13 g) was added to a solution of $NaNH_2$ in liquid ammonia prepared from Na (0.93 g) and $FeCl_3$ (catalytic amount) in liquid ammonia (50 ml) After 15 min., a solution of 2,6-dichlorobenzylchloride (3.96 g) in THF (5 ml) was added and the mixture was stirred for 3 hr. The reaction mixture was quenched with $H_2O$ and ether. The pH of the aqueous layer was adjusted to pH 8 with 5% HCl followed by cooling. The resulting precipitate was collected by filtration, washed with $H_2O$, and dried to give 1-[(2,6-dichlorophenyl)methyl]-L-histidine (3.58 g). The obtained compound (0.80 g) was dissolved in MeOH (30 ml) and HCl gas was bubbled for 10 min. at 0° C. The reaction mixture was stirred for 15 hr. at room temperature and the solvent was removed in vacuo to give 1-[(2,6-Dichlorophenyl) methyl]-L-histidine methyl ester, dihydrochloride salt.

R. Example 7

3-Nitro-L-tyrosine methyl ester, hydrochloride salt.

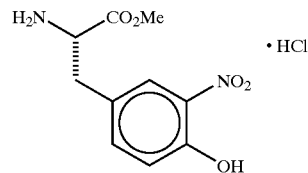

To a solution of N-(tert-butoxycarbonyl)-L-tyrosine methyl ester (5.64 g) in THF (10 ml) was added $NH_4NO_3$ (3 g) and concentrated $HNO_3$ (3 ml). After 30 sec., the reaction mixture turned to dark red with reflux occurring. The reaction mixture was quenched with solid $NaHCO_3$ and $H_2O$, and extracted with AcOEt. The extract was dried over $Na_2SO_4$ and the solvent was removed in vacuo. The residue was purified by column chromatography on silica gel (eluent; Hexane→1:1, Hexane/AcOEt) to give N-(tert-butoxycarbonyl)-3-nitro-L-tyrosine methyl ester (3.42 g). The obtained compound was treated in a similar manner as described in R. Example 4 to give 3-Nitro-L-tyrosine methyl ester, hydrochloride salt.

R. Example 8

3-[(2,6-Dichlorobenzoyl)amino]-L-tyrosine methyl ester, hydrochloride salt.

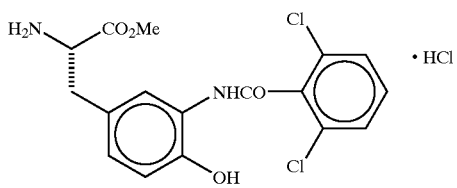

A mixture of N-(tert-butoxycarbonyl)-3-nitro-L-tyrosine methyl ester (2.0 g) and 10% Pd-C (1.0 g) in MeOH (10 ml) was subjected to catalytic hydrogenolysis at atmospheric pressure. The catalyst was filtered off and the filtrate was evaporated in vacuo. The residue was triturated with ether to give 3-amino-N-(tert-butoxycarbonyl)-L-tyrosine methyl ester (1.5 g) as a solid. To a solution of the obtained compound (1.0 g) in $CH_2Cl_2$ (10 ml) was added 2,6-dichlorobenzoyl chloride (0.74 g) and DIEA (1.1 g) and the mixture was stirred at room temperature overnight. The solvent was removed in vacuo and the residue was purified by column chromatography on silica gel (eluent; 2:1, Hexane/AcOEt) to give N-(tert-butoxycarbonyl)-3-(2,6-dichlorobenzamido)-L-tyrosine methyl ester (1.2 g). The obtained compound was treated in a similar manner as described in R. Example 4 to give 3-[(2,6-Dichlorobenzoyl)amino]-L-tyrosine methyl ester, hydrochloride salt.

R. Example 9

4-[[(2,6-Dichlorophenyl)methyl]amino]-L-phenylalanine methyl ester, hydrochloride salt.

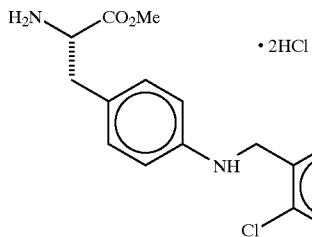

To a mixture of 4-amino-N-(tert-butoxycarbonyl)-L-phenylalanine methyl ester (0.59 g) and 2,6-dichlorobenzaldehyde (0.35 g) in MeOH (9 ml) was added $NaCNBH_3$ (0.38 g), AcOH (1 ml), and molecular sieves 4A (catalytic amount) and the mixture was stirred overnight at room temperature.

The reaction mixture was quenched with brine and 1N HCl. The solvent was removed in vacuo and the residue was extracted with AcOEt. The extract was washed with 1N HCl, brine, dried over $MgSO_4$, and the solvent was removed in vacuo. The residue was purified by column chromatography on silica gel (eluent; 10% $EtOH/CH_2Cl_2$) to give N-(tert-butoxycarbonyl)-4-[[(2,6-dichlorophenyl)methyl]amino]-L-phenylalanine (0.36 g) as a colorless solid. The obtained compound (0.5 g) was dissolved in MeOH (5 ml) and HCl gas was bubbled for 5 min. at 0° C. The mixture was stirred for 2 hr. and the solvent was removed in vacuo to give 4-[[(2,6-Dichlorophenyl)methyl]amino]-L-phenylalanine methyl ester, hydrochloride salt.

R. Example 10

(S)-α-Amino-2-naphthalenepropanoic acid phenylmethyl ester, 4-methylphenylsulfonic acid salt.

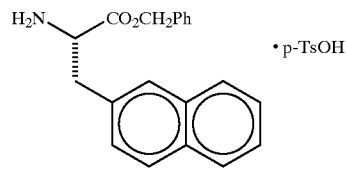

A mixture of (S)-2-amino-3-(2-naphthyl)-propanoic acid (0.40 g), benzyl alcohol (2 ml), and p-toluenesulfonic acid monohydrate (0.42 g) in toluene (5 ml) was heated for 6 hr. under reflux.

The reaction mixture was cooled and diluted with ether (10 ml)/hexane (10 ml). The resulting precipitate was collected by filtration and recrystallized from EtOH/ether to give (S)-α-Amino-2-naphthalenepropanoic acid phenylmethyl ester, 4-methylphenylsulfonic acid salt (0.73 g), mp 174–176° C.

R. Example 11

4-[[(2,6-Dichlorophenyl)amino]carbonyl]-L-phenylalanine methyl ester, hydrochloride salt.

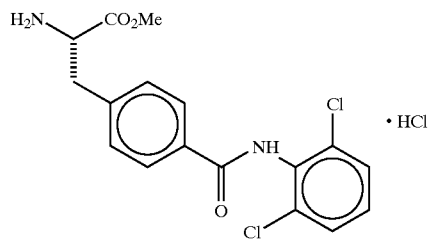

A solution of 4-bromo-N-(tert-butoxycarbonyl)-L-phenylalanine (359 mg) in THF was added to a THF solution of n-BuLi (2.7 ml of 1.6 M solution in hexane) at −78° C. The mixture was stirred for 2 hr. at room temperature, quenched with 1N HCl (15 ml), and extracted with AcOEt. The extract was dried over $Na_2SO_4$ and the solvent was removed in vacuo. The residue was purified by column chromatography on silica gel (eluent: Hexane→AcOEt) to give N-(tert-butoxycarbonyl)-4-[(2,6-dichlorophenyl)-carbamoyl]-L-phenylalanine (95 mg). The obtained compound was treated in a similar manner as described in R. Example 4 to give 4-[[(2,6-Dichlorophenyl)amino]carbonyl]-L-phenylalanine methyl ester, hydrochloride salt.

R. Examples 12–46 were prepared in a similar manner as described in R. Examples 4–11, and are shown in the Tables 6–8.

TABLE 6

R. Examples 12 through 26:

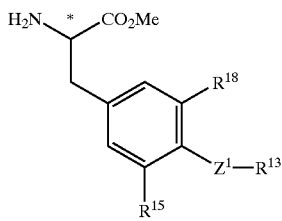

(*: R—— or S—— form)

| R. Ex. No. | * | $R^{15}$ | $Z^1$ | $R^{13}$ | $R^{18}$ |
|---|---|---|---|---|---|
| 12 | S | H | single bond | t-BuO— | H |
| 13 | S | H | —OCH$_2$— | 1-naphthyl | H |
| 14 | S | H | —OCH$_2$— | 2-naphthyl | H |
| 15 | S | H | —OCH$_2$— | 2,6-dichlorophenyl | H |
| 16 | S | H | —OCH$_2$— | CH(Et)(n-Bu) | H |
| 17 | S | I | —OCH$_2$— | 3-bromophenyl | I |
| 18 | S | H | —OCH$_2$— | 3,4-dichlorophenyl | H |
| 19 | S | PhCH$_2$O | —OCH$_2$— | Ph | H |
| 20 | S | H | —OCH$_2$— | 4-biphenylyl | H |
| 21 | S | H | —OCH$_2$— | Ph | H |
| 22 | R | H | —OCH$_2$— | Ph | H |

TABLE 6-continued

R. Examples 12 through 26:

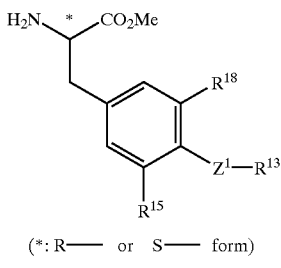

(*: R—— or S—— form)

| R. Ex. No. | * | R$^{15}$ | Z$^1$ | R$^{13}$ | R$^{18}$ |
|---|---|---|---|---|---|
| 23 | S | NO$_2$ | —OCH$_2$— | 2,6-dichlorophenyl | H |
| 24 | S | OH | —OCH$_2$— | 2,6-dichlorophenyl | H |
| 25 | S | 2,6-dichlorobenzyloxy (–CH$_2$O–) | —OCH$_2$— | 2,6-dichlorophenyl | H |
| 26 | S | 2,6-dichlorobenzyloxy (–CH$_2$O–) | single Bond | OH | H |

TABLE 7

R. Examples 27 through 35:

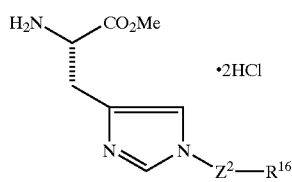

·2HCl

| R. Ex. No. | Z$^2$ | R$^{16}$ |
|---|---|---|
| 27 | single bond | Ph$_3$C— |

TABLE 7-continued

R. Examples 27 through 35:

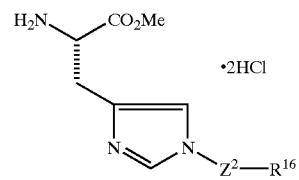

·2HCl

| R. Ex. No. | Z$^2$ | R$^{16}$ |
|---|---|---|
| 28 | CH$_2$ | 4-chlorophenyl |

TABLE 7-continued
R. Examples 27 through 35:
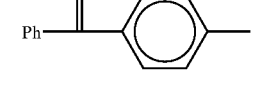
| R. Ex. No. | $Z^2$ | $R^{16}$ |
|---|---|---|
| 29 | $CH_2$ | Ph |
| 30 | $CH_2$ | 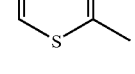 |
| 31 | $CH_2$ | $PhCH_2O$ |
| 32 | $CH_2$ | 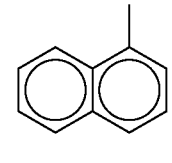 |
| 33 | $CH_2$ | 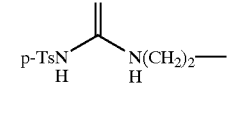 |
| 34 | $CH_2$ | 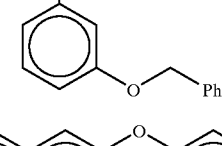 |
| 35 | $CH_2$ |  |
TABLE 8
R. Examples 36 through 46:
(*: R—— or S—— form)
| R. Ex. No. | * | $R^6$ |
|---|---|---|
| 36 | S | 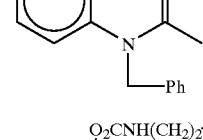 |
| 37 | S | 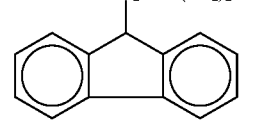 |
| 38 | S |  |
| 39 | S |  |
| 40 | S | Ph |
| 41 | S |  |
| 42 | S |  |
| 43 | S |  |
| 44 | S |  |
| 45 | S |  |

TABLE 8-continued

R. Examples 36 through 46:

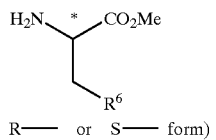

(*: R—— or S—— form)

| R. Ex. No. | * | R⁶ |
|---|---|---|
| 46 | R | ![phenol] |

R. Example 47

(1S-cis)-1,2,2-trimethylcyclopentane-1,3-dicarboxylic acid 3-methyl ester ($C_{11}H_{18}O_4$), 36-B

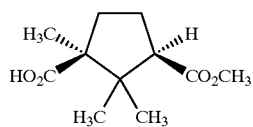

Reference Example 47 was prepared according to Scheme 36: 36-B where $R^{36-1}$ is $CH_3$, and the stereochemistry is (1S-cis) as follows: The preparation follows that of Preparation 10-A using (1S, 3R)-(−)-Camphoric acid as the starting material. Physical properties as follows: $^1$H NMR (CDCl$_3$) δ11.45 (1H), 3.69 (3H), 2.82 (1H), 2.54 (1H), 2.24 (1H), 1.82 (1H), 1.52 (1H), 1.27 (3H), 1.25 (3H), 0.86 (3H); Anal: Calcd. for $C_{11}H_{18}O_4$: C, 61.66; H, 8.47; Found: C, 61.60; H, 8.30.

R. Example 48

(1S-cis)-1,2 2-trimethylcyclopentane-1,3-dicarboxylic acid 1-(1,1-dimethylethyl)-3-methyl diester ($C_{15}H_{26}O_4$), 36-C

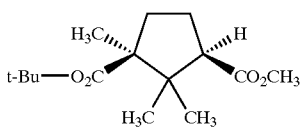

Reference Example 48 was prepared according to Scheme 36: 36-C where $R^{36-1}$ is $CH_3$, $R^{36-2}$ is t-Bu, and the stereochemistry is (1S-cis) as follows: To a solution of (1S-cis)-1,2,2-trimethylcyclopentane-1,3-dicarboxylic acid 3-methyl ester (9.69 g), 36-B, in 3 mL of $CH_2Cl_2$ and 80 mL of cyclohexane was added t-Butyl-2,2,2-trichloroacetimidate (16.18 mL) and 35 μL of $BF_3.Et_2O$. The reaction was stirred at ambient temperature for 18 hours and then filtered. The filtrate was purified by flash chromatography silica gel eluting with AcOEt-hexane to obtain (1S-cis)-1,2,2-trimethylcyclopentane-1,3-dicarboxylic acid 1-(1,1-dimethylethyl)-3-methyl diester (12.89 g), 36-C. Physical properties as follows: m.p.=35–37° C.; $^1$H NMR (CDCl3) δ 3.68 (3H), 2.79 (1H), 2.53 (1H), 2.17 (1H), 1.76 (1H), 1.24 (3H), 1.17 (3H), 0.81 (3H); Anal: Calcd. for $C_{15}H_{26}O_4$: C, 66.64; H, 9.67; Found: C, 66.61; H, 9.64.

R. Example 49

(1S-cis)-1,2,2-Trimethylcyclopentane-1,3-dicarboxylic acid 1-(1,1-dimethylethyl)ester ($C_{14}H_{24}O_4$), 36-D

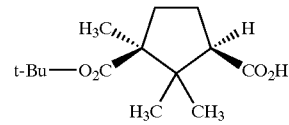

Reference Example 49 was prepared according to Scheme 36 in the Preparation of 36-D where $R^{36-2}$ is t-Bu and the stereochemistry is (1S-cis) as follows: The preparation follows that of Preparation 15-D using 36-C, (1S-cis)-1,2,2-trimethylcyclopentane-1,3-dicarboxylic acid 1-(1,1-dimethylethyl)-3-methyl diester, as starting material. Physical properties as follows: m.p.=95.7–97.5° C.; $^1$H NMR (CDCl3) δ 2.82 (1H), 2.53 (1H), 2.13 (1H), 1.82 (1H), 1.45 (10H), 1.29 (3H), 1.17 (3H), 0.88 (3H); Anal: Calcd. for $C_{15}H_{26}O_4$: C, 65.60; H, 9.44; Found: C, 65.60; H, 9.44.

R. Example 50

(1S-trans)-[3-(Phenylmethoxy)carbonyl]-1,2,2-trimethylcyclopentane-1-carboxylic acid 1-(1,1-dimethylethyl)ester ($C_{21}H_{30}O_4$), 36-E-1

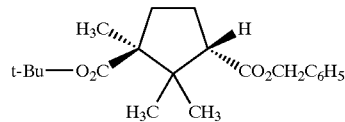

Reference Example 50 was prepared according to Scheme 36: Preparation of 36-E-1 where $R^{36-1}$ is —$CH_2C_6H_5$, $R^{36-2}$ is t-Bu, and the stereochemistry is (1S-trans) as follows: To a solution of (1S-cis)-1,2,2-Trimethylcyclopentane-1,3-dicarboxylic acid 1-(1,1-dimethylethyl)ester 36-D (20.0 g) in 300 mL of $CH_3CN$ was added benzyl bromide(16.01 g) and DIEA(12.1 g). The reaction was stirred at ambient temperature for 22 hours, concentrated in vacuo, and diluted with $CH_2Cl_2$. The solution was consecutively washed with water, 10% HCl, water, and brine. The organic layer was dried($Na_2SO_4$) and concentrated in vacuo. The concentrate was purified by chromatography on silica gel eluting with AcOEt-hexane to obtain (1S-cis)-[3-(Phenylmethoxy) carbonyl]-1,2,2-trimethylcyclopentane-1-carboxylic acid 1-(1,1-dimethylethyl)ester (18.94 g) Physical properties as follows: $^1$H NMR (CDCl$_3$) δ7.34 (5H), 5.12 (2H), 2.82 (1H), 2.51 (1H), 2.19 (1H), 1.82 (1H), 1.44 (10H), 1.23 (3H), 1.15 (3H), 0.78 (3H); MS (EI) m/z (rel. intensity) 0 (M+, 0), 181 (64), 180 (64), 179 (17), 166 (22), 155 (16), 153 (15), 109 (18), 92 (15), 91 (99), 57 (40); Anal. Calcd for $C_{21}H_{30}O_4$: C, 72.80; H, 8.73; Found: C, 70.76; H, 8.38; N, 0.36.

The product of the above reaction was combined with THF(44 mL) and NaH(634 mg) and refluxed for 0.5 hour then cooled, diluted with saturated $NaHCO_3$, and extracted with AcOEt. The organic layer was concentrated to obtain a mixture of starting material and (1S-trans)-[3-(Phenylmethoxy)carbonyl]-1,2,2-trimethylcyclopentane-1-carboxylic acid 1-(1,1-dimethylethyl)ester. These were separated by HPLC on an (R, R)Whelk-O, 5×25 cm column, eluting with 2% isopropanol in hexane at 50 mL/minute. The detector monitored 215 nm. The first peak at 19 minutes contained (1S-trans)-[1-(Phenylmethoxy)carbonyl]-1,2,2-trimethylcyclopentane-1-carboxylic acid 1-(1,1-dimethylethyl)ester 36-E-1(3.88 g). Physical properties as follows: $^1$H NMR (CDCl$_3$) 67 7.34 (5H), 5.12 (2H), 3.02 (1H), 2.18 (2H), 1.98 (1H), 1.58 (1H), 1.44 (9H), 1.08 (3H), 1.06 (3H), 0.79 (3H); MS (FAB) m/z 347 (MH+), 501, 292, 291, 245, 183, 109, 92, 91, 57, 41; HPLC 0.46×25 cm (R, R)Whelk-O column eluted at 0.5 mL/minute with 2% isopropanol in hexane, monitoring 215 nm, RT=13.65 minutes.

R. Example 51

(1R-trans)-[3-(Phenylmethoxy)carbonyl]-1,2,2-trimethylcyclopentane-1-carboxylic acid 1-(1,1-dimethylethyl)ester (C$_{21}$H$_{30}$O$_4$), 36-E-2

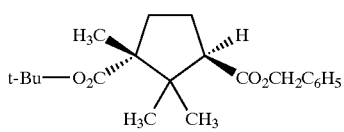

Reference Example 51 was prepared according to Scheme 36: Preparation of 36-E-2 where R$^{36-1}$ is —CH$_2$C$_6$H$_5$, R$^{36-2}$ is t-Bu, and the stereochemistry is (1R-trans) as follows: The preparation follows that of Preparation 36-E-1 using 15-D, (1R-cis)-1,2,2-Trimethylcyclopentane-1,3-dicarboxylic acid 1-(1,1-dimethylethyl)ester, as starting material. Physical properties as follows: $^1$H NMR (CDCl$_3$) δ 7.35 (5H), 5.12 (2H), 3.02 (1H), 2.13 (2H), 1.98 (1H), 1.58 (1H), 1.44 (9H), 1.08 (3H), 1.05 (3H), 0.78 (3H); HPLC 0.46×25 cm (R, R)Whelk-O column eluted at 1.0 mL/minute with 2% isopropanol in hexane, monitoring 254 nm, RT=5.54 minutes R. Example 52

(1S-trans)-[3-(Phenylmethoxy)carbonyl]-1,2,2-trimethylcyclopentane-1-carboxylic acid (C$_{17}$H$_{22}$O$_4$), 36-F-1

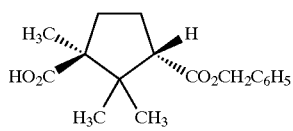

Reference Example 52 was prepared according to Scheme 36: Preparation of 36-F-1 where R$^{36-1}$ is —CH$_2$C$_6$H$_5$, and the stereochemistry is (1S-trans) as follows: A sample of 36-E-1,(1S-trans)-[3-(Phenylmethoxy)carbonyl]-1,2,2-trimethylcyclopentane-1-carboxylic acid 1-(1,1-dimethylethyl)ester (2.95 g), was dissolved in TFA at 0° C. and then allowed to come to ambient temperature. The solution was stirred for 19 hours then concentrated, redissolved in t-butyl methyl ether and washed with a saturated solution of NaHCO$_3$. The organic layer was concentrated in vacuo to obtain (1S-trans)-[3-(phenylmethoxy)carbonyl]-1,2,2-trimethylcyclopentane-1-carboxylic acid 36-F-1 (2.44 g). Physical properties as follows: $^1$H NMR (CDCl$_3$) δ 7.34 (, 5H), 5.13 (, 2H), 3.08 (, 1H), 2.16 (, 2H), 2.02 (, 1H), 1.64 (, 1H), 1.16 (, 3H), 1.10 (, 3 H), 0.83 (, 3H); Anal. Calcd for C$_{17}$H$_{22}$O$_4$: C, 70.32; H, 7.64. Found: C, 70.94; H, 7.63; N, 0.04.

R. Example 53

(1R-trans)-[3-(Phenylmethoxy)carbonyl]-1,2,2-trimethylcyclopentane-1-carboxylic acid (C$_{17}$H$_{22}$O$_4$), 36-F-2

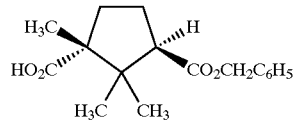

Reference Example 53 was prepared according to Scheme 36: Preparation of 36-F-2 where R$^{36-1}$ is —CH$_2$C$_6$H$_5$, and the stereochemistry is (1R-trans) as follows: The preparation follows that of Preparation 36-F-1 using 36-E-2, (1R-trans)-[3-(Phenylmethoxy)carbonyl]-1,2,2-trimethylcyclopentane-1-carboxylic acid 1-(1,1-dimethylethyl)ester, as starting material. Physical properties as follows: MS (EI) m/z (rel. intensity) 290 (M+, 5), 183 (15), 182 (9), 164 (8), 153 (22) 136 (10), 109 (22), 92 (24), 91 (99), 65 (9), 55 (9); Anal. Calcd for C$_{17}$H$_{22}$O$_4$: C, 70.32; H, 7.64. Found: C, 70.66; H, 7.74; N, 0.22.

R. Example 54

(1S-trans)-1,2,2-trimethylcyclopentane-1,3-dicarboxylic acid 1-(1,1-dimethylethyl)ester (C$_{14}$H$_{24}$O$_4$), 36-G-1

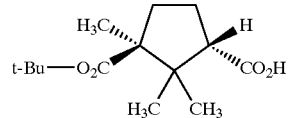

Reference Example 54 was prepared according to Scheme 36: Preparation of 36-G-1 where R$^{36-2}$ is t-Bu and the stereochemistry is (1S-trans) as follows: A sample of 36-E-1, (1S-trans)-[3-(Phenylmethoxy)carbonyl]-1,2,2-trimethylcyclopentane-1-carboxylic acid 1-(1,1-dimethylethyl)ester (3.27 g), was dissolved in EtOH (100 mL) and added 5% palladium on carbon (1.0 g) and cyclohexene (50 mL). The mixture was refluxed for 4 hours and then stirred at ambient temperature for 18 hours. The reaction was then filtered and the filtrate concentrated in vacuo to obtain 36-G-1, (1S-trans)-1,2,2-trimethylcyclopentane-1-carboxylic acid 1-(1,1-dimethylethyl)ester (2.45 g). Physical properties as follows: $^1$H NMR (CDCl$_3$) δ 3.05 (1H), 2.11 (2H), 1.99 (1H), 1.60 (1H), 1.45 (9H), 1.11 (3H), 1.10 (3H), 0.89 (3H); MS (FAB) m/z (rel. intensity) 257 (MH+, 43), 411 (23), 257 (43), 201 (99), 183 (20), 177 (14), 155 (26), 109 (36), 57 (81), 41 (22), 29 (15); Anal. Calcd for C$_{14}$H$_{24}$O$_4$: C, 65.60; H, 9.44. Found: C, 65.62; H, 9.42; N, 0.03.

R. Example 55

(1R-trans)-1,2,2-trimethylcyclopentane-1,3-dicarboxylic acid 1-(1,1-dimethylethyl)ester ($C_{14}H_{24}O_4$), 36-G-2

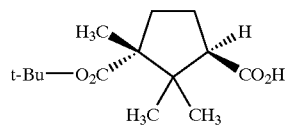

Reference Example 55 was prepared according to Scheme 36: Preparation of 36-G-2 where $R^{36-2}$ is t-Bu and the stereochemistry is (1R-trans) as follows: The preparation follows that of Preparation 36-G-1 using 36-E-2, (1R-trans)-[3-(Phenylmethoxy)carbonyl]-1,2,2-trimethylcyclopentane-1-carboxylic acid 1-(1,1-dimethylethyl)ester, as starting material. Physical properties as follows: $^1$H NMR (CDCl$_3$) δ 3.03 (, 1H), 2.13 (, 2H), 1.98 (, 1H), 1.59 (, 1H), 1.45 (, 9H), 1.11 (, 3H), 1.10 (, 3H), 0.89 (, 3H); MS (FAB) m/z (rel. intensity) 257 (MH+, 35), 411 (19), 279 (14), 257 (35), 201 (99), 183 (18), 155 (26), 109 (35), 57 (74), 41 (19), 29 (12); Anal. Calcd for $C_{14}H_{24}O_4$: C, 65.60; H, 9.44. Found: C, 65.56; H, 9.44; N, 0.18.

R. Example 56

3-Bromo-4-[(2,6-dichlorobenzoyl)amino]-L-phenylalanine methyl ester hydrochloride salt ($C_{17}H_{15}BrCl_2N_2O_3 \cdot HCl$).

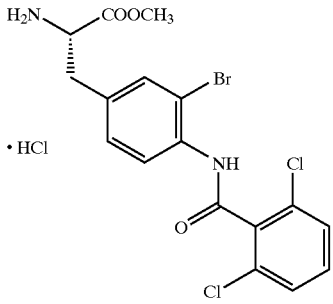

Reference Example 56 was prepared as follows: To a solution of 4-[(2,6-Dichlorobenzoyl)amino]-L-phenylalanine methyl ester hydrochloride salt, 37-B-1, (205.7 mg) in acetic acid(5 mL) was added an excess of bromine (5.55 g) in acetic acid (5 mL) and iron powder (416.2 mg). The reaction was stirred at ambient temperature for 3 hours. The reaction concentrated in vacuo and the remaining acetic acid removed as an azeotrope with toluene. The crude material was diluted with water, made basic with saturated sodium bicarbonate and extracted with AcOEt. The extract was purified by flash chromatography on silica gel eluting with methanol-methylene chloride. The purified material was dissolved in methanol saturated with hydrogen chloride and concentrated in vacuo and then crystallized from methanol with AcOEt to obtain 3-Bromo-4-[(2,6-dichlorobenzoyl)amino]-L-phenylalanine methyl ester hydrochloride salt (540.4 mg). Physical properties as follows: m.p. 200–205; $^1$H NMR (CD$_3$OD) δ 7.76 (1H), 7.64 (1H), 7.46 (3H), 7.34 (1H), 4.38 (1H), 3.85 (3H), 3.30 (1H), 3.15 (1H); HRMS (FAB) Calcd for $C_{17}H_{15}BrCL_2N_2O_3+H_1$ 444.9722, found 444.9724.

R. Example 57

N-[(1,1-Dimethylethoxy)carbonyl]-3-iodo-L-alanine methyl ester ($C_9H_{16}INO_4$).

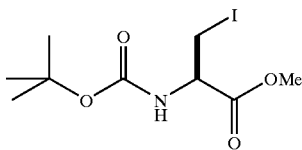

The preparation of Reference Example 57 is taught by Scheme 39 under the heading Preparation of Reference Example 57.

R. Example 58

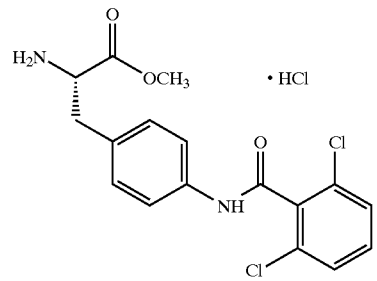

The aminoester product of Reference Example 58 is useful as a synthetic intermediate (for example, reagent 37-B of Scheme 37). Reference Example 58 is prepared as follows:

To a cold (0–5° C.) solution of anhydrous methanolic HCl was added 100 g of L-4-nitrophenylalanine (Advanced ChemTech) portionwise over 15 min. The mechanically stirred mixture was heated to gentle reflux for 48 h. The mixture was allowed to cool and then filtered through a sintered glass filter funnel, washing the collected solids with hot MeOH until only insoluble residues remained. The filtrate was concentrated in vacuo to afford the methyl ester (120 g) as waxy off white solid which was used without further purification.

To a suspension of methyl ester described above (87 g, 0.33 mole) in CH$_2$Cl$_2$ (1500 mL) at ambient temperature was added di-t-butyldicarbonate (109 g, 0.50 mole) followed by the dropwise addition of Et$_3$N (51 mL, 0.37 mole). After 15 min additional Et$_3$N (40 mL, 0.29 mol) was added to maintain a slightly basic mixture (ca. pH 8). The reaction mixture was stirred 18 h and additional. CH$_2$Cl$_2$ (1400 mL) and Et$_3$N (15 mL, 0.11 mol) were added. After an additional 2 h the reaction mixture was quenched by the slow addition of MeOH (100 mL), stirred for 1 h and then partitioned between CH$_2$Cl$_2$ and cold 10% aqueous KHSC$_4$. The organic layer was washed with saturated NaHCO$_3$ and brine, dried (Na$_2$SO$_4$), filtered and concentrated in vacuo. Flash chromatography of the residue using hexane and a gradient of a 1:1 mixture of EtOA$_c$/CH$_2$Cl$_2$ (25–33%) afforded the Boc-methyl ester (69 g) as a white solid. Physical properties as follows: $^1$H NMR (300 MHz; CDCl$_3$) δ 8.16 (2H), 7.31 (2H), 5.04 (1H), 4.63 (1H), 3.73 (3H), 3.18 (2H), 1.41 (9H); MS (ES+) for $C_{15}H_{20}N_2O_6$ m/z 325.2 (M+H)$^+$.

Palladium on carbon (10% w/w, 1.25 g) was added to a Parr hydrogenation flask under a N$_2$ atmosphere and carefully wetted with 100 mL of MeOH/THF (1:1). A solution of the Boc-methyl ester described above (25 g, 77 mmol) in 400 mL of MeOH/THF (1:1) was added and the mixture shaken on a hydrogenation apparatus under a hydrogen atmosphere (20 psi) for 1 h at ambient temperature. The reaction mixture was filtered through a pad of Celite and the solids washed several times with MeOH. The combined filtrates were concentrated in vacuo to afford the 4-aminophenylalanyl derivative (22.7 g) which was used without further purification. Physical properties as follows: $^1$H NMR (300 MHz, CDCl$_3$) δ 6.89 (2H), 6.61 (2H), 4.96 (1H), 4.50 (1H), 3.69 (3H), 2.95 (2H), 1.41 (9H); MS (ES+) for $C_{15}H_{22}N_2O_4$ m/z 295.2 (M+H)$^+$.

A cold (0–5° C.) solution of 2,6-dichlorobenzoyl chloride (11.1 mL, 77.5 mmol) in 125 mL of THF was treated dropwise with a solution of the 4-aminophenylalanyl derivative described above (22.7 g, 77.1 mmol) and Et$_3$N (16 mL, 115 mmol) in 125 mL of THF. The reaction mixture was allowed to warm to temperature and stir an additional 18 h. The mixture was diluted with EtOAc (2 L) and then washed with 1N HCl, H$_2$O, 1N NaOH and brine. The organic extract was dried (Na$_2$SO$_4$), filtered, and concentrated in vacuo to give the crude product as a pale yellow solid. This material was recrystallized from acetone/hexanes (ca. 1:1) to afford the amide (30.8 g) as a crystalline solid. Physical properties as follows: mp 192.2–193.1° C.; IR (mull) 3305, 1747, 1736, 1690, 1665, 1609, 1548, 1512, 1433, 1414, 1325, 1277, 1219, 1171, 781 cm$^{-1}$; $^1$H NMR (300 MHz; CDCl$_3$) δ 7.57 (2H), 7.34 (4H), 7.14 (2H), 4.98 (1H), 4.60 (1H), 3.74 (3H), 3.11 (2H), 1.42 (9H); MS (ES+) for $C_{22}H_{24}Cl_2N_2O_5$ m/z 467.0 (M+H)$^+$.

To 650 mL of anhydrous 4M HCl in dioxane at ambient temperature was added the amide described above (30.6 g, 65.5 mmol) portionwise and the resulting mixture was stirred until all the solids had dissolved (ca. 1 h). Volatiles were removed in vacuo to give a light yellow solid which was partitioned between water (500 mL) and ether (1 L). The water layer was separated and concentrated in vacuo to approximately 200 mL. The aqueous solution was then frozen and lyophilized to afford the aminoester product Reference Example 58 (25.6 g) as a light yellow solid. Physical properties as follows: $[\alpha]^{25}_D$=+5 (c 1, MeOH); IR (mull) 3244, 3186, 3112, 1747, 1660, 1604, 1562, 1539, 1516, 1431, 1416, 1327, 1273, 1243, 799 cm$^{-1}$; $^1$H NMR (300 MHz; CD$_3$OD) δ 7.69 (2H), 7.45 (3H), 7.29 (2H), 4.34 (1H), 3.83 (3H), 3.21 (2H); $^{13}$C NMR (300 MHz; CD$_3$OD) δ 169.0, 163.9, 137.8, 136.08, 131.8, 131.0, 130.3, 129.7, 127.9, 120.6, 53.8, 52.3, 35.4; MS (ES+) for $C_{17}H_{16}Cl_2N_2O_3$ m/z 367.1 (M+H)$^+$.

Biological Assays

Jurkat-Endothelial Cell Adhesion Assay

The following assay established the activity of the present compounds in inhibiting β$_1$-mediated cell adhesion in a representative in vitro system. This assay measures the adhesive interactions of a T-cell line, Jurkat, known to express the α$_4$β$_1$ integrin, to endothelial monolayers in the presence of test compounds. The test compounds were added in increasing concentrations to T-cells and then the T-cell compound mixture was added to IL-1 stimulated endothelial cell monolayers. The plates were incubated, washed and the percentage of attached cells was quantitated. The present assay directly demonstrates the cell adhesion inhibitory activity and adhesion modulatory activity of the compounds. Human umbilical vein endothelial cells were purchased from Clonetics (San Diego, Calif.) at passage number 2. The cells were grown on 0.5% porcine skin gelatin pre-coated flasks (Sigma, St. Louis Mo.) in EGM-UV media (Clonetics, San Diego, Calif.) supplemented with 10% fetal bovine serum. Cells are refed every 2–3 days reaching confluence by day 4 to 6. The cells are monitored for factor VIII antigen and results show that at passage 12, the cells are positive for this antigen. The endothelial cells are not used following passage 6. The T-cell line Jurkat was obtained from American Type Tissue Culture Collection (Rockville, Md.) and the cells were cultured in RPMI containing 10% fetal calf serum. The cells were washed twice in Hank's Balanced Salt Solution (HBSS) and resuspended in Dulbecco's Minimal Eagle's Media (DMEM) containing 2.5 mg/ml Human Serum Albumin (HSA). Jurkat cells (1×10$^6$ cells/ml) were stained with 10 ng/ml BCECF-AM (Molecular Probes, Eugene, Oreg.)) in HBSS without phenol red. The cells were loaded with BCECF for 60 minutes in the dark at 37° C., washed 2 times, and resuspended in DMEM-HSA solution. Confluent endothelial monolayers, grown in 96-well tissue culture plates, were stimulated for 4 hr. at 37° C. with 0.1 ng/ml (~50 U/ml) recombinant IL-1 (Amgen, Thousand Oaks, Calif.). Following this incubation, the monolayers were washed twice with HBSS and 0.1 ml of DMEM-HSA solution was added. Jurkat cells (5×10$^5$ cells) were combined with the appropriate concentration of the test compound and 0.1 ml of the Jurkat cell-compound mixture was added to the endothelial cell monolayers. Generally, 100, 20, 5 and 1.25 μM compound concentrations were tested. These concentrations are adjusted downward for analogs found or thought to be more potent. The plates were placed on ice for 5 minutes to allow for Jurkat cell settling and the plates were incubated at 37° C. for 20 minutes. Following this incubation, the monolayers were washed twice with PBS containing 1 mM calcium chloride and 1 mM magnesium chloride and the plates were read using a Millipore Cytofluor 2300 (Marlboro, Mass.). Fluorescence in each well was measured as Arbitrary Fluorescence Units and percent adhesion in the absence of compound was adjusted to 100% and the % adhesion in the presence of compound was calculated. Monolayers were also fixed in 3% paraformaldehyde and evaluated microscopically to verify the adhesion. This procedure is a modification of a previously published method (Cardarelli et al., J. Biol. Chem. 269:18668–18673 (1994)).

Jurkat-CS-1 Assay

The CS-1 derived peptide, CLHPGEILDVPST, and the scrambled control peptide, CLHGPIELVSDPT, were synthesized on a Beckman 990 synthesizer using t-Boc methodology. The peptides were immobilized onto microtiter plates using the heterobifunctional crosslinker 3-(2-pyridyldithio)propionic acid N-hydroxysuccinimide ester (SPDP) as reported by Pierschbacher et al., Proc. Natl. Acad. USA, 80:1224–1227 (1983). Microtiter plates were coated with 20 μg/ml HSA for 2 hr. at room temperature, washed once with PBS and derivatized with 10 μg/ml SPDP for 1 hr. After washing, 100 μl of a 100 μg/ml cysteine containing peptide solution which had been recently dissolved was added to the wells and allowed to crosslink to the plates overnight at 4° C. Unbound peptide was removed from plates by washing with PBS. To block non-reacted sites, the plates are coated with 100 μl of a 2.5 mg/ml BSA solution in PBS for 1 hr. at 37° C. 100 μl of Jurkat cells (2.5×10$^6$ cells/ml) in DMEM plus BSA (2.5 mg/ml) was mixed with an appropriate concentration of the compound to be tested and the mixture was added to peptide coated dishes and incubated for 1 hr. at 37° C. Generally 100, 20, 5 and 1.25 μM concentrations of the compound were tested. The concentrations of the compound were adjusted downward for compounds thought or found to be more potent.

Following this incubation the plates were washed once with PBS and the attached cells were fixed with 3% paraformaldehyde in PBS and stained with 0.5% toluidine blue in 3.7% formaldehyde. The cells were stained overnight at room temperature and the optical density at 590 nm of toluidine blue stained cells was determined using a vertical pathway spectrophotometer to quantitate attachment (VMAX Kinetic Microplate Reader, Molecular Devices, Menlo Park, Calif.). This procedure is a modification of a previously published method (Cardarelli et al, J. Biol. Chem., 269:18668–18673 (1994) and Cardarelli et al, Proc. Natl. Acad. Sci. USA, 83:2647–2651 (1986)).

The preferred compounds are those which have low $IC_{50}$ values in the Jurkat EC assay or the Jurkat-CS-1 assay described above or which have at least moderate activity in both assays. All of the compounds of the present invention have an activity of less than 50 μM in the Jurkat CS-1 assay or less than 500 μM in the Jurkat EC assay. Compounds with activity in the Jurkat CS-1 assay preferably have $IC_{50}$ values of less than 1 μM, more preferably less than 0.5 μM, most preferably less than or equal to 0.08 μM. Compounds with activity in the Jurkat EC assay preferably have $IC_{50}$ values of less than 10 μM, more preferably less than 5 μM, most preferably less than or equal to 0.8 μM.

In the Jurkat EC Assay, $IC_{50}$ value ranges (μM) are depicted by A, B, and C and in the Jurkat CS-1 Assay, $IC_{50}$ value ranges are depicted by D, E, and F. These ranges are as follows:

Jurkat EC: 5≦A<10, 0.8<B<5, and C≦0.8

Jurkat CS-1: 0.5≦D<1, 0.08<E<0.5, and F≦0.08

The following chart illustrates the $IC_{50}$ values for selected compounds of the present invention in the Jurkat EC Assay and the Jurkat-CS-1 Assay. The ranges are as described above.

Additional in Vitro Biological Data

| Example No. | Jurkat EC | Jurkat CS-1 |
|---|---|---|
| 2 | — | D |
| 4 | B | E |
| 10 | B | E |
| 12 | C | F |
| 13 | A | D |
| 14 | A | — |
| 16 | A | — |
| 24 | B | E |
| 26 | B | D |
| 28 | B | E |
| 29 | A | D |
| 31 | A | — |
| 36 | A | D |
| 38 | B | E |
| 46 | B | — |
| 53 | B | D |
| 54 | C | F |
| 61 | B | E |
| 62 | A | — |
| 63 | B | F |
| 65 | C | E |
| 75 | B | — |
| 77 | B | E |
| 79 | A | — |
| 81 | C | E |
| 83 | C | F |
| 85 | A | E |
| 86 | — | D |
| 87 | C | F |
| 89 | B | E |
| 91 | B | F |
| 92 | C | F |
| 93 | C | F |
| 95 | B | E |
| 96 | A | — |
| 97 | C | F |
| 100 | C | F |
| 102 | C | F |
| 103 | C | F |
| 104 | C | F |
| 105 | B | E |
| 106 | C | F |
| 108 | C | F |
| 110 | C | F |
| 112 | C | F |
| 113 | — | D |
| 114 | C | E |
| 116 | C | F |
| 118 | B | D |
| 120 | B | E |
| 121 | B | D |
| 122 | B | — |
| 124 | B | E |
| 126 | B | E |
| 128 | B | E |
| 130 | B | E |
| 132 | B | E |
| 134 | B | — |
| 136 | A | D |
| 137 | — | E |
| 141 | B | D |
| 142 | B | E |
| 143 | — | D |
| 144 | B | E |
| 146 | B | E |
| 148 | C | E |
| 150 | B | D |
| 152 | C | F |
| 153 | B | E |
| 155 | A | D |
| 161 | B | — |
| 163 | — | D |
| 166 | C | F |
| 170 | A | — |
| 179 | A | F |
| 180 | C | F |
| 181 | C | F |
| 182 | C | F |
| 183 | C | F |
| 184 | C | F |
| 185 | B | E |
| 186 | B | E |
| 187 | B | E |
| 188 | B | E |
| 189 | B | — |
| 194 | B | E |
| 208 | C | E |
| 209 | C | F |
| 210 | C | F |
| 211 | C | F |
| 212 | A | E |
| 213 | B | E |
| 214 | C | F |
| 215 | C | E |
| 216 | C | F |
| 217 | C | F |
| 219 | C | F |
| 220 | B | E |
| 221 | A | D |
| 222 | C | E |
| 223 | C | F |
| 225 | C | F |
| 231 | C | D |
| 232 | C | F |
| 236 | C | E |
| 253 | B | E |
| 254 | B | E |

Activity of Camphoric Acids in Dextran Pleurisy Model

Certain compounds of the present invention were tested in a Dextran® pleurisy model.

Rationale for Developing an $\alpha_4\beta_1$ Integrin Antagonist to Treat Inflammatory Diseases VLA-4, a member of the $\beta1$ integrin family of adhesion molecules, is thought to play a critical role in several types of inflammatory disease processes by promoting leukocyte adhesion to vascular cell adhesion molecule (VCAM-1) and the CS-1 domain of fibronectin in extracellular tissue matrix (Elices M J, Osborn L, Takada Y, Crouse C, Luhowskyj S, Hemler M, Lobb R R. *VCAM-1 on activated endothelium interacts with the leukocyte integrin VLA-4 at a site distinct from the VLA-4-fibronectin binding site*. Cell; 60: 577–584, 1990, Humphries M J, Akiyama S K, Komoriya A, Olden K, Yamada K M. *Identification of an alternatively-spliced site in human plasma fibronectin that mediates cell type-specific adhesion*. J Cell Biol; 103: 2637–2647, 1986, Wayner E A, Garcia-Pardo A, Humphries M J, McDonald J A, Carter W G. *Identification and characterization of the T lymphocyte adhesion receptor for an alternative cell attachment domain (CS-1) in plasma fibronectin*. J Cell Biol; 109: 1321–1330, 1989, Guan J-L, Hynes R O. *Lymphoid cells recognize an alternatively-spliced segment of fibronectin via the integrin $\alpha_4\beta_1$*. Cell; 60: 53–61, 1990) Of the cell types expressing VLA-4, the major emphasis has been on eosinophils, lymphocytes, and monocytes. Validation of the role of VLA-4 has relied predominantly on the use of anti-VLA-4 antibodies which have been shown to suppress delayed-type hypersensitivity responses (Issekutz T B. *Dual inhibition of VLA-4 and LFA-1 maximally inhibits cutaneous delayed-type hypersensitivity-induced inflammation*. Am J Pathol; 143: 1286–1293, 1993, Scheynius A, Camp R L, Puré E. *Reduced contact sensitivity reactions in mice treated with monoclonal antibodies to leukocyte function-associated molecule-1 and intercellular adhesion molecule-1*. J Immunol; 150: 655–663, 1993, Ferguson T A, Kupper T S. *Antigen-independent processes in antigen-specific immunity*. J Immunol; 150: 1172–1182, 1993, Chisholm P L, Williams C A, Lobb R R. *Monoclonal antibodies to the integrin $\alpha$-4 subunit inhibit the murine contact hypersensitivity response*. Eur J Immunol; 23: 682–688, 1993, Elices M J, Tamraz S, Tollefson V, Vollger L W. *The integrin VLA-4 mediates leukocyte recruitment to skin inflammatory sites in vivo*. Clin Exp Rheumatol; 11 (Suppl 8) S77–80), 1993, experimental allergic encephalomyelitis (Yednock T A, Cannon C, Fritz L C, Sanchez-Madrid F, Steinman L M, Karin N. *Prevention of experimental autoimmune encephalomyelitis by antibodies against $\alpha_4\beta_1$ integrin*. Nature; 356: 63–66, 1992, Canella B, Raine C S. *The VCAM-1/VLA-4 pathway is involved in chronic lesion expression in multiple sclerosis (MS)*. J Neuropathol Exp Neurol; 52: 311, 1993), HIV-induced encephalitis (Sasseville V G, Newman W, Brodie S J, Hesterberg P, Pauley D, Ringler D J. *Monocyte adhesion to endothelium in simian immunodeficiency virus-induced AIDS encephalitis is mediated by vascular cell adhesion molecule-1/$\alpha_4\beta_1$ integrin reactions*. Am J Pathol; 144: 27–40, 1994), pulmonary inflammation and airway hyperreactvity in asthma (Abraham W M, Sielczak M W, Ahmed A, Cortes A, Lauredo I T, Kim J. Pepinsky, B, et al. *$\alpha_4$-integrins mediate antigen-induced late bronchial responses and prolonged airway hyperresponsiveness in sheep*. J Clin Invest; 93: 776–787, 1994, Pretolani M, Ruffié C, Roberto LapaeSilva J, Joseph D, Lobb R R, Vargaftig B B. *Antibody to very late activation antigen 4 prevents antigen-induced bronchial hyperreactivity and cellular infiltration in the guinea-pig airways*. J Exp Med; 180: 795–805, 1994), experimental models of autoimmune-mediated diabetes (Yang X-D, Karin N, Tisch R, Steinman L, McDevitt H O. *Inhibition of insulitis and prevention of diabetes in non-obese diabetic mice by blocking L-selectin and very late antigen 4 adhesion receptors*. Proc Natl Acad Sci USA; 90: 10494–10498, 1993, Burkly L C, Jakubowski A, Hattori M. *Protection against adoptive transfer of autoimmune diabetes medicated through very late antigen-4 integrin*. Diabetes; 43: 529–534, 1994), and experimental colitis (Podolsky D K, Lobb R, King N, Benjamin C D, Pepinsky B, Sehgal P, et al. *Attentuation of colitis in the cotton-top Tamarin by anti-$\alpha4$ integrin monoclonal antibody*. J Clin Invest; 92: 372–380, 1993). Since eosinophils represent a major component of the inflammatory cell influx in asthmatic lung tissue we developed a simple acute inflammatory model of VLA-4 integrin-dependent eosinophil infiltration which could be used to identify VLA-4 antagonists; such compounds would be of potential value in the treatment of asthma as well as other diseases in which VLA-4 played a role.

Materials and Methods

Animals, Housing and Viral Testing

C57BL/6 mice (Jackson, Bar Harbor, Me.;), 6–8 weeks old, weighing 20–25 g were used throughout. All mice were acclimated for at least 7–14 days after arrival. and maintained under controlled temperature (20–22° C.) and a 12 hr daily light cycle (6.00 A.M.–6.00 P.M.). Mice werehoused in laminar flow racks and checked biweekly for viral infections (mouse hepatitis virus, minute virus of mice, rodent orphan parvovirus, Sendai) with kits obtained from Oreganon Teknika (Durham, N.C.) using established enzyme-linked immunoabsorbent assays. Mice testing positive for any of the above were omitted from the study. All mice were fed standard laboratory chow (Upjohn Lab Rodent irradiated Mouse Chow, #5011-3, PMI Feeds, St. Louis, Mo.) and acidified drinking water (pH 5.0) ad libitum.

Induction of Inflammation by Intrapleural Injection of Dextran

Intrapleural injections were made using a 27G needle cut to 3–4 mm and blunted by filing. Injections were made by inserting the needle between the mid-intercostal ribs on the right side of the thoracic cavity.

Dextran (MW 5–40×$10^6$, St Louis, Mo.) was injected as a 10% solution in saline in a volume of 100 $\mu$l/mouse. Care was taken to avoid bleeding at the site of injection at which the intercostal muscles were cut to facilitate smooth insertion of the needle.

Quantitation of Pleural Inflammatory Leukocyte Responses

Pleural leukocytes were collected as follows: 4 h post-induction, pleural inflammatory exudate was removed by washing with 2×1.0 ml $Ca^{++}/Mg^{++}$ free HBSS (Gibco, Grand Island, N.Y.) containing 45 mg EDTA/100 ml HBSS, 4° C. Total leukocyte counts were made by hemocytometer following erythrocyte lysis in 2% acetic acid in PBS buffer; exudate leukocyte pellets were resuspended in serum for cytospin preparations and stained (Diff Quik, Baxter Healthcare, McGraw Park, Ill.) for differential leukocyte counts (neutrophils, eosinophils, and mononuclear leukocytes). The pleural cavities of mice receiving either no intrapleural injection, or saline were washed and the cells counted in the same way to estimate baseline or saline-induced pleural leukocyte counts respectively.

Administration of Drugs

All drugs were dissolved in PBS and the pH adjusted to 7.5 with NaOH. Each drug was administered intravenously through the retroorbital sinus at hourly intervals (0–3 h) starting from time "0" as indicated. Mice were carefully monitored for side effects; none were noted for the series of compounds reported herein.

The following camphoric acid analogues were tested for their inhibitory effects on dextran-induced leukocyte infiltration: Examples 4, 12, 54, 63, 166, 93, 180, 181, 183, 184, 217, Camphoric acid or PBS (saline) was administered iv. as a control. Inhibition of eosinophil infiltration, which was suppressed by anti-alpha-4 Mab (PS/2, 50%), was used as a readout of VLA-4 antagonist activity of the camphoric acids tested. Data for neutrophils are also reported.

Results

Dextran pleural leukocyte response. The total pleural leukocyte counts were $255\times10^4(+/-16$ SEM) cells in the normal pleural cavity; of the normal pleural leukocyte population, all cells were mononuclear (a similar response was observed following intrapleural saline injection). Four hours after intrapleural injection of dextran total pleural leukocyte counts increased to $719\times10^4(+/-67$ SEM) and comprised $36.8\times10^4(+/-4.1$ SEM) eosinophils, $292\times10^4(+/-25$ SEM) neutrophils and $391\times10^4(+/-48$ SEM) mononuclear leukocytes.

Inhibition of neutrophils and eosinophil (%Δ) are depicted by A, B and C according to the following ranges: $A\leq-50$, $-50<B\leq-10$, $-10<C\leq0$ Inhibition of Dextran Pleural Leukocyte Infiltration by Camiphoric Acids

|  |  | %Δ Pleural Leukocytes | |
| --- | --- | --- | --- |
| Treatment | Dose(mg/kg)# | Neutro | Eos |
| Ex. 12 | 50 × 4 iv | B | A |
|  | 50 × 2 iv | B | A |
| Ex. 54 | 50 × 4 iv | B | A |
| Ex. 4 | 25 × 2 iv | — | — |
|  | 50 × 2 iv | B | A |
| Ex. 63 | 25 × 2 iv | B | B |
|  | 50 × 2 iv | B | B |
| Ex. 166 | 25 × 2 iv | — | — |
|  | 50 × 2 iv | C | B |
| Ex. 93 | 25 × 2 iv | — | — |
|  | 50 × 2 iv | C | B |
| Ex. 181 | 25 × 2 iv | B | B |
|  | 50 × 2 iv | B | B |
| Ex. 180 | 25 × 2 iv | B | B |
|  | 50 × 2 iv | B | B |
| Ex. 183 | 25 × 2 iv | B | B |
|  | 50 × 2 iv | B | B |
| Ex. 184 | 25 × 2 iv | B | B |
|  | 50 × 2 iv | B | A |
| Ex. 217 | 25 × 2 iv | — | — |
|  | 50 × 2 iv | C | B |

Compounds given at 0 h, +1 h (×2 iv) or 0 h, +1 h, +2 h, +3 h (×4 iv) relative to dextran.
p < 0.05* Drug treated vs camphoric acid or PBS treated control.

What is claimed is:

1. A compound of the formula (I):

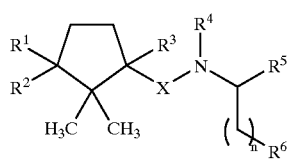

wherein n is an integer of 0 or 1;

$R^1$ is a hydrogen atom or methyl group, $R^2$ is a group of the formula: —CN, —COOH, —($C_{1-6}$ alkylene)OH, —CH$_2$O($C_{1-6}$ alkyl), —($C_{1-6}$ alkylene)COOH, —CH$_2$O($C_{1-6}$ alkylene)O($C_{1-6}$ alkyl), —CH$_2$O($C_{1-6}$ alkylene)COOH, —($C_{2-7}$ alkenylene)COOH, —CO($C_{1-6}$ alkylene)COOH, —CO($C_{2-7}$ alkenylene)COOH, —CO($C_{1-6}$ alkylene)O($C_{1-6}$ alkyl), —CO($C_{1-6}$ alkylene)CO($C_{1-6}$ alkyl), —CONH($C_{1-6}$ alkyl), —CONHO($C_{1-6}$ alkyl), —CONH($C_{1-6}$ alkylene)COOH, —CONH$_2$, —CONH($C_{3-7}$ cycloalkyl),

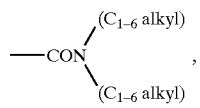

—CONHOCH$_2$Ph, —CONH($C_{1-6}$ alkylene)CN, —COO($C_{1-6}$ alkyl), —CH$_2$O($C_{1-6}$ alkylene)CONH$_2$, —CONH($C_{1-6}$ alkylene)CONH$_2$, —CONHOH, —NHCOOCH$_2$Ph,

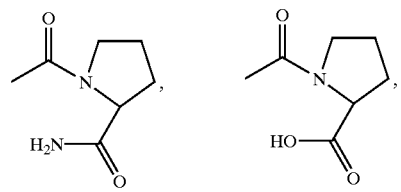

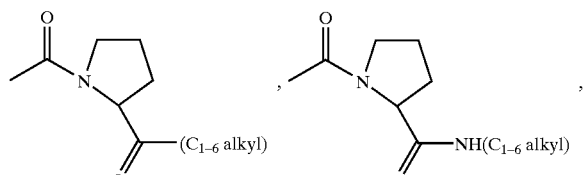

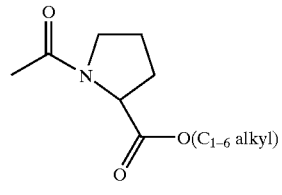

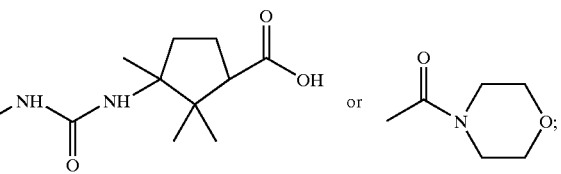

$R^3$ is a hydrogen atom or a methyl group;

X is a methylene group or a group of the formula: —CO—, $R^4$ is a hydrogen atom or a $C_{1-6}$ alkyl group;

$R^5$ s a group of the formula: —COOH or an ester or an amide thereof, —($C_{1-6}$ alkylene)COOH or an ester or an amide thereof, —($C_{1-7}$ alkylene)O($C_{1-6}$ alkyl), —($C_{1-7}$ alkylene)OH, —COO($C_{1-6}$ alkyl), —CONH($C_{1-6}$ alkyl), or —CONH$_2$;

237

$R^6$ is a substituent of the formula:

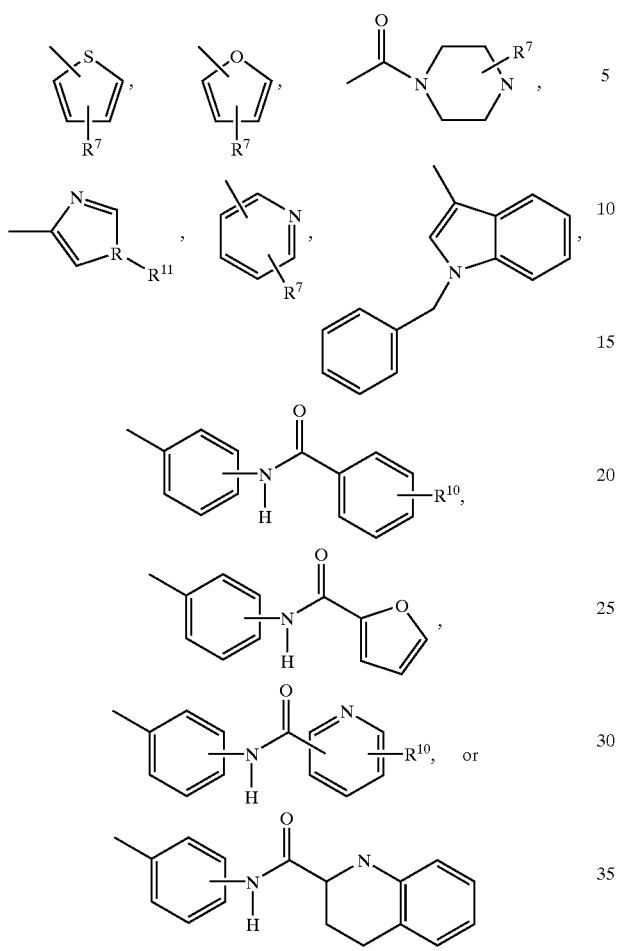

wherein, $R^7$, which occurs one or more times and which may be the same or different in each occurrence, is —H, —OH, —NO$_2$, —NH$_2$, —C$_1$-C$_5$ alkyl, —F, —Cl, —Br, —I, —COOH, —COO(C$_{1-6}$ alkyl), —O(C$_1$-C$_8$ alkyl), —CONH (C$_{1-6}$ alkylene)COOH, —OCH$_2$(C$_3$-C$_7$ cycloalkyl) or a substituent of the formula

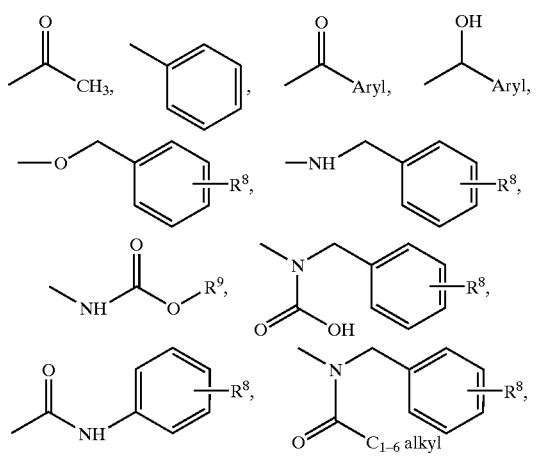

238

-continued

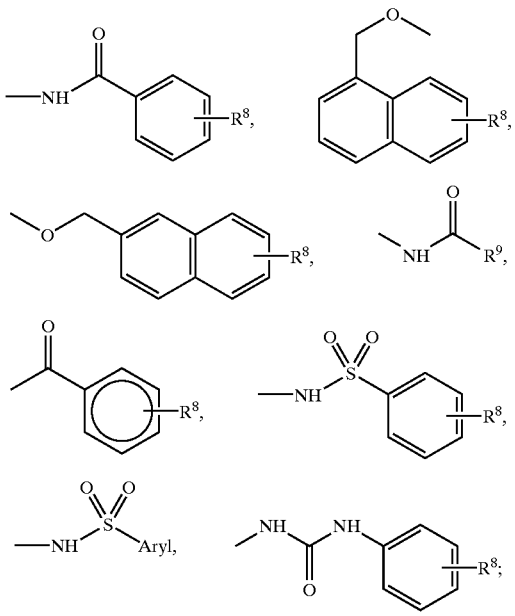

$R^8$, which occurs one or more times and which may be the same or different in each occurrence, is —H, —OH, —NH$_2$, —NO$_2$, —C$_1$-C$_7$ alkyl, —F, —Cl, —Br, —I, —CF$_3$, phenyl, or —O(C$_{1-6}$ alkyl);

$R^9$ is selected from a group of the formula: —H, —C$_1$-C$_5$ alkyl, —C$_3$-C$_7$ cycloalkyl, —(—C$_1$-C$_6$ alkylene)aryl, aryl, or a substituent of the formula:

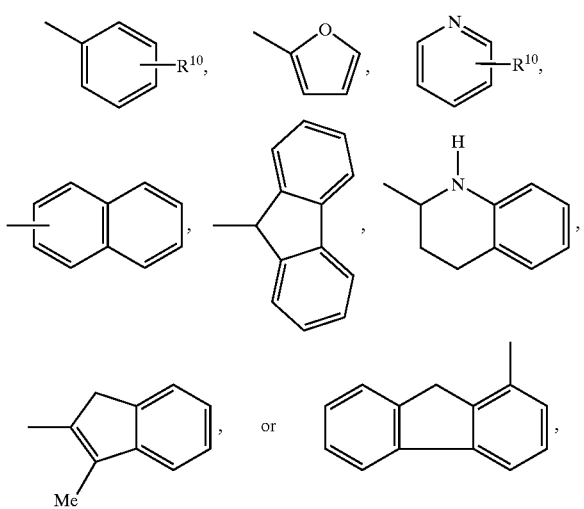

$R^{10}$, which occurs one or more times and which may be the same or different in each occurrence, is —H, —F, —Cl, —Br, or —I, —NO$_2$, —C$_{1-6}$ alkyl or —C$_{1-6}$ alkyl);

$R^{11}$ is selected from a group of the formula:

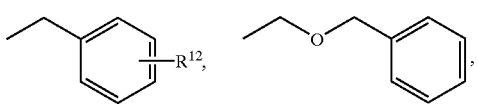

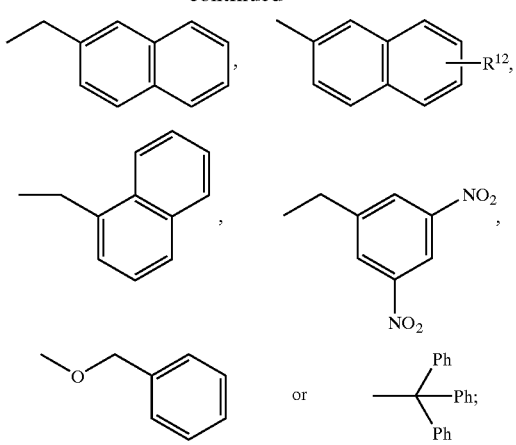

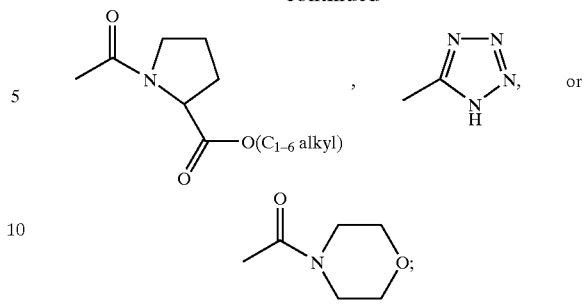

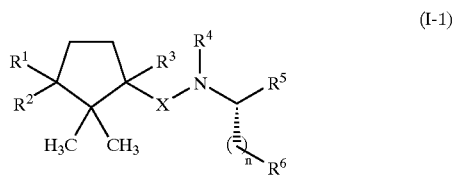

15 or a pharmaceutically acceptable salt thereof.

2. The compound according to claim 1, which is a compound of the formula (I-1):

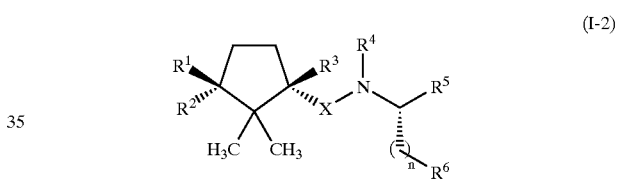

(I-1)

wherein n, $R^1$ through $R^6$ and X are as defined above.

3. The compound according to claim 1, which is a compound of the formula (I-2):

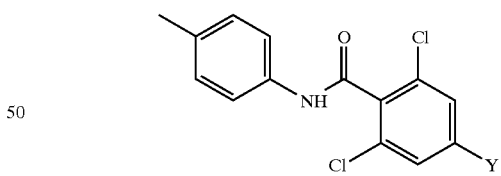

(I-2)

$R^{12}$, which occurs one or more times and which may be the same or different in each occurrence, is —H, —$CF_3$, —$OCF_3$, —F, —Br, —Cl, or —I;

with the proviso that $R^1$ and $R^3$ must be different and also with the proviso that when $R^2$ or $R^6$ is a moiety of the formula —COOH or contains a moiety of the formula —COOH, then a pharmaceutically acceptable ester or a pharmaceutically acceptable amide thereof are included, and also with the proviso that when $R^7$ is the formula

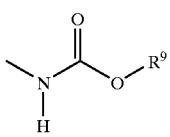

$R^9$ is other than hydrogen, and also with the proviso that when $R^6$ is the formula

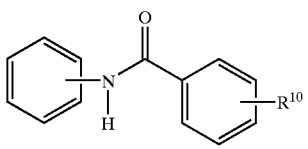

$R^2$ is

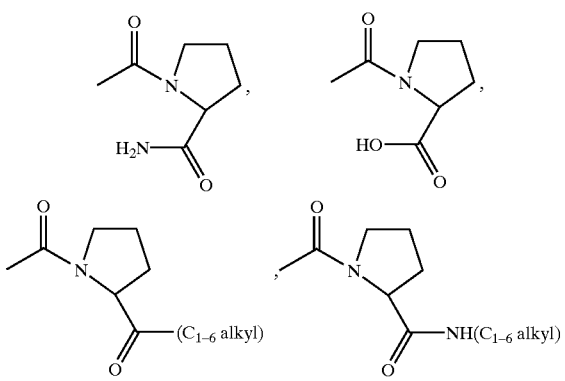

wherein n, $R^1$ through $R^4$, $R^6$ and X are as defined above and $R^5$ is a group of the formula: —COOH, —($C_{1-6}$ alkylene)COOH, —($C_{1-7}$ alkylene)O($C_{1-6}$ alkyl), —($C_{1-7}$ alkylene)OH, —COO($C_{1-6}$ alkyl), —CONH($C_{1-6}$ alkyl), or —$CONH_2$.

4. The compound according to claim 1, wherein $R^6$ is

[structure with dichlorobenzamide and Y substituent]

wherein Y is a hydrogen atom or a chlorine atom.

5. The compound according to claim 1, wherein $R_2$ is a group of the formula: is a group of the formula: —COOH or an ester or an amide thereof, —$CONHCH_2COOH$, —$CONHOCH_2Ph$ or —$CONHCH_2CONH_2$.

6. The compound according to claim 1, wherein said compound is selected from the group consisting of Examples 4, 24, 26, 28, 29, 31, 36, 38, 77, 130, 146, 194, 208, 209, 210, 212, 213, 215, and 225.

7. The compound according to claim 6, wherein said compound is selected from the group consisting of Examples 4, 24, 26, 28, 38, 77, 130, 146, 194, 208, 209, 210, 213, 215, and 225.

8. The compound according to claim 7, wherein said compound is selected from the group consisting of Examples 208, 209, 210, 215, and 225.

9. The compound according to claim 1, wherein said compound is selected from the group consisting of Examples 4, 24, 26, 28, 29, 36, 38, 77, 130, 194, 208, 209, 210, 212, 213, 215, and 225.

10. The compound according to claim 9, wherein said compound is selected from the group consisting of Examples 4, 24, 28, 38, 77, 130, 194, 208, 209, 210, 212, 213, 215, and 225.

11. The compound according to claim 10, wherein said compound is selected from the group consisting of Examples 209, 210, and 225.

12. The compound according to claim 1, wherein said compound is (1S-cis)-N-[3-carboxy-2,2,3-trimethylcyclopentyl)-carbonyl]-1-[(3,4-dichlorophenyl)methyl]-L-histidine.

13. A pharmaceutical composition comprising:
a therapeutically effective amount of the compound as set forth in claims 1, 2, 3, 4, 5, 6, 7, 8, 9, 10, 11, or 12; and
a pharmaceutically acceptable carrier or diluent.

14. A method for treating or preventing $\alpha_4\beta_1$ adhesion mediated conditions in a human which comprises administering to a patient an effective amount of the compound according to claim 1, 2, 3, 4, 5, 6, 7, 8, 9, 10, 11, or 12.

15. A method according to claim 14, wherein said condition is selected from the group consisting of rheumatoid arthritis, asthma, allergy conditions, allograft rejection, psoriasis, eczema, contact dermatitis and other skin inflammatory diseases, inflammatory and immunoinflammatory conditions including ophthalmic inflammatory conditions, inflammatory bowel diseases, atherosclerosis, and ulcerative colitis.

* * * * *